United States Patent
Andersen et al.

(10) Patent No.: US 6,410,556 B1
(45) Date of Patent: *Jun. 25, 2002

(54) MODULATORS OF PROTEIN TYROSINE PHOSPHATESES (PTPASES)

(75) Inventors: Henrik Sune Andersen, Lyngby; Thomas Kruse Hansen, Herlev; Jesper Lau, Farum; Niels Peter Hundahl Møller, København Ø ; Ole Hvilsted Olsen, Brønshøj, all of (DK); Frank Urban Axe, Escondido, CA (US); Yu Ge; Daniel Dale Holsworth, both of San Diego, CA (US); Todd Kevin Jones, Solana Beach, CA (US); Luke Milburn Judge, Seattle, WA (US); Wiliam Charles Ripka, San Diego, CA (US); Barry Zvi Shapira, Acton, CA (US); Roy Teruyuki Uyeda, San Diego, CA (US)

(73) Assignees: Novo Nordisk A/S, Bagsvaerd (DK); Ontogen Corporation, Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/659,547

(22) Filed: Sep. 11, 2000

Related U.S. Application Data

(60) Provisional application No. 60/156,742, filed on Sep. 30, 1999.

(30) Foreign Application Priority Data

Sep. 10, 1999 (DK) .................................. PA 1999 01277
Jul. 7, 2000 (DK) .................................. PA 2000 01069

(51) Int. Cl.$^7$ ..................... A61K 31/435; C07D 471/04
(52) U.S. Cl. ................... 514/301; 514/229.8; 514/302; 540/476; 540/593; 546/114; 546/115; 546/116; 548/453
(58) Field of Search ................................. 546/114, 115, 546/116; 514/301, 302

(56) References Cited

U.S. PATENT DOCUMENTS 3,953,468 A 4/1976 Wechter et al. ....... 260/332.2 R
6,262,044 B1 * 7/2001 Møller et al. ................ 514/202

FOREIGN PATENT DOCUMENTS

| GB | 1 583 679 | 1/1981 |
|---|---|---|
| WO | WO 99/46237 | 9/1999 |
| WO | WO 99/46267 | 9/1999 |
| WO | WO 99/46268 | 9/1999 |

OTHER PUBLICATIONS

Peters et al., The Journal of Biological Chemistry, vol. 275, pp. 18201–18209 (2000).
Iversen et al., The Journal of Biological Chemistry, vol. 275, pp. 10300–10307 (2000).

* cited by examiner

*Primary Examiner*—Bernard Dentz
(74) *Attorney, Agent, or Firm*—Reza Green, Esq.; Peter J. Waibel, Esq.

(57) ABSTRACT

Disclosed are novel compounds, novel compositions, methods of their use, and methods of their manufacture, where such compounds of Formula 1 are pharmacologically useful inhibitors of Protein Tyrosine Phosphatases (PTPase's) including PTP1B, T cell PTP,

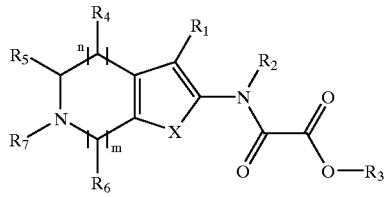

Formula 1 wherein n, m, X, $R_1$, $R_2$, $R_3$, $R_4$, $R_5$, $R_6$, and $R_7$ are defined more fully in the description. The compounds are useful in the treatment of type I diabetes, type II diabetes, impaired glucose tolerance, insulin resistance, obesity, and other diseases.

77 Claims, No Drawings

MODULATORS OF PROTEIN TYROSINE PHOSPHATESES (PTPASES)

CROSS-REFERENCE TO RELATED APPLICATIONS

This application claims priority under 35 USC 119 of provisional application No. 60/156,742 filed Sep. 30, 1999 and of Danish application nos. PA 1999 01277 and PA 2000 01069 filed Sep. 10, 1999 and Jul. 7, 2000, the contents of which are fully incorporated herein by reference.

FIELD OF THE INVENTION

The present invention relates to novel compounds, to methods for their preparation, to compositions comprising the compounds, to the use of these compounds as medicaments and their use in therapy, where such compounds of Formula 1 are pharmacologically useful inhibitors of Protein Tyrosine Phosphatases (PTPases) such as PTP1B, CD45, SHP-1, SHP-2, PTPα, LAR and HePTP or the like,

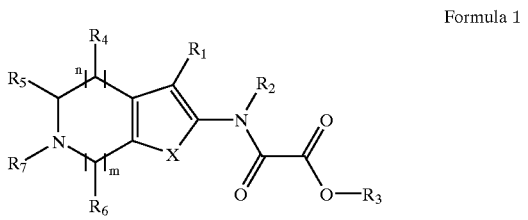

Formula 1 wherein n, m, X, Y, $R_1$, $R_2$, $R_3$, $R_4$, $R_5$ and $R_6$ are defined more fully below. It has been found that PTPases plays a major role in the intracellular modulation and regulation of fundamental cellular signaling mechanisms involved in metabolism, growth, proliferation and differentiation (Hunter, Phil. Trans. R. Soc. Lond. B 353: 583–605 (1998); Chan et al., Annu. Rev. Immunol. 12: 555–592 (1994); Zhang, Curr. Top. Cell. Reg. 35: 21–68 (1997); Matozaki and Kasuga, Cell. Signal. 8: 113–19 (1996); Flint et al., The EMBO J. 12:1937–46 (1993); Fischer et al, Science 253:401–6 (1991)). Overexpression or altered activity of tyrosine phosphatases can also contribute to the symptoms and progression of various diseases (Wiener, et al., J. Natl. cancer Inst. 86:372–8 (1994); Hunter and Cooper, Ann. Rev. Biochem, 54:897–930 (1985)). Furthermore, there is increasing evidence which suggests that inhibition of these PTPases may help treat certain types of diseases such as diabetes type I and II , autoimmune disease, acute and chronic inflammation, osteoporosis and various forms of cancer.

BACKGROUND OF THE INVENTION

Protein phosphorylation is now well recognized as an important mechanism utilized by cells to transduce and regulate signals during different stages of cellular function (Hunter, Phil. Trans. R. Soc. Lond. B 353: 583–605 (1998); Chan et al., Annu. Rev. Immunol. 12: 555–592 (1994); Zhang, Curr. Top. Cell. Reg. 35: 21–68 (1997); Matozaki and Kasuga, Cell. Signal. 8: 113–19 (1996); Fischer et al, Science 253:401–6 (1991); Flint et al., EMBO J. 12:1937–46 (1993)). There are at least two major classes of phosphatases: (1) those that dephosphorylate proteins (or peptides) that contain a phosphate group(s) on a serine or threonine moiety (termed Ser/Thr phosphatases) and (2) those that remove a phosphate group(s) from the amino acid tyrosine (termed protein tyrosine phosphatases or PTPases or PTPs).

The PTPases are a family of enzymes that can be classified into two groups: a) intracellular or nontransmembrane PTPases and b) receptor-type or transmembrane PTPases.

Intracellular PTPases

Most known intracellular type PTPases contain a single conserved catalytic phosphatase domain consisting of 220–240 amino acid residues. The regions outside the PTPase domains are believed to play important roles in localizing the intracellular PTPases subcellularly (Mauro, L. J. and Dixon, J. E. TIBS 19: 151–155 (1994)). The first intracellular PTPase to be purified and characterized was PTP1B, which was isolated from human placenta (Tonks et al., J. Biol. Chem. 263: 6722–6730 (1988)). Shortly after, PTP1B was cloned (Charbonneau et al., Proc. Natl. Acad. Sci. USA 86: 5252–5256 (1989); Chernoff et al., Proc. Natl. Acad. Sci. USA 87: 2735–2789 (1989)). Other examples of intracellular PTPases include (1) T-cell PTPase/TC-PTP (Cool et al. Proc. Natl. Acad. Sci. USA 86: 5257–5261 (1989)), (2) rat brain PTPase (Guan et al., Proc. Natl. Acad. Sci. USA 87:1501–1502 (1990)), (3) neuronal phosphatase STEP (Lombroso et al., Proc. Natl. Acad. Sci. USA 88: 7242–7246 (1991)), (4) ezrin-domain containing PTPases: PTPMEG1 (Guet al., Proc. Natl. Acad. Sci. USA 88: 5867–57871 (1991)), PTPH1 (Yang and Tonks, Proc. Natl. Acad. Sci. USA 88: 5949–5953 (1991)), PTPD1 and PTPD2 (Møller et al., Proc. Natl. Acad. Sci. USA 91: 7477–7481 (1994)), FAP-1/BAS (Sato et al., Science 268: 411–415 (1995); Banville et al., J. Biol. Chem. 269: 22320–22327 (1994); Maekawa et al., FEBS Letters 337: 200–206 (1994)), and SH2 domain containing PTPases: PTP1C/SH-PTP1/SHP-1 (Plutzky et al., Proc. Natl. Acad. Sci. USA 89: 1123–1127 (1992); Shen et al., Nature Lond. 352: 736–739 (1991)) and PTP1D/Syp/SH-PTP2/SHP-2 (Vogel et al., Science 259: 1611–1614 (1993); Feng et al., Science 259: 1607–1611 (1993); Bastein et al., Biochem. Biophys. Res. Comm. 196: 124–133 (1993)).

Receptor-type PTPases consist of a) a putative ligand-binding extracellular domain, b) a transmembrane segment, and c) an intracellular catalytic region. The structures and sizes of the putative ligand-binding extracellular domains of receptor-type PTPases are quite divergent. In contrast, the intracellular catalytic regions of receptor-type PTPases are very homologous to each other and to the intracellular PTPases. Most receptor-type PTPases have two tandemly duplicated catalytic PTPase domains.

The first receptor-type PTPases to be identified were (1) CD45/LCA (Ralph, S. J., EMBO J. 6: 1251–1257 (1987)) and (2) LAR (Streuli et al., J. Exp. Med. 168: 1523–1530 (1988)) that were recognized to belong to this class of enzymes based on homology to PTP1B (Charbonneau et al., Proc. Natl. Acad. Sci. USA 86: 5252–5256 (1989)). CD45 is a family of high molecular weight glycoproteins and is one of the most abundant leukocyte cell surface glycoproteins and appears to be exclusively expressed upon cells of the hematopoietic system (Trowbridge and Thomas, Ann. Rev. Immunol. 12: 85–116 (1994)).

The identification of CD45 and LAR as members of the PTPase family was quickly followed by identification and cloning of several different members of the receptor-type PTPase group. Thus, 5 different PTPases, (3) PTPα, (4) PTPβ, (5) PTPδ, (6) PTPε, and (7) PTPζ, were identified in one early study (Krueger et al., EMBO J. 9: 3241–3252 (1990)). Other examples of receptor-type PTPases include (8) PTPγ (Barnea et al., Mol. Cell. Biol. 13: 1497–1506 (1995)) which, like PTPζ (Krueger and Saito, Proc. Natl. Acad. Sci. USA 89: 7417–7421 (1992)) contains a carbonic anhydrase-like domain in the extracellular region, (9) PTPμ

(Gebbink et al., *FEBS Letters* 290: 123–130 (1991)), (10) PTPκ (Jiang et al., *Mol. Cell. Biol.* 13: 2942–2951 (1993)). Based on structural differences the receptor-type PTPases may be classified into subtypes (Fischer et al., *Science* 253: 401–406 (1991)): (I) CD45; (II) LAR, PTPδ, (11) PTPσ; (III) PTP, (12) SAP-1 (Matozaki et al., *J. Biol. Chem.* 269: 2075–2081 (1994)), (13) PTP-U2/GLEPP1 (Seimiya et al., *Oncogene* 10: 1731–1738 (1995); Thomas et al., *J. Biol. Chem.* 269: 19953–19962 (1994)), and (14) DEP-1; (IV) PTPα, PTPε. All receptor-type PTPases except Type III contain two PTPase domains. Novel PTPases are continuously identified. In the early days of PTPase research, it was believed that the number of PTPs would match that of protein tyrosine kinases (PTKs) (Hanks and Hunter, *FASEB J.* 9: 576–596 (1995)). However, although about 90 open reading frames in *C. elegans* contain the hallmark motif of PTPs, it now seems that the estimate of 'classical' PTPases must be downsized, perhaps to between 100 and 200 in humans.

PTPases are the biological counterparts to protein tyrosine kinases Therefore, one important function of PTPases is to control, down-regulate, the activity of PTKs. However, a more complex picture of the function of PTPases has emerged. Thus, several studies have shown that some PTPases may actually act as positive mediators of cellular signaling. As an example, the SH2 domain-containing SHP-2 seems to act as a positive mediator in insulin-stimulated Ras activation (Noguchi et al., *Mol. Cell. Biol.* 14: 6674–6682 (1994)) and of growth factor-induced mitogenic signal transduction (Xiao et al., *J. Biol. Chem.* 269: 21244–21248 (1994)), whereas the homologous SHP-1 seems to act as a negative regulator of growth factor-stimulated proliferation (Bignon and Siminovitch, *Clin.Immunol. Immunopathol.* 73: 168–179 (1994)). Another example of PTPases as positive regulators has been provided by studies designed to define the activation of the Src-family of tyrosine kinases. In particular, several lines of evidence indicate that CD45 is positively regulating the activation of hematopoietic cells, possibly through dephosphorylation of the C-terminal tyrosine of Fyn and Lck (Chan et al., *Annu. Rev. Immunol.* 12: 555–592 (1994)).

PTPases were originally identified and purified from cell and tissue lysates using a variety of artificial substrates and, therefore, their natural function of dephosphorylation was not well known. Since tyrosine phosphorylation by tyrosine kinases is usually associated with cell proliferation, cell transformation and cell differentiation, it was assumed that PTPases were also associated with these events. This association has now been proven to be the case with many PTPases. PTP1 B, a phosphatase whose structure was the first PTPase to be elucidated (Barford et al., *Science* 263:1397–1404 (1994)) has been shown to be involved in insulin-induced oocyte maturation (Flint et al., *The EMBO J.* 12:1937–46 (1993)) and it has been suggested that the overexpression of this enzyme may be involved in p185$^{c-erb}$ $_{B2}$-associated breast and ovarian cancers (Wiener, et al., *J. Natl. cancer Inst.* 86:372–8 (1994); Weiner et al., *Am. J. Obstet. Gynecol.* 170:1177–883 (1994)). The association with cancer is recent evidence which suggests that overexpression of PTP1B is statistically correlated with increased levels of p185$^{c-erb\ B2}$ in ovarian and breast cancer. The role of PTP1B in the etiology and progression of the disease has not yet been elucidated. Inhibitors of PTP1B may therefore help clarify the role of PTP1B in cancer and in some cases provide therapeutic treatment for certain forms of cancer.

PTPases: The Insulin Receptor Signaling Pathway/diabetes

Insulin is an important regulator of different metabolic processes and plays a key role in the control of blood glucose. Defects related to its synthesis or signaling lead to diabetes mellitus. Binding of insulin to the insulin receptor (IR) causes rapid (auto)phosphorylation of several tyrosine residues in the intracellular part of the β-subunit. Three closely positioned tyrosine residues (the tyrosine-1150 domain) must all be phosphorylated to obtain full activity of the insulin receptor tyrosine kinase (IRTK) which transmits the signal further downstream by tyrosine phosphorylation of other cellular substrates, including insulin receptor substrate-1 (IRS-1) (Wilden et al., *J. Biol. Chem.* 267: 16660–16668 (1992); Myers and White, *Diabetes* 42: 643–650 (1993); Lee and Pilch, *Am. J. Physiol.* 266: C319–C334 (1994); White et al., *J. Biol. Chem.* 263: 2969–2980 (1988)). The structural basis for the function of the tyrosine-triplet has been provided by X-ray crystallographic studies of IRTK that showed tyrosine-1150 to be autoinhibitory in its unphosphorylated state (Hubbard et al., *Nature* 372: 746–754 (1994)) and of the activated IRTK (Hubbard, *EMBO J.* 16:5572–5581 (1997)).

Several studies clearly indicate that the activity of the auto-phosphorylated IRTK can be reversed by dephosphorylation in vitro (reviewed in Goldstein, *Receptor* 3: 1–15 (1993); Mooney and Anderson, *J. Biol. Chem.* 264: 6850–6857 (1989)), with the tri-phosphorylated tyrosine-1150 domain being the most sensitive target for protein-tyrosine phosphatases (PTPases) as compared to the di- and mono-phosphorylated forms (King et al., *Biochem. J.* 275: 413–418 (1991)). This tyrosine-triplet functions as a control switch of IRTK activity and the IRTK appears to be tightly regulated by PTP-mediated dephosphorylation in vivo (Khan et al., *J. Biol. Chem.* 264: 12931–12940 (1989); Faure et al., *J. Biol. Chem.* 267: 11215–11221 (1992); Rothenberg et al., *J. Biol. Chem.* 266: 8302–8311 (1991)). The intimate coupling of PTPases to the insulin signaling pathway is further evidenced by the finding that insulin differentially regulates PTPase activity in rat hepatoma cells (Meyerovitch et al., *Biochemistry* 31: 10338–10344 (1992)) and in livers from alloxan diabetic rats (Boylan et al., *J. Clin. Invest.* 90: 174–179 (1992)).

Until recently, relatively little was known about the identity of the PTPases involved in IRTK regulation. However, the existence of PTPases with activity towards the insulin receptor can be demonstrated as indicated above. Further, when the strong PTPase-inhibitor pervanadate is added to whole cells an almost full insulin response can be obtained in adipocytes (Fantus et al., *Biochemistry* 28: 8864–8871 (1989); Eriksson et al., *Diabetologia* 39: 235–242 (1995)) and skeletal muscle (Leighton et al., *Biochem. J.* 276: 289–292 (1991)). In addition, other studies show that a new class of peroxovanadium compounds act as potent hypoglycemic compounds in vivo (Posner et al.,supra). Two of these compounds were demonstrated to be more potent inhibitors of dephosphorylation of the insulin receptor than of the EGF-receptor, thus indicating that even such relatively unselective inhibitors may convey some specificity in regulating different signal transduction pathways.

It was recently found by Montreal-based research groups that mice lacking the protein tyrosine phosphatase-1B gene (PTP1B) (Elchebly et al., *Science* 283: 1544–1548 (1999)) yielded healthy mice that showed increased insulin sensitivity and resistance to diet-induced obesity. Importantly, these results have been confirmed and extended independently by another research team from Boston (Klaman et al., *Mol. Cell. Biol.* 20: 5479–5489 (2000)). The enhanced insulin sensitivity of the PTP$^{-/-}$ mice was also evident in glucose and insulin tolerance tests. The PTP-1B knock-out mouse showed many characteristics which would be highly desirable to have for an anti-diabetes treatment. Most importantly, the knock-out mice grew normally and were fertile and have exhibited no increased incidence of cancer, as obviously there could have been concerns when one considers the mitogenic properties of insulin. From the diabetes perspective, the first notable features of the knock-out animals were that blood glucose and insulin levels were lowered, and the consequent marked increase in insulin sensitivity in the knock-out animals. Moreover, the insulin-stimulated tyrosine phosphorylation levels of IR and IRS-1 were found to be increased/prolonged in muscle and liver—but not in fat tissue. Thus, the main target tissues for this type of approach would appear to be insulin action in liver and muscle. This is in contrast to the main target tissue for the PPARγ agonist class of insulin sensitizers (the "-diones"), which is adipose tissue (Murphy & Nolan, *Exp. Opin. Invest. Drugs* 9: 1347–1361 (2000)). Several other "diabetic" parameters were also improved, such as plasma triglycerides being decreased in the knock-out mice. However, perhaps even more remarkably and unexpectedly, the knock-out animals also exhibited a resistance to weight gain when placed on a high-fat diet. This is again in contrast to the action of the PPARγ agonist class of insulin sensitizers, which rather induce weight gain (Murphy & Nolan, supra), and would suggest that inhibition of PTP-1B could be a particularly attractive option for treatment of obese Type II diabetics. This is also supported by the fact that the heterozygous mice from this study showed many of these desirable features. In the Montreal study, there appeared to be no gender differences, whereas in the Boston study in general the male animals had larger responses to PTP-1B being knocked out. In both studies, the reduction in weight gain of the knock-out animals on the high fat diet was found to be due to a decreased fat cell mass, although differences were observed with respect to fat cell number. Leptin levels were also lower in the knock-out mice, presumably as a reflection of the decreased fat mass. Significantly, the Boston group also found that the knock-out animals had an increased energy expenditure of around 20% and an increased respiratory quotient compared to the wild-type; again, heterozygote animals displayed an intermediate level of energy expenditure. Whether this increase in metabolic rate is a reflection of the effects of PTP-1B on insulin-signaling or on other cellular components remains to be established, but the bottom-line message that inhibition of this enzyme may be an effective anti-diabetic and perhaps also anti-obesity therapy is clear.

It should also be noted that in the PTP-1B knock-out mice the basal tyrosine phosphorylation level of the insulin receptor tyrosine kinase does not appear to be increased, which is in contrast to the situation after insulin treatment where there is an increased or prolonged phosphorylation. This might indicate that other PTPs are controlling the basic phosphorylation state of the insulin receptor in the knock-out mice—and perhaps in man.

Previous findings are in accordance with the results reported by Elchebly et al. (supra) (recently reviewed in Kennedy, *Biomed. Pharmacother.* 53: 466–470 (1999)). Thus, it has been found that high glucose concentration induce insulin resistance and increase the expression of PTP1B in rat (fibroblasts expressing the human insulin receptor (Maegawa et al., *J. Biol. Chem.* 270: 7724–7730 (1995)). In rat L6 cells, insulin and insulin-like growth factor I (IGF-I) were found to induce increased PTPase activity, including increased PTP1B expression (Kenner et al. *J. Biol. Chem.* 266: 25455–25462 (1993)). In addition, the same group has shown that PTP1B may interact directly with the activated IR (Seely et al. *Diabetes* 45: 1379–1385 (1996)) and act directly as a negative regulator of insulin and IGF-I-stimulated signaling (Kenner et al. *J. Biol. Chem.* 271: 19810–19816 (1996)). Osmotic loading of rat KRC-7 hepatoma cells with neutralizing anti-PTP1B antibodies also indicated a role for PTP1B in negative regulating of the insulin signaling pathway (Akmad et al. *J. Biol. Chem.* 270: 20503–20508 (1995)).

Also other PTPases have been implicated as regulators of the insulin signaling pathway. Thus, it was found that the ubiquitously expressed SH2 domain containing PTPase, PTP1D/SHP-2 (Vogel et al., 1993, supra), associates with and dephosphorylates IRS-1, but apparently not the IR itself (Kuhné et al., *J. Biol. Chem.* 268: 11479–11481 (1993); (Kuhné et al., *J. Biol. Chem.* 269: 15833–15837 (1994)).

Other studies suggest that receptor-type or membrane-associated PTPases are involved in IRTK regulation (Faure et al., *J. Biol. Chem.* 267: 11215–11221 (1992), (Haring et al., *Biochemistry* 23: 3298–3306 (1984); Sale, *Adv. Prot. Phosphatases* 6: 159–186 (1991)). Hashimoto et al. have proposed that LAR might play a role in the physiological regulation of insulin receptors in intact cells (Hashimoto et al., *J. Biol. Chem.* 267: 13811–13814 (1992)). Their conclusion was reached by comparing the rate of dephosphorylation/inactivation of purified IR using recombinant PTP1B as well as the cytoplasmic domains of LAR and PTPα. Antisense inhibition was used to study the effect of LAR on insulin signaling in a rat hepatoma cell line (Kulas et al., *J. Biol. Chem.* 270: 2435–2438 (1995)). A suppression of LAR protein levels by about 60 percent was paralleled by an approximately 150 percent increase in insulin-induced auto-phosphorylation. However, only a modest 35 percent increase in IRTK activity was observed, whereas the insulin-dependent phosphatidylinositol 3-kinase (PI 3-kinase) activity was significantly increased by 350 percent. Reduced LAR levels did not alter the basal level of IRTK tyrosine phosphorylation or activity. The authors speculate that LAR could specifically dephosphorylate tyrosine residues that are critical for PI 3-kinase activation either on the insulin receptor itself or on a downstream substrate. Conflicting results have been reported for PTP-LAR knock-out mice. Thus, Goldstein and coworkers reported that transgenic mice deficient in PTP-LAR exhibit profound defects in glucose-homeostasis (Ren et al., *Diabetes* 47: 493–497 (1998)). However, it is difficult to fully assess the contribution of LAR deficiency to the glucose homeostasis in these mice due to the fact that the control mice were of a different genetic background than the knock-out mice. Moreover, normal glucose homeostasis was reported in a different strain of PTP-LAR knock-out mice (Sorensen et al., *Diabetologia* 40: A143 (1997)).

While previous reports indicate a role of PTPα in signal transduction through src activation (Zheng et al., *Nature* 359: 336–339 (1992); den Hertog et al., *EMBO J.* 12: 3789–3798 (1993)) and interaction with GRB-2 (den Hertog et al., *EMBO J.* 13: 3020–3032 (1994); Su et al., *J. Biol. Chem.* 269: 18731–18734 (1994)), Møller, Lammers and coworkers provided results that suggest a function for this phosphatase and its close relative PTP as negative regulators of the insulin receptor signal (Møller et al, 1995 supra; Lammers, et al., *FEBS Lett.* 404:37–40 (1997). These studies also indicated that receptor-like PTPases might play a significant role in regulating the IRTK.

Other studies have shown that PTP1B and TC-PTP are likely to be involved in the regulation of several other cellular processes in addition to the described regulatory roles in insulin signaling. Therefore, PTP1B and/or TC-PTP as well as other PTPases showing key structural features with PTP1B and TC-PTP are likely to be important therapeutic targets in a variety of human and animal diseases. The compounds of the present invention are useful for modulating or inhibiting PTP1B and/or TC-PTP and/or other PTPases showing key structural features with said PTPases and for treating diseases in which said modulation or inhibition is indicated. A few examples that are not intended in any way to limit the scope of the invention of substrates that may be regulated by PTP1B will be given below.

Tonks and coworkers have developed an elegant 'substrate trapping' technique that has allowed identification of the epidermal growth factor receptor (EGF-R) as a major substrate of PTP1B in COS cells (Flint et al. *Proc. Natl. Acad. Sci. USA* 94: 1680–1685 (1997)). In addition, three other as yet unidentified substrates of PTP1B were isolated. As an example of these studies, it has been found—using the above substrate-trapping technique—that PTP1B in addition to the EGF-R associates with activated platelet-derived growth factor receptor (PDGF-R), but not with colony-stimulating factor 1 receptor (CSF-1R) (Liu & Chernoff, *Biochem. J.* 327: 139–145 (1997)).

Early studies have shown that the subcellular localization as well as the enzyme activity of PTP1B may be regulated by agonist-induced calpain-catalyzed cleavage in human platelets (Frangioni et al. *EMBO J.* 12: 4843–4856 (1993)). Moreover, PTP1B cleavage correlated with the transaction from reversible to irreversible platelet aggregation. Thus, as a non-limiting example compounds of the present invention might be used to prevent or induce irreversible platelet aggregation in individuals in need thereof. It was proposed that the cleavage-induced change in the subcellular localization of PTP1B (from membrane to cytosol) results in different substrate specificity not only in platelet but also in other cell types (Frangioni et al., supra).

The above substrate trapping method has further been used to identify the protein tyrosine kinase p210$^{bcr-abl}$ as a substrate for PTP1B (LaMontagne, Jr. et al. *Mol. Cell. Biol.* 18: 2965–2975 (1998)). These studies suggest that PTP1B might function as a negative regulator of p210$^{bcr-abl}$ signaling in vivo. In addition, PTP1B was recently found to bind to and dephosphorylate the docking protein p130$^{Cas}$ in rat fibroblasts and thereby suppress transformation by v-crk, v-src, and v-ras, but not by v-raf (Liu et al. *Mol. Cell. Biol.* 18: 250–259 (1998)).

The transmembrane PTPase CD45, which is believed to be hematopoietic cell-specific, was found to negatively regulate the insulin receptor tyrosine kinase in the human multiple myeloma cell line U266 (Kulas et al., *J. Biol. Chem.* 271: 755–760 (1996)).

Further, PTPases influences the following hormones or diseases or disease states: somatostatin, the immune system/autoimmunity, cell-cell interactions/cancer, platelet aggregation, osteoporosis, and microorganisms, as disclosed in PCT Publication WO 99/15529.

Somatostatin inhibits several biological functions including cellular proliferation (Lamberts et al., *Molec. Endocrinol.* 8: 1289–1297 (1994)). While part of the antiproliferative activities of somatostatin are secondary to its inhibition of hormone and growth factor secretion (e.g. growth hormone and epidermal growth factor), other antiproliferative effects of somatostatin are due to a direct effect on the target cells. As an example, somatostatin analogs inhibit the growth of pancreatic cancer presumably via stimulation of a single PTPase, or a subset of PTPases, rather than a general activation of PTPase levels in the cells (Liebow et al., *Proc. Natl. Acad. Sci. USA* 86: 2003–2007 (1989); Colas et al., *Eur. J. Biochem.* 207:1017–1024 (1992)).

PTPases: The Immune System/autoimmunity

Several studies suggest that the receptor-type PTPase CD45 plays a critical role not only for initiation of T cell activation, but also for maintaining the T cell receptor-mediated signaling cascade. These studies are reviewed in: (Weiss A., *Ann. Rev. Genet.* 25: 487–510 (1991); Chan et al., *Annu. Rev. Immunol.* 12: 555–592 (1994); Trowbridge and Thomas, *Annu. Rev. Immunol.* 12: 85–116 (1994)).

CD45 is one of the most abundant of the cell surface glycoproteins and is expressed exclusively on hemopoetic cells. In T cells, it has been shown that CD45 is one of the critical components of the signal transduction machinery of lymphocytes. In particular, evidence has suggested that CD45 phosphatase plays a pivotal role in antigen-stimulated proliferation of T lymphocytes after an antigen has bound to the T cell receptor (Trowbridge, *Ann. Rev. Immunol*, 12: 85–116 (1994)). Several studies suggest that the PTPase activity of CD45 plays a role in the activation of Lck, a lymphocyte-specific member of the Src family protein-tyrosine kinase (Mustelin et al., *Proc. Natl. Acad. Sci. USA* 86: 6302–6306 (1989); Ostergaard et al., *Proc. Natl. Acad. Sci. USA* 86: 8959–8963 (1989)). These authors hypothesized that the phosphatase activity of CD45 activates Lck by dephosphorylation of a C-terminal tyrosine residue, which may, in turn, be related to T-cell activation. Thus, it was found that recombinant p56lck specifically associates with recombinant CD45 cytoplasmic domain protein, but not to the cytoplasmic domain of the related PTPα (Ng et al., *J. Biol. Chem.* 271: 1295–1300 (1996)). The p56lck-CD45 interaction seems to be mediated via a nonconventional SH2 domain interaction not requiring phosphotyrosine. In immature B cells, another member of the Src family protein-tyrosine kinases, Fyn, seems to be a selective substrate for CD45 compared to Lck and Syk (Katagiri et al., *J. Biol. Chem.* 270: 27987–27990 (1995)).

Studies using transgenic mice with a mutation for the CD45-exon6 exhibited lacked mature T cells. These mice did not respond to an antigenic challenge with the typical T cell mediated response (Kishihara et al., *Cell* 74:143–56 (1993)). Inhibitors of CD45 phosphatase would therefore be very effective therapeutic agents in conditions that are associated with autoimmune diseases with rheumatoid arthritis, systemic lupus erythematosus, type I diabetes, and inflammatory bowel disease as non-limiting examples. Another important use of CD45 inhibitors is for immunosuppression in connection with tissue or cell transplantation and other condtions with need for immunosuppressive treatment.

CD45 has also been shown to be essential for the antibody mediated degranulation of mast cells (Berger et al., *J. Exp. Med.* 180:471–6 (1994)). These studies were also done with mice that were CD45-deficient. In this case, an IgE-mediated degranulation was demonstrated in wild type but not CD45-deficient T cells from mice. These data suggest that CD45 inhibitors could also play a role in the symptomatic or therapeutic treatment of allergic disorders with asthma, allergic rhinitis, food allergy, eczema, urticaria and anaphylaxis as non-limiting examples.

Another PTPase, an inducible lymphoid-specific protein tyrosine phosphatase (HePTP) has also been implicated in the immune response. This phosphatase is expressed in both resting T and B lymphocytes, but not non-hemopoetic cells. Upon stimulation of these cells, mRNA levels from the HePTP gene increase 10–15 fold (Zanke et al., *Eur. J. Immunol.* 22: 235–239 (1992)). In both T and B cells HePTP may function during sustained stimulation to modulate the immune response through dephosphorylation of specific residues. Its exact role, however remains to be defined.

Likewise, the hematopoietic cell specific SHP-1 seems to act as a negative regulator and play an essential role in immune cell development. In accordance with the above-mentioned important function of CD45, HePTP and SHP-1, selective PTPase inhibitors may be attractive drug candidates both as immunosuppressors and as immunostimulants. Recent studies illustrate the potential of PTPase inhibitors as immunmodulators by demonstrating the capacity of the non-selective vanadium-based PTPase inhibitor, BMLOV, to induce apparent B cell selective apoptosis compared to T cells (Dawson et al., *FEBS Lett.* 478: 233–236; Schieven et al., *J. Biol. Chem.* 270: 20824–20831 (1995)).

PTPases: Cell-cell Interactions/cancer

Focal adhesion plaques, an in vitro phenomenon in which specific contact points are formed when fibroblasts grow on appropriate substrates, seem to mimic, at least in part, cells and their natural surroundings. Several focal adhesion proteins are phosphorylated on tyrosine residues when fibroblasts adhere to and spread on extracellular matrix (Gumbiner, *Neuron* 11: 551–564 (1993)). However, aberrant tyrosine phosphorylation of these proteins can lead to cellular transformation. The intimate association between PTPases and focal adhesions is supported by the finding of several intracellular PTPases with ezrin-like N-terminal domains, e.g. PTPMEG1 (Gu et al., *Proc. Natl. Acad. Sci. USA* 88: 5867–5871 (1991), PTPH1 (Yang and Tonks, *Proc. Natl. Acad. Sci. USA* 88: 5949–5953 (1991)) and PTPD1 (Møller et al., *Proc. Natl. Acad. Sci. USA* 91: 7477–7481 (1994)). The ezrin-like domain shows similarity to several proteins that are believed to act as links between the cell membrane and the cytoskeleton. PTPD1 was found to be phosphorylated by and associated with c-src in vitro and is hypothesized to be involved in the regulation of phosphorylation of focal adhesions (Møller et al., supra).

PTPases may oppose the action of tyrosine kinases, including those responsible for phosphorylation of focal adhesion proteins, and may therefore function as natural inhibitors of transformation. TC-PTP, and especially the truncated form of this enzyme (Cool et al., *Proc. Natl. Acad. Sci. USA* 87: 7280–7284 (1990)), can inhibit the transforming activity of v-erb and v-fms (Lammers et al., *J. Biol. Chem.* 268: 22456–22462 (1993), Zander et al., *Oncogene* 8: 1175–1182 (1993)). Moreover, it was found that transformation by the oncogenic form of the HER2/neu gene was suppressed in NIH 3T3 fribroblasts overexpressing PTP1B (Brown-Shimer et al., *Cancer Res.* 52: 478–482 (1992)).

The expression level of PTP1B was found to be increased in a mammary cell line transformed with neu (Zhay et al., *Cancer Res.* 53: 2272–2278 (1993)). The intimate relationship between tyrosine kinases and PTPases in the development of cancer is further evidenced by the finding that PTPε is highly expressed in murine mammary tumors in transgenic mice over-expressing c-neu and v-Ha-ras, but not c-myc or int-2 (Elson and Leder, *J. Biol. Chem.* 270: 26116–26122 (1995)). Further, the human gene encoding PTPγ was mapped to 3p21, a chromosomal region, which is frequently deleted in renal and lung carcinomas (LaForgia et al., *Proc. Natl. Acad. Sci. USA* 88: 5036–5040 (1991)).

In this context, it seems significant that PTPases appear to be involved in controlling the growth of fibroblasts. Thus, it was found that Swiss 3T3 cells harvested at high density contain a membrane-associated PTPase whose activity on an average is 8-fold higher than that of cells harvested at low or medium density (Pallen and Tong, *Proc. Natl. Acad. Sci. USA* 88: 6996–7000 (1991)). It was hypothesized by the authors that density-dependent inhibition of cell growth involves the regulated elevation of the activity of the PTPase (s) in question. In accordance with this view, a membrane-bound, receptor-type PTPase, DEP-1, showed enhanced (>=10-fold) expression levels with increasing cell density of WI-38 human embryonic lung fibroblasts and in the AG1518 fibroblast cell line (Östman et al., *Proc. Natl. Acad. Sci. USA* 91: 9680–9684 (1994)).

Two closely related receptor-type PTPases, PTPκ and PTPμ, can mediate homophilic cell-cell interaction when expressed in non-adherent insect cells, suggesting that these PTPases might have a normal physiological function in cell-to-cell signalling (Gebbink et al., *J. Biol. Chem.* 268: 16101–16104 (1993), Brady-Kalnay et al., *J. Cell Biol.* 122: 961–972 (1993); Sap et al., *Mol. Cell. Biol.* 14: 1–9 (1994)). Interestingly, PTPκ and PTPμ do not interact with each other, despite their structural similarity (Zondag et al., *J. Biol. Chem.* 270: 14247–14250 (1995)). From the studies described above it is apparent that PTPases may play an important role in regulating normal cell growth. However, as pointed out above, other studies indicate that PTPases may also function as positive mediators of intracellular signaling and thereby induce or enhance mitogenic responses. Increased activity of certain PTPases might therefore result in cellular transformation and tumor formation. Indeed, in one study over-expression of PTPα was found to lead to transformation of rat embryo fibroblasts (Zheng, supra). In addition, SAP-1 was found to be highly expressed in pancreatic and colorectal cancer cells. SAP-1 is mapped to chromosome 19 region q13.4 and might be related to carcinoembryonic antigen mapped to 19q13.2 (Uchida et al., *J. Biol. Chem.* 269: 12220–12228 (1994)). Further, the dsPTPase, cdc25, dephosphorylates cdc2 at Thr14/Tyr-15 and thereby functions as positive regulator of mitosis (reviewed by Hunter, *Cell* 80: 225–236 (1995)). Inhibitors of specific PTPases are therefore likely to be of significant therapeutic value in the treatment of certain forms of cancer.

PTPases: Platelet Aggregation

PTPases seem to be centrally involved in platelet aggregation. Thus, agonist-induced platelet activation results in calpain-catalyzed cleavage of PTP1B with a concomitant 2-fold stimulation of PTPase activity (Frangioni et al., *EMBO J.* 12: 4843–4856 (1993)). The cleavage of PTP1B leads to subcellular relocation of the enzyme and correlates with the transition from reversible to irreversible platelet aggregation in platelet-rich plasma. In addition, the SH2 domain containing PTPase, SHP-1, was found to translocate to the cytoskeleton in platelets after thrombin stimulation in an aggregation-dependent manner (Li et al., *FEBS Lett.* 343: 89–93 (1994)).

Although some details in the above two studies have been questioned, there is over-all agreement that PTP1B and SHP-1 play significant functional roles in platelet aggregation (Ezumi et al., *J. Biol. Chem.* 270: 11927–11934 (1995)). In accordance with these observations, treatment of platelets with the PTPase inhibitor pervanadate leads to significant increase in tyrosine phosphorylation, secretion and aggregation (Pumiglia et al., *Biochem. J.* 286: 441–449 (1992)).

PTPases: Osteoporosis

The rate of bone formation is determined by the number and the activity of osteoblasts, which in term are determined by the rate of proliferation and differentiation of osteoblast progenitor cells, respectively. Histomorphometric studies indicate that the osteoblast number is the primary determinant of the rate of bone formation in humans (Gruber et al., *Mineral Electrolyte Metab.* 12: 246–254 (1987), reviewed in Lau et al., *Biochem. J.* 257: 23–36 (1989)). Acid phosphatases/PTPases may be involved in negative regulation of osteoblast proliferation. Thus, fluoride, which has phosphatase inhibitory activity, has been found to increase spinal bone density in osteoporotics by increasing osteoblast proliferation (Lau et al., supra). Consistent with this observation, an osteoblastic acid phosphatase with PTPase activity was found to be highly sensitive to mitogenic concentrations of fluoride (Lau et al., *J. Biol. Chem.* 260: 4653–4660 (1985), Lau et al., *J. Biol. Chem.* 262: 1389–1397 (1987), Lau et al., *Adv. Protein Phosphatases* 4: 165–198 (1987)). Interestingly, the level of membrane-bound PTPase activity was increased dramatically when the osteoblast-like cell line UMR 106.06 was grown on collagen type-I matrix compared to uncoated tissue culture plates. Since a significant increase in PTPase activity was observed in density-dependent growth arrested fibroblasts (Pallen and Tong, *Proc. Natl. Acad. Sci.* 88: 6996–7000 (1991)), it might be speculated that the increased PTPase activity directly inhibits cell growth. The mitogenic action of fluoride and other phosphatase inhibitors (molybdate and vanadate) may thus be explained by their inhibition of acid phosphatases/PTPases that negatively regulate the cell proliferation of osteoblasts. The complex nature of the involvement of PTPases in bone formation is further suggested by the identification of a novel parathyroid regulated, receptor-like PTPase, OST-PTP, expressed in bone and testis (Mauro et al., *J. Biol. Chem.* 269: 30659–30667 (1994)). OST-PTP is up-regulated following differentiation and matrix formation of primary osteoblasts and subsequently down-regulated in the osteoblasts which are actively mineralizing bone in culture. It may be hypothesized that PTPase inhibitors may prevent differentiation via inhibition of OST-PTP or other PTPases thereby leading to continued proliferation. This would be in agreement with the above-mentioned effects of fluoride and the observation that the tyrosine phosphatase inhibitor orthovanadate appears to enhance osteoblast proliferation and matrix formation (Lau et al., *Endocrinology* 116: 2463–2468 (1988)). In addition, it was observed that vanadate, vanadyl and pervanadate all increased the growth of the osteoblast-like cell line UMR106. Vanadyl and pervanadate were stronger stimulators of cell growth than vanadate. Only vanadate was able to regulate the cell differentiation as measured by cell alkaline phosphatase activity (Cortizo et al., *Mol. Cell. Biochem.* 145: 97–102 (1995)). It is of particular interest to the current invention that several studies have shown that bisphosphonates, such as alendronate and tiludronate, inhibit the PTPase activity in osteoclasts, and that the inhibition of PTPase activity correlated with the inhibition of in vitro osteoclast formation and boneresorption (Schmidt et al., *Proc. Natl. Acad. Sci. U.S.A.* 93: 3068–3073 (1996); Murakami et al., *Bone* 20: 399–404 (1997); Opas et al., *Biochem. Pharmacol.* 54: 721–727 (1997); Skorey et al., *J. Biol. Chem.* 272: 22472–22480 (1997)). Thus, PTPase inhibitors—other than bisphophonates—can potentially be effective for prevention and/or treatment of osteoporosis.

PTPases: Microorganisms

Dixon and coworkers have called attention to the fact that PTPases may be a key element in the pathogenic properties of Yersinia (reviewed in Clemens et al. *Molecular Microbiology* 5: 2617–2620 (1991)). This finding was rather surprising since tyrosine phosphate is thought to be absent in bacteria. The genus Yersinia comprises 3 species: *Y. pestis* (responsible for the bubonic plague), *Y. pseudoturberculosis* and *Y. enterocolitica* (causing enteritis and mesenteric lymphadenitis). Interestingly, a dual-specificity phosphatase, VH1, has been identified in Vaccinia virus (Guan et al., *Nature* 350: 359–263 (1991)). These observations indicate that PTPases may play critical roles in microbial and parasitic infections, and they further point to PTPase inhibitors as a novel, putative treatment principle of infectious diseases.

WO 99/46267 discloses compounds which are pharmacologically useful inhibitors of PTPases. However, the present invention which represents a novel selection under WO 99/46267, discloses a class of compounds which surprisingly are more potent against protein tyrosine phosphatases (e.g. PTP1B) than those disclosed in WO 99/46267.

DESCRIPTION OF THE INVENTION

The present invention relates to Compounds of the Formula 1 wherein n, m, X, $R_1$, $R_2$, $R_3$, $R_4$, $R_5$ and $R_6$ are defined below;

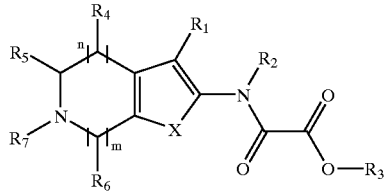

Formula 1

In the above Formula 1
n is 0, 1 or 2;
m is 1 or 2;
X is S or O;
$R_1$ is hydrogen, $COOR_3$, or $R_1$ is selected from the group consisting of the following 5-membered heterocycles:

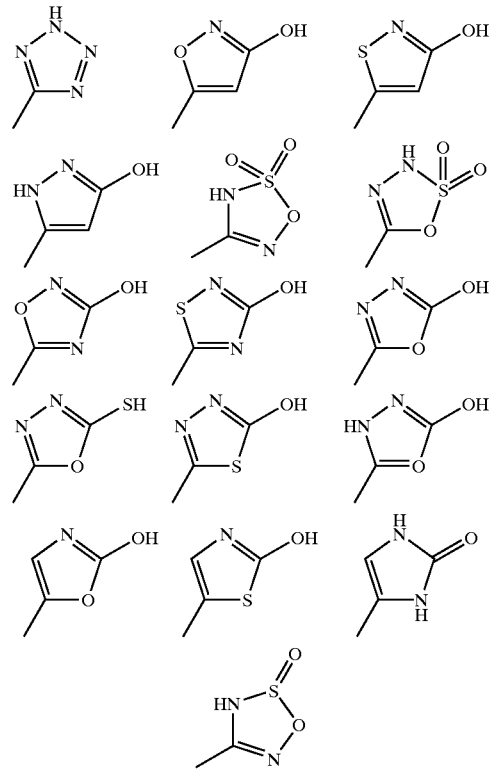

$R_2$ is hydrogen, $C_1$–$C_6$alkyl, hydroxy or $NR_8R_9$;
$R_3$ is hydrogen, $C_1$–$C_6$alkyl, aryl$C_1$–$C_6$alkyl, $C_1$–$C_6$alkylcarbonyloxy$C_1$–$C_6$alkyl or $C_1$–$C_6$alkylcarbonyloxyaryl$C_1$–$C_6$alkyl;

$R_4$, $R_5$ and $R_6$ are independently hydrogen, trihalomethyl, $C_1$–$C_6$alkyl, aryl, aryl$C_1$–$C_6$alkyl, hydroxy, oxo, carboxy, carboxy$C_1$–$C_6$alkyl, $C_1$–$C_6$alkyloxycarbonyl, aryloxycarbonyl, aryl$C_1$–$C_6$alkyloxycarbonyl, $C_1$–$C_6$alkyloxy, $C_1$–$C_6$alkyloxy$C_1$–$C_6$alkyl, aryloxy, aryl$C_1$–$C_6$alkyloxy, aryl$C_1$–$C_6$alkyloxy$C_1$–$C_6$alkyl, thio, $C_1$–$C_6$alkylthio, $C_1$–$C_6$alkylthio$C_1$–$C_6$alkyl, arylthio, aryl$C_1$–$C_6$alkylthio, aryl$C_1$–$C_6$alkylthio$C_1$–$C_6$alkyl, $NR_8R_9$, $R_8R_9NC_1$–$C_6$alkyl, $C_1$–$C_6$alkylamino$C_1$–$C_6$alkyl, arylamino$C_1$–$C_6$alkyl, aryl$C_1$–$C_6$alkylamino$C_1$–$C_6$alkyl, di(aryl$C_1$–$C_6$amino$C_1$–$C_6$alkyl, $C_1$–$C_6$alkylcarbonyl, $C_1$–$C_6$alkyl-carbonyl$C_1$–$C_6$alkyl, aryl$C_1$–$C_6$alkylcarbonyl, aryl$C_1$–$C_6$alkylcarbonyl$C_1$–$C_6$alkyl, $C_1$–$C_6$alkylcarboxy, $C_1$–$C_6$alkylcarboxy$C_1$–$C_6$-alkyl, arylcarboxy, arylcarboxy$C_1$–$C_6$alkyl, aryl$C_1$–$C_6$alkylcarboxy, aryl$C_1$–$C_6$alkylcarboxy$C_1$–$C_6$alkyl, $C_1$–$C_6$alkylcarbonylamino, $C_1$–$C_6$alkylcarbonylamino$C_1$–$C_6$alkyl, arylcarbonylamino$C_1$–$C_6$alkyl, -carbonylN$R_8C_1$–$C_6$alkylCO$R_{12}$, aryl$C_1$–$C_6$alkylcarbonylamino, aryl$C_1$–$C_6$alkylcarbonylamino$C_1$–$C_6$alkyl, $CONR_8R_9$, or $C_1$–$C_6$alkyl$CONR_8R_9$ wherein the alkyl and aryl groups are optionally substituted and $R_{12}$ is $NR_8R_9$, or $C_1$–$C_6$alkyl$NR_8R_9$;

$R_7$ is hydrogen, $C_1$–$C_6$alkyl, aryl, aryl$C_1$–$C_6$alkyl, $C_1$–$C_6$alkylcarbonyl, $C_1$–$C_6$alkoxycarbonyl, arylcarbonyl, aryloxocarbonyl, aryl$C_1$–$C_6$alkylcarbonyl, aryl$C_1$–$C_6$alkoxycarbonyl, $C_1$–$C_6$alkylcarboxy, aryl$C_1$–$C_6$alkylcarboxy, $R_{10}R_{11}$Ncarbonyl$C_1$–$C_6$alkyl wherein $R_{10}$ and $R_{11}$ are independently selected from hydrogen, $C_1$–$C_6$alkyl, aryl, aryl$C_1$–$C_6$alkyl, $C_1$–$C_6$alkylcarbonyl, arylcarbonyl, aryl$C_1$–$C_6$alkylcarbonyl, $C_1$–$C_6$alkylcarboxy or aryl$C_1$–$C_6$alkyl-carboxy; wherein the alkyl and aryl groups are optionally substituted;

$R_8$ and $R_9$ are independently selected from hydrogen, $C_1$–$C_6$alkyl, aryl, aryl$C_1$–$C_6$alkyl, $C_1$–$C_6$alkylcarbonyl, $C_1$–$C_6$alkoxycarbonyl, arylcarbonyl, aryloxocarbonyl, aryl$C_1$–$C_6$alkylcarbonyl, aryl$C_1$–$C_6$alkoxycarbonyl, $C_1$–$C_6$alkylcarboxy, aryl$C_1$–$C_6$alkylcarboxy, $R_{10}R_{11}$Ncarbonyl$C_1$–$C_6$alkyl wherein the alkyl and aryl groups are optionally substituted; or $R_8$ and $R_9$ are together with the nitrogen to which they are attached forming a saturated, partially saturated or aromatic cyclic, bicyclic or tricyclic ring system containing from 3 to 14 carbon atoms and from 0 to 3 additional heteroatoms selected from nitrogen, oxygen or sulphur, the ring system can optionally be substituted with at least one $C_1$–$C_6$alkyl, aryl, aryl$C_1$–$C_6$alkyl, hydroxy, oxo, $C_1$–$C_6$alkyloxy, aryl$C_1$–$C_6$alkyloxy, $C_1$–$C_6$alkyloxy$C_1$–$C_6$alkyl, $NR_{10}R_{11}$ or $C_1$–$C_6$alkylamino$C_1$–$C_6$alkyl, wherein $R_{10}$ and $R_{11}$ are independently selected from hydrogen, $C_1$–$C_6$alkyl, aryl, aryl$C_1$–$C_6$alkyl, $C_1$–$C_6$alkylcarbonyl, arylcarbonyl, aryl$C_1$–$C_6$alkylcarbonyl, $C_1$–$C_6$alkylcarboxy or aryl$C_1$–$C_6$alkylcarboxy; wherein the alkyl and aryl groups are optionally substituted; or $R_8$ and $R_9$ are independently a saturated or partial saturated cyclic 5, 6 or 7 membered amine, imide or lactam;

or a salt thereof with a pharmaceutically acceptable acid or base, or any optical isomer or mixture of optical isomers, including a racemic mixture, or any tautomeric form, or prodrug thereof.

The compounds of the invention can be further modified to act as prodrugs.

It is a well known problem in drug discovery that compounds, such as enzyme inhibitors, may be very potent and selective in biochemical assays, yet be inactive in vivo. This lack of so-called bioavailability may be ascribed to a number of different factors such as lack of or poor absorption in the gut, first pass metabolism in the liver, poor uptake in cells. Although the factors determining bioavailability are not completely understood, there are many examples in the scientific literature—well known to those skilled in the art—of how to modify compounds, which are potent and selective in biochemical assays but show low or no activity in vivo, into drugs that are biologically active. It is within the scope of the invention to modify the compounds of the invention, termed the 'original compound', by attaching chemical groups that will improve the bioavailability of said compounds in such a way that the uptake in cells or mammals is facilitated. Examples of said modifications, which are not intended in any way to limit the scope of the invention, include changing of one or more carboxy groups to esters (for instance methyl esters, ethyl esters, acetoxymethyl esters or other acyloxymethyl esters). Compounds of the invention, original compounds, such modified by attaching chemical groups are termed 'modified compounds'. Said chemical groups may or may not be apparent in the claims of this invention. Other examples of modified compounds, which are not intended in any way to limit the scope of the invention, are compounds that have been cyclized at specific positions—socalled 'cyclic compounds'—which upon uptake in cells or mammals become hydrolyzed at the same specific position(s) in the molecule to yield the compounds of the invention, the original compounds, which are then said to be 'non-cyclic'. For the avoidance of doubt, it is understood that the latter original compounds in most cases will contain other cyclic or heterocyclic structures that will not be hydrolyzed after uptake in cells or mammals. Generally, said modified compounds will not show a behaviour in bio-chemical assays similar to that of the original compound, i.e. the corresponding compounds of the invention without the attached chemical groups or said modifications. Said modified compounds may even be inactive in biochemical assays. However, after uptake in cells or mammals these attached chemical groups of the modified compounds may in turn be removed spontaneously or by endogenous enzymes or enzyme systems to yield compounds of the invention, original compounds. 'Uptake' is defined as any process that will lead to a substantial concentration of the compound inside cells or in mammals. After uptake in cells or mammals and after removal of said attached chemical group or hydrolysis of said cyclic compound, the compounds may have the same structure as the original compounds and thereby regain their activity and hence become active in cells and/or in vivo after uptake. A number of procedures, well known to those skilled in the art, may be used to verify that the attached chemical groups have been removed or that the cyclic compound has been hydrolyzed after uptake in cells or mammals. An example, which is not intended in any way to limit the scope of the invention, is given in the following. A mammalian cell line, which can be obtained from the American Tissue Type Collection or other similar governmental or commercial sources, is incubated with said modified compound. After incubation at conditions well known to those skilled in the art, the cells are washed appropriately, lysed and the lysate is isolated. Appropriate controls, well known to those skilled in the art, must be included. A number of different procedures, well known to those skilled in the art, may in turn be used to extract and purify said compound from said lysate. Said compound may or may not retain the attached chemical group or said cyclic compound may or may not have been hydrolyzed. Similarly, a number of different procedures—well known to those skilled in the art—may be used to structurally and chemically characterize said purified compound. Since said purified compound has been isolated from said cell lysate and hence has been taken up by said cell line, a comparison of said structurally and chemically characterized compound with that of the original unmodified compound (i.e. without said attached chemical group or said non-cyclic compound) will immediately provide those skilled in the art information on whether the attached chemical group as been removed in the cell or if the cyclic compound has been hydrolyzed. As a further analysis, said purified compound may be subjected to enzyme kinetic analysis as described in detail in the present invention. If the kinetic profile is similar to that of the original compound without said attached chemical group, but different from said modified compound, this confirms that said chemical group has been removed or said cyclic compounds has been hydrolyzed. Similar techniques may be used to analyze compounds of the invention in whole animals and mammals.

A preferred prodrug is acetoxymethyl esters of the compounds of the present invention which may be prepared by the following general procedure (C. Schultz et al, *The Journal of Biological Chemistry*, 1993, 268, 6316–6322.):

A carboxylic acid (1 equivalent) is suspended in dry acetonitrile (2 ml per 0.1 mmol). Diisopropyl amine (3.0 equivalents) is added followed by bromomethyl acetate (1.5 equivalents). The mixture is stirred under nitrogen overnight at room temperature. Acetonitrile is removed under reduced pressure to yield an oil which is diluted in ethylacetate and washed with water (3×). The organic layer is dried over anhydrous magnesium sulfate. Filtration followed by solvent removal under reduced pressure afford a crude oil. The product is purified by column chromatography on silica gel, using an appropriate solvent system.

DEFINITIONS

As used herein, the term "attached" or "—" (e.g. —$COR_{11}$ which indicates the carbonyl attachment point to the scaffold) signifies a stable covalent bond, certain preferred points of attachment points being apparent to those skilled in the art.

The terms "halogen" or "halo" include fluorine, chlorine, bromine, and iodine.

The term "alkyl" includes $C_1$–$C_6$ straight chain saturated, methylene and $C_2$–$C_6$ unsaturated aliphatic hydrocarbon groups, $C_1$–$C_6$ branched saturated and $C_2$–$C_6$ unsaturated aliphatic hydrocarbon groups, $C_3$–$C_6$ cyclic saturated and $C_5$–$C_6$ unsaturated aliphatic hydrocarbon groups, and $C_1$–$C_6$ straight chain or branched saturated and $C_2$–$C_6$ straight chain or branched unsaturated aliphatic hydrocarbon groups substituted with $C_3$–$C_6$ cyclic saturated and unsaturated aliphatic hydrocarbon groups having the specified number of carbon atoms. For example, this definition shall include but is not limited to methyl (Me), ethyl (Et), propyl (Pr), butyl (Bu), pentyl, hexyl, heptyl, ethenyl, propenyl, butenyl, penentyl, hexenyl, isopropyl (i-Pr), isobutyl (i-Bu), tert-butyl (t-Bu), sec-butyl (s-Bu), isopentyl, neopentyl, cyclopropyl, cyclobutyl, cyclopentyl, cyclohexyl, cyclopentenyl, cyclohexenyl, methylcyclopropyl, ethylcyclohexenyl, butenylcyclopentyl, and the like.

The term "substituted alkyl" or "optionally substituted alkyl" represents an alkyl group as defined above wherein the substitutents are independently selected from halo, cyano, nitro, trihalomethyl, carbamoyl, hydroxy, oxo, $COOR_3$, $CONR_8R_9$, $C_1$–$C_6$alkyl, $C_1$–$C_6$alkyloxy, aryloxy, aryl$C_1$–$C_6$alkyloxy, thio, $C_1$–$C_6$alkylthio, arylthio, aryl$C_1$–$C_6$alkylthio, $NR_8R_9$, $C_1$–$C_6$alkylamino, arylamino, aryl$C_1$–$C_6$alkylamino, di(aryl$C_1$–$C_6$alkyl)amino, $C_1$–$C_6$alkylcarbonyl, aryl$C_1$–$C_6$-alkylcarbonyl, $C_1$–$C_6$alkylcarboxy, arylcarboxy, aryl$C_1$–$C_6$alkylcarboxy, $C_1$–$C_6$alkylcarbonylamino, -$C_1$–$C_6$alkylamino$COR_{12}$, aryl$C_1$–$C_6$alkylcarbonylamino, tetrahydrofuranyl, morpholinyl, piperazinyl, —$CONR_8R_9$, —$C_1$–$C_6$alkyl$CONR_8R_9$, or a saturated or partial saturated cyclic 5, 6 or 7 membered amine, imide or lactam; wherein $R_{11}$ is hydroxy, $C_1$–$C_6$alkyl, aryl, aryl$C_1$–$C_6$alkyl, $C_1$–$C_6$alkyloxy, aryloxy, aryl$C_1$–$C_6$alkyloxy and $R_3$ is defined as above or NR8R9, wherein $R_8$, $R_9$ are defined as above.

The term "saturated, partially saturated or aromatic cyclic, bicyclic or tricyclic ring system" represents but are not limit to aziridinyl, pyrrolyl, pyrrolinyl, pyrrolidinyl, imidazolyl, 2-imidazolinyl, imidazolidinyl, pyrazolyl, 2-pyrazolinyl, 1,2,3-triazolyl, 1,2,4-triazolyl, morpholinyl, piperidinyl, thiomorpholinyl, piperazinyl, indolyl, isoindolyl, 1,2,3,4-tetrahydro-quinolinyl, 1 ,2,3,4-tetrahydro-isoquinolinyl, 1,2,3,4-tetrahydro-quinoxalinyl, indolinyl, indazolyl, benzimidazolyl, benzotriazolyl, purinyl, carbazolyl, acridinyl, phenothiazinyl, phenoxazinyl, iminodibenzyl, iminostilbenyl.

The term "alkyloxy" (e.g. methoxy, ethoxy, propyloxy, allyloxy, cyclohexyloxy) represents an "alkyl" group as defined above having the indicated number of carbon atoms attached through an oxygen bridge.

The term "alkyloxyalkyl" represents an "alkyloxy" group attached through an alkyl group as defined above having the indicated number of carbon atoms.

The term "alkyloxyalkyloxy" represents an "alkyloxyalkyl" group attached through an oxygen atom as defined above having the indicated number of carbon atoms.

The term "aryloxy" (e.g. phenoxy, naphthyloxy and the like) represents an aryl group as defined below attached through an oxygen bridge.

The term "arylalkyloxy" (e.g. phenethyloxy, naphthylmethyloxy and the like) represents an "arylalkyl" group as defined below attached through an oxygen bridge.

The term "arylalkyloxyalkyl" represents an "arylalkyloxy" group as defined above attached through an "alkyl" group defined above having the indicated number of carbon atoms.

The term "arylthio" (e.g. phenylthio, naphthylthio and the like) represents an "aryl" group as defined below attached through an sulfur bridge.

The term "alkyloxycarbonyl" (e.g. methylformiat, ethylformiat and the like) represents an "alkyloxy" group as defined above attached through a carbonyl group.

The term "aryloxycarbonyl" (e.g. phenylformiat, 2-thiazolylformiat and the like) represents an "aryloxy" group as defined above attached through a carbonyl group.

The term "arylalkyloxycarbonyl" (e.g. benzylformiat, phenyletylformiat and the like) represents an "arylalkyloxy" group as defined above attached through a carbonyl group.

The term "alkyloxycarbonylalkyl" represents an "alkyloxycarbonyl" group as defined above attached through an "alkyl" group as defined above having the indicated number of carbon atoms.

The term "arylalkyloxycarbonylalkyl" represents an "arylalkyloxycarbonyl" group as defined above attached through an "alkyl" group as defined above having the indicated number of carbon atoms.

The term "alkylthio" (e.g. methylthio, ethylthio, propylthio, cyclohexenylthio and the like) represents an "alkyl" group as defined above having the indicated number of carbon atoms attached through a sulfur bridge.

The term "arylalkylthio" (e.g. phenylmethylthio, phenylethylthio, and the like) represents an "arylalkyl" group as defined above having the indicated number of carbon atoms attached through a sulfur bridge.

The term "alkylthioalkyl" represents an "alkylthio" group attached through an alkyl group as defined above having the indicated number of carbon atoms.

The term "arylalkylthioalkyl" represents an "arylalkylthio" group attached through an alkyl group as defined above having the indicated number of carbon atoms.

The term "alkylamino" (e.g. methylamino, diethylamino, butylamino, N-propyl-N-hexylamino, (2-cyclopentyl)propylamino, hexenylamino, pyrrolidinyl, piperidinyl and the like) represents one or two "alkyl" groups as defined above having the indicated number of carbon atoms attached through an amine bridge. The two alkyl groups may be taken together with the nitrogen to which they are attached forming a saturated, partially saturated or aromatic cyclic, bicyclic or tricyclic ring system containing 3 to 14 carbon atoms and 0 to 3 additional heteroatoms selected from nitrogen, oxygen or sulfur, the ring system can optionally be substituted with at least one $C_1$–$C_6$alkyl, aryl, aryl$C_1$–$C_6$alkyl, hydroxy, oxo, $C_{1-6}$alkyloxy, $C_1$–$C_6$alkyloxy$C_1$–$C_6$alkyl, $NR_8R_9$, $C_1$–$C_6$alkylamino$C_1$–$C_6$alkyl substituent wherein the alkyl and aryl groups are optionally substituted as defined in the definition section and $R_8$ and $R_9$ are defined as above.

The term "arylalkylamino" (e.g. benzylamino, diphenylethylamino and the like) represents one or two "arylalkyl" groups as defined above having the indicated number of carbon atoms attached through an amine bridge. The two "arylalkyl" groups may be taken together with the nitrogen to which they are attached forming a saturated, partially saturated or aromatic cyclic, bicyclic or tricyclic ring system containing 3 to 14 carbon atoms and 0 to 3 additional heteroatoms selected from nitrogen, oxygen or sulfur, the ring system can optionally be substituted with at least one $C_1$–$C_6$alkyl, aryl, aryl$C_1$–$C_6$alkyl, hydroxy, oxo, $C_1$–$C_6$alkyloxy, $C_1$–$C_6$alkyloxy$C_1$–$C_6$alkyl, $NR_8R_9$, $C_1$–$C_6$alkylamino$C_1$–$C_6$alkyl substituent wherein the alkyl and aryl groups are optionally substituted as defined in the definition section and $R_8$ and $R_9$ are defined as above.

The term "alkylaminoalkyl" represents an "alkylamino" group attached through an alkyl group as defined above having the indicated number of carbon atoms.

The term "arylalkylaminoalkyl" represents an "arylalkylamino" group attached through an alkyl group as defined above having the indicated number of carbon atoms. 10 The term "arylamino" represents an "aryl" group as defined below attached through an amino group.

The term "arylaminoalkyl" represents an "arylamino" group attached through an alkyl group as defined above having the indicated number of carbon atoms.

The term "arylalkyl" (e.g. benzyl, phenylethyl) represents an "aryl" group as defined below attached through an alkyl having the indicated number of carbon atoms or substituted alkyl group as defined above.

The term "alkylcarbonyl" (e.g. cyclooctylcarbonyl, pentylcarbonyl, 3-hexenylcarbonyl) represents an "alkyl" group as defined above having the indicated number of carbon atoms attached through a carbonyl group.

The term "arylcarbonyl" (benzoyl) represents an "aryl" group as defined above attached through a carbonyl group.

The term "arylalkylcarbonyl" (e.g. phenylcyclopropylcarbonyl, phenylethylcarbonyl and the like) represents an "arylalkyl" group as defined above having the indicated number of carbon atoms attached through a carbonyl group.

The term "alkylcarbonylalkyl" represents an "alkylcarbonyl" group attached through an "alkyl" group as defined above having the indicated number of carbon atoms.

The term "arylalkylcarbonylalkyl" represents an "arylalkylcarbonyl" group attached through an alkyl group as defined above having the indicated number of carbon atoms.

The term "arylcarbonylamino" represents an "arylcarbonyl" group as defined above attached through an amino group.

The term "arylcarbonylaminoalkyl" represents an "arylcarbonylamino" group attached through an alkyl group as defined above having the indicated number of carbon atoms.

The term "alkylcarboxy" (e.g. heptylcarboxy, cyclopropylcarboxy, 3-pentenylcarboxy) represents an "alkylcarbonyl" group as defined above wherein the carbonyl is in turn attached through an oxygen bridge.

The term "arylcarboxyalkyl" (e.g. phenylcarboxymethyl) represents an "arylcarbonyl" group defined above wherein the carbonyl is in turn attached through an oxygen bridge to an alkyl chain having the indicated number of carbon atoms.

The term "arylalkylcarboxy" (e.g. benzylcarboxy, phenylcyclopropylcarboxy and the like) represents an "arylalkylcarbonyl" group as defined above wherein the carbonyl is in turn attached through an oxygen bridge.

The term "alkylcarboxyalkyl" represents an "alkylcarboxy" group attached through an "alkyl" group as defined above having the indicated number of carbon atoms.

The term "arylalkylcarboxyalkyl" represents an "arylalkylcarboxy" group attached through an "alkyl" group as defined above having the indicated number of carbon atoms.

The term "alkylcarbonylamino" (e.g. hexylcarbonylamino, cyclopentylcarbonyl- aminomethyl, methylcarbonylaminophenyl) represents an "alkylcarbonyl" group as defined above wherein the carbonyl is in turn attached through the nitrogen atom of an amino group. The nitrogen atom may itself be substituted with an alkyl or aryl group.

The term "arylalkylcarbonylamino" (e.g. benzylcarbonylamino and the like) represents an "arylalkylcarbonyl" group as defined above wherein the carbonyl is in turn attached through the nitrogen atom of an amino group. The nitrogen atom may itself be substituted with an alkyl or aryl group.

The term "alkylcarbonylaminoalkyl" represents an "alkylcarbonylamino" group attached through an "alkyl" group as defined above having the indicated number of carbon atoms. The nitrogen atom may itself be substituted with an alkyl or aryl group.

The term "arylalkylcarbonylaminoalkyl" represents an "arylalkylcarbonylamino" group attached through an "alkyl" group as defined above having the indicated number of carbon atoms. The nitrogen atom may itself be substituted with an alkyl or aryl group.

The term "alkylcarbonylaminoalkylcarbonyl" represents an alkylcarbonylaminoalkyl group attached through a carbonyl group. The nitrogen atom may be further substituted with an "alkyl" or "aryl" group.

The term "aryl" represents an unsubstituted, monocyclic, polycyclic, biaryl and heterocyclic aromatic groups covalently attached at any ring position capable of forming a stable covalent bond, certain preferred points of attachment being apparent to those skilled in the art (e.g., 3-indolyl, 4(5)-imidazolyl).

The definition of aryl includes but is not limited to phenyl, biphenyl, indenyl, fluorenyl, naphthyl (1-naphthyl, 2-naphthyl), pyrrolyl (2-pyrrolyl), pyrazolyl (3-pyrazolyl), imidazolyl (1-imidazolyl, 2-imidazolyl, 4-imidazolyl, 5-imidazolyl), triazolyl (1,2,3-triazol-1-yl, 1,2,3-triazol-2-yl 1,2,3-triazol4-yl, 1,2,4-triazol-3-yl), oxazolyl (2-oxazolyl, 4-oxazolyl, 5-oxazolyl), isoxazolyl (3-isoxazolyl, 4-isoxazolyl, 5-isoxazolyl), thiazolyl (2-thiazolyl, 4-thiazolyl, 5-thiazolyl), thiophenyl (2-thiophenyl, 3-thiophenyl, 4-thiophenyl, 5-thiophenyl), furanyl (2-furanyl, 3-furanyl, 4-furanyl, 5-furanyl), pyridyl (2-pyridyl, 3-pyridyl, 4-pyridyl, 5-pyridyl), 5-tetrazolyl, pyrimidiny (2-pyrimidinyl, 4-pyrimidinyl, 5-pyrimidinyl, 6-pyrimidinyl), pyrazinyl, pyridazinyl (3-pyridazinyl, 4-pyridazinyl, 5-pyridazinyl), quinolyl (2-quinolyl, 3-quinolyl, 4-quinolyl, 5-quinolyl, 6-quinolyl, 7-quinolyl, 8-quinolyl), isoquinolyl (1-isoquinolyl, 3-isoquinolyl, 4-isoquinolyl, 5-isoquinolyl, 6-isoquinolyl, 7-isoquinolyl, 8-isoquinolyl), benzo[b]furanyl (2-benzo[b]furanyl, 3-benzo[b]furanyl, 4-benzo[b]furanyl, 5-benzo[b]furanyl, 6-benzo[b]furanyl, 7-benzo[b]furanyl), 2,3-dihydro-benzo[b]furanyl (2-(2,3-dihydro-benzo[b]furanyl), 3-(2,3-dihydro-benzo[b]furanyl), 4-(2,3-dihydro-benzo[b]furanyl), 5-(2,3-dihydro-benzo-[b]furanyl), 6-(2,3-dihydro-benzo-[b]furanyl) 7-(2,3-dihydro-benzo[b]furanyl)), benzo[b]thiophenyl (2-benzo[b]thiophenyl, 3-benzo[b]thiophenyl, 4-benzo[b]thiophenyl, 5-benzo[b]thiophenyl, 6-benzo[b]thiophenyl, 7-benzo[b]thiophenyl), 2,3-dihydro-benzo[b]-thiophenyl (2-(2,3-dihydro-benzo[b]thiophenyl), 3-(2,3-dihydro-benzo[b]-thiophenyl), 4-(2,3-dihydro-benzo[b]thiophenyl), 5-(2,3-dihydro-benzo[b]-thiophenyl), 6-(2,3-dihydro-benzo[b]thiophenyl), 7-(2, 3-dihydro-benzo[b]-thiophenyl)), 4,5,6,7-tetrahydro-benzo[b]thiophenyl (2-(4,-5,6,7=tetrahydro-benzo-[b]thiophenyl), 3-(4,5,6,7-tetrahydro-benzo-[b]thiophenyl), 4-(4,5,6,7-tetrahydro-benzo[b]thiophenyl), 5-(4,5,6,7-tetrahydro-benzo-[b]thiophenyl), 6-(4, 5,6,7tetrahydro-benzo-[b]thiophenyl), 7-(4,5,6,7-tetrahydro-benzo[b]thiophenyl)), 4-,5,6,7-tetrahydro-thieno[2,3-c]pyridyl (4-(4,5,6,7-tetrahydro-thieno[2,3-c]pyridyl), 5-4,5,6,7-tetrahydro-thieno[2,3-c]pyridyl) 6-(4,5,6,7-tetrahydro-thieno[2,3-c]pyridyl), 7-(4,5,6,7-tetrahydro-thieno[2,3-c]pyridyl)), indolyl (1-indolyl, 2-indolyl, 3-indolyl, 4-indolyl, 5-indolyl, 6-indolyl, 7-indolyl), isoindolyl (1-isoindolyl, 2-isoindolyl, 3-isoindolyl, 4-isoindolyl, 5-isoindolyl, 6-isoindolyl, 7-isoindolyl), 1,3-dihydro -isoindolyl (1-(1,3-dihydro-isoindolyl), 2-(1,3-dihydro-isoindolyl), 3-(1,3-dihydro-isoindolyl), 4-(1,3-dihydro-isoindolyl), 5-(1,3-dihydro-isoindolyl), 6-(1,3-dihydro-isoindolyl), 7-(1,3-dihydro-isoindolyl)), indazole (1-indazolyl, 3-indazolyl, 4-indazolyl, 5-indazolyl, 6-indazolyl, 7-indazolyl), benzimidazolyl (1-benzimidazolyl, 2-benzimidazolyl, 4-benzimidazolyl, 5-benzimidazolyl, 6-benzimidazolyl, 7-benzimidazolyl, 8-benzimidazolyl), benzoxazolyl (1-benzo-oxazolyl, 2-benzoxazolyl), benzothiazolyl (1-benzothiazolyl, 2-benzo-thiazolyl, 4-benzothiazolyl, 5-benzothiazolyl, 6-benzothiazolyl, 7-benzothiazolyl), carbazolyl (1-carbazolyl, 2-carbazolyl, 3-carbazolyl, 4-carbazolyl), 5H-dibenz[b,f]azepine (5H-dibenz[b,f] azepin-1-yl, 5H-dibenz-[b,f]azepine-2-yl, 5H-dibenz[b,f] azepine-3-yl, 5H-dibenz-[b,f]azepine4-yl, 5H-dibenz[b,f]-azepine-5-yl), 10,11-dihydro-5H-dibenz[b,f]azepine (10,11 -dihydro-5H-dibenz[b,f]azepine-1-yl, 10,11-dihydro-5H-dibenz[b,f]azepine-2-yl, 10,11-dihydro-5H-dibenz[b,f] azepine-3-yl, 10,11-dihydro-5H-dibenz-[b,f]azepine-4-yl, 10,11-dihydro-5H-dibenz [b,f]azepine-5-yl), piperidinyl (2-piperidinyl, 3-piperidinyl, 4-piperidinyl), pyrrolidinyl (1-pyrrolidinyl, 2-pyrrolidinyl, 3-pyrrolidinyl), phenylpyridyl (2-phenyl-pyridyl, 3-phenyl-pyridyl, 4-phenylpridyl), phenylpyrimidinyl (2-phenylpyrimidinyl, 4-phenyl-pyrimidinyl, 5-phenylpyrimidinyl, 6-phenylpyrimidinyl), phenylpyrazinyl, phenylpyridazinyl (3-phenylpyridazinyl, 4-phenylpyridazinyl, 5-phenyl-pyridazinyl).

The term "optionally substituted aryl" represents an mono-, di- or trisubstituted aryl as defined above wherein the substituents are independently selected from the group consisting of halo, nitro, cyano, trihalomethyl, $C_1$–$C_6$alkyl, aryl, aryl$C_1$–$C_6$alkyl, hydroxy, COOR$_3$, CONR$_8$R$_9$, $C_1$–$C_6$alkyloxy, $C_1$–$C_6$alkyloxy$C_1$–$C_6$alkyl, aryloxy, aryl$C_1$–$C_6$alkyloxy, aryl$C_1$–$C_6$alkyloxy$C_1$–$C_6$alkyl, thio, $C_1$–$C_6$alkylthio, $C_1$–$C_6$alkylthio$C_1$–$C_6$alkyl, arylthio, aryl$C_1$–$C_6$alkylthio, aryl$C_1$–$C_6$alkylthio$C_1$–$C_6$alkyl, NR$_8$R$_9$, $C_1$–$C_6$-alkylamino, $C_1$–$C_6$(alkyl-amino$C_1$–$C_6$alkyl, arylamino, aryl$C_1$–$C_6$alkylamino, aryl$C_1$–$C_6$alkyl-amino$C_1$–$C_6$alkyl, di(aryl$C_1$–$C_6$alkyl)amino$C_1$–$C_6$alkyl, $C_1$–$C_6$alkylcarbonyl, $C_1$–$C_6$alkyl-carbonyl$C_1$–$C_6$alkyl, aryl$C_1$–$C_6$alkylcarbonyl, aryl$C_1$–$C_6$alkylcarbonyl$C_1$–$C_6$alkyl, $C_1$–$C_6$alkyl-carboxy, $C_1$–$C_6$alkylcarboxy$C_1$–$C_6$alkyl, aryl$C_1$–$C_6$alkylcarboxy, aryl$C_1$–$C_6$alkyl-carboxy$C_1$–$C_6$alkyl, carboxy$C_1$–$C_6$-alkyloxy, $C_1$–$C_6$alkylcarbonylamino, $C_1$–$C_6$alkyl-carbonylamino$C_1$–$C_6$alkyl, -carbonylNR$_7$$C_1$–$C_6$alkylCOR$_{11}$, aryl$C_1$–$C_6$alkylcarbonylamino, aryl$C_1$–$C_6$-alkylcarbonylamino$C_1$–$C_6$alkyl, —CONR$_8$R$_9$, or —$C_1$–$C_6$alkylCONR$_8$R$_9$; wherein R$_3$, R$_8$, R$_9$, and R$_{11}$, are defined as above and the alkyl and aryl groups are optionally substituted as defined in the definition section;

The term "arylcarbonyl" (e.g. 2-thiophenylcarbonyl, 3-methoxy-anthrylcarbonyl, oxazolylcarbonyl) represents an "aryl" group as defined above attached through a carbonyl group.

The term "arylalkylcarbonyl" (e.g. (2,3-dimethoxyphenyl)propylcarbonyl, (2-chloronaphthyl) pentenylcarbonyl, imidazolylcyclopentylcarbonyl) represents an "arylalkyl" group as defined above wherein the "alkyl" group is in turn attached through a carbonyl.

The compounds of the present invention have asymmetric centers and may occur as racemates, racemic mixtures, and as individual enantiomers or diastereoisomers, with all isomeric forms being included in the present invention as well as mixtures thereof.

Pharmaceutically acceptable salts of the Compounds of Formula 1, where a basic or acidic group is present in the structure, are also included within the scope of this invention. When an acidic substituent is present, such as —COOH, 5-tetrazolyl or —P(O)(OH)$_2$, there can be formed the ammonium, morpholinium, sodium, potassium, barium, calcium salt, and the like, for use as the dosage form. When a basic group is present, such as amino or a basic heteroaryl radical, such as pyridyl, an acidic salt, such as hydrochloride, hydrobromide, phosphate, sulfate, trifluoroacetate, trichloroacetate, acetate, oxalate, maleate, pyruvate, malonate, succinate, citrate, tartarate, fumarate, mandelate, benzoate, cinnamate, methanesulfonate, ethane sulfonate, picrate and the like, and include acids related to the pharmaceutically acceptable salts listed in Journal of Pharmaceutical *Science*, 66, 2 (1977) and incorporated herein by reference, can be used as the dosage form.

Also, in the case of the —COOH or —P(O)(OH)$_2$ being present, pharmaceutically acceptable esters can be employed, e.g., methyl, tert-butyl, pivaloyloxymethyl, and the like, and those esters known in the art for modifying solubility or hydrolysis characteristics for use as sustained release or prodrug formulations.

In addition, some of the compounds of the present invention may form solvates with water or common organic solvents. Such solvates are encompassed within the scope of the invention.

The term "therapeutically effective amount" shall mean that amount of drug or pharmaceutical agent that will elicit the biological or medical response of a tissue, system, animal, or human that is being sought by a researcher, veterinarian, medical doctor or other. In a preferred embodiment, the present invention is concerned with compounds of Formula I

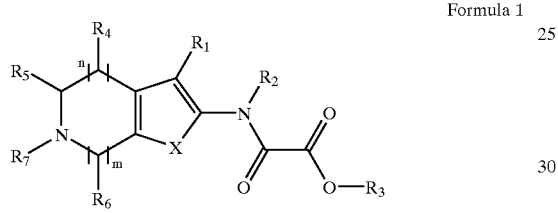

Formula 1 wherein n is 0, 1 or 2;

m is 1 or 2;

X is S or O;

$R_1$ is hydrogen or $COOR_3$, or $R_1$ is selected from the group consisting of the following 5-membered heterocycles:

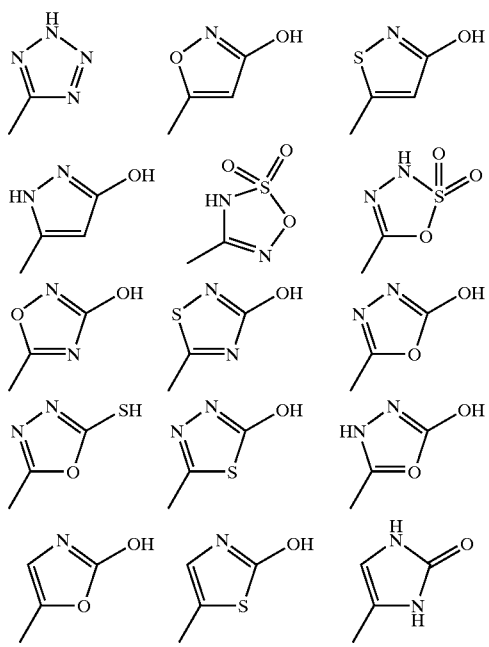

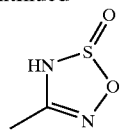

$R_2$ is hydrogen, $C_1$–$C_6$alkyl, hydroxy or $NR_8R_9$;

$R_3$ is hydrogen, $C_1$–$C_6$alkyl, aryl$C_1$–$C_6$alkyl, $C_1$–$C_6$alkylcarbonyloxy$C_1$–$C_6$alkyl or $C_1$–$C_6$alkylcarbonyloxyaryl$C_1$–$C_6$alkyl;

$R_4$, $R_5$ and $R_6$ are independently hydrogen, trihalomethyl, $C_1$–$C_6$alkyl, aryl, aryl$C_1$–$C_6$alkyl, hydroxy, oxo, carboxy, carboxy$C_1$–$C_6$alkyl, $C_1$–$C_6$alkyloxycarbonyl, aryloxycarbonyl, aryl$C_1$–$C_6$alkyloxycarbonyl, $C_1$–$C_6$alkyloxy, $C_1$–$C_6$alkyloxy$C_1$–$C_6$alkyl, aryloxy, aryl$C_1$–$C_6$alkyloxy, aryl$C_1$–$C_6$alkyloxy$C_1$–$C_6$alkyl, thio, $C_1$–$C_6$alkyl-thio, $C_1$–$C_6$alkylthio$C_1$–$C_6$alkyl, arylthio, aryl$C_1$–$C_6$alkylthio, aryl$C_1$–$C_6$alkylthio$C_1$–$C_6$alkyl, $NR_8R_9$, $C_1$–$C_6$alkylamino$C_1$–$C_6$alkyl, aryl$C_1$–$C_6$alkylamino$C_1$–$C_6$alkyl, di(aryl$C_1$–$C_6$alkyl)amino$C_1$–$C_6$alkyl, $C_1$–$C_6$alkylcarbonyl, $C_1$–$C_6$alkylcarbonyl$C_1$–$C_6$alkyl, aryl$C_1$–$C_6$alkylcarbonyl, aryl$C_1$–$C_6$alkylcarbonyl$C_1$–$C_6$alkyl, $C_1$–$C_6$alkylcarboxy, $C_1$–$C_6$alkylcarboxy$C_1$–$C_6$-alkyl, arylcarboxy, arylcarboxy$C_1$–$C_6$alkyl, $C_1$–$C_6$alkylcarboxy, aryl$C_1$–$C_6$alkylcarboxy$C_1$–$C_6$alkyl, $C_1$–$C_6$alkylcarbonylamino, $C_1$–$C_6$alkylcarbonylamino$C_1$–$C_6$alkyl, -carbonyl$NR_8C_1$–$C_6$alkyl$COR_{12}$, aryl$C_1$–$C_6$alkylcarbonylamino, aryl$C_1$–$C_6$alkylcarbonylamino$C_1$–$C_6$alkyl, $CONR_8R_9$, or $C_1$–$C_6$alkyl$CONR_8R_9$ wherein the alkyl and aryl groups are optionally substituted and $R_{12}$ is $NR_8R_9$, or $C_1$–$C_6$alkynyl$_8R_9$;

$R_7$ is hydrogen, $C_1$–$C_6$alkyl, aryl, aryl$C_1$–$C_6$alkyl, $C_1$–$C_6$alkylcarbonyl, $C_1$–$C_6$alkoxycarbonyl, arylcarbonyl, aryloxocarbonyl, aryl$C_1$–$C_6$alkylcarbonyl, aryl$C_1$–$C_6$alkoxycarbonyl, $C_1$–$C_6$alkylcarboxy, aryl$C_1$–$C_6$alkylcarboxy, $R_{10}R_{11}$Ncarbonyl$C_1$–$C_6$alkyl wherein $R_{10}$ and $R_{11}$ are independently selected from hydrogen, $C_1$–$C_6$alkyl, aryl, aryl$C_1$–$C_6$alkyl, $C_1$–$C_6$alkylcarbonyl, arylcarbonyl, aryl$C_1$–$C_6$alkylcarbonyl, $C_1$–$C_6$alkylcarboxy or aryl$C_1$–$C_6$alkylcarboxy; wherein the alkyl and aryl groups are optionally substituted; $R_8$ and $R_9$ are independently selected from hydrogen, $C_1$–$C_6$alkyl, aryl, aryl$C_1$–$C_6$alkyl, $C_1$–$C_6$alkylcarbonyl, $C_1$–$C_6$alkoxycarbonyl, arylcarbonyl, aryloxocarbonyl, aryl$C_1$–$C_6$alkylcarbonyl, aryl$C_1$–$C_6$alkoxycarbonyl, $C_1$–$C_6$alkylcarboxy, aryl$C_1$–$C_6$alkylcarboxy, $R_{10}R_{11}$Ncarbonyl$C_1$–$C_6$alkyl wherein the alkyl and aryl groups are optionally substituted; or $R_8$ and $R_9$ are together with the nitrogen to which they are attached forming a saturated, partially saturated or aromatic cyclic, bicyclic or tricyclic ring system containing from 3 to 14 carbon atoms and from 0 to 3 additional heteroatoms selected from nitrogen, oxygen or sulphur, the ring system can optionally be substituted with at least one $C_1$–$C_6$alkyl, aryl, aryl$C_1$–$C_6$alkyl, hydroxy, oxo, $C_1$–$_6$alkyloxy, aryl$C_1$–$C_6$alkyloxy, $C_1$–$C_6$alkyloxy$C_1$–$C_6$alkyl, $NR_{10}R_{11}$ or $C_1$–$C_6$alkylamino$C_1$–$C_6$alkyl, wherein $R_{10}$ and $R_{11}$ are independently selected from hydrogen, $C_1$–$C_6$alkyl, aryl, aryl$C_1$–$C_6$alkyl, $C_1$–$C_6$alkylcarbonyl, arylcarbonyl, aryl$C_1$–$C_6$alkylcarbonyl, $C_1$–$C_6$alkylcarboxy or aryl$C_1$–$C_6$alkylcarboxy; wherein the alkyl and aryl groups are optionally substituted; or $R_8$ and $R_9$ are independently a saturated or partial saturated cyclic 5, 6 or 7 membered amine, imide or lactam;

or a salt thereof with a pharmaceutically acceptable acid or base, or any optical isomer or mixture of optical isomers, including a racemic mixture, or any tautomeric form.

In another preferred embodiment, the present invention is concerned with compounds wherein X is sulphur.

In another preferred embodiment, the present invention is concerned with compounds wherein $R_1$ is COOR$_3$ and $R_2$ is hydrogen; wherein $R_3$ is defined as above.

In another preferred embodiment, the present invention is concerned with compounds wherein n and m are 1.

In another preferred embodiment, the present invention is concerned with compounds wherein $R_5$ is $C_1$–$C_6$alkylNR$_8$R$_9$.

In another preferred embodiment, the present invention is concerned with compounds wherein $R_4$ and $R_6$ are hydrogen.

In another preferred embodiment, the present invention is concerned with compounds wherein $R_1$ is 5-tetrazolyl, $R_2$ is hydrogen, and $R_5$ is $C_1$–$C_6$alkylNR$_8$R$_9$.

In another preferred embodiment, the present invention is concerned with compounds wherein $R_6$ is $C_1$–$C_6$alkylNR$_8$R$_9$.

In another preferred embodiment, the present invention is concerned with compounds wherein $R_4$ and $R_5$ are hydrogen.

In another preferred embodiment, the present invention is concerned with compounds wherein $R_1$ is 5-tetrazolyl, $R_2$ is hydrogen, and $R_6$ is $C_1$–$C_6$alkylNR$_8$R$_9$.

In another preferred embodiment, the present invention is concerned with compounds wherein $R_5$ and R6 are $C_1$–$C_6$alkylNR$_8$R$_9$.

In another preferred embodiment, the present invention is concerned with compounds wherein $R_1$ is COOR$_3$ and $R_2$ is hydrogen; wherein $R_3$ is defined as above.

In another preferred embodiment, the present invention is concerned with compounds wherein $R_1$ is 5-tetrazolyl.

In another preferred embodiment, the present invention is concerned with compounds wherein $R_8$ and $R_9$ are together with the nitrogen to which they are attached forming a partially saturated bicyclic ring system containing 8 carbon atoms, the ring system being optionally substituted with two oxo groups.

In another preferred embodiment, the present invention is concerned with compounds wherein the ring system is isoindolyl.

In another preferred embodiments, the present invention is concerned with compounds wherein $R_7$ is $C_1$–$C_6$alkoyxcarbonyl.

In another preferred embodiment, the present invention is concerned with compounds wherein $R_8$ and $R_9$ are together with the nitrogen to which they are attached forming a partially saturated bicyclic ring system containing 8 carbon atoms, the ring system being optionally substituted with two oxo groups.

In another preferred embodiment, the present invention is concerned with compounds wherein the ring system is isoindolyl.

In another preferred embodiment, the present invention is concerned with compounds wherein $R_8$ and $R_9$ are together with the nitrogen to which they are attached forming a partially saturated bicyclic ring system containing 7 carbon atoms and one sulfur atom, the ring system being optionally substituted with three oxo groups.

In another preferred embodiment, the present invention is concerned with compounds wherein the ring system is 2,3-dihydro-benzo[d]isothiazoly.

In another preferred embodiment, the present invention is concerned with compounds wherein $R_8$ and $R_9$ are together with the nitrogen to which they are attached forming a partially saturated bicyclic ring system containing 7 carbon atoms and one sulfur atom, the ring system being optionally substituted with two oxo groups.

In another preferred embodiment, the present invention is concerned with compounds wherein the ring system is 2,3-dihydro-benzo[d]isothiazoly.

In another preferred embodiment, the present invention is concerned with compounds wherein $R_7$ is $C_1$–$C_6$alkoxycarbonyl.

In another preferred embodiment, the present invention is concerned with compounds wherein $R_8$ and $R_9$ are together with the nitrogen to which they are attached forming a partially saturated bicyclic ring system containing 8 carbon atoms, the ring system being optionally substituted with one oxo group.

In another preferred embodiment, the present invention is concerned with compounds wherein the ring system is optionally substituted isoindolyl.

In another preferred embodiment, the present invention is concerned with compounds wherein the ring system is optionally substituted 1-oxo-1,3-dihydro-isoindolyl.

In another preferred embodiment, the present invention is concerned with compounds wherein $R_7$ is $C_1$–$C_6$alkoxycarbonyl.

In another preferred embodiment, the present invention is concerned with compounds wherein $R_5$ and $R_6$ are $C_1$–$C_6$alkylNR$_8$R$_9$.

In another preferred embodiment, the present invention is concerned with compounds of Formula I wherein $R_5$ is 1,3-dihydro-isoindol, substituted with 1 or 2 oxo groups at the atom positions adjacent to the nitrogen atom and optionally substituted with hydroxy, $C_{1-6}$-alkyloxy, arylC$_{1-6}$-alkyloxy or $C_{1-6}$-alkylcarboxy, and wherein $R_7$ is hydrogen, alkyl, alkyloxycarbonyl, arylalkyl or aryl wherein aryl is optionally substituted with methoxy.

In another preferred embodiment, the present invention is concerned with compounds of Formula I wherein $R_5$ is 1,1,3-trioxo-1,2-dihydro-1H-benzo[d]isothiazol-2-yl and wherein $R_7$ is hydrogen or arylalkyl.

In another preferred embodiment, the present invention is concerned with compounds of Formula I wherein $R_5$ or $R_6$ is arylaminoalkyl, wherein aryl is 1,1-dioxo-1,2-dihydro-1H-benzo[d]isothiazol-3-yl.

In another preferred embodiment, the present invention is concerned with compounds of Formula I wherein $R_5$ or $R_6$ is arylcarbonylaminoalkyl, wherein aryl is phenyl, indol-3-yl, indol-2-yl, 1,2,3-triazol4-yl, quinolin-4-yl or naphth-1-yl wherein aryl is optionally substituted, and wherein $R_7$ is hydrogen or arylalkyl optionally substituted with methoxy.

In another preferred embodiment, the present invention is concerned with compounds of Formula I wherein $R_5$ is arylalkylaminoalkyl wherein aryl is phenyl, dibenzofuranyl, naphth-2-yl or indo-3-yl, and wherein alkyl and aryl are optionally substituted, and wherein $R_7$ is hydrogen or arylalkyl optionally substituted with methoxy.

In another preferred embodiment, the present invention is concerned with compounds of Formula I wherein $R_6$ is alkylNR$_8$R$_9$, wherein $R_8$ is alkylcarbonyl and $R_9$ is arylalkyl, wherein aryl is optionally substituted.

In a preferred embodiment of the invention X in formula 1 is sulphur. In another preferred embodiment of the invention $R_1$ is COOR$_3$ and $R_2$ is hydrogen; wherein $R_3$ is hydrogen, $C_1$–$C_6$alkyl or arylC$_1$–C$_6$alkyl.

In a further preferred embodiment of the invention n and m are 1.

In a further preferred embodiment of the invention $R_4$ and $R_6$ are both hydrogen and $R_5$ is $C_1$–$C_6$alkylNR$_8$R$_9$ and $R_8$ and $R_9$ are together with the nitrogen to which they are attached forming a partially saturated bicyclic ring system containing 8 carbon atoms, the ring system being optionally substituted with two oxo groups.

Most preferred are $R_8$ and $R_9$ together with the nitrogen to which they are attached forming an isoindolyl-1,3-dione optionally substituted.

In another preferred embodiment of the invention $R_4$ and $R_5$ are both hydrogen and $R_6$ is $C_1$–$C_6$alkylNR$_8$R$_9$ and $R_8$ and $R_9$ are together with the nitrogen to which they are attached forming a partially saturated bicyclic ring system containing 8 carbon atoms, the ring system being optionally substituted with three oxo groups.

Most preferred are $R_8$ and $R_9$ together with the nitrogen to which they are attached forming an 1,1-dioxo-1,2-dihydro-1H-benzo[d]isothiazolyl-3-one optionally substituted.

In a further preferred embodiment of the invention $R_4$ and $R_5$ are both hydrogen and $R_6$ is $C_1$–$C_6$alkylNR$_8$R$_9$ and $R_8$ and $R_9$ are together with the nitrogen to which they are attached forming a partially saturated bicyclic ring system containing 8 carbon atoms, the ring system being optionally substituted with two oxo groups.

Most preferred are $R_8$ and $R_9$ together with the nitrogen to which they are attached forming an isoindolyl-1,3-dione optionally substituted.

In a further preferred embodiment of the invention $R_4$ and $R_6$ are both hydrogen and $R_5$ is $C_1$–$C_6$alkylNR$_8$R$_9$ and $R_8$ and $R_9$ are together with the nitrogen to which they are attached forming a partially saturated bicyclic ring system containing 8 carbon atoms, the ring system being optionally substituted with one oxo group.

Most preferred are $R_8$ and $R_9$ together with the nitrogen to which they are attached forming an optionally substituted 1-oxo-1,3-dihydro-isoindolyl ring.

In another preferred embodiment of the invention $R_4$ and $R_5$ are both hydrogen and $R_6$ is $C_1$–$C_6$alkylNR$_8$R$_9$ and $R_8$ and $R_9$ are together with the nitrogen to which they are attached forming a partially saturated bicyclic ring system containing 8 carbon atoms, the ring system being optionally substituted with one oxo group.

Most preferred are $R_8$ and $R_9$ together with the nitrogen to which they are attached forming an optionally substituted 1-oxo-1,3-dihydro-isoindolyl ring.

In a preferred embodiment of the invention $R_7$ is $C_1$–$C_6$alkoxycarbonyl.

The following compounds are preferred:

5-(1,3-Dioxo-1,3-dihydro-isoindol-2-ylmethyl)-2-(oxalyl-amino)-4,5,6,7-tetrahydro-thieno[2,3-c]pyridine-3,6-dicarboxylic acid 6-ethyl ester;
5-(1,3-Dioxo-1,3-dihydro-isoindol-2-ylmethyl)-2-(oxalyl-amino)-4,5,6,7-tetrahydro-thieno[2,3-c]pyridine-3-carboxylic acid;
(L)-5-(1,3-Dioxo-1,3-dihydro-isoindol-2-ylmethyl)-2-(oxalyl-amino)-4,5,6,7-tetrahydro-thieno[2,3-c]pyridine-3-carboxylic acid;
7-(1,3-Dioxo-1,3-dihydro-isoindol-2-ylmethyl)-2-(oxalyl-amino)-4,5,6,7-tetrahydro-thieno[2,3-c]pyridine-3-carboxylic acid;
5-(4-Hydroxy-1,3-dioxo-1,3-dihydro-isoindol-2-ylmethyl)-2-(oxalyl-amino)-4,5,6,7-tetrahydro-thien [2,3-c]pyridine-3-carboxylic acid;
2-(Oxalyl-amino)-5-(1-oxo-1,3-dihydro-isoindol-2-ylmethyl)-4,5,6,7-tetrahydro-thieno[2,3-c]pyridine-3-carboxylic acid;
2-(Oxalyl-amino)-7-(1,1,3-trioxo-1,3-dihydro-1H-benzo[d]isothiazol-2-ylmethyl)-4,5,6,7-tetrahydro-thieno[2,3-c]pyridine-3-carboxylic acid;
7-(1,1-Dioxo-1,3-dihydro-1H-benzo[d]isothiazol-2-ylmethyl)-2-(oxalyl-amino)-4,5,6,7-tetrahydro-thieno[2,3-c]pyridine-3-carboxylic acid;
5-(7-Hydroxy-1-oxo-1,3-dihydro-isoindol-2-ylmethyl)-2-(oxalyl-amino)-4,5,6,7-tetrahydro-thieno[2,3-c]pyridine-3-carboxylic acid;
or a pharmaceutically acceptable salt thereof.

The following compounds are also preferred:

5-(1,3-Dioxo-1,3-dihydro-isoindol-2-ylmethyl)-2-(oxalyl-amino)-4,5,6,7-tetrahydro-thieno[2,3-c]pyridine-3,6-dicarboxylic acid 6-ethyl ester;
5-(1,3-Dioxo-1,3-dihydro-isoindol-2-ylmethyl)-2-(oxalyl-amino)-4,5,6,7-tetrahydro-thieno[2,3-c]pyridine-3-carboxylic acid;
(S)-5-(1,3-Dioxo-1,3-dihydro-isoindol-2-ylmethyl)-2-(oxalyl-amino)-4,5,6,7-tetrahydro-thieno[2,3-c]pyridine-3-carboxylic acid;
7-(1,3-Dioxo-1,3-dihydro-isoindol-2-ylmethyl)-2-(oxalyl-amino)-4,5,6,7-tetrahydro-thieno[2,3-c]pyridine-3-carboxylic acid;
5-(4-Hydroxy-1,3-dioxo-1,3-dihydro-isoindol-2-ylmethyl)-2-(oxalyl-amino)-4,5,6,7-tetrahydro-thieno[2,3-c]pyridine-3-carboxylic acid;
2-(Oxalyl-amino)-5-(1-oxo-1,3-dihydro-isoindol-2-ylmethyl)-4,5,6,7-tetrahydro-thieno[2,3-c]pyridine-3-carboxylic acid;
5-(4-Hydroxy-1-oxo-1,3-dihydro-isoindol-2-ylmethyl)-2-(oxalyl-amino)-4,5,6,7-tetrahydro-thieno [2,3-c]pyridine-3-carboxylic acid;
5-(4-Hydroxy-1-oxo-1,3-dihydro-isoindol-2-ylmethyl)-6-methyl-2-(oxalyl-amino)-4,5,6,7-tetrahydro-thieno[2,3-c]pyridine-3-carboxylic acid;
5-((1,1-Dioxo-1H-benzo[d]isothiazol-3-ylamino)-methyl)-2-(oxalyl-amino)-4,5,6,7-tetrahydro-thieno[2,3-c]pyridine-3-carboxylic acid;
7-((1,1-Dioxo-1H-benzo[d]isothiazol-3-ylamino)-methyl)-2-(oxalyl-amino)-4,5,6,7-tetrahydro-thieno[2,3-c]pyridine-3-carboxylic acid;
5-(7-Methoxy-1-oxo-1,3-dihydro-isoindol-2-ylmethyl)-2-(oxalyl-amino)-4,5,6,7-tetrahydro-thieno[2,3-c]pyridine-3-carboxylic acid;
5-(7-Hydroxy-1-oxo-1,3-dihydro-isoindol-2-ylmethyl)-2-(oxalyl-amino)-4,5,6,7-tetrahydro-thieno[2,3-c]pyridine-3-carboxylic acid;
5-(7-Benzyloxy-1-oxo-1,3-dihydro-isoindol-2-ylmethyl)-2-(oxalyl-amino)-4,5,6,7-tetrahydro-thieno[2,3-c]pyridine-3-carboxylic acid;
5-(7-Hydroxy-1-oxo-1,3-dihydro-isoindol-2-ylmethyl)-6-(4-methoxy-benzyl)-2-(oxalyl-amino)-4,5,6,7-tetrahydro-thieno[2,3-c]pyridine-3-carboxylic acid;
5-(1,3-Dioxo-1,3-dihydro-isoindol-2-ylmethyl)-6-(4-methoxy-benzyl)-2-(oxalyl-amino)-4,5,6,7-tetrahydro-thieno[2,3-c]pyridine-3-carboxylic acid;
7-(7-Hydroxy-1-oxo-1,3-dihydro-isoindol-2-ylmethyl)-2-(oxalyl-amino)-4,5,6,7-tetrahydro-thieno[2,3-c]pyridine-3-carboxylic acid;

7-(7-Hydroxy-1-oxo-1,3-dihydro-isoindol-2-ylmethyl)-6-(4-methoxy-benzyl)-2-(oxalyl-amino)-4,5,6,7-tetrahydro-thieno[2,3-c]pyridine-3-carboxylic acid;

7-(1,3-Dioxo-1,3-dihydro-isoindol-2-ylmethyl)-6-(4-methoxy-benzyl)-2-(oxalyl-amino)-4,5,6,7-tetrahydro-thieno[2,3-c]pyridine-3-carboxylic acid;

5-(S)-(7-Methoxy-1-oxo-1,3-dihydro-isoindol-2-ylmethyl)-2-(oxalyl-amino)-4,5,6,7-tetrahydro-thieno[2,3-c]pyridine-3-carboxylic acid;

5-(R)-(7-Methoxy-1-oxo-1,3-dihydro-isoindol-2-ylmethyl)-2-(oxalyl-amino)-4,5,6,7-tetrahydro-thieno[2,3-c]pyridine-3-carboxylic acid;

5-(4-Benzyloxy-1,3-dioxo-1,3-dihydro-isoindol-2-ylmethyl)-2-(oxalyl-amino)-4,5,6,7-tetrahydro-thieno[2,3-c]pyridine-3-carboxylic acid;

5-(6-Methoxy-4-methoxycarbonyl-1-oxo-1,3-dihydro-isoindol-2-ylmethyl)-2-(oxalyl-amino)-4,5,6,7-tetrahydro-thieno[2,3-c]pyridine-3-carboxylic acid;

2-(Oxalyl-amino)-5-(1,1,3-trioxo-1,3-dihydro-1H-benzo[d]isothiazol-2-ylmethyl)-4,7-dihydro-5H-thieno[2,3-c]pyridine-3-carboxylic acid;

2-(Oxalyl-amino)-7-(1,1,3-trioxo-1,3-dihydro-1H-benzo[d]isothiazol-2-ylmethyl)-4,7-dihydro-5H-thieno[2,3-c]pyridine-3-carboxylic acid;

7-Carbamoyl-2-(oxalyl-amino)-4,5,6,7-tetrahydro-thieno[2,3-c]pyridine-3-carboxylic acid;

2-(Oxalyl-amino)-5-(2-oxo-tetrahydro-thiophen-3-ylcarbamoyl)-4,5,6,7-tetrahydro-thieno[2,3-c]pyridine-3-carboxylic acid;

2-(Oxalyl-amino)-5-phenylcarbamoyl-4,5,6,7-tetrahydro-thieno[2,3-c]pyridine-3-carboxylic acid;

2-(Oxalyl-amino)-7-phenylcarbamoyl-4,5,6,7-tetrahydro-thieno[2,3-c]pyridine-3-carboxylic acid;

or a pharmaceutically acceptable salt thereof.

The following compounds are also preferred:

5-(1,3-Dioxo-1,3-dihydro-isoindol-2-ylmethyl)-2-(oxalyl-amino)-4,5,6,7-tetrahydro-thieno[2,3-c]pyridine-3,6-dicarboxylic acid 6-ethyl ester;

5-(1,3-Dioxo-1,3-dihydro-isoindol-2-ylmethyl)-2-(oxalyl-amino)-4,5,6,7-tetrahydro-thieno[2,3-c]pyridine-3-carboxylic acid;

5-(S)-(1,3-Dioxo-1,3-dihydro-isoindol-2-ylmethyl)-2-(oxalyl-amino)-4,5,6,7-tetrahydro-thieno[2,3-c]pyridine-3-carboxylic acid;

7-(1,3-Dioxo-1,3-dihydro-isoindol-2-ylmethyl)-2-(oxalyl-amino)-4,5,6,7-tetrahydro-thieno[2,3-c]pyridine-3-carboxylic acid;

5-(4-Hydroxy-1,3-dioxo-1,3-dihydro-isoindol-2-ylmethyl)-2-(oxalyl-amino)-4,5,6,7-tetrahydro-thieno[2,3-c]pyridine-3-carboxylic acid;

7-(4-Hydroxy-1,3-dioxo-1,3-dihydro-isoindol-2-ylmethyl)-2-(oxalyl-amino)-4,5,6,7-tetrahydro-thieno[2,3-c]pyridine-3-carboxylic acid;

2-(Oxalyl-amino)-5-(S)-(1-oxo-1,3-dihydro-isoindol-2-ylmethyl)-4,5,6,7-tetrahydro-thieno[2,3-c]pyridine-3-carboxylic acid;

5-(4-Hydroxy-1-oxo-1,3-dihydro-isoindol-2-ylmethyl)-2-(oxalyl-amino)-4,5,6,7-tetrahydro-thieno[2,3-c]pyridine-3-carboxylic acid;

5-(4-Hydroxy-1-oxo-1,3-dihydro-isoindol-2-ylmethyl)-6-methyl-2-(oxalyl-amino)-4,5,6,7-tetrahydro-thieno[2,3-c]pyridine-3-carboxylic acid;

5-((1,1-Dioxo-1H-benzo[d]isothiazol-3-ylamino)methyl)-2-(oxalyl-amino)-4,5,6,7-tetrahydro-thieno[2,3-c]pyridine-3-carboxylic acid;

7-((1,1-Dioxo-1H-benzo[d]isothiazol-3-ylamino)methyl)-2-(oxalyl-amino)-4,5,6,7-tetrahydro-thieno[2,3-c]pyridine-3-carboxylic acid;

5-(7-Methoxy-1-oxo-1,3-dihydro-isoindol-2-ylmethyl)-2-(oxalyl-amino)-4,5,6,7-tetrahydro-thieno[2,3-c]pyridine-3-carboxylic acid;

5-(7-Hydroxy-1-oxo-1,3-dihydro-isoindol-2-ylmethyl)-2-(oxalyl-amino)-4,5,6,7-tetrahydro-thieno[2,3-c]pyridine-3-carboxylic acid;

5-(7-Benzyloxy-1-oxo-1,3-dihydro-isoindol-2-ylmethyl)-2-(oxalyl-amino)-4,5,6,7-tetrahydro-thieno[2,3-c]pyridine-3-carboxylic acid;

5-(7-Hydroxy-1-oxo-1,3-dihydro-isoindol-2-ylmethyl)-6-(4-methoxy-benzyl1)-2-(oxalyl-amino-4,5,6,7-tetrahydro-thieno[2,3-c]pyridine-3-carboxylic acid;

5-(1,3-Dioxo-1,3-dihydro-isoindol-2-ylmethyl)-6-(4-methoxy-benzyl)-2-(oxalyl-amino)-4,5,6,7-tetrahydro-thieno[2,3-c]pyridine-3-carboxylic acid;

7-(7-Hydroxy-1-oxo-1,3-dihydro-isoindol-2-ylmethyl)-2-(oxalyl-amino)-4,5,6,7-tetrahydro-thieno[2,3-c]pyridine-3-carboxylic acid;

7-(7-Hydroxy-1-oxo-1,3-dihydro-isoindol-2-ylmethyl)-6-(4-methoxy-benzyl)-2-(oxalyl-amino)-4,5,6,7-tetrahydro-thieno[2,3-c]pyridine-3-carboxylic acid;

7-(1,3-Dioxo-1,3-dihydro-isoindol-2-ylmethyl)-6-(4-methoxy-benzyl)-2-(oxalyl-amino)-4,5,6,7-tetrahydro-thieno[2,3-c]pyridine-3-carboxylic acid;

7-(((5-Benzyloxy-1H-indole-2-carbonyl)amino)methyl)-6-(4-methoxy-benzyl)-2-(oxalyl-amino)-4,5,6,7-tetrahydro-thieno[2,3-c]pyridine-3-carboxylic acid;

7-(((6-Bromo-2-p-tolyl-quinoline-4-carbonyl)amino)methyl)-6-(4-methoxy-benzyl)-2-(oxalyl-amino)-4,5,6,7-tetrahydro-thieno[2,3-c]pyridine-3-carboxylic acid;

6-(4-Methoxy-benzyl)-7-(((5-methyl-2-phenyl-2H-[1,2,3]triazole4-carbonyl)amino)methyl)-2(oxalyl-amino)-4,5,6,7-tetrahydro-thieno[2,3-c]pyridine-3-carboxylic acid;

7-(((1H-Indole-3-carbonyl)amino)methyl)-6-(4-methoxy-benzyl)-2-(oxalyl-amino)-4,5,6,7-tetrahydro-thieno[2,3-c]pyridine-3-carboxylic acid;

7-((4-Ethoxy-2-hydroxy-benzoylamino)methyl)-6-(4-methoxy-benzyl)-2-(oxalyl-amino) -4,5,6,7-tetrahydro-thieno[2,3-c]pyridine-3-carboxylic acid;

7-((4-Benzoylamino-benzoylamino)methyl)-6-(4-methoxy-benzyl)-2-(oxalyl-amino)-4,5,6,7-tetrahydro-thieno[2,3-c]pyridine-3-carboxylic acid;

7-(((Biphenyl4-carbonyl)-amino)methyl)-6-(4-methoxy-benzyl)-2-(oxalyl-amino)-4,5,6,7-tetrahydro-thieno[2,3-c]pyridine-3-carboxylic acid;

7-(((1H-Indole-2-carbonyl)amino)methyl)-6-(4-methoxy-benzyl)-2-(oxalyl-amino)-4,5,6,7-tetrahydro-thieno[2,3-c]pyridine-3-carboxylic acid;

7-((3-Biphenyl4-yl-acryloylamino)methyl)-6-(4-methoxy-benzyl)-2-(oxalyl-amino)-4,5,6,7-tetrahydro-thieno[2,3-c]pyridine-3-carboxylic acid;

6-(4-Methoxy-benzyl)-7-(((5-methoxy-1H-indole-2-carbonyl)amino)methyl)-2-(oxalyl-amino)-4,5,6,7-tetrahydro-thieno[2,3-c]pyridine-3-carboxylic acid;

7-((4-Benzyl-benzoylamino)methyl)-6-(4-methoxy-benzyl)-2-(oxalyl-amino)-4,5,6,7-tetrahydro-thieno[2,3-c]pyridine-3-carboxylic acid;

6-(4-Methoxy-benzyl)-7-(((naphthalene-1-carbonyl)amino)methyl)-2-(oxalyl-amino)-4,5,6,7-tetrahydro-thieno[2,3-c]pyridine-3-carboxylic acid;

6-(4-Methoxy-benzyl)-5-((2-naphthalen-2-yl-ethylamino)methyl)-2-(oxalyl-amino)-4,5,6,7-tetrahydro-thieno[2,3-c]pyridine-3-carboxylic acid;

5-((2-Benzo[1,3]dioxol-5-yl-acetylamino)methyl)-2-(oxalyl-amino)-4,5,6,7-tetrahydro-thieno[2,3-c]pyridine-3-carboxylic acid;

5-((2-Dibenzofuran-2-yl-ethyl)amino)methyl)-6-(4-methoxy-benzyl)-2-(oxalyl-amino)-4,5,6,7-tetrahydro-thieno[2,3-c]pyridine-3-carboxylic acid;

6-(4-Methoxy-benzyl)-5-((2-(5-methoxy-2-methyl-1H-indol-3-yl)-acetylamino)methyl)-2-(oxalyl-amino)-4,5,6,7-tetrahydro-thieno[2,3-c]pyridine-3-carboxylic acid;

5-((2-(1H-Indol-3-yl)-2-oxo-acetylamino)methyl)-2-(Oxalyl-amino)-4,5,6,7-tetrahydro-thieno[2,3-c]pyridine-3-carboxylic acid;

5-(R)-(7-Methoxy-1-oxo-1,3-dihydro-isoindol-2-ylmethyl)-2-(oxalyl-amino)-4,5,6,7-tetrahydro-thieno[2,3-c]pyridine-3-carboxylic acid;

5-(S)-(7-Methoxy-1-oxo-1,3-dihydro-isoindol-2-ylmethyl)-2-(oxalyl-amino)-4,5,6,7-tetrahydro-thieno[2,3-c]pyridine-3-carboxylic acid;

5-(S)-(4-Hydroxy-1-oxo-1,3-dihydro-isoindol-2-ylmethyl)-2-(oxalyl-amino)-4,5,6,7-tetrahydro-thieno[2,3-c]pyridine-3-carboxylic acid;

2-(Oxalyl-amino)-5-(S)-((4-phenoxy-benzylamino)methyl)-4,5,6,7-tetrahydro-thieno[2,3-c]pyridine-3-carboxylic acid;

5-(S)-((4-Acetylamino-benzylamino)methyl)-2-(oxalyl-amino)-4,5,6,7-tetrahydro-thieno[2,3-c]pyridine-3-carboxylic acid;

7-(S)-((Acetyl-(4-phenoxy-benzyl)amino)methyl)-2-(oxalyl-amino)-4,5,6,7-tetrahydro-thieno[2,3-c]pyridine-3-carboxylic acid;

7-(S)-((Acetyl-benzyl-amino)methyl)-2-(oxalyl-amino)-4,5,6,7-tetrahydro-thieno[2,3-c]pyridine-3-carboxylic acid;

5-(S)-((1,1-Dioxo-1H-benzo[d]isothiazol-3-ylamino)methyl)-2-(oxalyl-amino)-4,5,6,7-tetrahydro-thieno[2,3-c]pyridine-3-carboxylic acid;

5-(4-Benzyloxy-1,3-dioxo-1,3-dihydro-isoindol-2-ylmethyl)-2-(oxalyl-amino)-4,5,6,7-tetrahydro-thieno[2,3-c]pyridine-3-carboxylic acid;

5-(6-Methoxy-4-methoxycarbonyl-1-oxo-1,3-dihydro-isoindol-2-ylmethyl)-2-(oxalyl-amino)-4,5,6,7-tetrahydro-thieno[2,3-c]pyridine-3-carboxylic acid;

2-(Oxalyl-amino)-5-(1,1,3-trioxo-1,3-dihydro-1H-benzo[d]isothiazol-2-ylmethyl)-4,7-dihydro-5H-thieno[2,3-c]pyridine-3-carboxylic acid;

2-(Oxalyl-amino)-7-(1,1,3-trioxo-1,3-dihydro-1H-benzo[d]isothiazol-2-ylmethyl)-4,7-dihydro-5H-thieno[2,3-c]pyridine-3-carboxylic acid;

7-(R)-Carbamoyl-2-(oxalyl-amino)-4,5,6,7-tetrahydro-thieno[2,3-c]pyridine-3-carboxylic acid;

2-(Oxalyl-amino)-5-(S)-(2-oxo-tetrahydro-thiophen-3-ylcarbamoyl)-4,5,6,7-tetrahydro-thieno[2,3-c]pyridine-3-carboxylic acid;

2-(Oxalyl-amino)-5-(S)-phenylcarbamoyl-4,5,6,7-tetrahydro-thieno[2,3-c]pyridine-3-carboxylic acid;

2-(Oxalyl-amino)-7-(R)-phenylcarbamoyl-4,5,6,7-tetrahydro-thieno[2,3-c]pyridine-3-carboxylic acid;

5-(R),7-(R)-Bis-benzyloxymethyl-2-(oxalyl-amino)-4,5,6,7-tetrahydro-thieno[2,3-c]pyridine-3-carboxylic acid;

6-Benzyl-2-(oxalyl-amino)-5-(1,1,3-trioxo-1,3-dihydro-1,6-benzo[d]isothiazol-2-ylmethyl)-4,5,6,7-tetrahydro-thieno[2,3-c]pyridine-3-carboxylic acid;

or a salt thereof with a pharmaceutically acceptable acid or base, or any optical isomer or mixture of optical isomers, including a racemic mixture, or any tautomeric form, or prodrug thereof.

PHARMACOLOGICAL METHODS

The compounds are evaluated for biological activity with a truncated form of PTPI B (corresponding to the first 321 amino acids), which was expressed in E. coli and purified to apparent homogeneity using published procedures well-known to those skilled in the art. The enzyme reactions are carried out using standard conditions essentially as described by Burke et al. (*Biochemistry* 35; 15989–15996 (1996)). The assay conditions are as follows. Appropriate concentrations of the compounds of the invention are added to the reaction mixtures containing different concentrations of the substrate, p-nitrophenyl phosphate (range: 0.16 to 10 mM—final assay concentration). The buffer used was 50 mM HEPES pH 7.0, 100 mM sodium chloride, 0.1% (w/v) bovine serum albumin, 5 mM glutathione, and 1 mM EDTA. The reaction was started by addition of the enzyme and carried out in microtiter plates at 25° C. for 60 minutes. The reactions are stopped by addition of NaOH. The enzyme activity was determined by measurement of the absorbance at 405 nm with appropriate corrections for absorbance at 405 nm of the compounds and p-nitrophenyl phosphate. The data are analyzed using nonlinear regression fit to classical Michaelis Menten enzyme kinetic models. Inhibition is expressed as $K_i$ values in nM. The results of representative experiments are shown in Table 1.

TABLE 1

| Inhibition of classical PTP1B by compounds of the invention | |
|---|---|
| Example no. | PTP1B $K_i$ values (nM) |
| 8 | 250 |
| 10 | 270 |
| 11 | 240 |
| 12 | 570 |
| 36 | 830 |
| 42 | 220 |
| 46 | 300 |

Analysis for Blood Glucose Lowering Effects

The compounds of the invention are tested for blood glucose lowering effects in diabetic, obese female ob/ob mice. The mice are of similar age and body weights and they are randomized into groups of ten mice. They have free access to food and water during the experiment. The compounds are administered by either by gavage, subcutaneous, intravenous or intraperitoneal injections. The control group receives the same volume of vehicle as the mice that receive the compounds. Non-limiting examples of dose-range: 0.1, 0.3, 1.0, 3.0, 10, 30, 100 mg per kg body weight. The blood glucose levels are measured two times before administration of the compounds of the invention and vehicle (to the control group). After administration of the compound, the blood glucose levels are measured at the following time points: 1, 2, 4, 6, and 8 hours. A positive response is defined either as (i) a more than 25 percent reduction in blood glucose levels in the group receiving the compound of the invention compared to the group receiving the vehicle at any time point or (ii) statistically significant (i.e. $p<0.05$) reduction in the area under the blood glucose curve during the whole period (i.e. 8 hrs) in the group treated with the compounds of the invention compared to the group receiving the vehicle.

Compounds that show positive response can be used as development candidates and used for treatment of human diseases such as diabetes and obesity.

THE SYNTHESIS OF THE COMPOUNDS

In accordance with one aspect of the invention, the compounds of the invention are prepared as illustrated in the following reaction scheme:

Method A

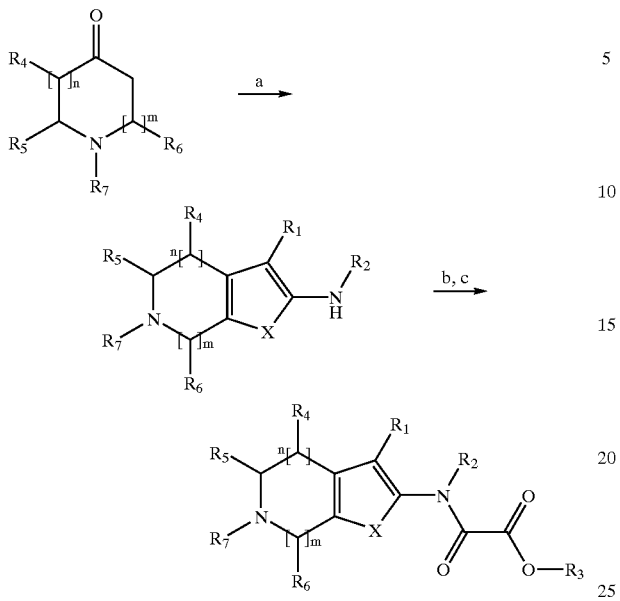

a) NCCH$_2$COOR$_3$, sulphur, morpholine or triethylamine, ethanol; b) R$_3$OCOCOimidazole, tetrahydrofuran; c) 25% trifluoroacetic acid/dichloromethane; wherein n, m, X, R$_1$, R$_2$, R$_3$, R$_4$, R$_5$, R$_6$ and R$_7$ are defined above;

When R$_4$ is hydrogen the reaction step a) in Method A gives a mixture of regioisomers which can be separated by use of column chromatography known to thus skilled in the art.

Method B

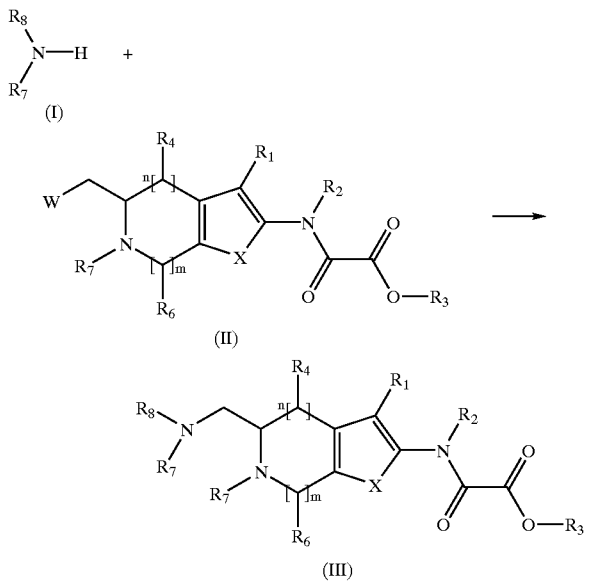

By allowing an amine (I) and a substituted oxalylamide (II) to react under basic conditions (e.g. K$_2$CO$_3$, in N,N-dimethylformamide or methylethylketone) or under Mitsunobu conditions (Oyo Mitsunobu, *Synthesis*, (1981) 1–28) to yield (III) wherein W is OH, OSO$_2$Me or halo, and n, m, X, R$_1$, R$_2$, R$_3$, R$_4$, R$_6$, R$_7$ and R$_8$ are defined above.

Method C

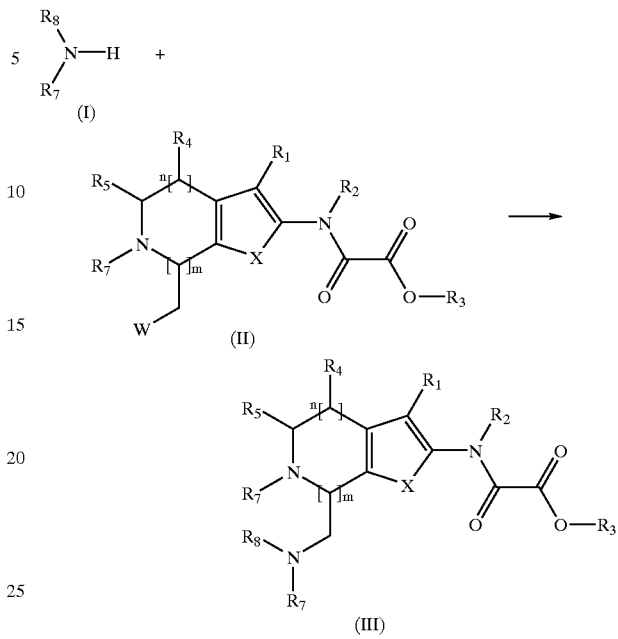

By allowing an amine (I) and a substituted oxalylamide (II) to react under basic conditions (e.g. K$_2$CO$_3$, in N,N-dimethylformamide or methylethylketone) or under Mitsunobu conditions (Oyo Mitsunobu, *Synthesis*, (1981) 1–28) to yield (III) wherein W is OH, OSO$_2$Me or halo, and n, m, X, R$_1$, R$_2$, R$_3$, R$_4$, R$_5$, R$_7$ and R$_8$ are defined above.

Pharmacological Preparations

In another aspect, the present invention includes within its scope pharmaceutical compositions comprising, as an active ingredient, at least one of the compounds of the general formula I or a pharmaceutically acceptable salt thereof together with a pharmaceutically acceptable carrier or diluent.

The present compounds may also be administered in combination with one or more further pharmacologically active substances e.g., selected from antiobesity agents, antidiabetics, antihypertensive agents, agents for the treatment and/or prevention of complications resulting from or associated with diabetes and agents for the treatment and/or prevention of complications and disorders resulting from or associated with obesity.

Thus, in a further aspect of the invention the present compounds may be administered in combination with one or more antiobesity agents or appetite regulating agents.

Such agents may be selected from the group consisting of CART (cocaine amphetamine regulated transcript) agonists, NPY (neuropeptide Y) antagonists, MC4 (melanocortin 4) agonists, orexin antagonists, TNF (tumor necrosis factor) agonists, CRF (corticotropin releasing factor) agonists, CRF BP (corticotropin releasing factor binding protein) antagonists, urocortin agonists, β3 agonists, MSH (melanocyte-stimulating hormone) agonists, MCH (melanocyte-concentrating hormone) antagonists, CCK (cholecystokinin) agonists, serotonin re-uptake inhibitors, serotonin and noradrenaline re-uptake inhibitors, mixed serotonin and noradrenergic compounds, 5HT (serotonin) agonists, bombesin agonists, galanin antagonists, growth hormone, growth hormone releasing compounds, TRH (thyreotropin releasing hormone) agonists, UCP 2 or 3 (uncoupling protein 2 or 3) modulators, leptin agonists, DA agonists (bromocriptin, doprexin), lipase/amylase inhibitors, PPAR (peroxisome proliferator activated receptor) modulators, RXR (retinoid X receptor) modulators or TR β agonists.

In one embodiment of the invention the antiobesity agent is leptin.

In another embodiment the antiobesity agent is dexamphetamine or amphetamine.

In another embodiment the antiobesity agent is fenfluramine or dexfenfluramine.

In still another embodiment the antiobesity agent is sibutramine.

In a further embodiment the antiobesity agent is orlistat.

In another embodiment the antiobesity agent is mazindol or phentermine.

Suitable antidiabetics comprise insulin, GLP-1 (glucagon like peptide-1) derivatives such as those disclosed in WO 98/08871 to Novo Nordisk A/S, which is incorporated herein by reference as well as orally active hypoglycaemic agents.

The orally active hypoglycaemic agents preferably comprise sulphonylureas, biguanides, meglitinides, oxadiazolidinediones, thiazolidinediones, glucosidase inhibitors, glucagon antagonists such as those disclosed in WO 99/01423 to Novo Nordisk A/S and Agouron Pharmaceuticals, Inc., GLP-1 agonists, potassium channel openers such as those disclosed in WO 97/26265 and WO 99/03861 to Novo Nordisk A/S which are incorporated herein by reference, insulin sesitizers, DPP-IV (dipeptidyl peptidase-IV) inhibitors, inhibitors of hepatic enzymes involved in stimulation of gluconeogenesis and/or glycogenolysis, glucose uptake modulators, compounds modifying the lipid metabolism such as antihyperlipidemic agents and antilipidemic agents as HMG CoA inhibitors (statins), compounds lowering food intake, PPAR and RXR agonists and agents acting on the ATP-dependent potassium channel of the β-cells.

In one embodiment of the invention the present compounds are administered in combination with insulin.

In a further embodiment the present compounds are administered in combination with a sulphonylurea e.g. tolbutamide, glibenclamide, glipizide or glicazide.

In another embodiment the present compounds are administered in combination with a biguanide e.g. metformin.

In yet another embodiment the present compounds are administered in combination with a meglitinide e.g. repaglinide.

In still another embodiment the present compounds are administered in combination with a thiazolidinedione e.g. troglitazone, ciglitazone, pioglitazone, rosiglitazone or compounds disclosed in WO 97/41097 such as 5-[[4-[3-Methyl-4-oxo-3,4-dihydro-2-quinazolinyl]methoxy]phenyl-methyl] thiazolidine-2,4-dione or a pharmaceutically acceptable salt thereof, preferably the potassium salt.

Furthermore, the present compounds may be administered in combination with the insulin sensitizers disclosed in WO 99/19313 such as (-) 3-[4-[2-Phenoxazin-10-yl)ethoxy]phenyl]-2-ethoxypropanoic acid or a pharmaceutically acceptable salts thereof, preferably the arginine salt.

In a further embodiment the present compounds are administered in combination with an α-glucosidase inhibitor e.g. miglitol or acarbose.

In another embodiment the present compounds are administered in combination with an agent acting on the ATP-dependent potassium channel of the β-cells e.g. tolbutamide, glibenclamide, glipizide, glicazide or repaglinide.

Furthermore, the present compounds may be administered in combination with nateglinide.

In still another embodiment the present compounds are administered in combination with an antihyperlipidemic agent or antilipidemic agent e.g. cholestyramine, colestipol, clofibrate, gemfibrozil, lovastatin, pravastatin, simvastatin, probucol or dextrothyroxine.

In a further embodiment the present compounds are administered in combination with more than one of the above-mentioned compounds e.g. in combination with a sulphonylurea and metformin, a sulphonylurea and acarbose, repaglinide and metformin, insulin and a sulphonylurea, insulin and metformin, insulin, insulin and lovastatin, etc.

Furthermore, the present compounds may be administered in combination with one or more antihypertensive agents. Examples of antihypertensive agents are β-blockers such as alprenolol, atenolol, timolol, pindolol, propranolol and metoprolol, ACE (angiotensin converting enzyme) inhibitors such as benazepril, captopril, enalapril, fosinopril, lisinopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin. Further reference can be made to Remington: The Science and Practice of Pharmacy, 19$^{th}$ Edition, Gennaro, Ed., Mack Publishing Co., Easton, Pa., 1995.

It should be understood that any suitable combination of the compounds according to the invention with one or more of the above-mentioned compounds and optionally one or more further pharmacologically active substances are considered to be within the scope of the present invention.

For the above indications the dosage will vary depending on the compound of the invention employed, on the mode of administration and on the therapy desired. However, in general, satisfactory results are obtained with a dosage of from about 0.5 mg to about 1000 mg, preferably from about 1 mg to about 500 mg of compounds of the invention, conveniently given from 1 to 5 times daily, optionally in sustained release form. Usually, dosage forms suitable for oral administration comprise from about 0.5 mg to about 1000 mg, preferably from about 1 mg to about 500 mg of the compounds of the invention admixed with a pharmaceutical carrier or diluent.

The compounds of the invention may be administered in a pharmaceutically acceptable acid addition salt form or where possible as a metal or a $C_{1-6}$-alkylammonium salt. Such salt forms exhibit approximately the same order of activity as the free acid forms.

This invention also relates to pharmaceutical compositions comprising a compound of the invention or a pharmaceutically acceptable salt thereof and, usually, such compositions also contain a pharmaceutical carrier or diluent. The compositions containing the compounds of this invention may be prepared by conventional techniques and appear in conventional forms, for example capsules, tablets, solutions or suspensions.

The pharmaceutical carrier employed may be a conventional solid or liquid carrier. Examples of solid carriers are lactose, terra alba, sucrose, talc, gelatine, agar, pectin, acacia, magnesium stearate and stearic acid. Examples of liquid carriers are syrup, peanut oil, olive oil and water.

Similarly, the carrier or diluent may include any time delay material known to the art, such as glyceryl monostearate or glyceryl distearate, alone or mixed with a wax.

If a solid carrier for oral administration is used, the preparation can be tabletted, placed in a hard gelatine capsule in powder or pellet form or it can be in the form of a troche or lozenge. The amount of solid carrier will vary widely but will usually be from about 25 mg to about 1 g. If a liquid carrier is used, the preparation may be in the form of a syrup, emulsion, soft gelatin capsule or sterile injectable liquid such as an aqueous or non-aqueous liquid suspension or solution.

Generally, the compounds of this invention are dispensed in unit dosage form comprising 10–200 mg of active ingredient in or together with a pharmaceutically acceptable carrier per unit dosage.

The dosage of the compounds according to this invention is 1–500 mg/day, e.g. about 100 mg per dose, when administered to patients, e.g. humans, as a drug.

A typical tablet that may be prepared by conventional tabletting techniques contains

| Core: | |
| --- | --- |
| Active compound (as free compound or salt thereof) | 100 mg |
| Colloidal silicon dioxide (Areosil ®) | 1.5 mg |
| Cellulose, microcryst. (Avicel ®) | 70 mg |
| Modified cellulose gum (Ac-Di-Sol ®) | 7.5 mg |
| Magnesium stearate | |
| Coating: | |
| HPMC | approx. 9 mg |
| Mywacett ® 9-40 T | approx. 0.9 mg |

* Acylated monoglyceride used as plasticiser for film coating.

The route of administration may be any route, which effectively transports the active compound to the appropriate or desired site of action, such as oral or parenteral e.g. rectal, transdermal, subcutaneous, intranasal, intramuscular, topical, intravenous, intraurethral, ophthalmic solution or an ointment, the oral route being preferred.

EXAMPLES

The process for preparing compounds of Formula 1 and preparations containing them is further illustrated in the following examples, which, however, are not to be construed as limiting.

Hereinafter, TLC is thin layer chromatography, $CDCl_3$ is deuterio chloroform, $CD_3OD$ is tetradeuterio methanol and DMSO-$d_6$ is hexadeuterio dimethylsulfoxide. The structures of the compounds are confirmed by either elemental analysis or NMR, where peaks assigned to characteristic protons in the title compounds are presented where appropriate. $^1$H NMR shifts ($\delta^H$) are given in parts per million (ppm) down field from tetramethylsilane as internal reference standard. M.p.: is melting point and is given in ° C. and is not corrected. Column chromatography was carried out using the technique described by W. C. Still et al., *J. Org. Chem.* 43:2923 (1978) on Merck silica gel 60 (Art. 9385). HPLC analyses are performed using 5 μm C18 4×250 mm column eluted with various mixtures of water and acetonitrile, flow=1 ml/min, as described in the experimental section.

Compounds used as starting material are either known compounds or compounds, which can readily be prepared by methods known per se.

Example 1

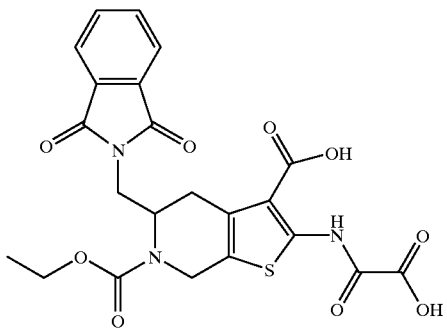

5-(1,3-Dioxo-1,3-dihydro-isoindol-2-ylmethyl)-2-(oxalyl-amino)-4,5,6,7-tetrahydro-thieno[2,3-c]pyridine-3,6-dicarboxylic acid 6-ethyl ester To a solution of 4-(2-spiro[1,3]dioxolane)-piperidine (51.5 g, 0.36 moles) in a mixture of dichloromethane (500 ml) and saturated sodium bicarbonate (500 ml) was added di-tert-butyldicarbonate (69.8 g, 0.32 moles) and the reaction was vigorously stirred for 3 hours and the layers separated. The organic layer was washed with 1N hydrochloric acid (2×150 ml), brine (100 ml), dried ($MgSO_4$), filtered and the solvent evaporated in vacuo affording 75.5 g (97%) of 4-(2-spiro[1,3]dioxolane)-piperidine-1-carboxylic acid tert-butyl ester as a crystallizing oil.

$^1$H-NMR (400 MHz, $CDCl_3$): δ3.96 (s, 4H), 3.49 (bm, 4H), 1.65 (bm, 4H), 1.45 (s, 9H)

To the above 4-(2-spiro[1,3]dioxolane)-piperidine-1-carboxylic acid tert-butyl ester (4.0 g, 16.4 mmol) dissolved in dry diethyl ether (32 ml) was added 2,2' bipyridyl (1 mg) and the solution was cooled to −75° C. Tetramethylethylenediamine (3.2 ml, 21.4 mmol) was added followed by dropwise addition of sec-butyl lithium (16.4 ml, 21.4 mmol, 1.3M in cyclohexane). The mixture was stirred at −75° C. for 10 min, then slowly warmed to −20° C. and stirred at that temperature for 0.5 hour, then cooled to −30° C. At this temperature, formaldehyde was generated by heating paraformaldehyde at 150° C. and passed through the mixture with dry nitrogen until the color faded to off-white, at which time water (40 ml) was added. The layers were separated, and the aqueous layer was extracted with diethyl ether (2×50 ml). The combined organic extracts were washed with 1 N hydrochloric acid (2×75 ml), saturated sodium bicarbonate solution (50 ml), dried ($MgSO_4$), filtered and the solvent evaporated in vacuo. The residue (2.9 g) was purified by silica gel chromatography (hexane/ethyl acetate, 10% ethyl acetate to 30% ethyl acetate, gradient). Pure fractions were collected and the solvent evaporated in vacuo affording 1.3 g (29%) of 2-hydroxymethyl-4-(2-spiro[1,3]dioxolane)-piperidine-1-carboxylic acid tert-butyl ester as a thick oil.

$^1$H-NMR (400 MHz, $CDCl_3$): δ4.42 (bm, 1H), 4.08–3.96 (m, 5H), 3.96–3.88 (m, 1H), 3.78–3.70 (m, 1H), 3.30–3.16 (bm, 1H), 2.30–1.98 (bs, 1H), 1.96–1.78 (m, 2H), 1.74–1.64 (m, 2H), 1.49 (s, 9H).

To 2-hydroxymethyl-4-(2-spiro[1,3]dioxolane)-piperidine-1-carboxylic acid tert-butyl ester (0.4 g, 1.5 mmol) dissolved in dry tetrahydrofuran (20 ml) was added phthalimide (0.28 g, 1.9 mmol), triphenylphosphine (0.5 g, 1.9 mmol) and the mixture was cooled to 0° C. in an ice bath. Diethyl azodicarboxylate (0.29 ml, 1.82 mmol) was added dropwise and the mixture was stirred at 0° C. for 0.5 hour, then at ambient temperature for 18 hours. The solvent was removed in vacuo and the residue was purified by silica gel chromatography (hexane/ethyl acetate, 18% ethyl acetate to 25% ethyl acetate, gradient). Pure fractions were collected and the solvent evaporated in vacuo affording 0.29 g (48%) of 2-(1,3-dioxo-1,3-dihydro-isoindol-2-ylmethyl)-4-(2-spiro[1,3]dioxolane)-piperidine-1-carboxylic acid tert-butyl ester.

$^1$H-NMR (400 MHz, CDCl$_3$): δ7.94–7.80 (bs, 2H), 7.80–7.64 (bd, 2H), 4.96–4.70 (2bs, 1H) 4.66–4.52 (m, 1H), 4.30–4.14 (bm, 1H), 4.12–4.04 (m, 2H), 4.04–3.94 (m, 2H), 3.56–3.32 (m, 2H), 2.04–1.92 (m, 1H), 1.90–1.60 (m, 4H), 1.22–1.00 (bs, 9H).

MS: m/z: 403 [M+H]$^+$, 303 [M−Boc]

To the above 2-(1,3-dioxo-1,3-dihydro-isoindol-2-ylmethyl)-4-(2-spiro[1,3]dioxolane) -piperidine1-carboxylic acid tert-butyl ester (1.1 g, 2.7 mmol) dissolved in dichloromethane (6 ml) was added 1.0 N hydrogen chloride in diethyl ether (50 ml) and the solution kept at ambient temperature for 62 hours. The precipitate was filtered off and washed with diethyl ether and dried with nitrogen which afforded 0.83 g (90%) of 2-(1,3-dioxo-1,3-dihydro-isoindol-2-ylmethyl)-4-(2-spiro[1,3]dioxolane)-piperidine hydrochloride as a solid.

$^1$H-NMR (400 MHz, DMSO-d$_6$): δ9.2–8.8 (2bs, 2H), 7.8–8.1 (m, 2H), 4,1–3.6 (m, 5H), 2.9 (bs, 1H), 2.2–1.6 (m, 5H).

MS: m/z: 303.5 [M+H]$^+$

To a suspension of the above 2-(1,3-dioxo-1,3-dihydro-isoindol-2-ylmethyl)-4-(2-spiro[1,3]dioxolane)-piperidine hydrochloride (0.7 g, 2.1 mmol) and ethyl chloroformate (0.24 ml, 2.5 mmol) in dry tetrahydrofuran (14 ml) cooled in an ice bath under nitrogen was added diisopropyl-ethylamine (0.95 ml, 5.4 mmol) and the reaction mixture was stirred at ambient temperature for 3 hours. The volatiles were removed in vacuo and the residue was partitioned between dichloromethane (25 ml) and 1 N hydrochloric acid (25 ml). The layers were separated, and the aqueous layer extracted with dichloromethane (20 ml). The combined organic extracts were washed with a saturated sodium bicarbonate solution (50 ml), dried (MgSO$_4$), filtered and the solvent evaporated in vacuo. The residue was triturated with n-butylchloride, filtered and dried with nitrogen which afforded 0.47 g (61%) of 2-(1,3-dioxo-1,3-dihydro-isoindol-2-ylmethyl)-4-(2-spiro[1,3]dioxolane)-piperidine-1-carboxylic acid ethyl ester as an oil.

$^1$H-NMR (400 MHz, CDCl$_3$): δ7.9 (s, 2H), 7.7(s, 2H), 4.9–4.7 (bs, 1H), 4.7–4.5 (m, 1H), 4.3–3.9 (m, 5H), 3.9–3.6 (bs, 1H), 3.6–3.3 (m, 2H), 2.0–1.9 (m, 1H), 1.9–1.5 (m, 4H), 1.1–0.7 (bs, 3H).

MS: m/z: 373 [M−H]$^{31}$.

A solution of the above 2-(1,3-dioxo-1,3-dihydro-isoindol-2-ylmethyl)-4-(2-spiro[1,3]dioxolane)-piperidine-1-carboxylic acid ethyl ester (0.44 g, 1.2 mmol) in a mixture of 1 N hydrochloric acid (18 ml) and tetrahydrofuran (18 ml) was heated a 75° C. under nitrogen with stirring for 18 hours. The tetrahydrofuran was removed in vacuo and the residue was extracted with dichloromethane (2×75 ml). The combined organic extracts were washed with a saturated sodium bicarbonate solution (50 ml), dried (MgSO$_4$), filtered and the solvent removed in vacuo affording 0.42 g (>100%) of 2-(1,3-dioxo-1,3-dihydro-isoindol-2-ylmethyl)-4-oxo-piperidine-1-carboxylic acid ethyl ester as a solid.

$^1$H-NMR (400 MHz, CDCl$_3$): δ7.9 (s, 2H), 7.8 (s, 2H), 5.3–5.0 (bm, 1H), 4.6–4.2 (bm, 1H), 4.0 (m, 2H), 3.8–3.6 (bm, 3H), 2.8 (m, 1H), 2.7–2.4 (bm, 3H), 1.0 (bs, 3H).

MS: m/z: 330.6 [M+H]$^+$.

A mixture of the above 2-(1,3-dioxo-1,3-dihydro-isoindol-2-ylmethyl)-4-oxo-piperidine-1-carboxylic acid ethyl ester (0.39 g, 1.2 mmol), tert-butyl cyanoacetate (0.22 g, 1.55 mmol), sulfur (42 mg, 1.3 mmol) in ethanol (1.5 ml) was degassed. To this mixture, under nitrogen, morpholine (205 μl) was added and the mixture was heated a 50° C. for 13 hours. The solvent was removed in vacuo. The residue (0.74 g) was purified by silica gel chromatography using a mixture of hexane/ethyl acetate (7:3) as eluent. Pure fractions were collected and the solvent evaporated in vacuo. The residue (0.29 g) was titurated with acetonitrile, filtered, and dried with nitrogen affording 84 mg (15%) of 2-amino-5-(1,3-dioxo-1,3-dihydro-isoindol-2-ylmethyl)-4,5,6,7-tetrahydro-thieno[2,3-c]pyridine-3,6-dicarboxylic acid 3-tert-butyl ester 6-ethyl ester.

$^1$H-MNR (400 MHz, CDCl$_3$): δ7.9–7.7 (2m, 4H), 6.0 (bs, 2H), 5.1–4.8 (bm, 1H), 4.8–4.5 (m, 1H), 4.5–4.2 (m, 1H), 4.1–3.4 (3m, 4H), 3.0 (m, 2H), 1.8–1.4 (m, 10H), 1.1–0.9 (m, 3H).

MS: m/z: 486 [M+H]$^+$.

To the above 2-amino-5-(1,3-dioxo-1,3-dihydro-isoindol-2-ylmethyl)-4,5,6,7-tetrahydro-thieno[2,3-c]pyridine-3,6-dicarboxylic acid 3-tert-butyl ester 6-ethyl ester (48 mg, 0.1 mmol) dissolved in dry tetrahydrofuran (1 ml) was added imidazol-1-yl-oxo-acetic acid tert-butyl ester (0.4 ml) and the solution stirred for 18 hours at ambient temperature. The solvent was removed in vacuo and the residue was dissolved in dichloromethane (25 ml) and a saturated sodium bicarbonate solution (25 ml) was added. The layers were separated and the aqueous layer was extracted with dichloromethane (25 ml). The combined organic extracts were dried (Na$_2$SO$_4$), filtered and the solvent evaporated in vacuo. The residue (63 mg) was dissolved in ethyl acetate and passed through 1 g of silica gel and the solvent evaporated in vacuo affording 55 mg (90%) of 2-(tert-butoxyoxalyl-amino)-5-(1,3-dioxo-1,3-dihydro-isoindol-2-ylmethyl)-4,5,6,7-tetrahydro-thieno[2,3-c]pyridine-3,6-dicarboxylic acid 3-tert-butyl ester 6-ethyl ester as a solid.

The above 2-(tert-butoxyoxalyl-amino)-5-(1,3-dioxo-1,3-dihydro-isoindol-2-ylmethyl)-4,5,6,7-tetrahydro-thieno[2,3-c]pyridine-3,6-dicarboxylic acid 3-tert-butyl ester 6-ethyl ester (55 mg, 0.09 mmol) was dissolved in 50% trifluoroacetic acid in dichloromethane (2 ml) and stirred at ambient temperature for 18 hours. The volatiles were removed in vacuo and the residue was purified by preparative HPLC (column: Kromasil C18, 250×4.6 mm., flow: 2 ml/min., gradient: acetonitrile/water, 20% acetonitrile to 60% acetonitrile over 20 min.) affording after evaporation of the solvent in vacuo 13.8 mg (31%) of the title compound as a solid trifluoroacetate.

$^1$H-NMR (400 MHz, DMSO-d$_6$): δ14–13 (bs, 1H), 12.4 (s, 1H), 7.9 (s, 4H), 4.9 (m, 2H), 4.4 (m, 1H), 4.0–2.8 (m, 13H), 0.8 (m, 3H).

MS: m/z: 502 [M+H]+.

Example 2

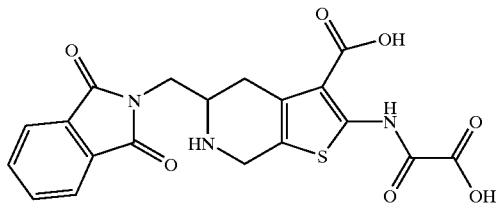

5-(1,3-Dioxo-1,3-dihydro-isoindol-2-ylmethyl)-2-(oxalyl-amino)-4,5,6,7-tetrahydro-thieno[2,3-c]pyridine-3-carboxylic acid 2-(1,3-Dioxo-1,3-dihydro-isoindol-2-ylmethyl)-4-(2-spiro[1,3]dioxolane)-piperidine-1-carboxylic acid tert-butyl ester (353 mg, 0.88 mmol) was cooled in an ice bath and then dissolved in a solution of 20% trifluoroacetic acid/dichloromethane (7 ml). The reaction was stirred for 5 minutes in the ice bath then another 3 hours at ambient temperature, after which it was concentrated in vacuo affording a solid residue. To the solid was added 2N hydrochloric acid (9 ml) and the mixture was heated at 50° C. (oil bath) with stirring for 24 hours. The cooled reaction mixture was quenched with saturated sodium bicarbonate solution until the pH was basic. The aqueous layer was extracted with chloroform (3×20 ml) and the combined organic extracts dried ($K_2CO_3$), filtered, and the solvent evaporated in vacuo to give 205 mg (91%) of 2-(4-oxo-piperidin-2-ylmethyl)-isoindole-1,3-dione as a solid.

$^1$H-NMR (400 MHz, $CDCl_3$): δ7.90–7.83 (m, 2H), 7.78–7.71 (m, 2H), 3.81–3.73 (m, 2H), 3.43–3.35 (m, 1H), 3.30–3.22 (m, 1H), 2.83 (dt, 1H, J=13 Hz and J=3 Hz), 2.46 (d, 1H, J=15 Hz), 2.42–2.32 (m, 2H), 2.21 (dd, 1H, J=14 Hz and J=13 Hz).

APCl-MS: m/z: 259 [M+H]+

The above 2-(4-oxo-piperidin-2-ylmethyl)-isoindole-1,3-dione (0.20 g, 0.76 mmol) was dissolved in dichloromethane (5 ml). Saturated sodium bicarbonate solution (5 ml) was added followed by di-tert-butyl dicarbonate (0.20 g, 0.91 mmol). The reaction was stirred vigorously for 16 hours after which the organic phase was separated. The aqueous layer was extracted with dichloromethane (2×10 ml) and the combined organic extracts were dried ($Na_2SO_4$), filtered, and the solvent evaporated in vacuo. The residue was purified by silica gel chromatography using a gradient of ethyl acetate/dichloromethane (0 to 10% gradient) as eluent. Pure fractions were collected and the solvent evaporated in vacuo affording 0.23 g (85%) of 2-(1,3-dioxo-1,3-dihydro-isoindol-2-ylmethyl)-4-oxo-piperidine-1-carboxylic acid tert-butyl ester.

$^1$H-NMR (400 MHz, $CDCl_3$): δ7.86 (bs, 2H), 7.72 (bs, 2H), 5.15–4.98 (m, 1H), 4.23–4.14 (m, 1H), 3.90 (t, 1H, J=12 Hz), 3.61–3.52 (m, 2H), 2.78–2.70 (m, 1H), 2.57–2.39 (m, 3H), 1.15 (s, 9H).

APCI-MS: m/z: 359 [M+H]+

The above 2-(1,3-dioxo-1,3-dihydro-isoindol-2-ylmethyl)-4-oxo-piperidine-1-carboxylic acid tert-butyl ester (0.43 g, 1.2 mmol) was dissolved in absolute ethanol (9 ml). To the solution was added sulfur (42 mg, 1.32 mmol) and tert-butyl cyanoacetate (0.22 g, 1.56 mmol). The mixture was placed under nitrogen and stirred in a 50° C. oil bath. Morpholin (0.21 ml, 2.4 mmol) was added and the reaction was stirred for 16 hours. The precipitate formed was filtered off and washed with acetonitrile (2×3 ml) and dried which afforded 0.18 g of 2-amino-5-(1,3-dioxo-1,3-dihydro-isoindol-2-ylmethyl)-4,5,6,7-tetrahydro-thieno[2,3-c]pyridine-3,6-dicarboxylic acid di-tert-butyl ester (A) (30%). The filtrate was concentrated in vacuo and the residue purified by silica gel chromatography using a gradient of ethyl acetate/hexane (1:4 to 1:3 gradient) as eluent. Pure fractions were collected and the solvent evaporated in vacuo affording 0.3 g of a mixture of 2-amino-5-(1,3-dioxo-1,3-dihydro-isoindol-2-ylmethyl)-4,5,6,7-tetrahydro-thieno[2,3-c]pyridine-3,6-dicarboxylic acid di-tert-butyl ester and 2-amino-7-(1,3-dioxo-1,3-dihydro-isoindol-2-ylmethyl)-4,5,6,7-tetrahydro-thieno[2,3-c]pyridine-3,6-dicarboxylic acid di-tert-butyl ester. HPLC purification of a small portion of the mixture gave 28 mg of pure 2-amino-7-(1,3-dioxo-1,3-dihydro-isoindol-2-ylmethyl)-4,5,6,7-tetrahydro-thieno[2,3-c]pyridine-3,6-dicarboxylic acid di-tert-butyl ester (B).

(A)
$^1$H-NMR (400 MHz, $CDCl_3$): δ7.87–7.82 (m, 2H) 7.73–7.66 (m, 2H), 6.00 (bs, 2H), 5.02–4.87 (m, 1H), 4.72–4.21 (m, 2H), 4.03–3.93 (m, 1H), 3.51 (t, 1H, J=14 Hz), 2.97–2.91 (m, 2H), 1.56 (s, 9H), 1.12–1.09 (s, 9H).

LC-MS: $R_t$=3.96 min, m/z: 514.4 [M+H]+

(B)
$^1$H-NMR (400 MHz, $CDCl_3$): δ7.88–7.82 (m, 2H), 7.74–7.66 (m, 2H), 5.39–5.19 (m, 1H), 4.30–4.02 (m, 2H), 3.78–3.70 (m, 1H), 3.33–3.18 (m, 1H), 2.86 (dd, 1H, J=18 Hz and J=4 Hz), 2.75–2.61 (m, 1H), 1.54 (s, 9H), 1.13–1.05 (s, 9H).

LC-MS: $R_t$=4.01 min, m/z: 514.4 [M+H]+

To a solution of the above 2-amino-5-(1,3-dioxo-1,3-dihydro-isoindol-2-ylmethyl)-4,5,6,7-tetrahydro-thieno[2,3-c]pyridine-3,6-dicarboxylic acid di-tert-butyl ester (50 mg, 0.097 mmol) in dichloromethane (3 ml) was added imidazol-1-yl-oxo-acetic acid tert-butyl ester (60 mg, 0.29 mmol). The reaction was placed under nitrogen and stirred for 3 hours at ambient temperature. The solution was concentrated in vacuo and the residue purified by silica gel chromatography using a 5% mixture of ethyl acetate/dichloromethane as eluent. Pure fractions were collected and the solvent evaporated in vacuo affording 54 mg (87%) of 2-(tert-butoxyoxalyl-amino)-5-(1,3-dioxo-1,3-dihydro-isoindol-2-ylmethyl)-4,5,6,7-tetrahydro-thieno[2,3-c]pyridine-3,6-dicarboxylic acid di-tert-butyl ester.

$^1$H-NMR (400 MHz, $CDCl_3$): δ12.52 (s, 1H), 7.85 (bs, 2H), 7.74–7.67 (m, 2H), 5.08–4.92 (m, 1H), 4.93–4.40 (m, 2H), 3.97–3.87 (m, 1H), 3.53 (t, 1H, J=14 Hz), 3.11–2.99 (m, 2H), 1.62 (s, 18H), 1.14–1.12 (2s, 9H).

APCI-MS: m/z: 641 [M−H]−

The above 2-(tert-butoxyoxalyl-amino)-5-(1,3-dioxo-1,3-dihydro-isoindol-2-ylmethyl)-4,5,6,7-tetrahydro-thieno[2,3-c]pyridine-3,6-dicarboxylic acid di-tert-butyl ester (54 mg, 0.084 mmol) was dissolved in a solution of 50% trifluoroacetic acid/dichloromethane (2 ml). The reaction was stirred at ambient temperature for 7 hours, concentrated in vacuo and the residue evaporated in vacuo from dichloromethane (3×10 ml). The resulting precipitate was washed with dichloromethane, filtered off and dried in vacuo, which afforded 41 mg (90%) of the title compound as a solid trifluoroacetate.

$^1$H-NMR (400 MHz, DMSO-$d_6$): δ12.31 (s, 1H), 9.36 (bs, 2H), 7.93–7.90 (m, 2H), 7.88–7.85 (m, 2H), 4.43 (d, 1H, J=16 Hz), 4.26 (d, 1H, J=16 Hz), 4.03–3.91 (m, 2H), 3.83–3.76 (m, 1H), 3.31 (dd, 1H, J=18 Hz and J=4 Hz), 2.82 (dd, 1H, J=18 Hz and J=10 Hz).

APCI-MS: m/z: 430 [M+H]$^+$
HPLC (254.4 nm): $R_t$=6.72 min, 98%

Example 3

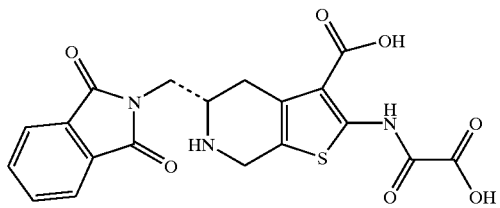

5-(S)-(1,3-Dioxo-1,3-dihydro-isoindol-2-ylmethyl)-
2-(oxalyl-amino)-4,5,6,7-tetrahydro-thieno[2,3-c]
pyridine-3-carboxylic acid To a solution of L-aspartic acid (120 g, 0.90 mol) in methanol (600 ml) cooled to −20° C. was added thionylchoride (93 ml, 1.29 mol) dropwise over 0.5 hour. The cooling bath was removed and the mixture was stirred for 1 hour, before diethyl ether (1.8 L, containing 50 ml 1 N hydrochloric acid in diethyl ether) was added upon cooling. The resulting precipitate was filtered off and washed with diethyl ether. The product was recrystallized twice: First recrystallization: The product was dissolved in warm methanol (600 ml) and reprecipitated with 1.8 ml diethyl ether (containing 50 ml 1 N hydrochloric acid in diethyl ether). Second recrystallization: The product was dissolved in warm methanol (250 ml) and reprecipitated with 1.0 m diethyl ether (containing 50 ml 1 N hydrochloric acid in diethyl ether).

This afforded 75 g (45%) of L-aspartic acid β-methyl ester hydrochloride as a solid.

To a solution of the above β-methyl ester (50 g, 0.27 mol) in water (120 ml) cooled to 0° C. was added triethylamine (95 ml, 0.68 mol) and methyl acrylate (74 ml, 0.82 mol). The reaction mixture was stirred for 3 hours before the cooling bath was removed. After stirring for an additional 1 hour the mixture was washed with petrol ether (2×400 ml), before tert-butanol (40 ml) and di-tert-butyl dicarbonate (74 g, 0.34 mol) was added and the reaction mixture was stirred for 16 hours. The mixture was washed with petrol ether (2×400 ml), cooled to 0° C. and the pH adjusted to 3 with concentrated hydrochloric acid. After extraction with ethyl acetate (3×200 ml) the organic phase was washed with brine (200 ml), dried (MgSO$_4$), filtered and the volatiles evaporated in vacuo. The residue was subjected to column chromatography on silicagel using a mixture of ethyl acetate/hexane/methanol/acetic acid (25:25:2.5:1) as eluent. Pure fractions were collected and the solvent evaporated in vacuo which afforded 60 g (66%) of 2-(tert-butoxycarbonyl-(2-methoxycarbonyl-ethyl)-amino)-succinic acid 4-methyl ester as a solid.

To a solution of the above di-ethyl ester (96.9 g, 0.29 mol) in dry degassed tetrahydrofuran (1.0 l) was added sodium methoxide (161 ml, 30% solution in methanol) and the reaction mixture was refluxed under nitrogen for 16 hours with mechanical stirring. The reaction mixture was cooled to room temperature; the volatiles remove in vacuo until a wet cage was observed. Water (500 ml) was added and the reaction mixture was refluxed for 16 hours. The remaining organic solvents were evaporated in vacuo before the pH was adjusted to 2.5 with concentrated hydrochloric acid. The aqueous phase was extracted with ethyl acetate (3×300 ml) and the combined organic phases were washed with brine (100 ml), dried (MgSO$_4$) and filtered. tert-Butyl amine (25.36 g, 0.350 mol) was added dropwise under stirring whereupon a off white precipitate was formed. The precipitate was filtered off and washed with ethyl acetate, dried in vacuo affording 74.4 g (81%) of 4-oxo-piperidine-1,2-dicarboxylic acid 1-tert-butyl ester, tert-butyl amine salt as a solid.

Analytically pure compound can be obtained from recrystallisation of the crude product from ethanol-diisopropyl ether by heating the compound in ethanol (ca 100 ml per 10 g compound) and while still hot diisopropyl ether is added (ca 250 ml per 10 g compound). Yield in recrystallisation is approximately 50%.

A solution of the above 4-oxo-piperidine-1,2-dicarboxylic acid 1-tert-butyl ester, tert-butyl amine salt (3.0 g, 9.48 mmol), tert-butyl cyanoacetate (2.01 g, 14.22 mmol), sulfur (0.46 g, 14.22 mmol) and diisopropyl-ethylamine (1.64 ml, 9.48 mmol) was heated to 50° C. under nitrogen for 12 hours. The solution was allowed to cool to room temperature before a small precipitate was filtered off. The filtrate was evaporated in vacuo and the residue was divided between ethyl acetate (50 ml) and saturated ammonium chloride (100 ml). The aqueous phase was extracted with ethyl acetate (3×50 m) and the combined organic phases were washed with brine (50 ml), dried (MgSO$_4$), filtered and the solvent evaporated in vacuo. The residue was subjected to column chromatography using a mixture of petrol ether/ethyl acetate/methanol (8:4:1) as eluent. Pure fractions were collected and the solvent evaporated in vacuo affording 2.22 g (58%) of 2-amino-4,5,6,7-tetrahydro-thieno[2,3-c]pyridine-3,5,6-tricarboxylic acid 3,6-di-tert-butyl ester as a solid.

To a solution of the above 3,5,6-tricarboxylic acid 3,6-di-tert-butyl ester (0.63 g, 1.58 mmol) in dimethoxyethane (10 ml) cooled to −20° C. was added N-methylmorpholine (174 ml, 1.58 mmol) followed by isobutylchoroformate (205 ml, 1.58 mmol) and the reaction mixture was stirred for two min. before a precipitate was filtered off. The precipitate was rapidly washed with dimethoxyethane (2×2.5 ml), recooled to −20° C. and a solution of sodium borohydride (90 mg, 2.37 mmol) in water (1 ml) was added in one lot to the filtrate. (Caution—gas evolution).

The reaction mixture was stirred until gas evolution ceases (app. 3 min.) and the mixture was poured into water (25 ml) and extracted with ethyl acetate (10 ml), washed with brine (5 ml), dried (MgSO$_4$), filtered and the solvent evaporated in vacuo affording 0.40 g (66% of 2-amino-5-(S)-hydroxymethyl-4,5,6,7-tetrahydro-thieno[2,3-c]pyridine-3,6-dicarboxylic acid di-tert-butyl ester as a solid.

To a mixture of the above 2-amino-5-(S)-hydroxymethyl-4,5,6,7-tetrahydro-thieno[2,3-c]pyridine-3,6-dicarboxylic acid di-tert-butyl ester (2.00 g, 5.20 mmol), phthalimide (0.92 g, 6.24 mmol) and triphenylphosphine (1.64 g, 6.24 mmol) in dry tetrahydrofuran (30 ml) cooled to 0° C. under a nitrogen atmosphere was added diethyl azodicarboxylate (DEAD) (0.98 ml, 6.24 mmol). The reaction mixture was allowed to stir overnight, slowly warming to room temperature. Next day the reaction mixture was again cooled to 0° C. and phthalimide (0.46 g, 3.12 mmol), triphenylphosphine (0.82 g, 3.12 mmol) and diethyl azodicarboxylate (DEAD) (0.49 ml, 3.12 mmol) was added in sequence and the reaction mixture was allowed to stir overnight, slowly warming to room temperature. The volatiles were evaporated in vacuo and the resultant solid dissolved in dichloromethane (20 ml). The residue was subjected to flash column chromatography using a mixture of ethyl acetate/ hexane (1:2) as eluent. Fractions were collected affording after evaporation in vacuo 1.0 g of the desired compound contaminated with phthalimide. Recrystallization from ethanol gave 0.23 g (9%) of pure 2-amino-5-(S)-(1,3-dioxo-1,3-dihydro-isoindol-2-ylmethyl)-4,5,6,7-tetrahydro-thieno[2,3-c]pyridine-3,6-dicarboxylic acid di-tert-butyl ester as a solid.

To the above di-tert-butyl ester (0.20 g, 0.39 mmol) dissolved in dichloromethane (4 ml) was added a mixture of imidazol-1-yl-oxo-acetic acid tert butyl ester (0.23 g, 1.17 mmol) in dichloromethane (1 ml) under nitrogen. The reaction mixture was allowed to stir at room temperature overnight. The reaction mixture was added dichloromethane (5 ml) and washed with 1% hydrochloric acid (10 ml), dried ($Na_2SO_4$), filtered and the organic phase evaporated in vacuo affording 0.25 g (100%) of 2-(tert-butoxyoxalyl-amino)-5-(S)-(1,3-dioxo-1,3-dihydro-isoindol-2-ylmethyl)-4,5,6,7-tetrahydro-thieno[2,3-c]pyridine-3,6-dicarboxylic acid di-tert-butyl ester.

The above tri-tert-butyl ester (0.25 g, 0.39 mmol) was dissolved in 20% trifluoroacetic acid in dichloromethane (5 ml). The reaction was stirred at room temperature for 24 hours before diethyl ether (5 ml) was added. The precipitate was filtered off, washed with diethyl ether, dried in vacuo to give 150 mg of a solid. NMR revealed the presence of a trace amount of material arising from incomplete deprotection. 100 mg of the crude product was redissolved in 20% trifluoroacetic acid in dichloromethane (5 ml), and stirred at room temperature for 24 hours before diethyl ether (5 ml) was added. The product was filtered off and washed with diethyl ether and dried in vacuo to give 50 mg (40%) of the title compound as a solid trifluoroacetate.

M.p.: dec.>240° C. Calculated for $C_{19}H_{15}N_3O_7S$, 1/3× $C_2HF_3O_2$, 0.5×$H_2O$: C, 49.58%; H, 3.46%; N, 8.82%. Found: C, 49.84%; H, 3.83%; N, 8.99%.

Example 4

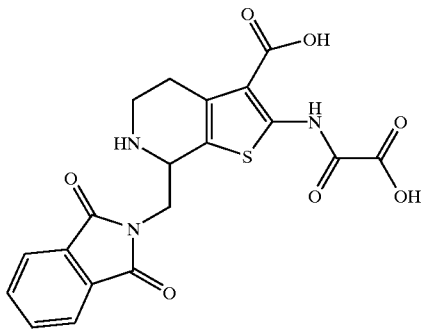

7-(1,3-Dioxo-1,3-dihydro-isoindol-2-ylmethyl)-2-(oxalyl-amino)-4,5,6,7-tetrahydro-thieno[2,3-c]pyridine-3-carboxylic acid To a solution of pure 2-amino-7-(1,3-dioxo-1,3-dihydro-isoindol-2-ylmethyl)-4,5,6,7-tetrahydro-thieno[2,3-c]pyridine-3,6-dicarboxylic acid di-tert-butyl ester (28 mg, 0.057 mmol) in dichloromethane (2 ml) was added midazol-1-yl-oxo-acetic acid tert-butyl ester (35 mg, 0.17 mmol). The reaction was placed under nitrogen and stirred for 12 hours at ambient temperature. The volatiles were evaporated in vacuo and the residue was purified by silica gel chromatography using a mixture of ethyl acetate/hexane (1:3) as eluent. Pure fractions were collected and the solvent evaporated in vacuo affording 25 mg (67%) of 2-(tert-butoxyoxalyl-amino)-7-(1,3-dioxo-1,3-dihydro-isoindol-2-ylmethyl)-4,5,6,7-tetrahydro-thieno[2,3c]pyridine-3,6-dicarboxylic acid di-tert-butyl ester as an oil.

$^1$H-NMR (400 MHz, CDCl$_3$): δ12.59–12.53 (bs, 1H), 7.89–7.84 (m, 2H), 7.75–7.67 (m, 2H), 5.61–5.41 (m, 1H), 4.36–4.15 (m, 1H), 4.12–4.06 (m, 1H), 3.90–3.82 (m, 1H), 3.34–3.21 (m, 1H), 2.99–2.93 (m, 1H), 2.84–2.68 (m, 1H), 1.62–1.59 (s, 18H), 1.12–1.06 (s, 9H).

The above 2-(tert-butoxyoxalyl-amino)-7-(1,3-dioxo-1,3-dihydro-isoindol-2-ylmethyl)-4,5,6,7-tetrahydro-thieno[2,3-c]pyridine-3,6-dicarboxylic acid di-tert-butyl ester (25 mg, 0.039 mmol) was dissolved in a solution of 50% trifluoroacetic acid/dichloromethane (1.5 ml). The reaction was stirred at ambient temperature for 7 hours, concentrated in vacuo and the residue evaporated in vacuo from dichloromethane (3×10 ml). The resulting precipitate was washed with dichloromethane, filtered off and dried in vacuo to give 41 mg (85%) of the title compound as a solid trifluoroacetate.

$^1$H-NMR (400 MHz, DMSO-d$_6$): δ12.32 (s, 1H), 9.48 (bs, 2H), 7.95–7.91 (m, 2H), 7.89–7.84 (m, 2H), 4.89 (s, 1H), 4.15–4.07 (m, 2H), 3.43–3.28 (2m, 2H, partially obsured by water), 3.04 (bs, 2H).

LC-MS: R$_t$=1.51 min, m/z: 428.4 [M–H]$^-$

Example 5

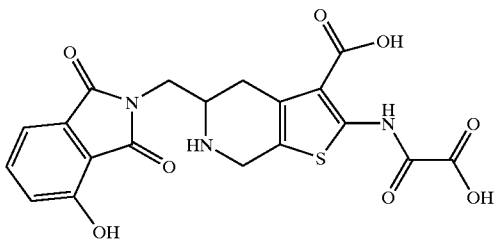

5-(4-Hydroxy-1,3-dioxo-1,3-dihydro-isoindol-2-ylmethyl)-2-(oxalyl-amino)-4,5,6,7-tetrahydro-thieno[2,3-c]pyridine-3-carboxylic acid 7-(1,3-Dioxo-1,3-dihydro-isoindol-2-ylmethyl)-1,4-dioxa-8-aza-spiro[4.5]decane-8-carboxylic acid tert-butyl ester (1.55 g, 3.85 mmol) was cooled in an ice bath and then dissolved in a solution of 20% trifluoroacetic acid/dichloromethane (15 ml). The reaction was stirred and allowed to slowly warm to ambient temperature during 3 hours. The solution was concentrated in vacuo to give crude 2-(1,4-dioxa-8-aza-spiro[4.5]dec-7-ylmethyl)isoindole-1,3-dione which was used directly in the following step (assumed 100% yield).

$^1$H-NMR (400 MHz, CDCl$_3$): δ9.26 (bs, 1H), 8.19 (bs, 1H), 7.78–7.75 (m, 2H), 7.74–7.71 (m, 2H), 4.11–3.98 (m, 5H), 3.90–3.79 (m, 3H), 3.26–3.17 (m, 1H), 2.10–2.00 (m, 3H), 1.92–1.88 (m, 1H).

To a suspension of the above 2-(1,4-dioxa-8-aza-spiro[4.5]dec-7-ylmethyl)isoindole-1,3-dione (3.85 mmol) in absolute ethanol (25 ml) was added hydrazine (0.36 ml, 11.55 mmol). The reaction was stirred at 80° C. (oil bath) for 6 hours, then cooled to ambient temperature and stirred for an additional 12 hours. The thick precipitate was filtered off and washed with ethanol. The filtrate was concentrated in vacuo and reconstituted in dichloromethane (20 ml), forming a small amount of a second precipitate, which was filtered off. The filtrate was evaporated in vacuo and the resulting oil was dissolved in water (10 ml) and basified with 1 N sodium hydroxide until pH=10. The aqueous layer was extracted with 20% isopropyl alcohol/chloroform (12×40 ml). The combined organic extracts were dried ($K_2CO_3$), filtered and the solvent evaporated in vacuo affording 0.42 g (63%) of (1,4-dioxa-8-aza-spiro[4.5]dec-7-yl) methylamine as an oil.

$^1$H-NMR (300 MHz, CDCl$_3$): δ3.94 (bs, 4H), 3.11–3.05 (m, 1H), 2.81 (dt, 1H, J=12 Hz and J=3 Hz), 2.76–2.65 (m, 2H), 2.58–2.50 (m, 1H), 1.70–1.57 (m, 3H), 1.31 (t, 1H, J=12 Hz).

APCI-MS: m/z: 173.2 [M+H]$^+$

To a solution of 4-hydroxy-isobenzofuran-1,3-dione (0.51 g, 3.09 mmol) in anhydrous N,N-dimethylformamide (7 ml) under nitrogen was added sodium hydride (130 mg, 3.25 mmol). Immediate evolution of gas and bright yellow color was observed. The mixture was stirred for 5 minutes after which benzyl bromide (1.8 ml, 15.45 mmol) was added. The reaction was stirred for 72 hours. Saturated sodium bicarbonate (2 ml) was added and the mixture stirred for 2 minutes, diluted in ethyl acetate (35 ml) and washed with saturated sodium bicarbonate (5 ml), 1N hydrochloric acid (5 ml), and brine (2×5 ml). The organic layer was dried (MgSO$_4$), filtered and the solvent evaporated in vacuo. To the crude material was added hexane and the formed precipitate was filtered off, washed further with hexane and dried in vacuo to give 0.54 g (69%) of 4-(benzyloxy)-isobenzofuran-1,3-dione as a solid.

$^1$H-NMR (300 MHz, CDCl$_3$): δ7.74 (t, 1H, J=8 Hz), 7.54 (d, 1H, J=8 Hz), 7.47–7.29 (m, 6H), 5.36 (s, 2H).

A solution of (1,4-dioxa-8-aza-spiro[4.5]dec-7-yl) methylamine (0.19 g, 1.1 mmol) and 4-(benzyloxy)-isobenzofuran-1,3-dione (0.27 g, 1.05 mmol) was prepared in a mixture of distilled dichloromethane (3 ml) and anhydrous N,N-dimethylformamide (2.5 ml) under nitrogen. 1-(3-dimethylaminopropyl)-3-ethylcarbodiimide hydrochloride (0.23 g, 1.21 mmol) was added followed by triethylamine (0.46 ml, 3.3 mmol) and the reaction stirred at ambient temperature for 18 hours. The solution was concentrated in vacuo and the residue diluted with ethyl acetate (25 ml) and washed with water (5 ml), saturated sodium bicarbonate (5 ml), and brine (5 ml). The organic layer was evaporated in vacuo and the residue purified by silica gel chromatography using a mixture of 5% methanol/dichloromethane/1% triethylamine as eluent. Pure fractions were collected and the solvent evaporated in vacuo affording 0.22 g (50%) of 4-benzyloxy-2-(1,4-dioxa-8-aza-spiro[4.5] dec-7-ylmethyl)-isoindole-1,3-dione as a semi-solid.

$^1$H-NMR (400 MHz, CDCl$_3$): δ7.57 (t, 1H, J=8 Hz), 7.48 (d, 2H, J=7 Hz), 7.42–7.29 (m, 4H), 7.18 (d, 1H, J=8 Hz), 5.31 (s, 2H), 3.94–3.90 (m, 4H), 3.65 (d, 2H, J=6 Hz) 3.16–3.09 (m, 1H), 3.07–3.02 (m, 1H), 2.76 (dt, 1H, J=13 Hz and J=3 Hz), 1.78 (d, 1H, J=12 Hz), 1.64–1.54 (m, 3H), 1.37 (t, 1H, J=12 Hz), 1.08 (t, 1H, J=7 Hz).

LC-MS: R$_t$=2.59 min, m/z: 409 [M+H]$^+$

To a solution of the above 4-benzyloxy-2-(1,4-dioxa-8-aza-spiro[4.5]dec-7-ylmethyl)-isoindole-1,3-dione (0.22 g, 0.54 mmol) in 1,4-dioxane (4 ml) was added 4N hydrochloric acid (4 ml) and the reaction stirred in a 65° C. (oil bath) for 6 hours. The mixture was basified with saturated sodium bicarbonate until pH=8 and extracted with dichloromethane (3×20 ml). The combined organic extracts were dried (MgSO$_4$), filtered, and the solvent evaporated in vacuo affording crude 4-benzyloxy-2-(4-oxo-piperidin-2-ylmethyl)-isoindole-1,3-dione as an oil. Which was used without further purification or characterization.

The above crude 4-benzyloxy-2-(4-oxo-piperidin-2-ylmethyl)-isoindole-1,3-dione (0.17 g, 0.47 mmol) was dissolved in dichloromethane (4 ml). Saturated sodium bicarbonate (4 ml) was added followed by di-tert-butyl dicarbonate (0.11 g, 0.52 mmol). The reaction was stirred vigorously for 16 hours, and then the layers were separated. The aqueous layer was extracted with dichloromethane (2×10 ml) and the combined organic phases were dried (MgSO$_4$), filtered and the solvent evaporated in vacuo. The residue was purified by silica gel chromatography using a mixture of ethyl acetate/hexane (1:2) as eluent. Pure fractions were collected and the solvent was evaporated in vacuo affording 0.14 g (64%) of 2-(4-benzyloxy-1,3-dioxo-1,3-dihydro-isoindol-2-ylmethyl)-4-oxo-piperidine-1-carboxylic acid tert-butyl ester.

$^1$H-NMR (400 MHz, CDCl$_3$): δ7.57 (bs, 1H), 7.47–7.31 (m, 6H), 7.18 (bs, 1H), 534 (s, 2H). 5.03 (bs, 1H), 4.45–4.14 (m, 1H), 3.89 (t, 1H, J=12 Hz), 3.55 (bs, 2H), 2.76–2.71 (m, 1), 2.57–2.38 (m, 3H), 1.17 (s, 9H).

A solution of 2-(4-benzyloxy-1,3-dioxo-1,3-dihydro-isoindol-2-ylmethyl)-4-oxo-piperidine-1-carboxylic acid tert-butyl ester (0.14 g, 0.30 mmol), sulfur (10.6 mg, 0.33 mmol), and tert-butyl cyanoacetate (55 mg, 0.39 mmol) in absolute ethanol (4 ml) was stirred at 50° C. (oil bath). Morpholine (53 μl, 0.6 mmol) was added and the reaction placed under nitrogen and stirred for 16 hours. The solution was cooled to ambient temperature, concentrated in vacuo and the residue purified by silica gel chromatography using a gradient of ethyl acetate/dichloromethane (0 to 5% gradient) as eluent. Pure fractions were collected and the solvent evaporated in vacuo affording a mixture of regioisomers 0.15 g (80%) of 2-amino-5-(4-benzyloxy-1,3-dioxo-1,3-dihydro-isoindol-2-ylmethyl)-4,5,6,7-tetrahydro-thieno[2,3-c]pyridine-3,6-dicarboxylic acid di-tert-butyl ester and 2-amino-7-(4-benzyloxy-1,3-dioxo-1,3-dihydro-isoindol-2-ylmethyl)-4,5,6,7-tetrahydro-thieno[2,3-c]pyridine-3,6-dicarboxylic acid di-tert-butyl ester which were not separable by chromatography.

To a solution of the above mixture of 2-amino-5-(4-benzyloxy-1,3-dioxo-1,3-dihydro-isoindol-2-ylmethyl)-4,5,6,7-tetrahydro-thieno[2,3-c]pyridine-3,6-dicarboxylic acid di-tert-butyl ester and 2-amino-7-(4-benzyloxy-1,3-dioxo-1,3-dihydro-isoindol-2-ylmethyl)-4,5,6,7-tetrahydro-thieno[2,3-c]pyridine-3,6-dicarboxylic acid di-tert-butyl ester (0.15 g, 0.24 mmol) in distilled dichloromethane (4 ml) under nitrogen was added imidazol-1-yl-oxo-acetic acid tert-butyl ester (0.14 g, 0.72 mmol) and the reaction mixture was stirred at ambient temperature for 1.5 hour. The volatiles were evaporated in vacuo and the crude residue was purified by silica gel chromatography using dichloromethane as eluent. Pure fractions were collected and the solvent evaporated in vacuo affording 50 mg of 2-(tert-butoxyoxalyl-amino)-5-(4-benzyloxy-1,3-dioxo-1,3-dihydro-isoindol-2-ylmethyl)-4,5,6,7-tetrahydro-thieno[2,3-c]pyridine-3,6-dicarboxylic acid di-tert-butyl ester (A) and 50 mg of 2-(tert-butoxyoxalyl-amino)-7-(4-benzyloxy-1,3-dioxo-1,3-dihydro-isoindol-2-ylmethyl)-4,5,6,7-tetrahydro-thieno[2,3-c]pyridine-3,6-dicarboxylic acid di-tert-butyl ester (B). Another 50 mg remained as a mixture of the two isomers (A) and (B).

(A)

$^1$H-NMR (300 MHz, CDCl$_3$): δ12.52 (s, 1H), 7.60–7.31 (m, 7H), 7.20–7.10 (m, 1H), 5.33 (s, 2H), 5.05–4.38 (m, 3H), 3.96–3.83 (m, 1H), 3.52–3.41 (m, 1H), 3.01 (bs, 2H), 1.60 (s, 9H), 1.59 (s, 9H), 1.17–1.14 (s, 9H).

LC-MS: R$_t$=4.93 min, m/z: 748.1 [M+H]$^+$ (B)

¹H-NMR (300 MHz, CDCl₃): δ12.58–12.52 (s, 1H), 7.60–7.30 (m, 7H), 7.20–7.10 (m, 1H), 5.60–5.39 (m, 1H), 5.34 (s, 2H), 4.36–4.02 (m, 2H), 3.86–3.75 (m, 1H), 3.33–3.18 (m, 1H), 2.97–2.90 (m, 1H), 2.83–2.68 (m, 1H), 1.60 (s, 9H), 1.58–1.57 (s, 9H), 1.15–1.09 (s, 9H)

LC-MS: $R_t$=4.93 min, m/z: 748.1 [M+H]⁺

The above 2-(tert-butoxyoxalyl-amino)-5-(4-benzyloxy-1,3-dioxo-1,3-dihydro-isoindol-2-ylmethyl)-4,5,6,7-tetrahydro-thieno[2,3-c]pyridine-3,6-dicarboxylic acid di-tert-butyl ester (50 mg, 0.067 mmol) was dissolved in a mixture of ethyl acetate/ethanol (3 ml, 1:1). Palladium on activated carbon (10%, 10 mg) was added and the solution degassed and stirred under hydrogen (1 atm.) for 72 hours. TLC analysis indicated that the reaction was incomplete. The mixture was filtered through celite and the filter cake washed with hot ethyl acetate. The filtrate was concentrated in vacuo and purified by silica gel chromatography using a gradient of ethyl acetate/dichloromethane (0 to 5% gradient) as eluent. Pure fractions were collected and the solvent evaporated in vacuo affording 15 mg (30%) of 2-(tert-butoxyoxalyl-amino)-5-(4-hydroxy-1,3-dioxo-1,3-dihydro-isoindol-2-ylmethyl)-4,5,6,7-tetrahydro-thieno[2,3-c]pyridine-3,6-dicarboxylic acid di-tert-butyl ester.

¹H-NMR (300 MHz, CDCl₃): δ12.50 (s, 1H), 7.61–7.51 (m, 1H), 7.39–7.34 (m, 1H), 7.17–7.09 (m, 1H), 5.04–4.64 (m, 2H), 4.49–4.34 (m, 1H), 3.90–3.78 (m, 1H), 3.51–3.42 (m, 1H), 3.02 (bs, 2H), 1.60 (s, 18H), 1.17–1.14 (2s, 9H).

The above 2-(tert-butoxyoxalyl-amino)-5-(4-hydroxy-1,3-dioxo-1,3-dihydro-isoindol-2-ylmethyl)-4,5,6,7-tetrahydro-thieno[2,3-c]pyridine-3,6-dicarboxylic acid di-tert-butyl ester (15 mg, 0.023 mmol) was dissolved in a solution of 50% trifluoroacetic acid/dichloromethane (2 ml). The reaction was stirred at ambient temperature for 12 hours, concentrated in vacuo and evaporated in vacuo from dichloromethane (3×10 ml). The resulting precipitate was washed with dichloromethane and dried in vacuo affording 6 mg (47%) of the title compound as a solid trifluoroacetate.

¹H-NMR (400 MHz, DMSO-d₆): δ12.32 (s, 1H), 11.17 (s, 1H), 9.25 (bs, 2H), 7.64 (t, 1H, J=8 Hz), 7.32 (d, 1H, J=8 Hz), 7.24 (d, 1H, J=8 Hz), 4.41–4.23 (m, 2H), 3.96–3.71 (m, 3H), 3.5–3.2 (obscured by water, 1H), 2.83–2.75 (m, 1H).

LC-MS: $R_t$=1.53 min, m/z: 446.2 [M+H]⁺

Example 6

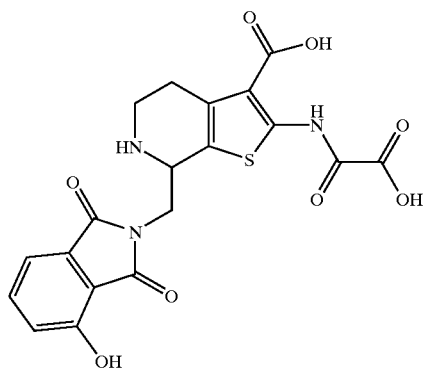

7-(4-Hydroxy-1,3-dioxo-1,3-dihydro-isoindol-2-ylmethyl)-2-(oxalyl-amino)-4,5,6,7-tetrahydro-thieno[2,3-c]pyridine-3-carboxylic acid 2-(tert-Butoxyoxalyl-amino)-7-(4-benzyloxy-1,3-dioxo-1,3-dihydro-isoindol-2-ylmethyl)-4,5,6,7-tetrahydro-thieno[2,3-c]pyridine-3,6-dicarboxylic acid di-tert-butyl ester (50 mg, 0.067 mmol) was dissolved in a mixture of ethyl acetate/ethanol (3 mL, 1:1). Palladium on activated carbon (10%, 10 mg) was added and the solution degassed and stirred under hydrogen (1 atm) for 72 hours. The mixture was filtered through celite and the filter cake washed with hot ethyl acetate. The filtrate was concentrated in vacuo and the residue purified by silica gel chromatography (10% ethyl acetate/dichloromethane) to obtain 42 mg (95%) of 2-(tert-butoxyoxalyl-amino)-7-(4-hydroxy-1,3-dioxo-1,3-dihydro-isoindol-2-ylmethyl)-4,5,6,7-tetrahydro-thieno[2,3-c]pyridine-3,6-dicarboxylic acid di-tert-butyl ester as an oil.

¹H-NMR (400 MHz, CDCl₃) δ12.59–12.53 (2s, 1H), 7.64–7.53 (m, 1H), 7.42–7.36 (m, 1H), 7.19–7.11 (m, 1H), 5.58–5.37 (m, 1H), 4.37–4.00 (m, 2H), 3.86–3.78 (m, 1H), 3.32–3.18 (m, 1H), 2.99–2.94 (m, 1H), 2.84–2.69 (m, 1H), 1.62–1.59 (3s, 18H), 1.17–1.11 (2s, 9);

LC-MS: $R_t$=4.55 min, m/z: 658 [M+H]⁺, 2-(tert-Butoxyoxalyl-amino)-7-(4-hydroxy-1,3-dihydro-isoindol-2-ylmethyl)-4,5,6,7-tetrahydro-thieno[2,3-c]pyridine-3,6-dicarboxylic acid di-tert-butyl ester (42 mg, 0.064 mmol) was dissolved in a solution of 50% trifluoroacetic acid/methylene chloride (3 mL). The reaction was stirred at ambient temperature for 7 hours, concentrated in vacuo and evaporated from dichloromethane (10 ml) three times. The resulting precipitate was washed with dichloromethane and dried in vacuo to give 29 mg (81%) of the title compound as a solid trifluoroacetate.

¹H-NMR (400 MHz, DMSO-d₆) δ12.32 (bs, 1H), 11.26 (s, 1H), 9.30 (bs, 2H), 7.64 (t, 1H, J=7 Hz), 7.33 (d, 1H, J=7 Hz), 7.25 (d, 1H, J=7 Hz), 4.84 (s, 1H), 4.06–3.96 (m, 2H), 3.56 (m, 2H), 3.05 (bs, 2H),

LC-MS: $R_t$=1.26 min, m/z: 446 [M+H]⁺,

Example 7

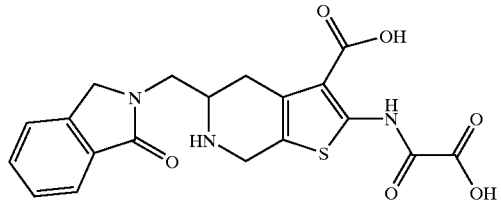

2-(Oxalyl-amino)-5-(S)-(1-oxo-1,3-dihydro-isoindol-2-ylmethyl)-4,5,6,7-tetrahydro-thieno[2,3-c]pyridine-3-carboxylic acid 2-Methyl-benzoic acid methyl ester (1.50 g 10 mmol), N-bromo-succinimide (1.96 g, 11 mmol) and 2,2'-azobis(2-methyl-propionitrile) (AIBN) (25 mg, 0.15 mmol) were dissolved in chloroform (3 ml). The solution was heated at reflux for 16 hours cooled and the solvent evaporated in vacuo. The residue was purified by silica gel chromatography using a gradient of ethyl acetate/hexane (1–2%) as eluent. Pure fractions were collected and the solvent evaporated in vacuo affording 2.05 g (89%) of 2-bromomethyl-benzoic acid methyl ester as a solid.

¹H-NMR (CDCl₃): δ7.97 (d, 1H, J=7.6 Hz), 7.45–7.52 (m, 2H), 7.38 (dt, 1H, J=1.2 Hz and J=7.6 Hz), 4.96 (s, 2H), 3.95 (s, 1H).

To a solution of 2-amino-5-(S)-(1,3-dioxo-1,3-dihydro-isoindol-2-ylmethyl)-4,5,6,7-tetrahydro-thieno[2,3-c]pyridine-3,6-dicarboxylic acid di-tert-butyl ester (100 mg, 0.20 mmol) and pyridine (0.18 ml, 2.0 mmol) in acetonitrile (1 ml) at room temperature was added benzyl chloroformate (0.28 ml, 2.0 mmol) in 10 aliquots over 48 hours. The solution was then taken into ethyl acetate (30 ml), washed with 0.5 N hydrochloric acid (3×10 ml), saturated sodium bicarbonate (3×10 ml), brine (10 ml), dried (MgSO$_4$) and filtered. The solvent was evaporated in vacuo. The resulting oil crystallized upon standing for 2 days. The precipitate was filtered off and washed with diethyl ether (3×1 ml) affording after drying in vacuo 59 mg (47%) of 2-benzyloxy-carbonylamino-5-(S)-(1,3-dioxo-1,3-dihydro-isoindol-2-ylmethyl)-4,5,6,7-tetrahydro-thieno[2,3-c]pyridine-3,6-dicarboxylic acid di-tert-butyl ester as a solid.

$^1$H-NMR (CDCl$_3$): δ10.60 (s, 1H), 7.60–7.92 (m, 4H), 7.38 (m, 5H), 5.26 (s, 2H), 4.30–5.10 (m, 3H), 3.40–4.00 (m, 2H), 1.57 (m, 9H), 1.15 (m, 9H).

To a solution of 1 N hydrochloric acid in ethyl acetate (1.0 ml) was added 2-benzyloxy-carbonylamino-5-(S)-(1,3-dioxo-1,3-dihydro-isoindol-2-ylmethyl)-4,5,6,7-tetrahydro-thieno[2,3-c]pyridine-3,6-dicarboxylic acid di-tert-butyl ester (52 mg, 0.08 mmol). The solution was stirred at room temperature for 48 hours. A precipitate was filtered off which afforded 42 mg (90%) of 2-benzyloxy-carbonylamino-5-(S)-(1,3-dioxo-1,3-dihydro-isoindol-2-ylmethyl)-4,5,6,7-tetrahydro-thieno[2,3-c]pyridine-3-carboxylic acid tert-butyl ester hydrochloride as a solid.

$^1$H-NMR (DMSO-d$_6$): δ10.45 (s, 1H), 9.40 (s, 1H), 9.25 (s, 1H), 7.89 (m, 4H), 7.39 (m, 5H), 5.22 (s, 2H), 4.39 (d, 1H, J=15 Hz), 4.28 (m, 1H), 3.95 (m, 2H), 3.79 (m, 1H), 3.20 (m, 1H), 2.70 (m, 1H), 1.48 (s, 9H).

To a solution of the above 2-benzyloxy-carbonylamino-5-(S)-(1,3-dioxo-1,3-dihydro-isoindol-2-ylmethyl)-4,5,6,7-tetrahydro-thieno[2,3-c]pyridine-3-carboxylic acid tert-butyl ester hydrochloride (42 mg, 0.072 mmol) in ethanol (0.5 ml) was added hydrazine (68 μl, 0.22 mmol). The solution was stirred at 80° C. for 5 hours and at room temperature for 16 hours. The mixture was filtered and the filtrate evaporated in vacuo. The residue was extracted with dichloromethane (5×1 ml). The combined dichloromethane washes were evaporated in vacuo affording 20 mg (67%) of 5-(S)-aminomethyl-2-benzyloxy-carbonylamino-4,5,6,7-tetrahydro-thieno[2,3-c]pyridine-3-carboxylic acid tert-butyl ester as an oil.

$^1$H-NMR (CDCl$_3$): δ10.55 (bs, 1H), 7.37 (m, 5H), 5.23 (s, 2H), 3.92 (s, 2H), 2.60–3.10 (m, 3H), 1.53 (s, 9H).

To a solution of the above 5-(S)-aminomethyl-2-benzyloxy-carbonylamino-4,5,6,7-tetrahydro-thieno[2,3-c]pyridine-3-carboxylic acid tert-butyl ester (20 mg, 0.048 mmol) in acetonitrile (1 ml) at 0° C. was added diisopropylethylamine (18 1, 0.15 mmol) and 2-bromomethyl-benzoic acid methyl (12 mg, 0.048 mmol). The solution was stirred at 0° C. for 3 hours and at room temperature for 16 hours. Di-tert-butyl dicarbonate (21 mg, 0.096 mmol) was then added to the solution. The solution was then stirred at room temperature for 16 hours. The solution was taken into ethyl acetate (30 ml), washed with 0.5 N hydrochloric acid (3×10 ml), saturated sodium bicarbonate (3×10 ml) and brine (10 ml), dried (MgSO$_4$) and filtered. The solvent was evaporated in vacuo. The solid residue was purified by silica gel chromatography using a 5% mixture of ethyl acetate/hexane as eluent. Pure fractions were collected and the solvent evaporated in vacuo affording 10 mg (33%) of 2-(benzyloxy-carbonylamino)-5-(S)-(1-oxo-1,3-dihydro-isoindol-2-ylmethyl)-4,5,6,7-tetrahydro-thieno[2,3-c]pyridine-3,6-dicarboxylic acid di-tert-butyl ester as a solid.

$^1$H-NMR (CDCl$_3$): δ10.59 (s, 1H), 7.81 (m, 1H), 7.52 (m, 1H), 7.39 (m, 7H), 5.25 (s, 2H), 4.22–5.00 (m, 4H), 4.40–4.80 (m, 2H), 2.80–3.10 (m, 2H), 1.55 (s, 9H), 1.25 (s, 9H).

To a solution of the above 2-benzyloxycarbonylamino-5-(S)-(1-oxo-1,3-dihydro-isoindol-2-ylmethyl)-4,5,6,7-tetrahydro-thieno[2,3-c]pyridine-3,6-dicarboxylic acid di-tert-butyl ester (9 mg, 0.014 mmol) in methanol (2 ml) was added 10% Pd/C (4 mg). The mixture was stirred under hydrogen (1 atm.) for 3 hours and then filtered. The filtrate was evaporated in vacuo affording 6 mg (93%) of 2-amino-5-(S)-(1-oxo-1,3-dihydro-isoindol-2-ylmethyl)-4,5,6,7-tetrahydro-thieno[2,3-c]pyridine-3,6-dicarboxylic acid di-tert-butyl ester as a solid.

$^1$H-NMR (CDCl$_3$): δ7.80 (m, 1H), 7.50 (m, 1H), 7.44 (m, 2H), 4.22–5.00 (m, 4H), 4.40–4.80 (m, 2H), 2.80–3.10 (m, 2H), 1.63 (s, 9H), 1.25 (s, 9H).

To a solution of the above 2-amino-5-(S)-(1-oxo-1,3-dihydro-isoindol-2-ylmethyl)-4,5,6,7-tetrahydro-thieno[2,3-c]pyridine-3,6-dicarboxylic acid di-tert-butyl ester (6 mg, 0.013 mmol) in acetonitrile (0.5 ml) at room temperature was added imidazol-1-yl-oxo-acetic acid tert-butyl ester (27 mg, 0.13 mmol). The solution was stirred for 3 hours at room temperature and then diluted with ethyl acetate (20 ml). washed with 0.5 N hydrochloric acid (2×5 ml), saturated sodium bicarbonate (2×5 ml), brine (5 ml), dried (MgSO$_4$) and filtered. The solvent was evaporated in vacuo. The residue was purified by silica gel chromatography using a gradient of ethyl acetate/hexane (10–25% gradient) as eluent. Pure fractions were collected and the solvent evaporated in vacuo affording 4 mg (50%) of 2-(tert-butoxyoxalyl-amino)-5-(S)-(1-oxo-1,3-dihydro-isoindol-2-ylmethyl)-4,5,6,7-tetrahydro-thieno[2,3-c]pyridine-3,6-dicarboxylic acid di-tert-butyl ester as a solid.

$^1$H-NMR (CDCl$_3$): δ12.49 (s, 1H), 7.80 (m, 1H), 7.50 (m, 1H), 7.44 (m, 2H), 4.22–5.00 (m, 4H), 4.20–4.90 (m, 2H), 2.90–3.20 (m, 2H), 1.63 (s, 9H), 1.60 (s, 9H), 1.25 (s, 9H).

To a solution of trifluoroacetic acid/dichloromethane (0.5 ml, 1:1) at room temperature was added the above 2-(tert-butoxyoxalyl-amino)-5-(S)-(1-oxo-1,3-dihydro-isoindol-2-ylmethyl)-4,5,6,7-tetrahydro-thieno[2,3-c]pyridine-3,6-dicarboxylic acid di-tert-butyl ester (4 mg, 0.006 mmol). The solution was stirred for 3 hours. The solvent was removed in vacuo. The residue was washed with dichloromethane affording in quantitative yield the title compound as a solid trifluoroacetate.

$^1$H-NMR (DMSO-d$_6$): δ12.32 (s, 1H), 4.62 (s, 1H), 4.12 (m, 1H), 3.62–3.78 (m, 2H), 3.40–3.52 (m, 2H), 2.83 (m, 2H).

MS: m/z: 416 [M+H]$^+$.

Example 8

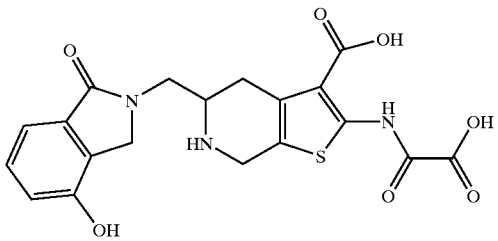

5-(4-Hydroxy-1-oxo-1,3-dihydro-isoindol-2-ylmethyl)-2-(oxalyl-amino)-4,5,6,7-tetrahydro-thieno[2,3-c]pyridine-3-carboxylic acid Acetyl chloride (5.4 ml, 5.96 g, 76 mmol) was added dropwise to methanol (15 ml) at 0° C. in a sealed 50 ml round-bottom flask. This solution was allowed to warm to room temperature for 1 hour while stirring. To this solution 3-hydroxy-2-methyl-benzoic acid (519 mg, 3.4 mmol) was added and the solution was stirred at room temperature for 42 hours. The reaction was quenched with saturated aqueous sodium bicarbonate and solid sodium bicarbonate. The volatiles were removed in vacuo and the basic aqueous solution was then extracted with dichloromethane (4×40 ml). The combined organic extracts were dried (MgSO$_4$), filtered, and the solvent evaporated in vacuo affording 493 mg (87%) of 3-hydroxy-2-methyl-benzoic acid methyl ester as a solid.

$^1$H-NMR (300 MHz, CDCl$_3$): δ7.43 (d, 1H, J=9 Hz), 7.12 (t, 1H, J=8 Hz), 6.95 (d, 1H, J=8 Hz), 5.05 (bs, 1H), 3.90 (s, 3H), 2.47 (s, 3H).

To a solution of the above methyl ester (256 mg, 1.54 mmol) and N,N-diisopropylethylamine (530 μl, 3.0 mmol) in dichloromethane (8 ml) at 0° C. methyloxymethyl chloride (175 μl, 2.3 mmol) was added dropwise. The solution was allowed slowly to warm to room temperature and stired for 24 hours. The solution was diluted with dichloromethane (12 ml), washed with water (20 ml), brine (20 ml), dried (MgSO$_4$), filtered, and concentrated in vacuo. The resulting oil was purified by silica gel chromatography using a mixture of hexanes/ethyl acetate (4:1) as eluent, which afforded 269 mg (85%) of 3-methoxymethoxy-2-methyl-benzoic acid methyl ester as an oil.

$^1$H-NMR (300 MHz, CDCl$_3$): δ7.48 (d, 1H, J=8 Hz), 7.24–7.15 (m, 2H), 5.22 (s, 2H), 3.90 (s, 3H), 3.50 (s, 3H), 2.47 (s, 3H).

In a 25 ml round-bottom flask, N-bromo succinimide (236 mg, 1.3 mmol) and azobis(cyclohexanecarbonitrile) (33 mg, 0.14 mmol) were added to a solution of 3-methoxymethoxy-2-methyl-benzoic acid methyl ester (265 mg, 1.26 mmol) in carbon tetrachloride (6.5 ml). The reaction was heated to reflux with stirring for 3.5 hours. The volatiles were removed in vacuo and the residue purified by silica gel chromatography using a mixture of hexanes/ethyl acetate (9:1) as eluent, which afforded 364 mg (100%) of 2-bromomethyl-3-methoxymethoxy-benzoic acid methyl ester as a solid.

$^1$H-NMR (300 MHz, CDCl$_3$): δ7.55 (dd, 1H, J=6,3 Hz), 7.29 (d, 2H, J=3 Hz), 5.27 (s, 2H), 5.05 (s, 2H), 3.91 (s, 3H), 3.50 (s, 3H).

In a 100 ml round-bottom flask, 2-amino-5-aminomethyl-6-(4-methoxy-benzyl)-4,5,6,7-tetrahydro-thieno[2,3-c]pyridine-3-carboxylic acid tert-butyl ester (298 mg, 0.74 mmol) and N,N-diisopropylethylamine (195 μl, 1.12 mmol) were dissolved in acetonitrile (40 ml). 2-Bromomethyl-3-methoxymethoxy-benzoic acid methyl ester (193 mg, 0.67 mmol) in acetonitrile (5 ml) was slowly added to the amine solution via gastight syringe over 24 hours, followed by stirring at room temperature for an additional 36 hours. The solution was concentrated in vacuo, the residue redissolved in ethyl acetate (25 ml), and washed with saturated aqueous sodium bicarbonate (25 ml) and brine (25 ml). The organic phase was dried (MgSO$_4$), filtered, and the solvent evaporated in vacuo. The residue was purified by silica gel chromatography using a mixture of hexanes/ethyl acetate (1:1) as eluent, which afforded 345 mg (81%) of 2-amino-6-(4-methoxy-benzyl)-5-(4-methoxymethoxy-1-oxo-1,3-dihydro-isoindol-2-ylmethyl)-4,5,6,7-tetrahydro[2,3-c]pyridine-3-carboxylic acid tert-butyl ester as a solid.

$^1$H-NMR (300 MHz, CDCl$_3$): δ7.67 (d, 1H, J=8 Hz), 7.57–7.38 (m, 5H), 7.14 (d, 2H, J=8 Hz), 6.96 (m, 2H), 6.77 (d, 2H, J=9 Hz), 6.20 (d, 2H, J=6 Hz), 5.96 (s, 2H), 4.69–2.58 (m, 17H), 1.55 (s, 9H).

In a 50 ml round-bottom flask a solution of 2-amino-6-(4-methoxy-benzyl)-5-(4-methoxymethoxy-1-oxo-1,3-dihydro-isoindol-2-ylmethyl)-4,5,6,7-tetrahydro[2,3-c]pyridine-3-carboxylic acid tert-butyl ester (338 mg, 0.58 mmol) in dichloromethane (20 ml) was treated with imidazol-1-yl-oxo-acetic acid tert-butyl ester (575 mg, 2.9 mmol). After stirring for 18 hours at room temperature, the mixture was concentrated to dryness in vacuo. The residue was purified by silica gel chromatography using a mixture of hexanes/ethyl acetate (1:1) as eluent, which afforded 310 mg (75%) of 2-(tert-Butoxyoxalyl-amino)-6-(4-methoxy-benzyl)-5-(4-methoxymethoxy-1-oxo-1,3-dihydro-isoindol-2-ylmethyl)-4,5,6,7-tetrahydro-thieno[2,3-c]pyridine-3-carboxylic acid tert-butyl ester as a solid.

$^1$H-NMR (300 MHz, CDCl$_3$): δ12.57 (s, 1H), 7.53 (d, 1H, J=8 Hz), 7.43 (t, 1H, J=8 Hz), 7.26 (d, 1H, J=8 Hz), 7.13 (d, 2H, J=9 Hz), 6.78 (d, 2H, J=9 Hz), 5.28 (s, 2H), 4.47 (q, 2H, J=18 Hz), 4.02–3.44 (m, 11H), 2.97 (dd, 1H, J=18 Hz and J=5 Hz), 2.76 (dd, 1H, J=17 Hz and J=5 Hz), 1.63 (s, 9H), 1.59 (s, 9H).

10% Pd/C (145 mg, 50% by weight) was added to a mixture of 2-(tert-butoxyoxalyl-amino)-6-(4-methoxy-benzyl)-5-(4-methoxymethoxy-1-oxo-1,3-dihydro-isoindol-2-ylmethyl)-4,5,6,7-tetrahydro-thieno[2,3-c]pyridine-3-carboxylic acid tert-butyl ester (283 mg, 0.40 mmol) in 10% formic acid and methanol (10 ml). After stirring at room temperature for 18 hours, more Pd/C (141 mg, 50% by weight) was added to the reaction mixture. After stirring at room temperature for an additional 20 hours, the catalyst was removed via fitration through celite. Fresh Pd/C (255 mg) and ammonium formate (1.0 g) were added to the residue (253 mg, 0.36 mmol) dissolved in 10% formic acid in methanol (10 ml). The solution was heated to 40° C. for 48 hours. Catalyst was removed via filtration through celite and liberal washing with methanol. Purification by chromatotron (ethyl acetate/triethylamine (99:1)) afforded 63 mg (27%) of 2-(tert-butoxyoxalyl-amino)-5-(4-methoxymethoxy-1-oxo-1,3-dihydro-isoindol-2-ylmethyl)-4,5,6,7-tetrahydro-thieno[2,3-c]pyridine-3-carboxylic acid tert-butyl ester A and 46 mg (19%) of 2-(tert-butoxyoxalyl-amino)-5-(4-methoxymethoxy-1-oxo-1,3-dihydro-isoindol-2-ylmethyl)-6-methyl-4,5,6,7-tetrahydro-thieno[2,3-c]pyridine-3-carboxylic acid tert-butyl ester B.

A $^1$H-NMR (300 MHz, CDCl$_3$): δ12.54 (s, 1H), 7.50 (d, 1H, J=8 Hz), 7.41 (t, 1H, J=8 Hz), 7.25 (d, 1H, J=8 Hz), 5.27 (s, 2H), 4.52 (dd, 2H, J=30 Hz and J=19 Hz), 4.08–3.90 (m, 2H), 3.86–3.67 (m, 2H), 3.51 (s, 3H), 3.27 (m, 1H), 2.99 (dd, 1H, J=18 and J=4 Hz), 2.53 (dd, 1H, J=18 Hz and J=11 Hz), 1.61 (s, 9H), 1.53 (s, 9H).

LC-MS (APCI$^+$) m/z: 588 [M+H]$^+$; R$_t$=1.32 min.

B $^1$H-NMR (300 MHz, CDCl$_3$): δ12.56 (s, 1H), 7.50 (d, 1H, J=7 Hz), 7.41 (t, 1H, J=8 Hz), 7.25 (d, 1H, J=8 Hz), 5.27 (s, 2H), 4.50 (dd, J=28 Hz and J=18 Hz), 3.93–3.68 (m, 4H), 3.51 (s, 1H), 3.51 (s, 3H), 3.31 (m, 1H), 2.88 (dd, 1H, J=18 Hz and J=4 Hz), 2.68 (dd, 1H, J=19 Hz and J=9 Hz), 2.46 (s, 3H), 1.61 (s, 9H), 1.54 (s, 9H).

LC-MS (APCI$^+$) m/z: 602 [M+H]$^+$; R$_t$=1.35 min.

2-(tert-Butoxyoxalyl-amino)-5-(4-methoxymethoxy-1-oxo-1,3-dihydro-isoindol-2-ylmethyl)-4,5,6,7-tetrahydro-thieno[2,3-c]pyridine-3-carboxylic acid tert-butyl ester A (63 mg, 0.11 mmol) was dissolved in 30% trifluoroacetic acid in dichloromethane (4 ml). The solution was left open to the atmosphere without stirring. After 24 hours the precipitate was filtered off and washed with diethyl ether, affording 57 mg (90%) of the title compound as a solid trifluoroacetate.

¹H-NMR (300 MHz, DMSO-d₆): δ12.30 (s, 1H), 10.17 (s, 1H), 9.23 (s, 2H, J=5 Hz and J=7 Hz), 7.34 (t, 1H, J=6 Hz), 7.19 (d, 1H, J=5 Hz), 7.03 (d, 1H, J=6 Hz), 5.76 (s, 2H), 4.53 (d, 1H, J=13 Hz), 4.43–4.22 (m, 3H), 4.07 (m, 1H), 3.91 (m, 1H), 3.70 (m, 1H), 3.10 (m, 1H), 2.82 (dd, 1H, J=14 Hz and J=8 Hz).

Example 9

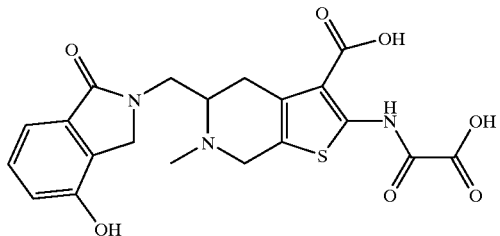

5-(4-Hydroxy-1-oxo-1,3-dihydro-isoindol-2-ylmethyl)-6-methyl-2-(oxalyl-amino)-4,5,6,7-tetrahydro-thieno[2,3-c]pyridine-3-carboxylic acid The above 2-(tert-butoxyoxalyl-amino)-5-(4-methoxymethoxy-1-oxo-1,3-dihydro-isoindol-2-ylmethyl)-6-methyl-4,5,6,7-tetrahydro-thieno[2,3-c]pyridine-3-carboxylic acid tert-butyl ester B (46 mg, 0.08 mmol) was dissolved in 30% trifluoroacetic acid in dichloromethane (4 ml). The solution was left open to the atmosphere without stirring. After 24 hours the precipitate was filtered off and washed with diethyl ether, affording 41 mg (90%) of the title compound as a solid trifluoroacetate.

¹H-NMR (400 MHz, CDCl₃): δ12.39 (s, 1H), 10.19 (s, 1H), 10.10 (s, 1H), 7.32 (t, 1H, J=7.6 Hz), 7.17 (d, 1H, J=7.2 Hz), 7.02 (t, 1H, J=7.2 Hz), 4.55 (d, 2H, J=15 Hz), 4.0–4.5 (m, 4H), 2.95–3.70 (m, 5H), 2.85 (s, 3H).

LC-MS (APCI⁺) m/z: 446 [M+H]⁺; $R_t$=1.02 min.

Example 10

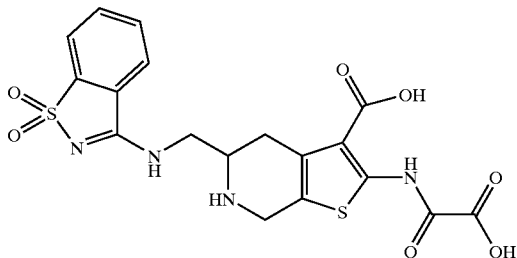

5-((1,1-Dioxo-1H-benzo[d]isothiazol-3-ylamino)methyl)-2-(oxalyl-amino)-4,5,6,7-tetrahydro-thieno[2,3-c]pyridine-3-carboxylic acid Saccharin (8.8 g, 48 mmol) and phosphorous pentachloride (15 g, 72 mmol) were added neat to a round bottom flask equipped with a short path distillation column. The mixture was heated to 175° C. After approximately 0.5 hour, phosphorous oxychloride slowly distilled off. Upon completion of the reaction, the mixture was cooled and the resultant solid recrystallized from benzene affording 3.6 g (37%) of 3-chloro-benzo[d]isothiazole 1,1-dioxide as a solid.

¹H-NMR (CDCl₃): δ7.92 (d, 1H, J=6.9 Hz), 7.8 (m, 3H).

To a solution of 2-amino-5-aminomethyl-6-(4-methoxybenzyl)-4,5,6,7-tetrahydro-thieno[2,3-c]pyridine-3-carboxylic acid tert-butyl ester (155 mg, 0.384 mmol) and triethylamine (59 μl, 0.423 mmol) in dichloromethane (2 ml) at 0° C., was added a solution of 3-chloro-benzo[d]isothiazole 1,1-dioxide (85.2 mg, 0.423 mmol) in dichloromethane (2 ml). The reaction mixture was stirred at 0° C. for 1 hour. The reaction was judged complete by tlc (dichloromethane/ethyl acetate (1:1)). The reaction mixture was washed with water (3×20 ml), dried (MgSO₄), filtered and the solvent evaporated in vacuo. The crude residue was subjected to flash chromatography using a gradient from 100% dichloromethane to dichloromethane/ethyl acetate (80/20) as eluent, which afforded 200 mg (92%) of 2-amino-5-((1,1-dioxo-1H-benzo[d]isothiazol-3-ylamino)methyl)-6-(4-methoxy-benzyl)-4,5,6,7-tetrahydro-thieno[2,3-c]pyridine-3-carboxylic acid tert-butyl ester as a foam.

¹H-NMR (CD₃OD): δ7.99 (m, 1H), 7.87 (m, 1H), 7.79 (m, 2H), 7.19 (d, 2H, J=8.4 Hz), 6.75 (d, 2H, J=8.7 Hz), 3.88–3.79 (m, 2H), 3.75–3.59 (m, 3H), 3.69 (s, 3H), 3.52–3.46 (m, 2H), 2.84 (dd, 1H, J=15.3 Hz and J=5.4 Hz), 2.68 (dd, J=18 Hz and J=4.5 Hz), 1.46 (s, 9H).

LC-MS: $R_t$=2.83, m/z: 569 [M+H]⁺

To a solution of 2-amino-5-((1,1-dioxo-1H-benzo[d]isothiazol-3-ylamino)-methyl)-6-(4-methoxy-benzyl)-4,5,6,7-tetrahydro-thieno[2,3-c]pyridine-3-carboxylic acid tert-butyl ester (129 mg, 0.227 mmol) in tetrahydrofuran (3 ml) was added imidazol-1-yl-oxo-acetic acid tert-butyl ester (1.1 ml, 1.1 mmol, 1 M in tetrahydrofuran). The reaction mixture was stirred at room temperature for 18 hours. The reaction mixture was concentrated in vacuo and the residue subjected to flash chromtography using a mixture of ethyl acetate/dichloromethane (10:90) as eluent, which afforded 142 mg (90%) of 2-(tert-butoxyoxalyl-amino)-5-((1,1-dioxo-1H-benzo[d]isothiazol-3-ylamino)methyl)-6-(4-methoxy-benzyl)-4,5,6,7-tetrahydro-thieno[2,3-c]pyridine-3-carboxylic acid tert-butyl ester as an oil.

¹H-NMR (CDCl₃): δ7.92 (d, 1H, J=6.3 Hz), 7.73 (m, 2H), 7.56 (d, 1H, J=5.7 Hz), 7.20 (d, 2H, J=6.3 Hz), 7.05 (bs, 1H), 6.87 (d, 2H, J=6.6 Hz), 3.91 (m, 2H), 3.82–3.72 (m, 2H), 3.79 (s, 3H), 3.61–3.49 (m, 2H), 3.44 (m, 1H), 3.11 (dd, 1H, J=15 Hz and J=3.6 Hz), 2.72 (dd, 1H, J=12 Hz and J=4.2 Hz), 1.63 (s, 18H);

LC-MS: $R_t$=3.48, m/z: 697 [M+H]⁺

2-(tert-Butoxyoxalyl-amino)-5-((1,1-dioxo-1H-benzo[d]isothiazol-3-ylamino)-methyl)-6-(4-methoxy-benzyl)-4,5,6,7-tetrahydro-thieno[2,3-c]pyridine-3-carboxylic acid tert-butyl ester (120 mg, 0.172 mmol) was dissolved in a mixture of ethanol (4 ml) and formic acid (0.5 ml). 10% Pd-C (20 mg) was added and the reaction mixture stirred at ambient temperature for 4 days (after the second day, 150 mg of additional 10% Pd-C was added). The reaction mixture was filtered through celite and the celite washed with dichloromethane. The organic fractions were combined and concentrated in vacuo. The resultant oil was subjected to preparative thin layer chromatography (dichloromethane/methanol (95:5)), which afforded 17 mg (17%) of 2-(tert-butoxyoxalyl-amino)-5-((1,1-dioxo-1H-benzo[d]isothiazol-3-ylamino)-methyl)-4,5,6,7-tetrahydro-thieno[2,3-c]pyridine-3-carboxylic acid tert-butyl ester as a solid.

¹H-NMR (CDCl₃): δ7.91 (m, 1H), 7.72 (m, 3H), 7.34 (bs, 1H), 4.16–4.08 (m, 1H), 4.07 (dd, 2H, J=36.3 Hz and J=8.7 Hz), 3.38–3.30 (m, 1H), 3.22–3.06 (m, 2H), 2.51 (dd, 1H, J=16.8 Hz and J=9.9 Hz), 1.61 (s, 18H).

2-(tert-Butoxyoxalyl-amino)-5-((1,1-dioxo-1H-benzo[d]isothiazol-3-ylamino)-methyl)-4,5,6,7-tetrahydro-thieno[2,3-c]pyridine-3-carboxylic acid tert-butyl ester (15 mg, 0.026 mmol) was dissolved in a solution of 50% trifluoroacetic acid/dichloromethane (3 ml). The reaction mixture was stirred at ambient temperature for 18 hours, concentrated in vacuo and re-evaporated from acetonitrile (2x). The residue was washed with dichloromethane and dried in vacuo to give 16 mg (90%) of the title compound as a solid trifluoroacetate.

¹H-NMR (CD₃OD): δ7.98 (d, 1H, J=7.2 Hz), 7.92 (d, 1H, J=6.6 Hz), 7.83 (m, 2H), 4.51–4.39 (m, 2H), 4.11–4.08 (m, 1H), 3.97–3.91 (m, 2H), 3.53–3.47 (m, 1H), 3.16–3.10 (m, 1H).

Example 11

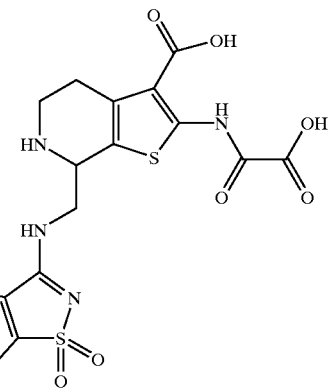

7-((1,1-Dioxo-1H-benzo[d]isothiazol-3-ylamino)methyl)-2-(oxalyl-amino)-4,5,6,7-tetrahydro-thieno[2,3-c]pyridine-3-carboxylic acid 3-Chloro-benzo[d]isothiazole-1,1-dioxide (160 mg, 0.79 mmol) and diisopropylethylamine (150 μl, 0.86 mmol) were dissolved in dichloromethane (7 ml) at 0° C. 2-Amino-7-aminomethyl- 6-(4-methoxy-benzyl)-4,5,6,7-tetrahydro-thieno[2,3-c]pyridine-3-carboxylic acid tert-butyl ester (284 mg, 0.70 mmol) was added and the mixture was stirred for 15 minutes at 0° C., diluted with dichloromethane (10 ml) and washed with water (20 ml) and brine (20 ml). The organic phase was dried (MgSO₄), filtered, and the solvent evaporated in vacuo. The residue was purified by silica gel chromatography using a gradient of hexanes/ethyl acetate (1:1) to pure ethyl acetate as eluent, which afforded 309 mg (77%) of 2-amino-7-((1,1-dioxo-1H-benzo[d]isothiazol-3-ylamino)methyl)-6-(4-methoxy-benzyl)-4,5,6,7-tetrahydro-thieno[2,3-c]pyridine-3-carboxylic acid tert-butyl ester as an foam.

¹H-NMR (300 MHz, CDCl₃): δ7.89 (d, 1H, J=8 Hz), 7.77–7.63 (m, 2H), 7.37 (d, 1H, J=7 Hz), 7.25 (d, 2H, J=10 Hz), 6.82 (d, 2H, J=8 Hz), 6.62 (bs, 1H), 6.08 (s, 2H), 3.91 (m, 1H), 3.71 (s, 3H), 3.49–2.65 (m, 8H), 1.59 (s, 9H).

LC-MS (APCI⁺) m/z: 569 [M+H]⁺, [M+Na] 591; R$_t$=2.85 min.

2-Amino-7-((1,1-dioxo-1H-benzo[d]isothiazol-3-ylamino)methyl)-6-(4-methoxy-benzyl)-4,5,6,7-tetrahydro-thieno[2,3-c]pyridine-3-carboxylic acid tert-butyl ester (102 mg, 0.18 mmol) in dichloromethane (10 ml) was treated with imidazol-1-yl-oxo-acetic acid tert-butyl ester (85 mg, 0.43 mmol). After stirring for 18 hours at room temperature, the reaction solution was concentrated to dryness in vacuo. The residue was purified by silica gel chromatography using a gradient of hexanes/ethyl acetate (1:1) to pure ethyl acetate as gradient, which afforded 98 mg (78%) of 2-(tert-butoxyoxalyl-amino)-7-((1,1-dioxo-1H-benzo[d]isothiazol-3-ylamino)-methyl)-6-(4-methoxy-benzyl)-4,5,6,7-tetrahydro-thieno[2,3-c]pyridine-3-carboxylic acid tert-butyl ester as a solid.

¹H-NMR (300 MHz, CDCl₃): δ12.57 (s, 1H), 7.89 (d, 1H, J=8 Hz), 7.77–7.63 (m, 2H), 7.39 (d, 1H, J=7 Hz), 7.25 (d, 2H, J=9 Hz), 6.84 (d, 2H, J=9 Hz), 6.64 (bs, 1H), 3.99–2.76 (m, 12H), 1.64 (s, 9H), 1.63 (s, 9H).

10% Pd/C (100 mg) was added to a mixture of 2-(tert-butoxyoxalyl-amino)-7-((1,1-dioxo-1H-benzo[d]isothiazol-3-ylamino)-methyl)-6-(4-methoxy-benzyl)-4,5,6,7-tetrahydro-thieno[2,3-c]pyridine-3-carboxylic acid tert-butyl ester (98 mg, 0.14 mmol) in 10% formic acid in methanol (10 ml). After stirring at room temperature for 48 hours, the catalyst was removed via filtration through celite and liberal washing with methanol. The volatiles were removed in vacuo and the residue purified by chromatotron (ethyl acetate/triethylamine, 99:1), which afforded 32 mg (40%) of 2-(tert-butoxyoxalyl-amino)-7-((1,1-dioxo-1H-benzo[d]isothiazol-3-ylamino)-methyl)-4,5,6,7-tetrahydro-thieno[2,3-c]pyridine-3-carboxylic acid tert-butyl ester as an oil.

¹H-NMR (300 MHz, CDCl₃): δ12.48 (s, 1H), 10.21–9.15 (m, 2H), 8.49–7.42 (m, 3H), 5.62–5.00 (bs, 1H), 4.53–2.87 (m, 8H), 1.61 (s, 18H).

HPLC (254.4 nm) R$_t$=3.67 minutes.

2-(tert-Butoxyoxalyl-amino)-7-((1,1-dioxo-1H-benzo[d]isothiazol-3-ylamino)-methyl)-4,5,6,7-tetrahydro-thieno[2,3-c]pyridine-3-carboxylic acid tert-butyl ester (32 mg) was dissolved in a mixture of 30% trifluoroacetic acid in dichloromethane (4 ml). The solution was left open to the atmosphere without stirring. After 24 hours the precipitate was filtered off and washed with diethyl ether, affording 29 mg (90%) of the title compound as a solid trifluoroacetate.

¹H-NMR (300 MHz, DMSO-d₆): δ12.36 (s, 1H), 9.92 (bs, 1H), 9.73 (bs, 1H), 9.38 (bs, 1H), 8.20 (m, 1H), 8.05 (m, 1H), 7.89 (m, 2H), 4.95 (s, 1H), 4.12–3.00 (m partially obscured by water, 8H).

LC-MS (APCI⁺) m/z: 466 [M+H]⁺; R$_t$=0.66 min.

Example 12

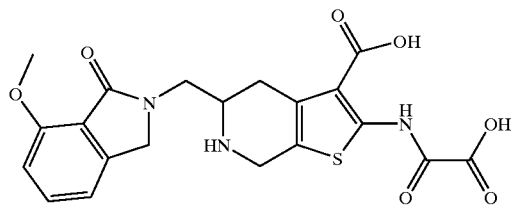

5-(7-Methoxy-1-oxo-1,3-dihydro-isoindol-2-ylmethyl)-2-(oxalyl-amino)-4,5,6,7-tetrahydro-thieno[2,3-c]pyridine-3-carboxylic acid 2-Methoxy-6-methylbenzoic acid ethyl ester (500 mg, 2.67 mmol), N-bromosuccinimide (483.8 mg, 2.72 mmol) and 2,2'-azobis(2-methyl-propionitrile) (30.2 mg, 0.123 mmol) in carbon tetrachloride (10 ml) were heated to reflux. After 18 hours, the reaction mixture was evaporated to dryness in vacuo. The residue was dissolved in dichloromethane (100 ml) and washed with water (2x50 ml). The organic layer was dried (MgSO₄), filtered and the solvent evaporated in vacuo. The residue (702 mg) was purified by column chromatography using a mixture of hexanes/dichloromethane (1:1) as eluent, which afforded 573 mg (85%) of 6-bromomethyl-2-methoxy-benzoic acid ethyl ester as an oil.

¹H-NMR (CDCl₃): δ7.37 (t, 1H, J=8.4 Hz), 7.01 (d, 1H, J=8.1 Hz), 6.90 (d, 1H, J=8.4 Hz), 4.54 (s, 2H), 4.45 (q, 2H, J=7.2 Hz), 3.82 (s, 3H), 1.42 (t, 3H, J=9 Hz).

6-Bromomethyl-2-methoxy-benzoic acid ethyl ester (71.1 mg, 0.260 mmol) dissolved in acetonitrile (5 ml) and diisopropylethylamine (453 μl, 2.60 mmol) was stirred at room temperature. To this mixture 2-amino-5-amino-methyl-6-(4-methoxy-benzyl)-4,5,6,7-tetrahydro-thieno[2,3-c]pyridine-3-carboxylic acid tert-butyl ester (200 mg, 0.52 mmol) dissolved in acetonitrile (5 ml) was added syringe pump (0.2 ml/min.). Once addition was complete, the reaction mixture was allowed to stir for 2 hours. The reaction mixture was concentrated in vacuo, and the residue diluted with ethylacetate (50 ml). The organic layer was washed with saturated sodium bicarbonate (2×25 ml) and brine (2×25 ml). The organic layer was dried (MgSO₄), filtered and concentrated in vacuo. The residue (308 mg) was subjected to column chromatography using a gradient of hexane/ethyl acetate (95:5) to (50:50) and then dichloromethane/ethyl acetate (95:5) as eluents, which afforded 106 mg (75%) of 2-amino-6-(4-methoxy-benzyl)-5-(7-methoxy-1-oxo-1,3-dihydro-isoindol-2-ylmethyl)-4,5,6,7-tetrahydro-thieno[2,3-c]pyridine-3-carboxylic acid tert-butyl ester as an oil.

¹H-NMR (CDCl₃): δ7.48 (t, 1H, J=7.5 Hz), 7.12 (d, 2H, J=8.4 Hz), 7.01 (d, 1H, J=7.5 Hz), 6.91 (d, 1H, J=8.4 Hz), 6.76 (d, 2H, J=7.8 Hz), 5.95 (bs, 2H), 4.37 (s, 2H), 4.05 (m, 1H), 3.97 (s, 3H), 3.88–3.78 (m, 2H), 3.81 (s, 3H), 3.71–3.39 (m, 4H), 2.90 (dd, 1H, J=18 Hz and J=5.4 Hz), 2.62 (dd, 1H, J=18 Hz and J=5.4 Hz), 1.53 (s, 9H).

To a solution of 2-amino-6-(4-methoxy-benzyl)-5-(7-methoxy-1-oxo-1,3-dihydro-isoindol-2-ylmethyl)-4,5,6,7-tetrahydro-thieno[2,3-c]pyridine-3-carboxylic acid tert-butyl ester (105 mg, 0.192 mmol) in tetrahydrofuran (3 ml) was added imidazol-1-yl-oxo-acetic acid tert-butyl ester (0.534 ml, 0.534 mmol, 1 M in tetrahydrofuran). The reaction mixture was stirred at room temperature for 18 hours. The reaction mixture concentrated in vacuo and the residue subjected to flash chromtography using a mixture of ethyl acetate/dichloromethane (10:90) as eluent, which afforded 85 mg (66%) of 2-(tert-butoxyoxalyl-amino)-6-(4-methoxy-benzyl)-5-(7-methoxy-1-oxo-1,3-dihydro-isoindol-2-ylmethyl)-4,5,6,7-tetrahydro-thieno[2,3-c]pyridine-3-carboxylic acid tert-butyl ester.

¹H-NMR (CDCl₃): δ7.47 (t, 1H, J=5.7 Hz), 7.10 (d, 2H, J=6 Hz), 6.99 (d, 1H, J=5.7 Hz), 6.90 (d, 1H, J=6.3 Hz), 6.76 (d, 2H, J=6.3 Hz), 4.37 (q, 2H, J=11.4 Hz), 3.99–3.92 (m, 1H), 3.97 (s, 3H), 3.79–3.76 (m, 2H), 3.77 (s, 3H), 3.66 (d, 1H, J=12.6 Hz), 3.58–3.50 (m, 3H), 2.95 (dd, 1H, J=13.5 Hz and J=3.6 Hz), 2.70 (dd, 1H, J=13.5 Hz and J=3.6 Hz) 1.61 (d, 9H), 1.57 (s, 9H).

2-(tert-Butoxyoxalyl-amino)-6-(4-methoxy-benzyl)-5-(7-methoxy-1-oxo-1,3-dihydro-isoindol-2-ylmethyl)-4,5,6,7-tetrahydro-thieno[2,3-c]pyridine-3-carboxylic acid tert-butyl ester (66 mg, 0.12 mmol) was dissolved in ethanol (2 ml) and formic acid (0.3 ml). 10% Pd-C (15 mg) was added and the reaction mixture stirred at room temperature for 3 days. TLC (hexane/ethyl acetate (1/1)) indicated reaction complete. The reaction mixture was filtered through celite and the celite washed with dichloromethane. The organic fractions were combined and subjected to preparative thin layer chromatography (hexane/ethyl acetate (1/1) to yield 14.7 mg (22%) of 2-(tert-butoxyoxalyl-amino)-5-(7-methoxy-1-oxo-1,3-dihydro-isoindol-2-ylmethyl)-4,5,6,7-tetrahydro-thieno[2,3-c]pyridine-3-carboxylic acid tert-butyl ester as an oil.

¹H-NMR (CDCl₃): δ7.48 (t, 1H, J=7.5 Hz), 7.01 (d, 1H, J=7.2 Hz), 6.90 (d, 1H, J=8.4 Hz), 5.50 (d, 2H, J=6.6 Hz), 4.04–3.90 (m, 1H), 3.97 (s, 3H), 3.24 (m, 1H), 3.01–2.95 (m, 1H), 2.57–2.43 (m, 2H), 1.62 (s, 9H), 1.57 (s, 9H).

2-(tert-Butoxyoxalyl-amino)-5-(7-methoxy-1-oxo-1,3-dihydro-isoindol-2-ylmethyl)-4,5,6,7-tetrahydro-thieno[2,3-c]pyridine-3-carboxylic acid tert-butyl ester (14.7 mg, 0.026 mmol) was dissolved in a solution of 50% trifluoroacetic acid/dichloromethane (2 ml). The reaction mixture was stirred at ambient temperature for 18 hours, concentrated in vacuo and re-evaporated from acetonitrile (2×). The resulting precipitate was washed with dichloromethane and dried in vacuo to give 13 mg (89%) of the title compound as a solid trifluoroacetate.

¹H-NMR (CD₃OD): δ7.56 (t, 1H, J=8.1 Hz), 7.13 (d, 1H, J=7.2 Hz), 7.01 (d, 1H, J=8.1 Hz), 4.87–4.44 (m, 4H), 4.15 (m, 1H), 3.90 (s, 3H), 3.88–3.79 (m, 1H), 3.43 (m, 1H), 2.98 (m, 2H);

LC-MS: R_f=0.71, m/z: 446 [M+H]⁺.

Example 13

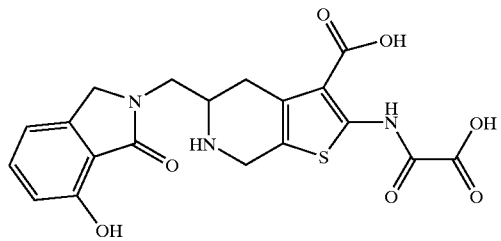

5-(7-Hydroxy-1-oxo-1,3-dihydro-isoindol-2-ylmethyl)-2-(oxalyl-amino)-4,5,6,7-tetrahydro-thieno[2,3-c]pyridine-3-carboxylic acid To a solution of 2-hydroxy-6-methyl-benzoic acid ethyl ester (5.00 g, 27.8 mmol) and t-butyl-di-methylsilyl chloride (6.27 g, 41.6 mmol) in dichloromethane (100 ml) was added diisopropyl ethylamine. The solution was stirred at 50° C. for 24 hours, washed with water, brine, dried (MgSO₄), filtered and the solvent evaporated in vacuo, which afforded 7.6 g (93%) of 2-(tert-butyl-dimethyl-silanyloxy)-6-methyl-benzoic acid ethyl ester as an oil.

¹H-NMR (CDCl₃): δ7.13 (t, 1H, J=7.5 Hz), 6.78 (d, 1H, J=7.5 Hz), 6.67 (d, 1H, J=7.5 Hz), 4.35 (q, 2H, J=7.2 Hz), 2.29 (s, 3H), 1.38 (t, 3H, J=7.2 Hz), 0.97 (s, 9H), 0.23 (s, 6H).

2-(tert-Butyl-dimethyl-silanyloxy)-6-methyl-benzoic acid ethyl ester (7.6 g, 25.8 mmol), N-bromosuccinimide (4.82 g, 27.1 mmol) and azobis(cyclohexanecarbonitrile) (0.32 g, 1.3 mmol) were dissolved in tetrachlormethane (130 ml). The solution was stirred at room temperature for 60 hours. The solvent was evaporated in vacuo and the residue was chromatographed on silica gel column using a gradient of 1–2% ethyl acetate/hexane as eluent, which afforded 8.0 g (83%) of 6-bromomethyl-2-(tert-butyl-dimethyl-silanyloxy)-benzoic acid ethyl ester as an oil.

¹H-NMR (CDCl₃): δ7.21 (t, 1H, J=8.4 Hz), 7.00 (d, 1H, J=8.4 Hz), 6.81 (d, 1H, J=8.4 Hz), 4.51 (s, 2H), 4.40 (q, 2H, J=7.2 Hz), 1.42 (t, 3H, J=7.2 Hz), 0.98 (s, 9H), 0.23 (s, 6H).

To a solution of 2-amino-5-aminomethyl-6-(4-methoxy-benzyl)-4,5,6,7-tetrahydro-thieno[2,3-c]pyridine-3-carboxylic acid tert-butyl ester (3.00 g, 7.45 mmol) and diisopropyl ethylamine (1.93 ml, 11.2 mmol) in acetonitrile at room temperature was added a solution of 6-bromomethyl-2-(tert-butyl-dimethyl-silanyloxy)-benzoic acid ethyl ester (2.78 g, 7.45 mmol) in acetonitril over 48 hours. The solution was stirred for 12 hours after the addition was complete. The volatiles were evaporated in vacuo and the residue was taken into ethyl acetate (50 ml) and washed with water, 1 N hydrochloric acid, brine, dried (MgSO$_4$), filtered and the solvent evaporated in vacuo. The residue was chromatographed on silica gel column eluted with a mixture of 20% ethyl acetate/Hexane, which afforded 3.2 g (66%) of 2-amino-5-(7-(tert-butyl-dimethyl-silanyloxy)-1-oxo-1,3-dihydro-isoindol-2-ylmethyl]-6-(4-methoxy-benzyl)-4,5,6,7-tetrahydro-thieno[2,3-c]pyridine-3-carboxylic acid tert-butyl ester as an oil.

$^1$H-NMR (CDCl$_3$): δ7.36 (t, 1H, J=8.0 Hz), 7.11 (d, 2H, J=8.8 Hz), 6.99 (d, 1H, J=8.0 Hz), 6.82 (d, 1H, J=8.0 Hz), 6.76 (d, 2H, J=8.8 Hz), 5.94 (s, 2H), 4.48 (d, 1H, J=16.8 Hz), 4.33 (d, 1H, J=16.8 Hz), 3.90–3.45 (m, 7H), 3.78 (s, 3H), 2.95 (dd, 1H, J=17.2 Hz and J=5.2 Hz), 2.72 (dd, 1H, J=17 Hz and J=5.6 Hz), 1.52 (s, 9H), 1.05 (s, 9H), 0.26 (s, 6H).

To a stirred solution of 2-amino-5-(7-(tert-butyl-dimethyl-silanyloxy)-1-oxo-1,3-dihydro-isoindol-2-ylmethyl)-6-(4-methoxy-benzyl)-4,5,6,7-tetrahydro-thieno[2,3-c]pyridine-3-carboxylic acid tert-butyl ester (2.37 g, 3.64 mmol) in tetrahydrofuran (50 ml) was added imidazol-1-yl-oxo-acetic acid tert-butyl ester (2.14 mg, 10.9 mmol) in tetrahydrofuran (10 ml). The mixture was stirred at room temperature for 24 hours. The solvent was removed in vacuo. The residue was taken into ethyl acetate (100 ml). The solution was washed with 0.5 N hydrochloric acid solution (2×20 ml), saturated sodium bicarbonate (2×20 ml) and brine (20 ml), dried (MgSO$_4$), filtered and the solvent removed in vacuo. The residue was chromatographed using a gradient of 10–20% ethyl acetate/Hexane as eluent, which afforded 2.40 g (92%) of 2-(tert-butoxyoxalyl-amino)-5-(7-(tert-butyl-dimethyl-silanyloxy)-1-oxo-1,3-dihydro-isoindol-2-ylmethyl)-6-(4-methoxy-benzyl)-4,5,6,7-tetrahydro-thieno[2,3-c]pyridine-3-carboxylic acid tert-butyl ester as a solid.

$^1$H-NMR (CDCl$_3$): δ12.59 (s, 1H), 7.37 (t, 1H, J=8.0 Hz), 7.10 (d, 2H, J=8.8 Hz), 7.00 (d, 1H, J=8.0 Hz), 6.83 (d, 1H, J=8.0 Hz), 6.77 (d, 2H, J=8.8 Hz), 4.50 (d, 1H, J=16.8 Hz), 4.34 (d, 1H, J=16.8 Hz), 3.90–3.45 (m, 7H), 3.77 (s, 3H), 2.95 (dd, 1H, J=17.2 Hz and J=5.2 Hz), 2.72 (dd, 1H, J=18 and J=5.6 Hz), 1.61 (s, 9H), 1.58 (s, 9H), 1.06 (s, 9H), 0.26 (s, 6H).

To a solution of 2-(tert-butoxyoxalyl-amino)-5-(7-(tert-butyl-dimethyl-silanyloxy)-1-oxo-1,3-dihydro-isoindol-2-ylmethyl)-6-(4-methoxy-benzyl)-4,5,6,7-tetrahydro-thieno[2,3-c]pyridine-3-carboxylic acid tert-butyl ester (2.40 g, 3.34 mmol) in 10% formic acid/methanol (50 ml) at room temperature under nitrogen was added 10% Pd/C (1.2 g). The mixture was stirred for 48 hours. The Pd/C was filtered off and the filtrate was evaporated in vacuo. The residue was dissolved in dichloromethane (10 ml). The resulting solution was poured into hexane. The precipitate was filtered off and dried in vacuo affording 1.3 g (61%) of 2-(tert-butoxyoxalyl-amino)-5-(7-(tert-butyl-dimethyl-silanyloxy)-1-oxo-1,3-dihydro-isoindol-2-ylmethyl)-4,5,6,7-tetrahydro-thieno[2,3-c]pyridine-3-carboxylic acid tert-butyl ester.

$^1$H-NMR (CDCl$_3$): δ12.45 (s, 1H), 8.05 (s, 1H), 7.39 (t, 1H, J=8.0 Hz), 7.00 (d, 1H, J=8.0 Hz), 6.83 (d, 1H, J=8.0 Hz), 4.50 (d, 1H, J=16.8 Hz), 4.45 (q, 2H, J=17 Hz), 4.05 (q, 2H, J=17 Hz), 3.82 (dd, 1H, J=17.2 Hz and J=5.2 Hz), 3.72 (dd, 1H, J=17 Hz and J=5.6 Hz), 3.40 (s, 1H), 3.08 (d, 1H, J=17 Hz), 2.61 (dd, 1H, J=18 Hz and J=7.2 Hz), 1.61 (s, 9H), 1.54 (s, 9H), 1.05 (s, 9H), 0.26 (s, 6H).

To a solution of trifluoroacetic acid (33.3 ml) and H$_2$O (2.7 ml) was added 2-(tert-butoxyoxalyl-amino)-5-(7-(tert-butyl-dimethyl-silanyloxy)-1-oxo-1,3-dihydro-isoindol-2-ylmethyl)-4,5,6,7-tetrahydro-thieno[2,3-c]pyridine-3-carboxylic acid tert-butyl ester (0.70 g, 1.04 mmol). The solution was stirred at room temperature for 40 hours. The solvent was poured into ethyl ether (400 ml). The precipitate was filtered off and dried in vacuo, which afforded 450 mg (80%) of the title compound as a solid trifluoroacetate.

$^1$H-NMR (DMSO-d$_6$): δ12.30 (s, 1H), 9.71 (s, 1H), 9.20 (s, 2H), 7.39 (t, 1H, J=8.0 Hz), 6.99 (d, 1H, J=8.0 Hz), 6.82 (d, 1H, J=8.0 Hz), 4.52 (d, 1H, J=16.8 Hz), 4.36 (d, 2H, J=17 Hz), 4.22 (d, 2H, J=17 Hz), 4.00 (dd, 1H, J=17.2 Hz and J=5.2 Hz), 3.86 (s, 1H), 3.62 (d, 1H, J=17 Hz), 2.81 (dd, 1H, J=18 Hz and J=7.2 Hz);

LC-MS: R$_t$=1.20 min; m/z=432 [M+H]$^+$

Example 14

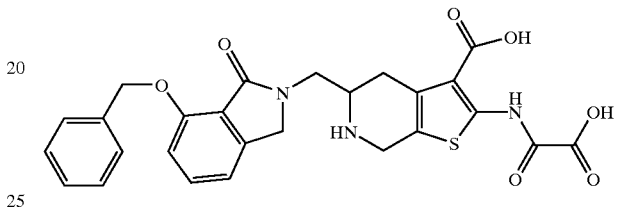

5-(7-Benzyloxy-1-oxo-1,3-dihydro-isoindol-2-ylmethyl)-2-(oxalyl-amino)-4,5,6,7-tetrahydro-thieno[2,3-c]pyridine-3-carboxylic acid To a solution of 2-(tert-butoxyoxalyl-amino)-5-(7-(tert-butyl-dimethyl-silanyloxy)-1-oxo-1,3-dihydro-isoindol-2-ylmethyl)-6-(4-methoxy-benzyl)-4,5,6,7-tetrahydro-thieno[2,3-c]pyridine-3-carboxylic acid tert-butyl ester (2.40 g, 3.34 mmol) in 10% formic acid/methanol (50 ml) at room temperature under nitrogen was added 10% Pd/C (1.2 g). The mixture was stirred for 48 hours. The Pd/C was filtered off and the filtrate was evaporated in vacuo. The residue was dissolved in dichloromethane (10 ml) and the resulting solution was poured into hexane. The precipitate was filtered off (1.3 g) and the filtrate was evaporated in vacuo. The residual foam (1.1 g) was taken into dichloromethane (50 ml) and treated with di-tert-butyl-dicarbonate (1.1 g, 5.0 mmol) and saturated sodium bicarbonate (20 ml). The mixture was stirred for 2 hours and the organic layer was separated and dried (MgSO$_4$). The solvent was evaporated in vacuo and the residue was chromatographed using a gradient of 10–30% ethyl acetate/Hexane as eluent, which afforded 175 mg of 2-(tert-butoxyoxalyl-amino)-5-(7-hydroxy-1-oxo-1,3-dihydro-isoindol-2-ylmethyl)-4,7-dihydro-5H-thieno[2,3-c]pyridine-3,6-carboxylic acid di-tert-butyl ester.

$^1$H-NMR (CDCl$_3$): δ12.55 (s, 1H), 8.53 (s, 1H), 7.37 (t, 1H, J=7.6 Hz), 6.92 (d, 1H, J=7.6 Hz), 6.83 (d, 1H, J=7.6 Hz), 4.95 (s, 1H), 4.84 (d, 1H, J=16.4 Hz), 4.72 (d, 1H, J=16.0 Hz), 4.56 (d, 1H, J=16.0 Hz), 4.28 (d, 1H, J=17.6 Hz), 4.13 (m, 1H), 3.68 (s, 0.5H), 3.42 (s, 0.5H), 3.16–2.94 (m, 2H), 1.62 (s, 9H), 1.61 (s, 9H), 1.26 (s, 9H).

To a solution of 2-(tert-butoxyoxalyl-amino)-5-(7-hydroxy-1-oxo-1,3-dihydro-isoindol-2-ylmethyl)-4,7-dihydro-5H-thieno[2,3-c]pyridine-3,6-carboxylic acid di-tert-butyl ester (16 mg, 0.025 mmol) in N,N-dimethylformamide (0.5 ml) under nitrogen was added sodium hydride (1.0 mg, 0.026 mmol) at room temperature. The solution was stirred for 2 hours and followed by addition of benzyl bromide (5.9 ml, 0.050 mmol). The solution was stirred for 16 hours, diluted with ethyl acetate (20 ml) and washed with 0.5 N hydrochloric acid solution (2×10 ml), saturated sodium bicarbonate (2×10 ml), brine (10 ml), dried (MgSO$_4$), and filtered. The solvent was removed in vacuo. The residue was chromatographed using a gradient of 10–20% ethyl acetate/Hexane as eluent, which afforded 14 mg (76%) of 5-(7-benzyloxy-1-oxo-1,3-dihydro-isoindol-2-ylmethyl)-2-(tert-butoxyoxalyl-amino)-4,7-dihydro-5H-thieno[2,3-c]pyridine-3,6-carboxylic acid di-tert-butyl ester as a solid.

$^1$H-NMR (CDCl$_3$): δ12.49 (s, 1H), 7.48 (d, 2H, J=7.2 Hz), 7.35 (m, 3H), 7.28 (d, 1H, J=7.2 Hz), 6.97 (d, 1H, J=7.6 Hz), 6.80 (d, 1H, J=7.6 Hz), 5.32 (s, 2H), 4.97 (m, 2H), 4.82–4.62 (m, 2H), 4.45–4.15 (m, 2H), 3.68 (s, 0.5H), 3.48 (s, 0.5H), 316–2.94 (m, 2H) 1.62 (s, 9H), 1.60 (s, 9H), 1.26 (s, 9H).

To a solution of trifluoroacetic acid (0.5 ml) and dichloromethane (2.7 ml) was added 5-(7-benzyloxy-1-oxo-1,3-dihydro-isoindol-2-ylmethyl)-2-(tert-butoxyoxalyl-amino)-4,7-dihydro-5H-thieno[2,3-c]pyridine-3,6-carboxylic acid di-tert-butyl ester (14 mg, 0.019 mmol).

The solution was stirred at room temperature for 40 hours. The reaction mixture was poured into ethyl ether (20 ml). The precipitate was filtered off and dried in vacuo affording 8.0 mg (68%) of the title compound as a solid trifluoroacetate.

$^1$H-NMR (DMSO-d$_6$): δ12.25 (s, 1H), 9.28 (s, 1H), 9.02 (s, 1H), 7.53 (m, 3H), 7.39 (t, 2H, J=7.6 Hz), 7.13 (d, 1H, J=7.6 Hz), 7.11 (d, 1H, J=8.4 Hz), 5.27 (m, 2H), 4.54 (d, 1H, J=17.2 Hz), 4.38 (d, 2H, J=17.6 Hz), 4.22 (m, 2H), 4.00 (dd, 1H, J=17.2 Hz and J=5.2 Hz), 3.86 (s, 1H), 3.64 (d, 1H, J=17.2 Hz), 2.81 (dd, 1H, J=18 Hz and J=7.2 Hz);

LC-MS: R$_t$=2.96 min; m/z: 522 [M+H]$^+$

Example 15

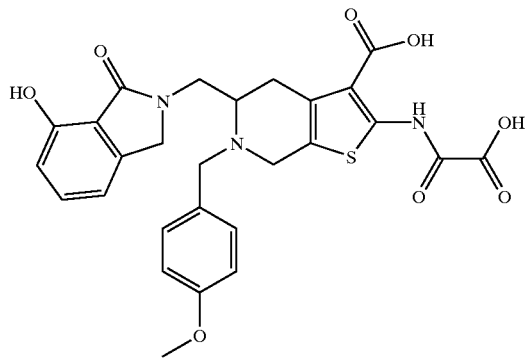

5-(7-Hydroxy-1-oxo-1,3-dihydro-isoindol-2-ylmethyl)-6-(4-methoxy-benzyl)-2-(oxalyl-amino)-4,5,6,7-tetrahydro-thieno[2,3-c]pyridine-3-carboxylic acid To a solution of trifluoroacetic acid (0.5 ml) and dichloromethane (0.5 ml) was added 2-(tert-butoxyoxaly-amino)-5-(7-(tert-butyl-dimethyl-silanyloxy)-1-oxo-1,3-dihydro-isoindol-2-ylmethyl)-6-(4-methoxy-benzyl)-4,5,6,7-tetrahydro-thieno[2,3-c]pyridine-3-carboxylic acid tert-butyl ester (11 mg, 0.014 mmol). The solution was stirred at room temperature for 16 hours. The reaction mixture was poured into ethyl ether (20 ml). The precipitate was filtered off and dried in vacuo, which afforded 7.0 mg (79%) of the title compound as a solid trifluoroacetate.

$^1$H-NMR (DMSO-d$_6$): δ12.39 (s, 1H), 9.95 (s, 1H), 9.75 (s, 2H), 7.42 (t, 1H, J=8.0 Hz), 7.30 (s, 2H), 7.02 (d, 1H, J=7.2 Hz), 6.96 (s, 2H), 6.85 (d, 1H, J=7.2 Hz), 4.95–3.65 (m, 11H), 3.76 (s, 3H).

LC-MS: R$_t$=1.93 min, m/z: 553 [M+H]$^+$

Example 16

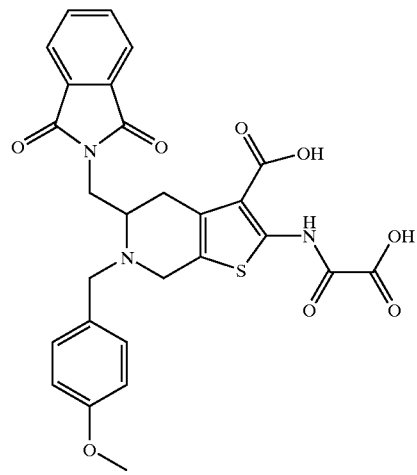

5-(1,3-Dioxo-1,3-dihydro-isoindol-2-ylmethyl)-6-(4-methoxy-benzyl)-2-(oxalyl-amino)-4,5,6,7-tetrahydro-thieno[2,3-c]pyridine-3-carboxylic acid To a stirred solution of 2-amino-5-(1,3-dioxo-1,3-dihydro-isoindol-2-ylmethyl)-6-(4-methoxy-benzyl)-4,5,6,7-tetrahydro-thieno[2,3-c]pyridine-3-carboxylic acid tert-butyl ester (15 mg, 0.028 mmol) in tetrahydrofuran (1.0 ml) was added imidazol-1-yl-oxo-acetic acid tert-butyl ester (27 mg, 0.11 mmol) in tetrahydrofuran (1.0 ml). The mixture was stirred at room temperature for 24 hours. The solvent was removed in vacuo. The residue was taken into ethyl acetate (20 ml). The solution was washed with 0.5 N hydrochloric acid solution (2×10 ml), saturated sodium bicarbonate (2×10 ml) and brine (10 ml), dried (MgSO$_4$) and filtered. The solvent was removed in vacuo. The residue was chromatographed using a gradient of 10–25% ethyl acetate/hexane as eluent, which afforded 17 mg (93%) of 2-(tert-butoxyoxalyl-amino)-5-(1,3-dioxo-1,3-dihydro-isoindol-2-ylmethyl)-6-(4-methoxy-benzyl)-4,5,6,7-tetrahydro-thieno[2,3-c]pyridine-3-carboxylic acid tert-butyl ester as a solid.

$^1$H-NMR (CDCl$_3$): δ12.54 (s, 1H), 7.86 (m, 2H), 7.40 (m, 2H), 7.08 (d, 2H, J=8.4 Hz), 6.72 (d, 2H, J=8.4 Hz), 4.08 (dd, 1H, J=13.6 Hz and J=8.8 Hz), 3.94 (d, 1H, J=16.8 Hz), 3.82 (d, 1H, J=12.8 Hz), 3.78 (s, 3H), 3.92 (s, 3H), 3.70–3.56 (m, 3H), 3.53 (d, 1H, J=12.8), 2.93 (dd, 1H, J=16.8 Hz and J=4.8 Hz), 2.75 (dd, 1H, J=18.0 Hz and J=5.6 Hz), 1.61 (s, 9H), 1.58 (s, 9H).

To a solution of trifluoroacetic acid (0.5 ml) and dichloromethane (0.5 ml) was added 2-(tert-butoxyoxalyl-amino)-5-(1,3-dioxo-1,3-dihydro-isoindol-2-ylmethyl)-6-(4-methoxy-benzyl)-4,5,6,7-tetrahydro-thieno[2,3-c]pyridine-3-carboxylic acid tert-butyl ester (15 mg, 0.023 mmol). The solution was stirred at room temperature for 40 hours. The reaction mixture was poured into ethyl ether (20 ml). The precipitate was filtered off and dried in vacuo, which afforded 13 mg (87%) of the title compound as a solid trifluoroacetate.

$^1$H-NMR (DMSO-d$_6$): δ12.38 (s, 1H), 7.89 (d, 4H, J=11.2 Hz), 7.18 (s, 2H), 6.85 (s, 2H), 4.20–3.60 (m, 9H), 3.71 (s, 3H);

LC-MS: $R_t$=2.05 min, m/z: 550 [M+H]$^+$

Example 17

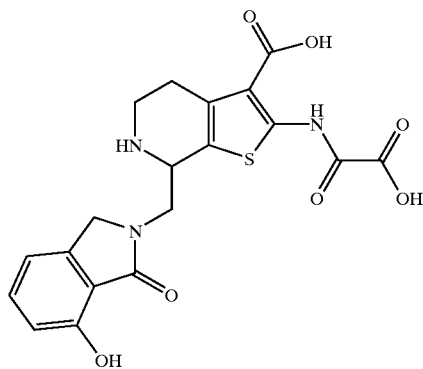

7-(7-Hydroxy-1-oxo-1,3-dihydro-isoindol-2-ylmethyl)-2-(oxalyl-amino)-4,5,6,7-tetrahydro-thieno[2,3-c]pyridine-3-carboxylic acid To a solution of 2-amino-7-aminomethyl-6-(4-methoxy-benzyl)-4,5,6,7-tetrahydro-thieno[2,3-c]pyridine-3-carboxylic acid tert-butyl ester (80 mg, 0.20 mmol) and diisopropyl ethylamine (35 μl, 0.40 mmol) in acetonitrile (10 ml) at room temperature was added a solution of 6-bromomethyl-2-(tert-butyl-dimethyl-silanyloxy)-benzoic acid ethyl ester (69 mg, 0.20 mmol). The solution was stirred for 12 hours at room temperature and the solvent was evaporated in vacuo. The residue was dissolved in ethyl acetate (50 ml) and washed with water, 1 N hydrochloric acid, brine, dried (MgSO$_4$), filtered and the solvent evaporated in vacuo. The residue was chromatographed on silica gel column eluted with 20% ethyl acetate/hexane to yield 42 mg (33%) of 2-amino-7-(7-(tert-butyl-dimethyl-silanyloxy)-1-oxo-1,3-dihydro-isoindol-2-ylmethyl)-6-(4-methoxy-benzyl)-4,5,6,7-tetrahydro-thieno[2,3-c]pyridine-3-carboxylic acid tert-butyl ester as an oil.

$^1$H-NMR (CDCl$_3$): δ7.64 (d, 1H, J=8.8 Hz), 7.39 (t, 1H, J=8.0 Hz), 7.10–6.80 (m, 5H), 6.09 (s, 2H), 5.0–4.2 (m, 4H), 3.80 (s, 3H), 3.66–2.92 (m, 3H), 1.55 (s, 9H), 1.04 (s, 9H), 0.22 (s, 6H).

To a stirred solution of 2-amino-7-(7-(tert-butyl-dimethyl-silanyloxy)-1-oxo-1,3-dihydro-isoindol-2-ylmethyl)-6-(4-methoxy-benzyl)-4,5,6,7-tetrahydro-thieno[2,3-c]pyridine-3-carboxylic acid tert-butyl ester (40 mg, 0.060 mmol) in tetrahydrofuran (1 ml) was added imidazol-1-yl-oxo-acetic acid tert-butyl ester (59 mg, 0.30 mmol) in tetrahydrofuran (1 ml). The mixture was stirred at room temperature for 24 hours. The solvent was removed in vacuo. The residue was dissolved in ethyl acetate (20 ml) and the solution was washed with 0.5 N hydrochloric acid (2×20 ml), saturated sodium bicarbonate (2×20 ml), brine (20 ml), dried (MgSO$_4$) and filtered. The solvent was removed in vacuo and the residue was chromatographed using a gradient of 10–20% ethyl acetate/Hexane as eluent, which afforded 40 mg (83%) of 2-(tert-butoxyoxalyl-amino)-7-(7-(tert-butyl-dimethyl-silanyloxy)-1-oxo-1,3-dihydro-isoindol-2-ylmethyl)-6-(4-methoxy-benzyl)-4,5,6,7-tetrahydro-thieno[2,3-c]pyridine-3-carboxylic acid tert-butyl ester as a solid.

$^1$H-NMR (CDCl$_3$): δ12.52 (s, 1H), 7.37 (t, 1H, J=8.0 Hz), 6.97 (d, 2H, J=8.4 Hz). 6.94 (d, 1H, J=8.0 Hz), 6.83 (d, 1H, J=8.0 Hz), 6.54 (d, 1H, J=8.4 Hz), 4.26 (d, 1H, J=16.8 Hz), 3.93–3.84 (m, 2H), 3.77 (d, 1H, J=16.8 Hz), 3.69 (s, 3H), 3.66–3.48 (m, 3H), 3.42–3.32 (m, 1H), 2.95 (dd, 1H, J=14.4 Hz and J=4.8 Hz), 2.92–2.82 (m, 1H), 2.73 (dd, 1H, J=14.4 Hz and J=4.8 Hz), 1.60 (s, 9H), 1.59 (s, 9H), 1.02 (s, 9H), 0.22 (d, 6H, J=1.6 Hz).

To a solution of 2-(tert-butoxyoxalyl-amino)-7-(7-(tert-butyl-dimethyl-silanyloxy)-1-oxo-1,3-dihydro-isoindol-2-ylmethyl)-6-(4-methoxy-benzyl)-4,5,6,7-tetrahydro-thieno[2,3-c]pyridine-3-carboxylic acid tert-butyl ester (4.0 mg, 5.1 mol) in 10% formic acid/methanol (1 ml) at room temperature under nitrogen was added 10% Pd/C (4 mg). The mixture was stirred for 1 hour. The Pd/C was filtered off and the filtrate was evaporated in vacuo to afford 2.8 mg (82%) of 2-(tert-butoxyoxalyl-amino)-7-(7-(tert-butyl-dimethyl-silanyloxy)-1-oxo-1,3-dihydro-isoindol-2-ylmethyl)-5H-4,5,6,7-tetrahydro-thieno[2,3-c]pyridine-3-carboxylic acid tert-butyl ester as a solid.

$^1$H-NMR (CDCl$_3$): δ12.45 (s, 1H), 8.05 (s, 1H), 7.39 (t, 1H, J=8.0 Hz), 6.99 (d, 1H, J=8.0 Hz), 6.79 (d, 1H, J=8.0 Hz), 4.50 (d, 1H, J=17.2 Hz), 4.45 (d, 1H, J=17.2 Hz), 4.24 (d, 1H, 8.4 Hz), 4.03 (dd, 1H, J=16.0 Hz and J=7.2 Hz), 3.78–3.68 (m, 2H), 3.38–3.28 (m, 1H), 3.21 (d, 1H, J=18.8 Hz), 3.08–2.98 (m, 1H), 1.57 (s, 9H), 1.56 (s, 9H), 0.98 (s, 9H), 0.15 (d, 6H, J=1 Hz).

To a solution of trifluoroacetic acid (0.5 ml) and dichloromethane (0.5 ml) was added 2-(tert-butoxyoxalyl-amino)-7-(7-(tert-butyl-dimethyl-silanyloxy)-1-oxo-1,3-dihydro-isoindol-2-ylmethyl)-5H-4,5,6,7-tetrahydro-thieno[2,3-c]pyridine-3-carboxylic acid tert-butyl ester (2.8 mg, 0.0042 mmol). The solution was stirred at room temperature for 16 hours. The solvent was removed in vacuo and the residue was washed with dichloromethane affording 1.8 mg (79%) of the title compound as a solid trifluoroacetate.

$^1$H-NMR (DMSO-d$_6$): δ12.30 (s, 1H), 9.76 (s, 1H), 9.40 (s, 1H), 8.95 (s, 1H), 7.40 (t, 1H, J=7.6 Hz), 7.00 (d, 1H, J=7.6 Hz), 6.83 (d, 1H, J=7.6 Hz), 4.92 (s, 1H), 4.54 (d, 1H, J=18.4 Hz), 4.40 (d, 2H, J=18.4 Hz), 4.08–4.00 (m, 1H), 3.91 (d, 1H, J=15.2 Hz), 3.60 (s, 2H), 3.06 (s, 2H);

LC-MS: $R_t$: 1.41 min, m/z: 432 [M+H]$^+$

Example 18

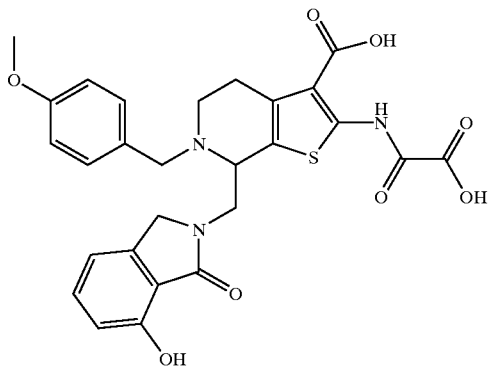

7-(7-Hydroxy-1-oxo-1,3-dihydro-isoindol-2-ylmethyl)-6-(4-methoxy-benzyl)-2-(oxalyl-amino)-4,5,6,7-tetrahydro-thieno[2,3-c]pyridine-3-carboxylic acid To a solution of trifluoroacetic acid (0.5 ml) and dichloromethane (0.5 ml) was added 2-(tert-butoxyoxalyl-amino)-7-(7-(tert-butyl-dimethyl-silanyloxy)-1-oxo-1,3-dihydro-isoindol-2-ylmethyl)-6-(4-methoxy-benzyl)-4,5,6,7- tetrahydro-thieno[2,3-c]pyridine-3-carboxylic acid tert-butyl ester (10 mg, 0.013 mmol). The solution was stirred at room temperature for 16 hours. The solvent was removed in vacuo and the residue was washed with dichloromethane, which afforded 6.8 mg (92%) of the title compound as a solid trifluoroacetate.

$^1$H-NMR (DMSO-$d_6$): δ12.35 (s, 1H), 9.90 (s, 1H), 9.70 (s, 2H), 7.41 (t, 1H, J=8.0 Hz), 7.28 (s, 2H), 7.04 (d, 1H, J=7.2 Hz), 6.92 (s, 2H), 6.83 (d, 1H, J=7.2 Hz), 4.90–3.60 (m, 11H), 3.80 (s, 3H).

LC-MS: $R_t$=1.92 min, m/z: 552 [M+H]$^+$

Example 19

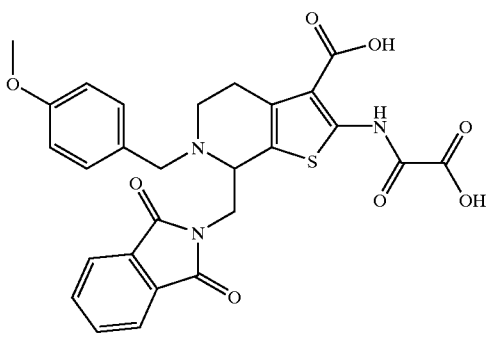

7-(1,3-Dioxo-1,3-dihydro-isoindol-2-ylmethyl)-6-(4-methoxy-benzyl)-2-(oxalyl-amino)-4,5,6,7-tetrahydro-thieno[2,3-c]pyridine-3-carboxylic acid To a stirred solution of 2-amino-7-(1,3-dioxo-1,3-dihydro-isoindol-2-ylmethyl)-6-(4-methoxy-benzyl)-4,5,6,7-tetrahydro-thieno[2,3-c]pyridine-3-carboxylic acid tert-butyl ester (10 mg, 0.019 mmol) in tetrahydrofuran (1.0 ml) was added imidazol-1-yl-oxo-acetic acid tert-butyl ester (18 mg, 0.092 mmol) in tetrahydrofuran (1.0 ml). The mixture was stirred at room temperature for 24 hours. The solvent was removed in vacuo. The residue was dissolved in ethyl acetate (20 ml) and washed with 0.5 N hydrochloric acid solution (2×10 ml), saturated sodium bicarbonate (2×10 ml), brine (10 ml), dried (MgSO$_4$), and filtered. The solvent was removed in vacuo and the residue was chromatographed using a gradient of 10–25% ethyl acetate/hexane as eluent, which afforded 11 mg (89%) of 2-(tert-butoxyoxalyl-amino)-7-(1,3-dioxo-1,3-dihydro-isoindol-2-ylmethyl)-6-(4-methoxy-benzyl)-4,5,6,7-tetrahydro-thieno[2,3-c]pyridine-3-carboxylic acid tert-butyl ester as a solid.

$^1$H-NMR (CDCl$_3$): δ12.54 (s, 1H), 7.76 (m, 4H), 6.82 (d, 2H, J=11.6 Hz), 6.33 (d, 2H, J=11.6 Hz), 4.02 (d, 1H, J=14.4 Hz), 3.98 (d, 1H, J=14.4 Hz), 3.62 (s, 3H), 3.62–3.54 (m, 2H), 3.48–3.34 (m, 2H), 3.02–2.70 (m, 3H), 1.60 (s, 9H), 1.59 (s, 9H).

To a solution of trifluoroacetic acid (0.5 ml) and dichloromethane (0.5 ml) was added 2-(tert-butoxyoxalyl-amino)-7-(1,3-dioxo-1,3-dihydro-isoindol-2-ylmethyl)-6-(4-methoxy-benzyl)-4,5,6,7-tetrahydro-thieno[2,3-c]pyridine-3-carboxylic acid tert-butyl ester (10 mg, 0.015 mmol). The solution was stirred at room temperature for 16 hours. The solvent was removed in vacuo and the residue was washed with dichloromethane, which afforded 6.8 mg (80%) of the title compound as a solid trifluoroacetate.

$^1$H-NMR (DMSO-$d_6$): δ12.38 (s, 1H), 7.86 (m, 4H), 6.82 (s, 2H), 6.30 (s, 2H), 4.00–2.86 (m, 9H), 3.58 (s, 3H);

LC-MS: $R_t$=2.02 min; m/z: 550 [M+H]$^+$

Example 20

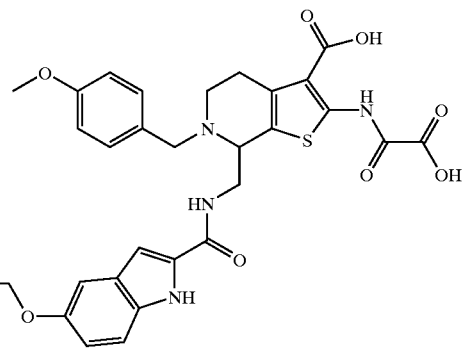

7-(((5-Benzyloxy-1H-indole-2-carbonyl)amino)methyl)-6-(4-methoxy-benzyl)-2-(oxalyl-amino)-4,5,6,7-tetrahydro-thieno[2,3-c]pyridine-3-carboxylic acid 2-Amino-7-aminomethyl-6-(4-methoxy-benzyl)-4,5,6,7-tetrahydro-thieno[2,3-c]pyridine-3-carboxylic acid tert-butyl ester (0.50 g; 1.2 mmol) was dissolved in N,N-dimethylformamide (20 ml). 1-Hydroxy-7-azabenzotriazole (0.19 g; 1.3 mmol) and N-(3-dimethylaminopropyl)-N'-ethylcarbodiimide hydrochloride (0.26 g; 1.3 mmol) and diisopropyl-ethylamine (0.23 ml; 1.3 mmol) were added and the mixture was stirred for 15 min. 5-Benzyloxyindole (0.36 g; 1.3 mmol) was dissolved in N,N-dimethylformamide (20 ml) and added. Diisopropylethylamine (0.23 ml; 1.3 mmol) was added and the mixture was stirred overnight. The solvent was removed in vacuo, the residue dissolved in dichloromethane (30 ml) and the organic phase washed with an aqueous solution of sodium hydrogencarbonate (15 ml). The organic phase was dried (MgSO$_4$), filtered and the solvent removed in vacuo. The residue was chromatographed on silica using ethyl acetate/heptane (1:1) as eluent affording 569 mg of 2-amino-7-(((5-benzyloxy-1H-indole-2-carbonyl)amino)methyl)-6-(4-methoxy-benzyl)-4,5,6,7-tetrahydro-thieno[2,3-c]pyridine-3-carboxylic acid tert-butyl ester as an oil.

The title compound was prepared in a similar way as described in Example 1 using the two last steps.

MS: m/z: 669.4 [M+H]$^+$

Calculated for $C_{35}H_{32}N_4O_8S$, 2/3×$C_2HF_3O_2$, 4/3×$H_2O$; C, 56.77%; H, 4.63%; N, 7.29%. Found: C, 56.43%; H, 4.57%; N, 7.13%.

Example 21

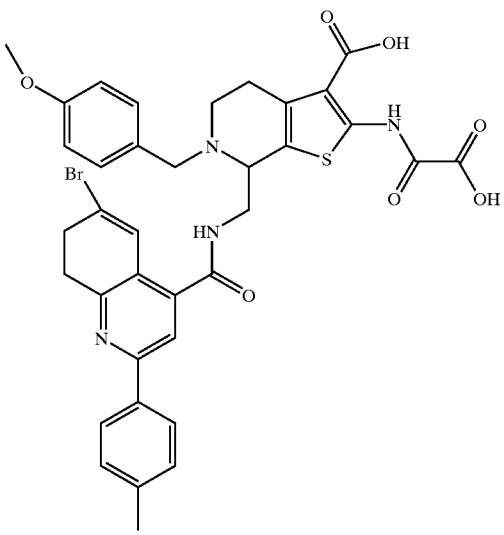

7-(((6-Bromo-2-p-tolyl-quinoline-4-carbonyl)amino)methyl)-6-(4-methoxy-benzyl)-2-(oxalyl-amino)-4,5,6,7-tetrahydro-thieno[2,3-c]pyridine-3-carboxylic acid The title compound was prepared in a similar way as in Example 19 using 6-bromo-2-p-tolyl-quinoline-4-carboxylic acid and 2-amino-7-aminomethyl6-(4-methoxy-benzyl)-4,5,6,7-tetrahydro-thieno[2,3-c]pyridine-3-carboxylic acid tert-butyl ester as the starting material.

LC-MS: m/z: 745.2 [M+H]$^+$

Calculated for $C_{36}H_{31}BrN_4O_7S$, $2 \times C_2HF_3O_2$; C, 49.44%; H, 3.42%; N, 5.77%. Found: C, 49.19%; H, 3.59%; N, 6.00%.

Example 22

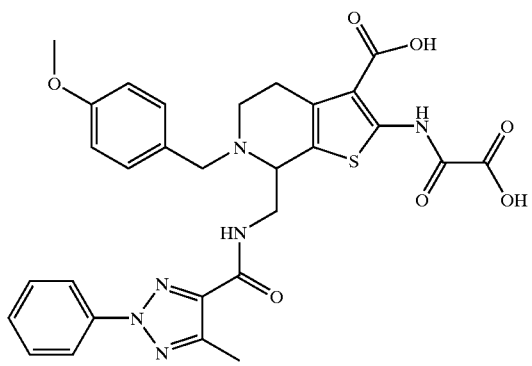

6-(4-Methoxy-benzyl)-7-(((5-methyl-2-phenyl-2H-[1,2,3]triazole-4-carbonyl)amino)methyl)-2-(oxalyl-amino)-4,5,6,7-tetrahydro-thieno[2,3-c]pyridine-3-carboxylic acid The title compound was prepared in a similar way as in Example 19 using 5-methyl-2-phenyl-2H-[1,2,3]triazole-4-carboxylic acid and 2-amino-7-aminomethyl-6-(4-methoxy-benzyl)-4,5,6,7-tetrahydro-thieno[2,3-c]pyridine-3-carboxylic acid tert-butyl ester as the starting material.

LC-MS: m/z: 605.2 [M+H]$^+$

Calculated for $C_{29}H_{28}N_6O_7S$, $1.3 \times C_2HF_3O_2$, $1.7 \times H_2O$; C, 48.14%; H, 3.94%; N, 10.94%. Found: C, 48.35%; H, 4.19%; N, 10.68%.

Example 23

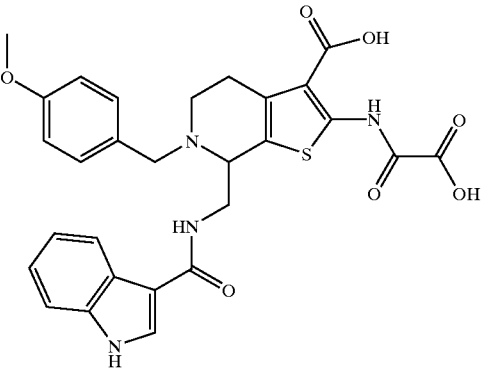

7-(((1H-indole-3-carbonyl)amino)methyl)-6-(4-methoxy-benzyl)-2-(oxalyl-amino)-4,5,6,7-tetrahydro-thieno[2,3-c]pyridine-3-carboxylic acid The title compound was prepared in a similar way as in Example 19 using 3-indole-carboxylic acid and 2-amino-7-aminomethyl-6-(4-methoxy-benzyl)-4,5,6,7-tetrahydro-thieno[2,3-c]pyridine-3-carboxylic acid tert-butyl ester as the starting material.

LC-MS: m/z: 563.2 [M+H]$^+$

Calculated for $C_{28}H_{26}N_4O_7S$, $5/3 \times C_2HF_3O_2$; C, 49.63%; H, 3.82%; N, 7.35%. Found: C, 50.00%; H, 3.71%; N, 7.44%.

Example 24

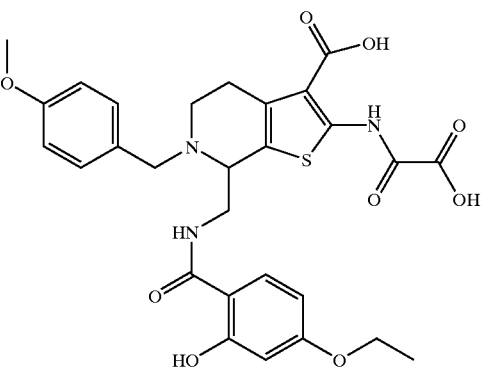

7-((4-Ethoxy-2-hydroxy-benzoylamino)methyl)-6-(4-methoxy-benzyl)-2-(oxalyl-amino)-4,5,6,7-tetrahydro-thieno[2,3-c]pyridine-3-carboxylic acid The title compound was prepared in a similar way as in Example 19 using 4-ethoxy-2-hydroxy-benzoic acid and 2-amino-7-aminomethyl-6-(4-methoxy-benzyl)-4,5,6,7-tetrahydro-thieno[2,3-c]pyridine-3-carboxylic acid tert-butyl ester as the starting material.

LC-MS: m/z: 584 [M+H]$^+$

HPLC: (B6): 23.8 min.

Example 25

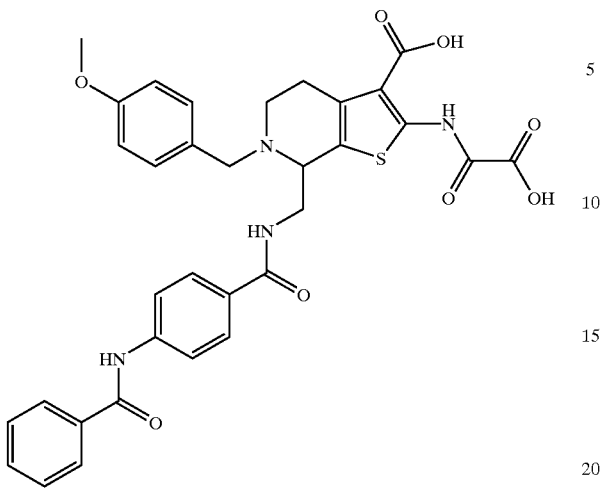

7-((4-Benzoylamino-benzoylamino)methyl)-6-(4-methoxy-benzyl)-2-(oxalyl-amino)-4,5,6,7-tetrahydro-thieno[2,3-c]pyridine-3-carboxylic acid The title compound was prepared in a similar way as in Example 19 using 4-benzoylaminobenzoic acid and 2-amino-7-aminomethyl-6-(4-methoxy-benzyl)-4,5,6,7-tetrahydro-thieno[2,3-c]pyridine-3-carboxylic acid tert-butyl ester as the starting material.

LC-MS: m/z: 643.1 [M+H]$^+$

Calculated for $C_{33}H_{30}N_4O_8S$, $3 \times C_2HF_3O_2$; C, 47.57%; H, 3.38%; N, 5.69%. Found: C, 47.34%; H, 3.55%; N, 5.62%.

Example 26

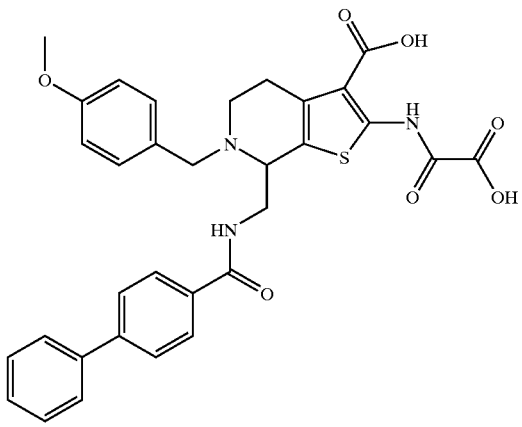

7-(((Biphenyl-4-carbonyl)amino)methyl)-6-(4-methoxy-benzyl)-2-(oxalyl-amino)-4,5,6,7-tetrahydro-thieno[2,3-c]pyridine-3-carboxylic acid The title compound was prepared in a similar way as in Example 19 using 4-phenylbenzoic acid and 2-amino-7-aminomethyl-6-(4-methoxy-benzyl)-4,5,6,7-tetrahydro-thieno[2,3-c]pyridine-3-carboxylic acid tert-butyl ester as the starting material.

LC-MS: m/z: 599.0 [M+H]$^+$

Calculated for $C_{32}H_{29}N_3O_7S$, $2 \times C_2HF_3O_2$, $1 \times H_2O$; C, 51.13%; H, 3.93%; N, 4.97%. Found: C, 52.02%; H, 4.02%; N, 5.16%.

Example 27

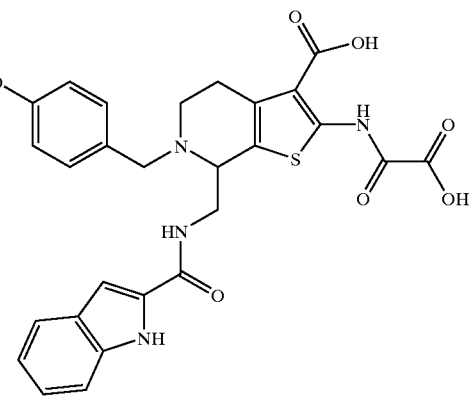

7-(((1H-Indole-2-carbonyl)amino)methyl)-6-(4-methoxy-benzyl)-2-(oxalyl-amino)-4,5,6,7-tetrahydro-thieno[2,3-c]pyridine-3-carboxylic acid The title compound was prepared in a similar way as in Example 19 using indole-2-carboxylic acid and 2-amino-7-aminomethyl-6-(4-methoxy-benzyl)-4,5,6,7-tetrahydro-thieno[2,3-c]pyridine-3-carboxylic acid tert-butyl ester as the starting material.

LC-MS: m/z: 563.2 [M+H]$^+$

HPLC (B6) $R_t$=23.07 min.

Example 28

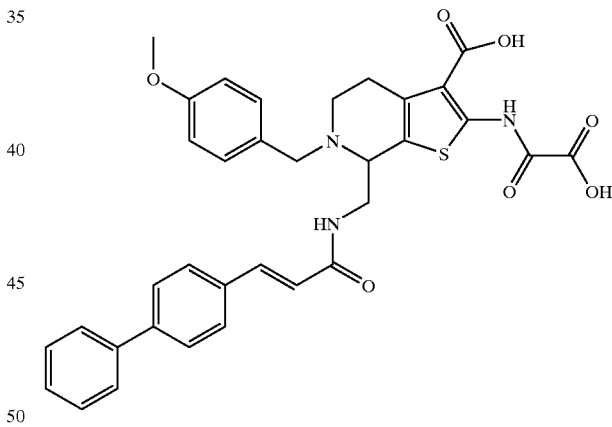

7-((3-Biphenyl-4-yl-acryloylamino)methyl)-6-(4-methoxy-benzyl)-2-(oxalyl-amino)-4,5,6,7-tetrahydro-thieno[2,3-c)pyridine-3-carboxylic acid The title compound was prepared in a similar way as in Example 19 using 3-biphenyl-4-yl-acrylic acid and 2-amino-7-aminomethyl-6-(4-methoxy-benzyl)-4,5,6,7-tetrahydro-thieno[2,3-c]pyridine-3-carboxylic acid tert-butyl ester as the starting material.

LC-MS: m/z: 626.2 [M+H]$^+$

HPLC (B6) $R_t$=28.74 min.

Calculated for $C_{34}H_{31}N_3O_7S$, $2 \times C_2HF_3O_2$; C, 53.46%; H, 3.90%; N, 4.92%. Found: C, 53.89%; H, 4.23%; N, 5.08%.

Example 29

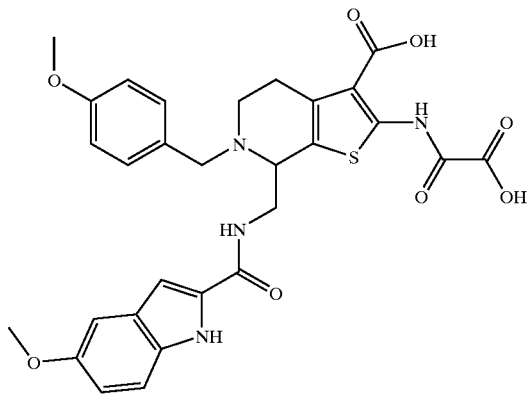

6-(4-Methoxy-benzyl)-7-(((5-methoxy-1H-indole-2-carbonyl)amino)-methyl)-2-(oxalyl-amino)-4,5,6,7-tetrahydro-thieno[2,3-c]pyridine-3-carboxylic acid The title compound was prepared in a similar way as in Example 19 using 5-methoxyindole-2-carboxylic acid and 2-amino-7-aminomethyl-6-(4-methoxy-benzyl)-4,5,6,7-tetrahydro-thieno[2,3-c]pyridine-3-carboxylic acid tert-butyl ester as the starting material.

LC-MS: m/z: 593.2 [M+H]$^+$

HPLC (B6) R$_t$=21.81 min.

Example 30

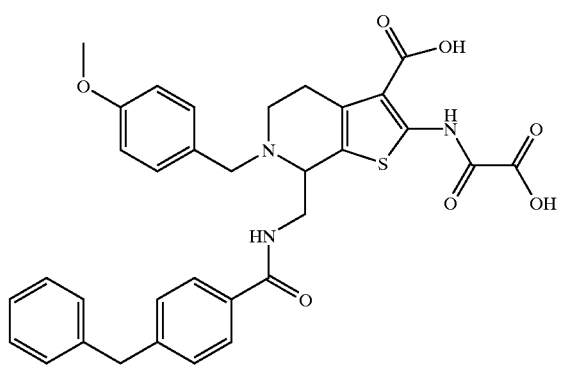

7-((4-Benzyl-benzoylamino)methyl)-6-(4-methoxy-benzyl)-2-(oxalyl-amino)-4,5,6,7-tetrahydro-thieno[2,3-c]pyridine-3-carboxylic acid The title compound was prepared in a similar way as in Example 19 using 4-benzylbenzoic acid and 2-amino-7-aminomethyl-6-(4-methoxy-benzyl)-4,5,6,7-tetrahydro-thieno[2,3-c]pyridine-3-carboxylic acid tert-butyl ester as the starting material.

LC-MS: m/z: 614.2 [M+H]$^+$

HPLC (B6) R$_t$=27.23 min.

Calculated for $C_{33}H_{31}N_3O_7S$, $1.5 \times C_2HF_3O_2$, $1 \times H_2O$; C, 53.87%; H, 4.33%; N, 5.23%. Found: C, 53.92%; H, 4.24%; N, 5.18%.

Example 31

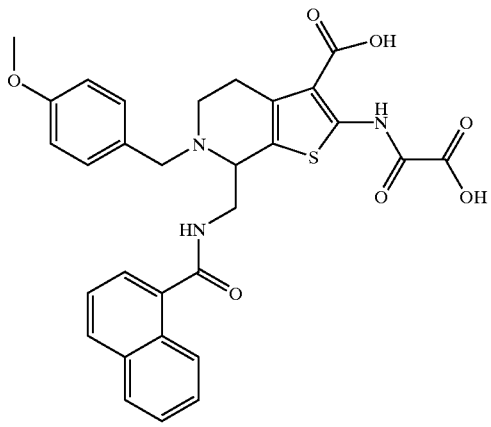

6-(4-Methoxy-benzyl)-7-(((naphthalene-1-carbonyl)amino)methyl)-2-(oxalyl-amino)-4,5,6,7-tetrahydro-thieno[2,3-c]pyridine-3-carboxylic acid The title compound was prepared in a similar way as in Example 19 using 1-napthylcarboxylic acid and 2-amino-7-aminomethyl-6-(4-methoxy-benzyl)-4,5,6,7-tetrahydro-thieno[2,3-c]pyridine-3-carboxylic acid tert-butyl ester as the starting material.

LC-MS: m/z: 574.0 [M+H]$^+$

HPLC (B6) R$_t$=22.51 min.

Calculated for $C_{30}H_{27}N_3O_7S$, $2 \times C_2HF_3O_2$; C, 50.94%; H, 3.65%; N, 5.24%. Found: C, 51.39%; H, 3.79%; N, 5.16%.

Example 32

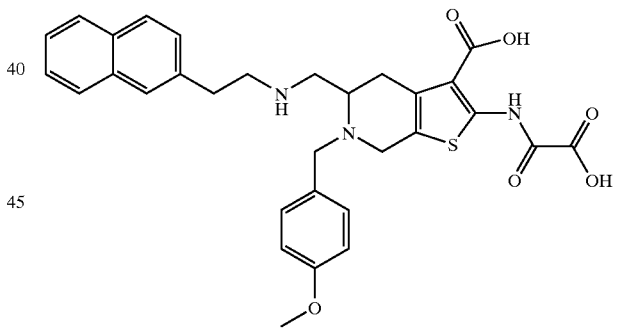

6-(4-Methoxy-benzyl)-5-((2-naphthalen-2-yl-ethylamino)methyl)-2-(oxalyl-amino)-4,5,6,7-tetrahydro-thieno[2,3-c]pyridine-3-carboxylic acid A solution of 2-naphthalen-2-yl-ethanol (1.02 g, 5.8 mmol), 2,2,6,6-tetramethyl-1-piperidinyloxy (TEMPO) (9 mg, 0.058 mmol) and sodium bromide (0.65 g, 6.4 mmol) in a mixture of toluene (18 mL), ethyl acetate (18 mL), and water (3 mL) was cooled to 0° C. and added dropwise over 1 hour a solution containing the following: sodium hypochlorite (17.2 mL, 0.37 M, 6.4 mmol) and sodium hydrogencarbonate (1.46 g, 17.4 mmol). The reaction mixture was stirred at 0° C. for 10 min., and the phases separated. The aqueous layer was extracted with ethyl acetate (150 mL). The combined organic phases were washed with a solution of potassium iodone (0.2 g) in 10% aqueous potassium hydrogensulfate (150 mL), water (150 mL), brine (150 mL), dried (MgSO₄), filtered, and concentrated in vacuo to provide 980 mg of a 3:1 mixture of naphthalen-2-yl-acetaldehyde and 2-naphthalen-2-yl-ethanol.

¹H-NMR (CDCl₃): δ9.81 (t, 1H, J=1.5 Hz), 7.92–7.80 (m, 3H), 7.68 (bs, 1H), 7.55–7.42 (m, 3H), 3.87 (d, 2H, J=1.5 Hz).

To a solution of 2-amino-5-aminomethyl-6-(4-methoxy-benzyl)-4,5,6,7-tetrahydro-thieno[2,3-c]pyridine-3-carboxylic acid tert-butyl ester (290 mg, 0.71 mmol) in 1,2-dichloroethane (3 ml) was added the above mixture of 2-naphthyl-acetaldehyde (100 mg, 0.59 mmol), sodium triacetoxyborohydride (190 mg, 0.88 mmol) and the mixture was stirred at room temperature under nitrogen for 2.5 hours. The crude reaction mixture was quenched with saturated sodium bicarbonate (50 ml) and the solution extracted with ethyl acetate (100 ml). The organic phase was dried (MgSO₄), filtered, and concentrated in vacuo providing a foam, which was taken directly to the next step. LC-MS showed that 2-amino-6-(4-methoxy-benzyl)-5-((2-naphthalen-2-yl-ethylamino)-methyl)-4,5,6,7-tetrahydro-thieno[2,3-c]pyridine-3-carboxylic acid tert-butyl ester was the major component. LC-MS: m/z: 558.1 [M+H]⁺, $R_f$=2.23 min.

To a solution of 2-amino-6-(4-methoxy-benzyl)-5-((2-naphthalen-2-yl-ethylamino)methyl)-4,5,6,7-tetrahydro-thieno[2,3-c]pyridine-3-carboxylic acid tert-butyl ester in tetrahydrofuran (3 ml) was added di-tert-butyl-dicarbonate (188 mg, 0.85 mmol) and N,N-dimethylformamide (18 mg, 0.14 mmol). The reaction was stirred at room temperature for 7 hours under nitrogen. The crude reaction mixture was diluted with dichloromethane (50 ml) and washed with water (50 ml) and brine (50 ml). The organic phase was dried (MgSO₄), filtered, and concentrated in vacuo affording a foam, which was used without further purification in the next step.

LC-MS showed that 2-amino-5-((tert-butoxycarbonyl-(2-naphthalen-2-yl-ethyl)-amino)-methyl)-6-(4-methoxy-benzyl)-4,5,6,7-tetrahydro-thieno[2,3-c]pyridine-3-carboxylic acid tert-butyl ester was the major component.

$R_f$=2.74, m/z: 658.1 [M+H]⁺, Calculated: 657.4.

To crude 2-amino-5-((tert-butoxycarbonyl-(2-naphthalen-2-yl-ethyl)-amino)-methyl)-6-(4-methoxy-benzyl)-4,5,6,7-tetrahydro-thieno[2,3-c]pyridine-3-carboxylic acid tert-butyl ester was added dichloromethane (5 ml) and imidazol-1-yl-oxo-acetic acid tert-butyl ester (400 mg, 1.78 mmol) and the reaction mixture stirred at room temperature for 12 hours. The crude reaction mixture was added to dichloromethane (50 ml) and washed with water (50 ml) and brine (50 ml). The organic phase was dried (MgSO₄), filtered, and concentrated in vacuo. The residue was purified by flash chromatography using a mixture of dichloromethane/ethyl acetate (10:1) as eluent, which afforded 20.3 mg (39% over tree steps) of 2-(tert-butoxyoxalyl-amino)-5-((tert-butoxycarbonyl-(2-naphthalen-2-yl-ethyl)-amino)methyl)-6-(4-methoxy-benzyl)-4,5,6,7-tetrahydro-thieno[2,3-c]pyridine-3-carboxylic acid tert-butyl ester as a foam.

¹H NMR (CDCl₃) δ7.99–7.92 (m, 3H), 7.88 (s, 1H), 7.68–7.57 (m, 3H), 7.45 (d, 2H, J=7.8 Hz), 6.99 (d, 2H, J=8.1 Hz), 3.90–3.75 (m, 7H), 3.56–3.42 (m, 5H), 3.19–3.13 (m, 2H), 2.88–2.82 (m, 2H), 1.79 (s, 9H), 1.71 (s, 18H);

LC-MS: m/z: 786.2 [M+H]⁺, $R_f$=3.03 min.

To a solution of 2-(tert-butoxyoxalyl-amino)-5-((tert-butoxycarbonyl-(2-naphthalen-2-yl-ethyl)-amino)methyl)-6-(4-methoxy-benzyl)-4,5,6,7-tetrahydro-thieno[2,3-c] pyridine-3-carboxylic acid tert-butyl ester (20 mg, 0.03 mmol) in dry dichloromethane (200 μl) at 0° C. was added 50% trifluoroacetic acid in dichloromethane (2.5 ml). The reaction was stirred for 14 hours at room temperature and then concentrated in vacuo. The resultant solid was re-suspended in dichloromethane, filtered, and dried in vacuo to provide 13 mg (90%) of the title compound as a solid.

¹H NMR (DMSO-d₆) δ9.15 (s, 1H), 8.09–8.01 (m, 3H), 7.93 (s, 1H), 7.68–7.57 (m, 3H), 7.45 (d, 2H, J=7.8 Hz), 6.99 (d, 2H, J=8.1 Hz), 4.18–4.12 (m, 2H), 3.90–3.75 (m, 7H), 3.56–3.42 (m, 3H), 3.19–3.13 (m, 2H), 2.88–2.82 (m, 2H);

LC-MS: m/z: 574.7 [M+H]⁺, $R_f$=1.36 min.

Example 33

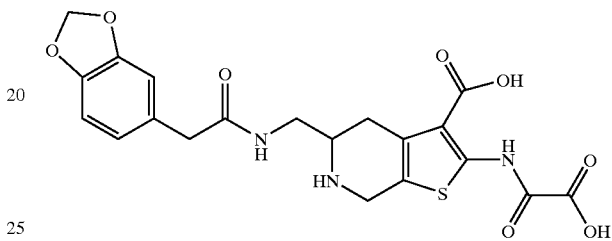

5-((2-Benzo[1,3]dioxol-5-yl-acetylamino)methyl)-2-(oxalyl-amino)-4,5,6,7-tetrahydro-thieno[2,3-c]pyridine-3-carboxylic acid To a mixture of 2-amino-5-aminomethyl-6-(4-methoxy-benzyl)-4,5,6,7-tetrahydro-thieno[2,3-c]pyridine-3-carboxylic acid tert-butyl ester (300 mg, 0.74 mmol), benzo[1,3]dioxol-5-yl-acetic acid (134 mg, 0.74 mmol), 1-hydroxybenzotriazole hydrate (111 mg, 0.82 mmol), and N,N-diisopropyl-ethylamine (258 μL, 1.48 mmol) in acetonitrile (5 ml) at room temperature was added 1-(3-dimethylaminopropyl)-3-ethylcarbodiimide hydrochloride (157 mg, 0.82 mmol). The reaction mixture was stirred for 16 hours and the solvent evaporated in vacuo. The residue was taken into ethylacetate (50 ml), washed with water, 1 N hydrochloric acid, saturated sodium bicarbonate, brine, dried (MgSO₄), filtered and the solvent evaporated in vacuo. The residue was subjected to flash chromatography using a gradient of 10–20% ethylacetate/hexanes as eluent, which afforded 268 mg (64%) of 2-amino-5-((2-benzo[1,3]dioxol-5-yl-acetylamino)methyl)-6-(4-methoxy-benzyl)-4,5,6,7-tetrahydro-thieno[2,3-c]pyridine-3-carboxylic acid tert-butyl ester as an oil.

¹H-NMR (CDCl₃) δ6.95 (bs, 2H), 6.75–6.85 (m, 5H), 5.96 (bs, 2H), 5.95 (s, 2H), 3.81 (s, 3H), 3.75–3.30 (m, 5H), 3.53 (s, 2H), 3.18 (bs, 2H), 2.82 (d, 1H, J=17 Hz), 2.52 (d, 1H, J=17 Hz).

To a solution of 2-amino-5-((2-benzo[1,3]dioxol-5-yl-acetylamino)methyl)-6-(4-methoxy-benzyl)-4,5,6,7-tetrahydro-thieno[2,3-c]pyridine-3-carboxylic acid tert-butyl ester (133 mg, 0.235 mmol) in tetrahydrofuran (1 ml) was added imidazol-1-yl-oxo-acetic acid tert-butyl ester (100 mg, 0.51 mmol). The mixture was stirred at room temperature for 24 hours. The solvent was removed in vacuo. The residue was taken into ethyl acetate (50 ml) washed with saturated sodium bicarbonate, brine, dried (Na₂SO₄) and filtered. The solvent was removed in vacuo and the residue was chromatographed using a gradient of 10–20% ethyl acetate/dichloromethane, which afforded 130 mg (80%) of 2-(tert-butoxyoxalyl-amino)-5-((2-benzo[1,3]

dioxol-5-yl-acetylamino)methyl)-6-(4-methoxy-benzyl)-4,5,6,7-tetrahydro-thieno[2,3-c]pyridine-3-carboxylic acid tert-butyl ester as an oil.

$^{1}$H-NMR (CDCl$_{3}$) δ12.50 (s, 1H), 7.95–7.75 (m, 7H), 5.96 (s, 2H), 3.81 (s, 3H), 3.80–3.40 (m, 5H), 3.15 (bs, 2H), 2.90 (d, 1H, J=17 Hz), 2.58 (d, 1H, J=17 Hz), 1.61 (s, 9H), 1.60 (s, 9H).

A solution of 2-(tert-butoxyoxalyl-amino)-5-((2-benzo[1,3]dioxol-5-yl-acetylamino)methyl)-6-(4-methoxy-benzyl)-4,5,6,7-tetrahydro-thieno[2,3-c]pyridine-3-carboxylic acid tert-butyl ester (130 mg, 0.188 mmol) in tetrahydrofuran (2 ml) was passed through a Raney Ni bed (120 mg, 50% Raney Ni-water washed with methanol (6 ml) and tetrahydrofuran (6 ml) and dried before use). The Raney Ni bed was washed with tetrahydrofuran (10 ml). The filtrate and washes were combined and the solvent evaporated in vacuo. The residue was dissolved in 10% formic acid/methanol (6 ml) and stirred with 10% Pd/C (120 mg) for 13 hours. Saturated sodium bicarbonate solution (60 ml) was added to the solution. The mixture was extracted with dichloromethane. The extracts were combined, dried (Na$_{2}$SO$_{4}$) and filtered. The solvent was removed in vacuo and the residue was washed with 50% hexane/diethyl ether to afford 62 mg (57%) of 2-(tert-butoxyoxalyl-amino)-5-((2-benzo[1,3]dioxol-5-yl-acetylamino)methyl)-4,5,6,7-tetrahydro-thieno[2,3-c]pyridine-3-carboxylic acid tert-butyl ester as an oil.

$^{1}$H-NMR (CDCl$_{3}$) δ12.59 (s, 1H), 6.80–6.70 (m, 3H), 5.96 (s, 2H), 4.05 (q, 2H, J=15 Hz), 3.85–3.60 (m, 2H), 3.25–3.00 (m, 4H), 2.58 (m, 1H), 1.61 (s, 9H), 1.59 (s, 9H); LC-MS: R$_{f}$=1.75 min, m/z: 574 [M+H]$^{+}$.

A solution of 2-(tert-butoxyoxalyl-amino)-5-((2-benzo[1,3]dioxol-5-yl-acetylamino)methyl)-4,5,6,7-tetrahydro-thieno[2,3-c]pyridine-3-carboxylic acid tert-butyl ester (62 mg, 0.11 mmol) in 50% trifluoroacetic acid-dichloromethane (2 ml) was left in an open flask over the weekend and then the solvent was removed in vacuo. The residue was washed with dichloromethane and the solid filtered off affording 39 mg (62%) of the title compounds as a solid trifluoroacetate.

$^{1}$H-NMR (DMSO-d$_{6}$) δ12.39 (s, 1H), 9.18 (bs, 1H), 9.10 (bs, 1H), 8.35 (s, 1H), 6.83 d, 1H, J=1.2 Hz), 6.82 (d, 1H, J=8.4 Hz), 6.70 (dd, 1H, J=8.4 Hz and J=1.2 Hz), 5.96 (s, 2H), 4.38 (d, 1H, J=14 Hz), 4.28 (m, 1H), 3.60–3.40 (m, 4H), 3.16 (d, 2H, J=14 Hz), 2.80 dd, 1H, J=14 Hz and J=11 Hz);

LC-MS: R$_{f}$=1.11 min, m/z: 462 [M+H]$^{+}$.

Example 34

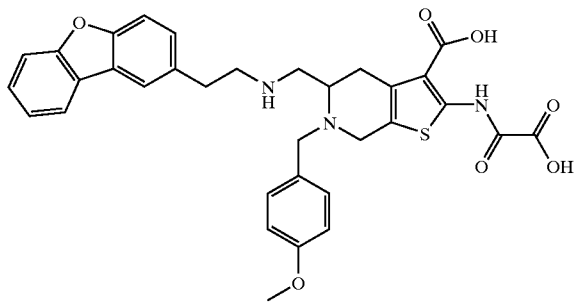

5-((2-Dibenzofuran-2-yl-ethyl)amino)methyl)-6-(4-methoxy-benzyl)-2-(oxalyl-amino)-4,5,6,7-tetrahydro-thieno[2,3-c]pyridine-3-carboxylic acid To a solution of 2-dibenzofuran-2-yl-ethanol (200 mg, 0.94 mmol) and 2,2,6,6-tetramethyl-1-piperidinyloxy (TEMPO) (2 mg, 0.009 mmol) in dichloromethane (2 mL) was added an aqueous solution of sodium bromide (97 mg in 1.3 mL of water for a 0.7M solution, 0.94mmol) and cooled to 0° C. To this mixture was added dropwise over 30 min., a solution containing the following: sodium hypochlorite (1.4 mL, 0.74 M, 1.03 mmol) and sodium hydrogencarbonate (120 mg, 1.4 mmol) and water (1.4 mL). The reaction mixture was stirred at 0° C. for 0.5 hour and allowed to warm to room temperature. The organic phase and aqueous layer were separated and the aqueous layer extracted with dichloromethane (20 mL). The combined organic phases were washed with a solution of potassium iodone (0.2 g) in 10% aq. Potassium hydrogensulfate (20 mL), water (20 mL), brine (20 mL), dried (MgSO$_{4}$) filtered, and concentrated in vacuo to provide 198 mg of a 5:1 mixture of dibenzofuran-2-yl-acetaldehyde and 2-dibenzofuran-2-yl-ethanol as an oil.

$^{1}$H-NMR (CDCl$_{3}$): δ9.80 (t, 1H, J=1.5 Hz), 8.02 (d, 2H, J=8.2 Hz), 7.71 (bs, 1H), 7.75–7.42 (m, 4H), 3.82 (d, 2H, J=1.5 Hz).

To a solution of 2-amino-5-aminomethyl-6-(4-methoxy-benzyl)-4,5,6,7-tetrahydro-thieno[2,3-c]pyridine-3-carboxylic acid tert-butyl ester (340 mg, 0.85 mmol) in 1,2-dichloroethane (3 ml) was added the above mixture of dibenzofuran-2-yl-acetaldehyde (150 mg, 0.70 mmol), and sodium triacetoxyborohydride (225 mg, 1.07 mmol) and the mixture was stirred at room temperature under nitrogen for 2.5 hours. The crude reaction mixture was quenched with saturated sodium bicarbonate (50 ml) and the solution extracted with ethylacetate (100 ml). The organic phase dried (MgSO$_{4}$), filtered, and the solvent evaporated in vacuo. The crude residue was taken directly to the next step. LC-MS showed that 2-amino-5-((2-dibenzofuran-2-yl-ethylamino)methyl]-6-(4-methoxy-benzyl)-4,5,6,7-tetrahydro-thieno[2,3-c]pyridine-3-carboxylic acid tert-butyl ester was the major component in the crude mixture: m/z: 598.1 [M+H]$^{+}$, R$_{f}$=2.40 min).

Crude 2-amino-5-((2-dibenzofuran-2-yl-ethylamino)methyl]-6-(4-methoxy-benzyl)-4,5,6,7-tetrahydro-thieno[2,3-c]pyridine-3-carboxylic acid tert-butyl ester was diluted in tetrahydrofuran (3 ml) and di-tert-butyl dicarbonate (262 mg, 1.20 mmol) and 4-(N,N-dimethylamino)pyridine (25 mg, 0.20 mmol) were added. The reaction was stirred at room temperature for 7 hours under nitrogen. The crude reaction mixture was added to dichloromethane (50 ml) and washed with water (50 ml) and brine (50 ml). The organic phase was dried (MgSO$_{4}$), filtered, and concentrated in vacuo. The residue was used directly in the next step. LC-MS showed that 2-amino-5-((tert-butoxycarbonyl-(2-dibenzofuran-2-yl-ethyl)amino)-methyl)-6-(4-methoxy-benzyl)-4,5,6,7-tetrahydro-thieno[2,3-c]pyridine-3-carboxylic acid tert-butyl ester was the major component in the crude: R$_{f}$=2.76, m/z: 698.2 [M+H]$^{+}$.

To compound 2-amino-5-((tert-butoxycarbonyl-(2-dibenzofuran-2-yl-ethyl)amino)-methyl)-6-(4-methoxy-benzyl)-4,5,6,7-tetrahydro-thieno[2,3-c]pyridine-3-carboxylic acid tert-butyl ester was added dichloromethane (5ml) and imidazol-1-yl-oxo-acetic acid tert-butyl ester (420 mg, 2.12 mmol). The reaction mixture was stirred at room temperature for 12 hours. The crude reaction mixture was added to dichloromethane (50 ml) and washed with water (50 ml) and brine (50 ml). The organic phase was dried (MgSO$_{4}$), filtered, and concentrated in vacuo. The residue was subjected to flash chromatography using a mixture of dichloromethane/ethyl acetate (10:1) as eluent, which afforded 35.2 mg (51% over 3 steps) of 2-(tert-butoxyoxalyl-amino)-5-((tert-butoxycarbonyl-(2-dibenzofuran-2-yl-ethyl)

amino)methyl)-6-(4-methoxy-benzyl)-4,5,6,7-tetrahydro-thieno[2,3-c]pyridine-3-carboxylic acid tert-butyl ester as a foam.

$^1$H-NMR (CDCl$_3$) δ7.95–7.90 (m, 3H), 7.84 (s, 1H), 7.68–7.57 (m, 3H), 7.45 (d, 2H, J==7.8 Hz), 6.95 (m, 3H), 3.90–3.75 (m, 7H), 3.56–3.42 (m, 5H), 3.19–3.13 (m, 2H), 2.88–2.82 (m, 2H), 1.79 (s, 9H), 1.71 (s, 18H);

LC-MS: R$_f$=3.03 min, m/z: 826.2 [M+H]$^+$.

To a solution of 2-(tert-butoxyoxalyl-amino)-5-((tert-butoxycarbonyl-(2-dibenzofuran-2-yl-ethyl)amino)methyl)-6-(4-methoxy-benzyl)-4,5,6,7-tetrahydro-thieno[2,3-c]pyridine-3-carboxylic acid tert-butyl ester (28 mg, 0.034 mmol) in dry dichloromethane (200 μL) at 0° C. was added 50% trifluoroacetic acid in dichloromethane (2.5 ml). The reaction was stirred for 14 hours at room temperature and then concentrated in vacuo. The resultant solid was re-suspended in dichloromethane, filtered, and dried in vacuo, which afforded 22 mg (90%) of the title compound as a solid trifluoroacetate.

$^1$H-NMR (DMSO-d$_6$) δ9.15 (s, 1H), 8.11–8.21 (m, 3H), 7.93 (s, 1H), 7.68–7.57 (m, 3H), 7.45 (d, 2H, J=7.8 Hz), 6.99 (d, 2H, J=8.1 Hz), 4.18–4.12 (m, 2H), 3.90–3.75 (m, 7H), 3.56–3.42 (m, 3H), 3.19–3.13 (m, 2H), 2.88–2.82 (m, 2H);

LC-MS: R$_f$=3.03, m/z: 614.7 [M+H]$^+$.

Example 35

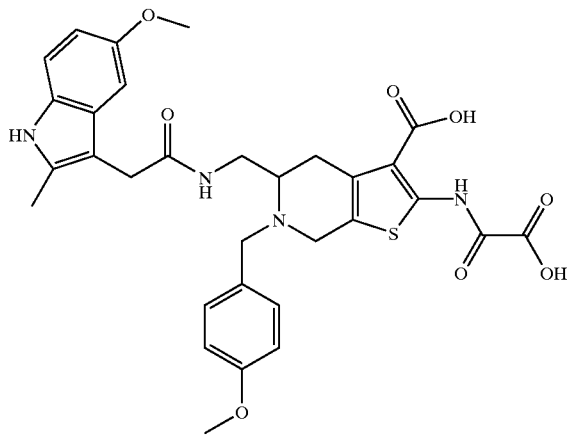

6-(4-Methoxy-benzyl)-5-((2-(5-methoxy-2-methyl-1H-indol-3-yl)-acetylamino)methyl)-2-(oxalyl-amino)-4,5,6,7-tetrahydro-thieno[2,3-c]pyridine-3-carboxylic acid To a solution of 2-amino-5-aminomethyl-6-(4-methoxy-benzyl)-4,5,6,7-tetrahydro-thieno[2,3-c]pyridine-3-carboxylic acid tert-butyl ester (202 mg, 0.50 mmol), in N,N-dimethylformamide (4 ml) was added 5-methoxy-2-methyl-3-indole acetic acid (170 mg, 0.74 mmol), 1-(3-dimethylamino-propyl)-3-ethylcarbodiimide, hydrochloride (150 mg, 0.75 mmol), and 1-hydroxybenzotriazole (105 mg, 0.74 mmol). The mixture was stirred at room temperature for 12 hours. The crude reaction mixture was diluted with dichloromethane (100 ml) and washed with water (100 ml), brine (100 ml), dried (MgSO$_4$), filtered, and concentrated in vacuo, which afforded 2-amino-6-(4-methoxy-benzyl)-5-((2-(5-methoxy-2-methyl-1H-indol-3-yl)acetylamino)methyl)-4,5,6,7-tetrahydro-thieno[2,3-c]pyridine-3-carboxylic acid tert-butyl ester as an oil.

$^1$H-NMR (CDCl$_3$) δ7.16 (d, 2H, J=10.8 Hz), 6.99 (d, 1H, J=2.5 Hz), 6.94 (m, 1H), 6.85 (dd, 1H, J=8.4 Hz and J=1.2 Hz), 6.78 (dd, 1H, J=8.3 Hz and J=1.2 Hz), 6.65 (m, 3H), 6.57 (m, 4H), 3.57 (t, 4H, J=3.0 Hz), 3.53 (m, 6H), 3.59–3.29 (m, 5), 3.12–2.92 (m, 4H), 2.39 (s, 3H), 1.6 (s, 9H);

LC-MS R$_f$=2.19, m/z: 605 [M+H]$^+$.

To a solution of 2-amino6-(4-methoxy-benzyl)-5-((2-(5-methoxy-2-methyl-1H-indol-3-yl)acetylamino)methyl)-4,5,6,7-tetrahydro-thieno[2,3-c]pyridine-3-carboxylic acid tert-butyl ester (96 mg, 0.5 mmol) in dichloromethane (5 ml) was added imidazol-1-yl-oxo-acetic acid tert-butyl ester (583 mg, 3.0 mmol) and the reaction stirred at room temperature for 24 hours. The mixture was then concentrated in vacuo. The residue was purified by flash column chromatography (25% ethylacetate/dichloromethane) to give 53 mg (15%) of 2-(tert-butoxyoxalyl-amino)-6-(4-methoxy-benzyl)-5-((2-(5-methoxy-2-methyl-1H-indol-3-yl)acetylamino)methyl)-4,5,6,7-tetrahydro-thieno[2,3-c]pyridine-3-carboxylic acid tert-butyl ester as an oil.

$^1$H-NMR (CDCl$_3$) δ7.16 (d, 2H, J=10.8 Hz), 6.99 (d, 1H, J=2.5 Hz), 6.94 (m, 1H), 6.85 (dd, 1H, J=8.4 Hz and J=1.2 Hz), 6.78 (dd, 1H, J=8.3 Hz and J=1.2 Hz), 6.65 (m, 3H), 6.56 (m, 3H), 3.57 (m, 3H), 3.53 (m, 6H), 3.59–3.29 (m, 5H), 3.12–2.92 (m, 4H), 2.39 (s, 3H), 1.6 (s, 18H);

LC-MS R$_f$=2.36 min, m/z: 733 [M+H]$^+$.

2-(tert-Butoxyoxalyl-amino)-6-(4-methoxy-benzyl)-5-((2-(5-methoxy-2-methyl-1H-indol-3-yl)acetylamino)methyl)-4,5,6,7-tetrahydro-thieno[2,3-c]pyridine-3-carboxylic acid tert-butyl ester was dissolved in 50% trifluoroacetic acid/dichloromethane (3 ml) and stirred at room temperature for 48 hours. The solvent was removed in vacuo and the residual trifluoroacetic acid was removed under reduced pressure to give 17 mg (49%) of the title compound as a solid trifluoroacetate.

$^1$H-NMR (DMSO-d$_6$) δ10.62 (s, 1H), 7.31 (s, 1H), 7.08 (d, 1H, J=10.2 Hz), 6.93 (s, 2H), 6.58 (dd, 1H, J$_1$=5.25 Hz and J$_2$=2.8 Hz), 3.84–3.44 (m, 19H, partially obscured by solvent), 2.95 (s, 1H), 2.28 (s, 3H), 1.31 (s, 1H), 1.19 (s, 2H);

LC-MS R$_f$=1.89 min, m/z: 621 [M+H]$^+$.

Example 36

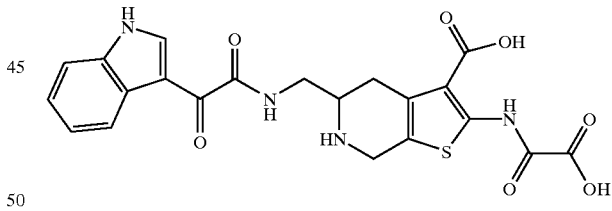

5-((2-(1H-indol-3-yl)-2-oxo-acetylamino)methyl)-2-(Oxalyl-amino)-4,5,6,7-tetrahydro-thieno[2,3-c]pyridine-3-carboxylic acid To a solution of 2-amino-5-aminomethyl-6-(4-methoxy-benzyl)-4,5,6,7-tetrahydro-thieno[2,3-c]pyridine-3-carboxylic acid tert-butyl ester (209 mg, 0.51 mmol) in dry N,N-dimethylformamide (4 ml) was added 3-indole-glyoxylic acid (141 mg, 0.74 mmol), 1-(3-dimethylaminopropyl)-3-ethylcarbodiimide, hydrochloride (152 mg, 0.76 mmol), and 1-hydroxy-benzotriazole (100 mg, 0.74 mmol). The mixture was stirred at room temperature for 16 hours, diluted with dichloromethane (100 ml) and washed with water (100 ml), brine (100 ml), dried (MgSO$_4$), filtered, and concentrated in vacuo. The residue was subjected to flash chromatography using a mixture of ethyl acetate/hexanes (2:5) as eluent, which afforded 143 mg (40%) of 2-amino-5-((2-(1H-indol-3-yl)-2-oxo-acetylamino)methyl)-6-(4-methoxy-benzyl)-4,5,6,7-tetrahydro-thieno[2,3-c]pyridine-3-carboxylic acid tert-butyl ester as an oil.

LC-MS $R_t$=2.31 min, m/z: 574.9 [M+H]$^+$.

To a solution of 2-amino-5-((2-(1H-indol-3-yl)-2-oxo-acetylamino)methyl)-6-(4-methoxy-benzyl)-4,5,6,7-tetrahydro-thieno[2,3-c]pyridine-3-carboxylic acid tert-butyl ester (143 mg, 0.25 mmol) in dichloromethane (5 ml) was added imidazol-1-yl-oxo-acetic acid tert-butyl ester (144 mg, 0.75 mmol) and the flask was purged with nitrogen. After 24 hours an additional portion of imidazol-1-yl-oxo-acetic acid tert-butyl ester (169 mg, 0.86 mmol) was added and the reaction mixture allowed stirred for an additional 24 hours. The mixture was then concentrated in vacuo. The residue was purified by flash chromatography using a mixture of ethyl acetate/hexanes (2:5) as eluent, which afforded 101 mg (58%) of 2-(tert-butyoxyoxalyl-amino)-5-((2-(1H-indol-3-yl)-2-oxo-acetylamino)methyl)-6-(4-methoxy-benzyl)-4,5,6,7-tetrahydro-thieno[2,3-c]pyridine-3-carboxylic acid tert-butyl ester as a oil.

$^1$H-NMR (CDCl$_3$) δ9.23 (s, 1H), 9.07 (d, 1H, J=3.6 Hz), 8.50 (d, 1H, J=7.6 Hz), 8.15 (d, 1H, J=4.0 Hz), 7.47 (d, 2H, J=7.2 Hz), 7.38–7.27 (m, 6H), 6.89 (d, 2H, J=8.8 Hz), 3.87–3.59 (m, 6H), 3.04 (dd, 2H, J=23.6 Hz), 2.74 (dd, 2H, J 22.4 Hz), 1.62 (s, 18H);

LC-MS $R_t$=2.49 min, m/z: 703 [M+H]$^+$.

2-(tert-Butyoxyoxalyl-amino)-5-((2-(1H-indol-3-yl)-2-oxo-acetylamino)methyl)-6-(4-methoxy-benzyl)-4,5,6,7-tetrahydro-thieno[2,3-c]pyridine-3-carboxylic acid tert-butyl ester (101 mg, 0.143 mmol) was dissolved in dry tetrahydrofuran (6 ml) and passed through a pipette, plugged with cotton containing Raney 2800 Nickel (0.38 g). The pipette was flushed with dry tetrahydrofuran (6 ml) and the filtrate was concentrated in vacuo. Pd on carbon (10%, 102 mg, source: Avocado) and formic acid (10% in methanol, 5 ml) were added to the flask containing 2-(tert-Butyoxyoxalyl-amino)-5-((2-(1H-indol-3-yl)-2-oxo-acetylamino) methyl)-6-(4-methoxy-benzyl)-4,5,6,7-tetrahydro-thieno[2,3-c]pyridine-3-carboxylic acid tert-butyl ester. After stirring for 18 hours, the solution was filtered through a pad of celite and concentrated in vacuo. The residue was diluted in ethyl acetate, washed with saturated sodium bicarbonate (2×25 ml), brine (2×25 ml), dried (MgSO$_4$), filtered and concentrated in vacuo. The residue was subjected to flash chromatography using a mixture of 10% methanol/dichloromethane as eluent, which afforded 2-(tert-butyoxyoxalyl-amino)-5-((2-(1H-indol-3-yl)-2-oxo-acetylamino)methyl)-4,5,6,7-tetrahydro-thieno[2,3-c]pyridine-3-carboxylic acid tert-butyl ester.

$^1$H-NMR (CDCl$_3$) δ9.23 (s, 1H), 9.07 (d, 1H, J=3.6 Hz), 8.50 (d, 1H, J=7.6 Hz), 8.15 (d, 1H, J=4.0 Hz), 7.27 (s, 2H), 7.09 (d, 1H, J=8.8 Hz), 6.81 (d, 1H, J=8.8 Hz), 3.79 (s, 1H), 2.29 (s, 1H), 1.62–1.57 (m, 18H), 0.08 (s, 5H);

LC-MS: $R_t$=2.17 min, m/z: 583 [M+H]$^+$.

The above 2-(tert-butyoxyoxalyl-amino)-5-((2-(1H-indol-3-yl)-2-oxo-acetylamino)methyl)-4,5,6,7-tetrahydro-thieno[2,3-c]pyridine-3-carboxylic acid tert-butyl ester was dissolved in 50% trifluoroacetic acid/dichloromethane (3 ml) and stirred at room temperature for 18 hours. The solvent was removed in vacuo and residual trifluoroacetic acid was removed under reduced pressure affording 17.1 mg of the title compound as a solid trifluoroacetate.

$^1$H-NMR (DMSO-d$_6$) δ12.28 (s, 2H), 9.26 (s, 1H), 9.13 (s, 1H), 8.83 (d, 1H, J=2.8 Hz), 8.26 (d, 1H, J=8.8 Hz), 7.55 (d, 1H, J=4.8 Hz), 7.27 (d, 2H, J=7.6 Hz), 4.42 (d, 1H, J=15.2 Hz), 4.29 (d, 1H, J=16.4 Hz), 3.76–3.22 (m, 4H, partially obscured by solvent), 2.91–2.834 (m, 1H), 1.23 (s, 1H);

LC-MS: $R_t$=0.99 min, m/z 471.4 [M+H]$^+$.

General Chiral Synthesis

4-Oxo-1-((S)-1-phenyl-ethyl)-piperidine-(R)-2-carboxylic acid ethyl ester

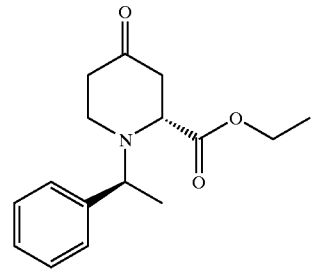

Dichloromethane (1 L) and mol sieves 3 Å (113 g) and amine (S)-(−)-α-methylbenzylamin (71,7 ml) were mixed in a 2 l three-necked bottle cooled to −5° C. (using a ethanol/water/ice bath). A 50% solution of ethylglyoxylate in toluene (117,6 ml) was added drop wise over 20 min., keeping the temperature between −5° C. and 0° C. The mixture was stirred for 0.5 hour before it was cooled to −30° C. Trifluoroacetic acid (45,2 ml) was added over 3–4 minutes. Boron trifluoride diethyl ether (69,8 ml) was added drop wise over 5 min at −55° C. The ice bath was removed and the mixture was allowed to warm up to −45° C. whereupon 2-(trimethylsilyloxy)-1,3-butadiene (100 ml) was added drop wise over 10 minutes. During the addition the mixture was cooled and the temperature kept below −20° C. The above additions are all exothermic hence the cooling bath should have sufficient capacity to remove the heat generated during the rapid addition. The reaction mixture was stirred for 2 hours at −15° C. and 1 hour at 0° C. and then poured on ice/water and stirred for 15 minutes. Solid sodium hydrogen carbonate was added until pH 7–8. The mixture was stirred overnight at room temperature. The layers wee separated and the aqueous phase extracted with dichloromethane. The combined organic phases were filtered through a plug of silica eluting with dichloromethane. The relevant fractions were concentrated in vacuo. The residue was dissolved in hot heptane and cooled. This leaves a yellowish gummy material on the side of the flask and crystals starts forming. The heptane solution was heated again to dissolve crystals, leaving the gummy material on the side of the flask and the mixture was filtered hot. The heptane solution was cooled to room temperature and the precipitate was filtered off and dried in vacuo, which afforded 38 g of 4-oxo-1-((S)-1-phenyl-ethyl)-piperidine-(R)-2-carboxylic acid ethyl ester as a solid.

The filtrate was put in a refrigerator and a second crop was formed which was less pure and needed recrystallization from heptane to yield another 7,5 g of 4-oxo-1-((S)-1-phenyl-ethyl)-piperidine-(R)-2-carboxylic acid ethyl ester.

4,4-Diethoxy-1-((S)-1-phenyl-ethyl)-piperidine-(S)-2-carboxylic acid ethyl ester

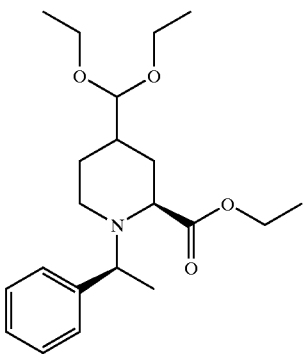

The mother liquor from the above crystallization was concentrated in vacuo. 5.0 g of the resulting material (18.16 mmol) was dissolved in ethanol (100 ml) and triethylorthoformate (26.9 g, 181.6 mmol) and para-toluensulphonic acid (6.9 g, 36.32 mmol) was added. The reaction was stirred at room temperature for 16 hours before the mixture was poured on aqueous sodium hydrogen carbonate (200 ml) and extracted with ethyl acetate (4×75 ml). The combined extracts were concentrated in vacuo and purified by column chromatography (SiO$_2$, Flash 40, petrol ether-ethyl acetate 10:1). Collection of the first band (R$_f$=0.68) gave 1.14 g (18%) of 4,4-diethoxy-1-((S)-1-phenyl-ethyl)-piperidine-(R)-2-carboxylic acid ethyl ester and collection of the second band (R$_f$=0.4) gave 3.60 g (57%) of the title compound.

4,4-Diethoxy-1-((S)-1-phenyl-ethyl)-piperidine-(R)-2-carboxylic acid ethyl ester

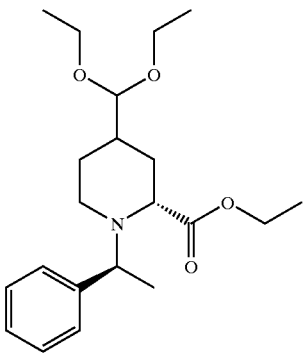

4-Oxo-1-((S)-1-phenyl-ethyl)-piperidine-(R)-2-carboxylic acid ethyl ester (11.0 g, 0.040 mmol) was dissolved in a 1:1 mixture of triethyl orthoformate and ethanol (140 ml) and para-toluene-4-sulphonic acid (15.2 g, 80 mmol) was added and the reaction mixture was stirred for 16 hours. The reaction mixture was neutralized with sodium bicarbonate (to pH 7–8), and extracted with dichloromethane (3×100 ml), dried (MgSO$_4$), filtered and concentrated in vacuo. The residue was purified by column chromatography (SiO$_2$, petrol ether/ethyl acetate 10:1), which afforded 12.0 g (86%) of the title compound as an oil.

4,4-Diethoxy-1-((S)1-phenyl-ethyl)-(R)-2-hydroxymethyl-piperidine

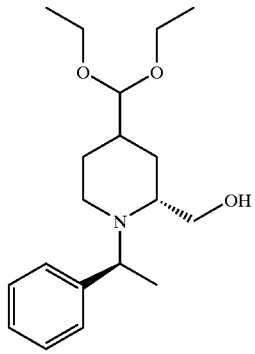

To a solution of 4,4-diethoxy-1-((S)-1-phenyl-ethyl)-piperidine-(R)-2-carboxylic acid ethyl ester (36.0 g, 0.103 mol) in dry diethyl ether (150 ml) was added a suspension of lithium aluminum hydride (5.88 g, 0.155 mol) in dry diethyl ether (300 ml) under an atmosphere of nitrogen at such a rate that the solution gently reflux. The reaction mixture was stirred over night before it was cooled to 0° C. and ethyl acetate (30 ml) was added drop wise to destroy excess lithium aluminum hydride. After stirring for another 0.5 hour, water (12 ml) was added drop wise. After stirring for 10–15 min the precipitate was filtered off through celite and the filter cage was washed with plenty of diethyl ether. The filtrate was washed with brine (100 ml), dried (MgSO$_4$), filtered and the solvent evaporated in vacuo, which afforded 30 g (95%) of the title compound as an oil.

4,4-Diethoxy-1-((S)-1-phenyl-ethyl)-(R)-2-phthalimidomethyl-piperidine

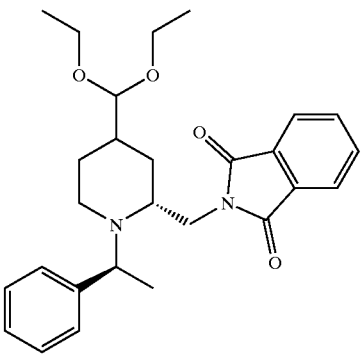

A solution of 4,4-Diethoxy-1-((S)1-phenyl-ethyl)-(R)-2-hydroxymethyl-piperidine (65.35 g, 0.213 mmol), triphenylphosphine (61.3 g, 0.234 mol) and phthalimide (34.4 g, 0.234 mol) in tetrahydrofuran (700 ml) cooled to 0° C. was added diethyl azodicarboxylate over the course of 1.5 hour. The reaction mixture was stirred at 0° C. for another 2 hours before the solvent was removed in vacuo. The residue was dissolved in hot heptane-toluene (3:2) (650 ml) before it was cooled on an ice bath. The precipitate consisting of triphenyl phosphine oxide was filtered off and washed with heptane. The filtrate was concentrated in vacuo and the residue subjected to column chromatography using a mixture of toluene-ethyl acetate-heptane (3:1:3) as eluent. The solvent was evaporated in vacuo whereupon a viscous oil was obtained. Upon addition of light petrol ether the product crystallized to give 67.4 g (73%) of the title compound as a solid.

Example 37

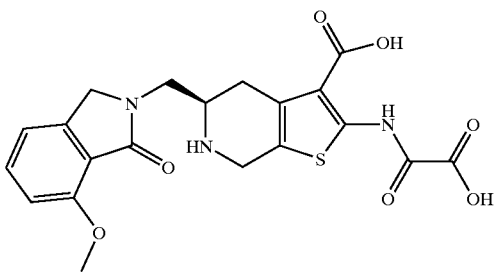

5-(R)-(7-Methoxy-1-oxo-1,3-dihydro-isoindol-2-ylmethyl)-2-(oxalyl-amino)-4,5,6,7-tetrahydro-thieno[2,3-c]pyridine-3-carboxylic acid A mixture of 4,4-diethoxy-1-((S)-1-phenyl-ethyl)-(R)-2-phthalimidomethyl-piperidine (5.25 g, 12.0 mmol) and hydrazine hydrate (2.92 ml, 60 mmol) was stirred overnight in ethanol (100 ml) at room temperature. The solvent was removed in vacuo and the solid residue was extracted with refluxing diethyl ether. The diethyl ether fractions were combined and evaporated in vacuo, which afforded 3.94 g (94%) of 4,4-diethoxy-1-((S)-1-phenyl-ethyl)-(R)-2-aminomethyl-piperidine as an oil.

4,4-Diethoxy-1-((S)-1-phenyl-ethyl)-(R)-2-aminomethyl-piperidine (2.25 g, 7.37 mmol), and triethyl amine (1.49 g, 14.7 mmol) in acetonitrile (50 ml) was heated to 60° C. before 2-chlormethyl-6-methoxy-benzoic acid methyl ester (1.58 g, 7.37 mmol) in acetonitrile (25 ml) was added over the course of 1.5 hour. After addition the reaction mixture was stirred overnight at 60° C. The solvent was removed in vacuo and the residue was dissolved in dichloromethane (50 ml) and washed with saturated sodium bicarbonate. After drying (MgSO$_4$), filtration and evaporation of the solvent in vacuo the residue was subjected to flash column chromatography (SiO$_2$, ethyl acetate-light petrol ether (1:1)) to give 2.3 g (69%) of 2-(R)-(7-methoxy-2,3-dihydro-isoindol-1-one-2-ylmethyl)-4,4-diethoxy-1-(1-(S)-phenyl-ethyl)-piperidine.

2-(R)-(7-Methoxy-2,3-dihydro-isoindol-1-one-2-ylmethyl)-4,4-diethoxy-1(1-(S)-phenyl-ethyl)-piperidine (2.0 g, 4.4 mmol) was dissolved in a ice cold mixture of trifluoroacetic acid and water (10 ml, 9:1) and stirred or 0.5 hour on an ice bath. The reaction mixture was poured on aqueous sodium carbonate (100 ml) and extracted with dichloromethane (2×50 ml). The organic phase was dried (MgSO$_4$), filtered and evaporated in vacuo, affording 1.67 g (100%) of 2-(R)-(7-methoxy-2,3-dihydro-isoindol-1-one-2-ylmethyl)-4-oxo-1(1-(S)-phenyl-ethyl)-piperidine.

2-(R)-(7-Methoxy-2,3-dihydro-isoindol-1-one-2-ylmethyl)-4-oxo-1(1-(S)-phenyl-ethyl)-piperidine (1.67 g, 4.41 mmol), sulphur (0.155 g, 4.85 mmol), tert-butylcyanoacetate (0.684 g, 4.85 mmol), N-methylmorpholine (0.892 g, 8.82 mmol) and molecular sieves (4 Å, 2 g) was heated to 50° C. in ethanol under an atmosphere of nitrogen for 16 hours. The reaction mixture was filtered through a plug (1 cm) of SiO$_2$, the silica was washed with dichloromethane-ethyl acetate and the solvent was removed in vacuo. The resulting residue was subjected to column chromatography (Flash 40, SiO$_2$, toluene-ethyl acetate (3:1)), which yielded 1.17 9 (50%) of 2-amino-5-(R)-(7-methoxy-1-oxo-1,3-dihydro-isoindol-2-ylmethyl)-6-(1-(S)-phenyl-ethyl)-4,5,6,7-tetrahydrothieno[2,3-c]pyridine-3-carboxylic acid tert-butyl ester and 2-amino-7-(S)-(7-methoxy-1-oxo-1,3-dihydro-isoindol-2-ylmethyl)-6-(1-(S)-phenyl-ethyl)-4,5,6,7-tetrahydrothieno[2,3-c]pyridine-3-carboxylic acid tert-butyl ester as a 3:1 mixture.

The above mixture of 5- and 7-regioisomers (1.17 g, 2.19 mmol) and imidazol-2-yl-oxo-acetic acid tert-butyl ester (1.29 g, 7.57 mmol) and triethylamine (0.66 g, 6.57 mmol) was stirred under an atmosphere of nitrogen in dichloromethane (25 ml) for 16 hours. The solvent was removed in vacuo and the residue was subjected to column chromatography (SiO$_2$, Flash 40, ethyl acetate-petrol ether (1:1)). Collection of relevant fractions gave 0.61 g (42%) of 2-(tert-butoxyoxalyl-amin)-5-(R)-(7-methoxy-1-oxo-1,3-dihydro-isoindo-2-ylmethyl)-6-(1-(S)-phenyl-ethyl-ethyl)-4,5,6,7-tetrahydro-thieno[2,3-c]pyridine-3-carboxylic acid tert-butyl ester.

2-(tert-Butoxyoxalyl-amin)-5-(R)-(7-methoxy-1-oxo-1,3-dihydro-isoindo-2-ylmethyl)-6-(1-(S)-phenyl-ethyl-ethyl)-4,5,6,7-tetrahydro-thieno[2,3-c]pyridine-3-carboxylic acid tert-butyl ester (0.60 g, 0.91 mmol) was stirred for 16 hours in a mixture of methanol and formic acid (10:1) (20 ml) in the presence of 10% palladium on carbon (50% water). The reaction mixture was filtered through a plug of Celite and washed with methanol. The volatiles were removed in vacuo and the residue was dissolved in dichloromethane (50 ml), washed with semi saturated aqueous sodium carbonate (50 ml), dried (MgSO$_4$), filtered and the solvent evaporated in vacuo. The residue was purified by column chromatography (SiO$_2$, Flash 40, ethyl acetate-methanol (100:15)), which afforded 0.36 g (71%) of 2-(tert-butoxyoxalyl-amin)-5-(R)-(7-methoxy-1-oxo-1,3-dihydro-isoindo-2-ylmethyl)-4,5,6,7-tetrahydro-thieno[2,3-c]pyridine-3-carboxylic acid tert-butyl ester.

2-(tert-Butoxyoxalyl-amin)-5-(R)-(7-methoxy-1-oxo-1,3-dihydro-isoindo-2-ylmethyl)-4,5,6,7-tetrahydro-thieno[2,3-c]pyridine-3-carboxylic acid tert-butyl ester (349 mg, 0.63 mmol) was stirred for 16 hours in a mixture of trifluoroacetic acid and dichloromethane (1:1) (10 ml) whereupon diethyl ether (20 ml) was added. The precipitate was filtered off and washed with diethyl ether, which afforded 215 mg (61%) of the title compound as a solid trifluoroacetate.

LC-MS: R$_t$=1.17 min, m/z: 446 [M+H]$^+$

Calculated for C$_{20}$H$_{19}$N$_3$O$_7$S, C$_2$HF$_3$O$_2$, 0.5×H$_2$O C, 46.48%; H, 3.72%; N, 7.39%; Found: C, 46.45%; H, 3.97%; N, 7.43%;

Example 38

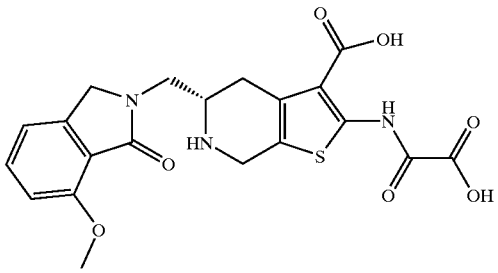

5-(S)-(7-Methoxy-1-oxo-1,3-dihydro-isoindol-2-ylmethyl)-2-(oxalyl-amino)-4,5,6,7-tetrahydro-thieno]2,3-c]pyridine-3-carboxylic acid A solution of 4,4-diethoxy-1-((S)-1-phenyl-ethyl)-piperidine-(S)-2-carboxylic acid ethyl ester (35.98 g, 0.103 mol) in diethyl ether (150 ml) was added drop wise to a suspension of lithium aluminum hydride (5.88 g, 0.155 mol) in diethyl ether (300 ml) over the course of 1 hour. The reaction mixture was stirred at room temperature overnight before it was cooled on an ice bath and the reaction was quenched by dropwise addition of ethyl acetate (30 ml), followed by drop wise addition of water (12 ml) whereupon a gray precipitate was formed. The mixture was filtered through a plug of Celite and the filter cage was washed with plenty of diethyl ether. The filtrate was dried ($MgSO_4$) before it was filtered and the solvent removed in vacuo, which afforded 24.5 g (79%) of 4,4-diethoxy-1-(1-(S)-phenyl-ethyl)-(S)-2-hydroxymethyl-piperidine as an oil.

A suspension of 4,4-diethoxy-1-(1-(S)-phenyl-ethyl)-(S)-2-hydroxymethyl-piperidine (20 g, 65 mmol), triphenylphosphine (18.76 g, 72 mmol) and phthalimide (10.52 g, 72 mmol) in tetrahydrofurane (200 ml) cooled to 0° C. was added diethyl azodicarboxylate (11.34 ml, 72 mmol) over the course of 1 hour. The reaction mixture was stirred at 0° C. for another 2 hours before the volatiles were removed in vacuo. The residue was dissolve in hot heptane-toluene (3:2) (100 ml) before it was cooled on an ice bath. The precipitate was filtered off and washed with heptane. The filtrate was concentrated in vacuo and the residue subjected to column chromatography using a mixture of toluene/ethyl acetate/heptane (3:1:3) as eluent. The solvent was evaporated in vacuo and the residue was crystallized by addition of light petrol ether (250 ml). The precipitate was filtered off, which afforded 24 g (85%) of 4,4-diethoxy-1-(1-(S)-phenyl-ethyl)-2-(S)-phthalimidomethyl-piperidine as a solid.

4,4-Diethoxy-1-(1-(S)-phenyl-ethyl)-2-(S)-phthalimidomethyl-piperidine (4.0 g, 9.2 mmol) was dissolved in a mixture of trifluoroacetic acid and water (9:1) (100 ml) at 0° C. and stirred for 2 hours at this temperature. The mixture was basified with half saturated aqueous sodium carbonate, extracted with ethyl acetate and dried ($MgSO_4$) for 2 hours. The solvent was removed in vacuo and the residue was dried in a vacuum own at 40° C. for to days. This afforded 3.23 g (98%) of 4-oxo-1-(1-(S)-phenyl-ethyl)-2-(S)-phthalimidomethyl-piperidine pure without further purification (98%).

A mixture of 4-oxo-1-(1-(S)-phenyl-ethyl)-2-(S)-phthalimidomethyl-piperidine (17.28 g, 47.73 mmol), tert-butylcyanoacetat (7.41 g, 52.17 mmol), sulphur (1.71 g, 52.17 mmol) and morpholine (8.31 g, 95.46 mmol) in ethanol (150 ml) was heated under an atmosphere of nitrogen at 50° C. The volatiles were removed in vacuo and the residue was subjected to column chromatography on silica gel (heptane-ethyl acetate 5:1). The fractions consisting of a mixture of 5- and 7-isomer were collected and the solvent evaporated in vacuo. The residue was purified on a reverse phase ($C_{18}$) column using a Flash 40 system. The residue was applied in a minimum volume of acetonitrile and eluted with 40% acetonitrile in water containing 0.1% trifluoroacetic acid. When the 5-isomer was collected the eluent was changed to 50% acetonitrile in water with 0.1% trifluoroacetic acid and the 7-isomer was collected. Yield of 2-amino-5-(S)-(1,3-dioxo-1,3-dihydro-isoindol-2-ylmethyl)-6-(1-(S)-phenyl-ethyl)-4,5,6,7-tetrahydro-thieno[2,3-c]pyridine-3-carboxylic acid tert-butyl ester was 7.96 g and yield of 2-amino-7-(R)-(1,3-dioxo-1,3-dihydro-isoindol-2-ylmethyl)-6-(1-(S)-phenyl-ethyl)-4,5,6,7-tetrahydro-thieno[2,3-c]pyridine-3-carboxylic acid tert-butyl ester was 3.72 g (47% total).

2-Amino-5-(S)-(1,3-dioxo-1,3-dihydro-isoindol-2-ylmethyl)-6-(1-(S)-phenyl-ethyl)-4,5,6,7-tetrahydro-thieno[2,3-c]pyridine-3-carboxylic acid tert-butyl ester (7.96 g, 15 mmol) and hydrazine hydrate (3.85 g, 77.0 mmol) in ethanol (250 ml) was stirred for 16 hours at room temperature. The solvent was removed in vacuo and the solid residue was extracted with diethyl ether (3×200 ml). The fractions were combined and the solvent removed in vacuo to give 5.9 g (100%) of 2-amino-5-(S)-aminomethyl-6-(1-(S)-phenyl-ethyl)-4,5,6,7-tetrahydrothieno[2,3-c]pyridine-3-carboxylic acid tert-butyl ester.

2-Amino-5-(S)-aminomethyl-6-(1-(S)-phenyl-ethyl)-4,5,6,7-tetrahydro-thieno[2,3-c]pyridine-3-carboxylic acid tert-butyl ester (0.55 g, 1.42 mmol) and triethylamine (396 I, 2.84 mmol) was heated in acetonitrile (15 ml) under an atmosphere of nitrogen to 60° C. whereupon a solution of 2-chloromethyl-6-methoxy-benzoic acid methyl ester (0.32 g, 1.49 mmol) in acetonitrile (5 ml) was added dropwise over the course of 3 hours, keeping the reaction mixture at 60° C. The reaction was allowed to cool to room temperature and was left for 16 hours before the solvent was evaporated in vacuo. The product was purified by column chromatography ($SiO_2$, Flash 40, ethyl acetate-petrol ether) to give 400 mg (53%) of 2-amino-5-(S)-(7-methoxy-1-oxo-1,3-dihydro-isoindol-2-ylmethyl)-6-((S)-1-phenyl-ethyl)-4,5,6,7-tetrahydro-thieno[2,3-c]pyridine-3-carboxylic acid tert-butyl ester as an oil.

The title compound was obtained as a trifluoroacetate in a similar way as described in example 32 using the last three steps.

Example 39

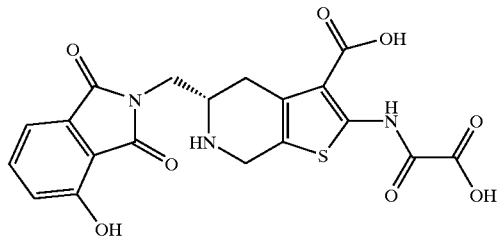

5-(S)-4-Hydroxy-1-oxo-1,3-dihydro-isoindol-2-ylmethyl)-2-(oxalyl-amino)-4,5,6,7-tetrahydro-thieno[2,3-c]pyridine-3-carboxylic acid 3-Hydroxy-2-methylbenzoic acid (0.5 g, 3.2 mmol) was dissolved in HPLC grade methanol (5 ml) and cooled to 0° C. under nitrogen. Acetyl chloride (5 ml) was added dropwise. Once the addition was complete, the ice bath was removed and the reaction mixture allowed warming to room temperature over a period of 18 hours. The reaction was complete by tlc ($R_f$=0.5, 1:1 ethyl acetate/hexanes) and quenched with saturated sodium bicarbonate. The reaction mixture was concentrated, diluted with dichloromethane and water and the layers separated. The aqueous layer was extracted with dichloromethane (3×). The organic layers were combined, dried ($MgSO_4$), filtered and concentrated in vacuo, which afforded 0.5 g (91%) of 3-hydroxy-2-methylbenzoic acid methyl ester as a solid.

$^1$H-NMR ($CDCl_3$) δ7.39 (dd, 1H, J=8.1 Hz and J=1.5 Hz), 7.09 (t, 1H, J=8.1 Hz), 6.92 (dd, 1H, J=8.1 Hz and J=1.2 Hz), 5.11 (bs, 1H), 3.87 (s, 3H), 2.43 (s, 3H).

3-Hydroxy-2-methylbenzoic acid methyl ester (0.5 g, 3.01 mmol) in dichloromethane (15 ml) and N,N-diisopropylethylamine (1.57 ml, 9.03 mmol) was cooled to 0° C. under nitrogen. Chloromethyl methyl ether (0.46 ml, 6.02 mmol) was added dropwise and the reaction allowed warming to room temperature over a period of 18 hours. The reaction was judged to be 50% complete by tlc (1:2 ethyl acetate/hexanes, 12) and therefore, N,N-diisopropylethylamine (1.57 ml, 9.03 mmol) was added, the reaction mixture cooled to 0° C. and chloromethyl methyl ether (0.46 ml, 6.02 mmol) added once more. The reaction mixture was warmed to room temperature and stirred for 5 hours. The reaction was quenched with water and the layers separated. The aqueous layer was extracted once with dichloromethane and the organic layers combined, dried ($MgSO_4$), filtered, and concentrated in vacuo. The crude residue was purified by column chromatography (20% ethyl acetate/hexanes) affording 0.44 g (69%) of 3-methoxymethoxy-2-methyl-benzoic acid methyl ester as an oil.

$^1$H-NMR ($CDCl_3$) δ7.46 (dd, 1H, J=7.6 Hz and J=1.2 Hz), 7.21 (dd, 1H, J=8 Hz and J=1.2 Hz), 7.18 (d, 1H, J=8 Hz), 5.21 (s, 2H), 3.88 (s, 3H), 3.48 (s, 3H), 2.46 (s, 3H).

To a mixture of 3-methoxymethoxy-2-methyl-benzoic acid methyl ester (0.44 g, 2.09 mmol) in carbon tetrachloride (10 ml) was added N-bromosuccinimide (0.39 g, 2.19 mmol) and 1,1'-azo bis(cyclohexane-carbonitrile) (0.051 g, 0.21 mmol). The mixture was heated at reflux for 3 hours, at which time the reaction was judged complete by tlc (1:4 ethyl acetate/hexanes). The reaction mixture was cooled to room temperature and concentrated in vacuo to a solid. The solid was recrystallized from hexane leaving 0.44 g (82%) of 2-bromomethyl-3-methoxymethoxy-benzoic acid methyl ester as a solid.

$^1$H-NMR ($CDCl_3$) δ7.58 (dd, 1H, J=6.8 Hz and J=2.4 Hz), 7.33–7.29 (m, 2H), 5.30 (s, 2H), 5.07 (s, 2H), 3.94 (s, 3H), 3.52 (s, 3H).

To a stirred mixture of 2-amino-5-(S)-aminomethyl-6-(1-(S)-phenyl-ethyl)-4,5,6,7-tetrahydro-thieno[2,3-c]pyridine-3-carboxylic acid tert-butyl ester (0.24 g, 0.67 mmol) in acetonitrile (30 ml) was added N,N-diisopropylethylamine (0.16 ml, 0.93 mmol) under nitrogen. 2-Bromo-methyl-3-methoxymethoxy-benzoic acid methyl ester (0.16 g, 0.55 mmol) dissolved in acetonitrile, was added via syringe pump at a rate of 0.3 ml/hour. Once the addition was complete, the reaction mixture was stirred at room temperature for 24 hours. Tlc analysis (1:1 ethyl acetate/hexanes) indicated the reaction to be complete. The volatiles were removed in vacuo and the resultant oil dissolved in ethyl acetate/water. The layers were separated and the aqueous layer extracted with ethyl acetate (3×). The organic layers were combined, dried ($MgSO_4$), filtered and the solvent evaporated in vacuo, which afforded 0.34 g (100%) of 2-amino-5-(S)-(4-methoxymethoxy-1-oxo-1,3-dihydro-isoindol-2-ylmethyl)-6-(1-(S)-phenyl-ethyl)-4,5,6,7-tetrahydro-thieno[2,3-c]pyridine-3-carboxylic acid tert-butyl ester, which was used without further purification in the next step.

$^1$H-NMR ($CDCl_3$) δ7.51 (d, 1H, J=6.8 Hz), 7.42 (t, 2H, J=7.6 Hz), 7.23–7.17 (m, 5H), 5.93 (s, 2H), 5.25 (s, 2H), 4.23 (s, 2H), 4.12 (q, 1H, J=7.2 Hz), 3.94 (m, 1H), 1H, J=6.4 Hz), 3.66 (d, 1H, J=16.4 Hz), 3.50 (s, 3H), 3.48–3.46 (m, 1H), 3.20 (dd, 1H, J=14 Hz and J=6 Hz), 2.94–2.87 (m, 1H), 2.60 (m, 1H), 1.49 (s, 9H), 1.36 (d, 3H, J=6.4 Hz);

LC-MS: m/z: 564.1 [M+H]$^+$.

To a solution of 2-amino-5-(S)-(4-methoxymethoxy-1-oxo-1,3-dihydro-isoindol-2-ylmethyl)-6-(1-(S)-phenyl-ethyl)-4,5,6,7-tetrahydro-thieno[2,3-c]pyridine-3-carboxylic acid tert-butyl ester (0.34 g, 0.60 mmol) in dichloromethane (10 ml) was added imidazol-1-yl-oxo-acetic acid tert-butyl ester (0.35 g, 1.8 mmol). The reaction mixture was stirred at room temperature for 18 hours and the solvent concentrated in vacuo. The residue was dissolved in ethyl acetate and washed with water (2×20 ml) and brine (2×25 ml). The organic layer was dried ($MgSO_4$), filtered and the solvent evaporated in vacuo. The residue was subjected to flash chromatography using a mixture of ethyl acetate/hexanes (1:1) as eluent. The obtained residue was then subjected to chromatotron purification (1% methanol/dichloromethane) and later to another flash chromatography (20% ethyl acetate/hexanes to 25% ethyl acetate/hexanes) to obtain 210 mg (50%) of 2-(tert-butoxyoxalyl-amino)-5-(S)-(4-methoxymethoxy-1-oxo-1,3-dihydro-isoindol-2-ylmethyl)-6-(1-(S)-phenyl-ethyl)-4,5,6,7-tetrahydro-thieno[2,3-c]pyridine-3-carboxylic acid tert-butyl ester as an oil.

$^1$H-NMR ($CDCl_3$) δ12.50 (s, 1H), 7.51 (dd, 1H, J=6.8 Hz and J=1.2 Hz), 7.42 (t, 2H, J=8 Hz), 7.25–7.17 (m, 5H), 5.23 (s, 2H), 4.24 (q, 2H, J=16.8 Hz), 4.08 (d, 1H, J=16.8 Hz), 4.01 (dd, 1H, J=14Hz and J=8.8Hz), 3.89 (d, 1H, J=17.6Hz), 3.82 (q, 1H, J=6.8 Hz), 3.56 (q, 1H, J=6.4 Hz), 3.51 (s, 3H), 2.28 (dd, 1H, J=14 Hz and J=6.4) 2.98–2.92 (m, 1H), 2.69 (d, 1H, J=17.2), 1.56 (s, 9H), 1.54 (s, 9H), 1.38 (d, 3H, J=6.8 Hz);

LC-MS: m/z: 692.5 [M+H]$^+$.

To a solution of 2-(tert-butoxyoxalyl-amino)-5-(S)-(4-methoxymethoxy-1-oxo-1,3-dihydro-isoindol-2-ylmethyl)-6-(1-(S)-phenyl-ethyl)-4,5,6,7-tetrahydro-thieno[2,3-c]pyridine-3-carboxylic acid tert-butyl ester (0.16 g, 0.23 mmol) in formic acid (10% in methanol, 5 ml total) was added 10% palladium on carbon (85 mg, source: Avacado) and the reaction mixture allowed to stir at room temperature. After 6 hours, tlc (1:1 ethyl acetate/hexanes) analysis indicated reaction complete. The reaction mixture was filtered through a pad of celite and concentrated in vacuo. The crude product was purified via flash chromatography (gradient: 3% isopropyl alcohol/dichloromethane to 5% isopropyl alcohol/dichloromethane (in 1% increments of isopropyl alcohol)) to provide 0.11 g (82%) of 2-(tert-butoxyoxalyl-amino)-5-(S)-(4-methoxymethoxy-1-oxo-1,3-dihydro-isoindol-2-ylmethyl)-4,5,6,7-tetrahydro-thieno[2,3-c]pyridine-3-carboxylic acid tert-butyl ester as an oil.

$^1$H-NMR ($CDCl_3$) δ12.50 (bs, 1H), 7.48 (dd, 1H, J=7.6 Hz and J=0.8 Hz), 7.38 (t, 1H, J=8 Hz), 7.22 (dd, 1H, J=8 Hz and J=0.8Hz), 5.24 (s, 2H), 4.50 (q, 2H, J=17.3 Hz), 4.02–3.90 (m, 2H), 3.74 (ddd, 2H, J=34 Hz, J=13.6 Hz and J=5.6 Hz), 3.49 (s, 3H), 3.24 (m, 1H), 2.97 (ddd, 1H, J=20 Hz, J=4.4 Hz and J=2.8 Hz), 2.50 (m, 1H), 1.59 (s, 9H), 1.51 (s, 9H);

LC-MS: m/z: 587.8 [M+H]$^+$.

2-(tert-Butoxyoxalyl-amino)-5-(S)-(4-methoxymethoxy-1-oxo-1,3-dihydro-isoindol-2-ylmethyl)-4,5,6,7-tetrahydro-thieno[2,3-c]pyridine-3-carboxylic acid tert-butyl ester (0.11 g, 0.18 mmol) was dissolved in neat trifluoroacetic acid (4 ml) and stirred at room temperature for 48 hours. The reaction mixture was concentrated in vacuo and the resultant solid washed with dichloromethane several times affording 100 mg (83%) of the title compound as a solid trifluoroaceatet.

$^1$H-NMR (DMSO-$d_6$) δ12.29 (bs, 1H), 10.13 (s, 1H), 9.29 (bs, 1H), 9.10 (bs, 1H), 7.32 (t, 1H, J=7.6 Hz), 7.17 (d, 1H, J=7.2 Hz), 7.01 (d, 1H, J=8 Hz), 4.52 (d, 1H, J=17.2 Hz), 4.40–4.22 (m, 3H), 4.05 (dd, 1H, J=14.4 Hz and J=9.6 Hz), 3.90 (bs, 1H), 3.69 (dm, 1H), 3.22 (dm, 1H), 2.80 (dm, 1H);

LC-MS: m/z: 432.2 [M+H]$^+$.

Example 40

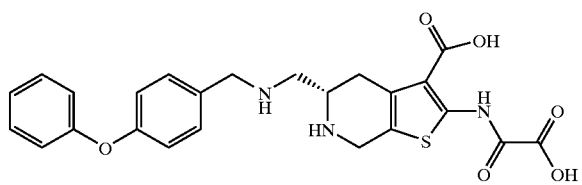

2-(S)-(Oxalyl-amino)-5-((4-phenoxy-benzylamino)methyl)-4,5,6,7-tetrahydro-thieno[2,3-c]pyridine-3-carboxylic acid A solution of 2-amino-5-(S)-aminomethyl-6-(1-(S)-phenyl-ethyl)-4,5,6,7-tetrahydro-thieno[2,3-c]pyridine-3-carboxylic acid tert-butyl ester (500 mg, 1.29 mmol) and 4-phenoxybenzaldehyde (256 mg, 1.29 mmol) was heated to 50° C. in ethanol (50 ml) for 1 hour in the presence of molecular sieves (4 A, 5 ml). The reaction mixture was cooled on an ice bath before sodium borohydride (98 mg, 2.59 mmol) was added in three portions over 45 min. The cooling bath was removed and the reaction mixture was allowed to reach room temperature. The mixture was filtered through a plug of Celite and the filter cage was washed with dichloromethane (3×25 ml). The solvent was removed in vacuo and the residue was redissolved in ethyl acetate (50 ml), washed with sodium bicarbonate (50 ml) and dried (MgSO$_4$). The solvent was removed in vacuo before the residue was redissolved in acetonitrile (20 ml). Triethylamine (130 mg, 1.29 mmol), di-tert-butyl dicarbonate (282 mg, 1.29 mmol) and 4-(N,N-dimethyl-amino)pyridine (5 mg, cat.) was added and the reaction mixture was stirred for 16 hours at room temperature. The volatiles were removed in vacuo and ethyl acetate (50 ml) was added and the solution was washed with saturated sodium bicarbonate (50 ml) and dried (MgSO$_4$). The crude product was purified by column chromatography (SiO$_2$, petroleum ether-ethyl acetate (9:1)) to give 325 mg (38% overall) of 2-amino-5-(S)-((4-phenoxy-benzylamino)methyl)-6-(1-(S)-phenyl-ethyl)-4,5,6,7-tetrahydro-thieno[2,3-c]pyridine-3-carboxylic acid tert-butyl ester.

The title compound was obtained as a trifluoroacetate in a similar way as described in example 32 using the last three steps.

Oxalation: Standard procedure (16 hours, 82%)
Hydrogenolysis: standard procedure (Pd/C, 10% Pd, methanol-formic acid, 16 hours, ((10:1)) (82% yield)
TFA cleavage: Standard procedure. Yield 150 mg (87%).
LC-MS m/z: 482 [M+H]$^+$, R$_t$=1.87 min
Calculated for C$_{24}$H$_{23}$N$_3$O$_6$S, 2×(C$_2$HF$_3$O$_2$) C, 47.40%; H, 3.55%; N, 5.92%; Found: C, 47.47%; H, 3.87%; N, 5.88%;

Example 41

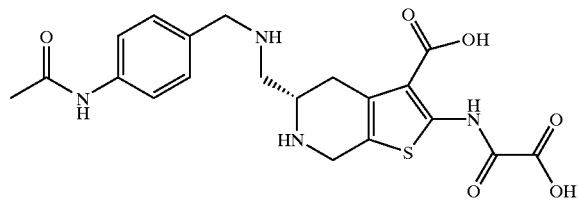

5-(S)-((4-Acetylamino-benzylamino)-methyl)-2-(oxalyl-amino)-4,5,6,7-tetrahydro-thieno[2,3-c]pyridine-3-carboxylic acid The title compound was prepared as a trifluoroacetate in a similar way as described in Example 35 using 2-amino-5-(S)-aminomethyl-6-(1-(S)-phenyl-ethyl)-4,5,6,7-tetrahydro-thieno[2,3-c]pyridine-3-carboxylic acid tert-butyl ester and N-(4-formyl-phenyl)acetamide as the starting material.

Calculated for C$_{20}$H$_{22}$N$_4$O$_6$S, 1.5×C$_2$HF$_3$O$_2$, 1.5×H$_2$O C, 43.78%; H, 3.99%; N, 8.88%; Found: C, 44.20%; H, 4.43%; N, 8.75%;

Example 42

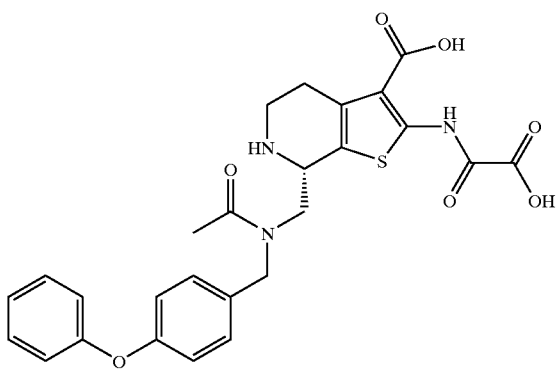

7-(S)-((Acetyl-(4-phenoxy-benzyl)amino)methyl)-2-(oxalyl-amino)-4,5,6,7-tetrahydro-thieno[2,3-c]pyridine-3-carboxylic acid A solution of 2-amino-7-(S)-aminomethyl-6-(1-(S)-phenyl-ethyl)-4,5,6,7-tetrahydro-thieno[2,3-c]pyridine-3-carboxylic acid tert-butyl ester (500 mg, 1.29 mmol) and 4-phenoxybenzaldehyde (256 mg, 1.29 mmol) was heated to 50° C. in ethanol (50 ml) for 1 hour in the presence of molecular sieves (4 A, 5 ml). The reaction mixture was cooled on an ice bath before sodium borohydride (98 mg, 2.59 mmol) was added in three portions over 45 min. The cooling bath was removed and the reaction mixture was allowed to reach room temperature. The mixture was filtered through a plug of Celite and the filter cage was washed with dichloromethane (3×25 ml). The solvent was removed in vacuo and the residue was redissolved in ethyl acetate (50 ml), washed with sodium bicarbonate (50 ml) and dried (MgSO$_4$). The solvent was removed in vacuo before the product was dissolved in dichloromethane (10 ml). The solution was cooled on an ice bath before di-isopropyl-ethyl amine (101 mg, 1.29 mmol) was added followed by drop wise addition of acetyl chloride (101 mg, 1.29 mmol) in dichloromethane (1 ml). The reaction mixture was stirred 1 hour at 0° C. and the solution was washed with sodium bicarbonate (10 ml) and dried (MgSO$_4$). The crude product was purified by flash column chromatography (SiO$_2$, ethyl acetate-petrol ether 1:3) to give 320 mg (41%) of 7-(S)-((acetyl-(4-phenoxy-benzyl)amino)methyl)-2-amino-6-(1-(S)-phenyl-ethyl)-4,5,6,7-tetrahydro-thieno[2,3-c]pyridine-3-carboxylic acid The title compound was obtained as a trifluoroacetate in a similar way as described in example 32 using the last three steps.

Oxalation: Standard procedure (Yield 69%)
Hydrogenolysis and trifluoroacetic acid cleavage in one step, Standard procedure (Overall yield 6%)
LC-MS m/z=524 [M+H]$^+$, R$_t$=2.58 min
Calculated for C$_{26}$H$_{25}$N$_3$O$_7$S, C$_2$HF$_3$O$_2$, 0.5×H$_2$O C, 52.01%; H, 4.21%; N, 6.50%; Found: C, 51.82%; H, 4.34%; N, 6.36%.

Example 43

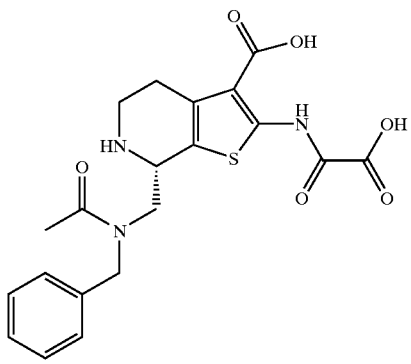

7-(S)-((Acetyl-benzyl-amino)methyl)-2-(oxalyl-amino)-4,5,6,7-tetrahydro-thieno[2,3-c]pyridine-3-carboxylic acid A solution of 2-amino-7-(S)-aminomethyl-6-(1-(S)-phenyl-ethyl)-4,5,6,7-tetrahydro-thieno[2,3-c]pyridine-3-carboxylic acid tert-butyl ester (400 mg, 1.03 mmol) and benzaldehyde (105 mg, 1.03 mmol) was heated to 50° C in ethanol (20 ml) for 1 hour in the presence of molecular sieves (4 A, 7 ml). The reaction mixture was cooled on an ice bath before sodium borohydride (78 mg, 2.06 mmol) was added in three portions over 45 min. The cooling bath was removed and the reaction mixture was allowed to reach room temperature. The mixture was filtered through a plug of Celite and the filter cage was washed with dichloromethane (3×25 ml). The solvent was removed in vacuo and the residue was redissolved in ethyl acetate (50 ml), washed with sodium bicarbonate (50 ml) and dried (MgSO$_4$). The solvent was removed in vacuo before the product was dissolved in dichloromethane (20 ml). The solution was cooled on an ice bath before di-isopropyl-ethyl amine (267 mg, 2.06 mmol) was added followed by drop wise addition of acetyl chloride (81 mg, 1.03 mmol) in dichloromethane (1 ml). The reaction mixture was stirred 1 hour at 0° C. before sodium bicarbonate (20 ml) was added. The mixture was extracted with dichloromethane (2×10 ml) and the combined organic fractions were dried (MgSO$_4$). The crude product was purified by flash column chromatography (petrol ether/ethyl acetate (3:1)), which afforded 250 mg (46%) of 7-(S)-((acetyl-benzyl-amino)methyl)-2-amino-6-(1-(S)-phenyl-ethyl)-4,5,6,7-tetrahydro-thieno[2,3-c]pyridine-3-carboxylic acid tert-butyl ester.

The title compound was obtained as a trifluoroacetate in a similar way as described in example 32 using the last three steps.

Oxalation: Standard procedure (54%)
Hydrogenolysis: Standard procedure (methanol-formic acid (10:1)) Yield 38 mg (26%)
Trifluoroacetic acid cleavage: Standard procedure 33 mg (80%)
LC-MS m/z: 432 [M+H]$^+$, R$_t$=1.52 min
Calculated for C$_{20}$H$_{21}$N$_3$O$_6$S×1.5×C$_2$HF$_3$O$_2$, 2×H$_2$O C, 43.26%; H, 4.18%; N, 6.58%; Found: C, 43:19%; H, 3.86%; N, 6.46%.

Example 44

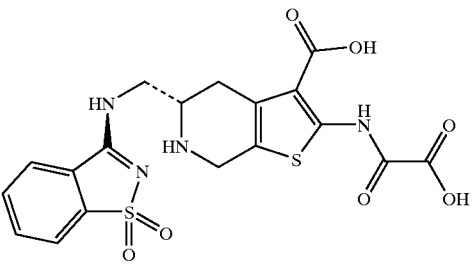

5-(S)-((1,1-Dioxo-1H-benzo[d]isothiazol-3-ylamino)methyl)-2-(oxalyl-amino)-4,5,6,7-tetrahydro-thieno[2,3-c]pyridine-3-carboxylic acid To a solution of (S)-2-amino-5-aminomethyl-6-(1-(S)-phenyl-ethyl)-4,5,6,7-tetrahydro-thieno[2,3-c]pyridine-3-carboxylic acid tert-butyl ester (1.0 g, 2.58 mmol) in dichloromethane (10 ml) at 0° C. was added N,N-diisopropylethylamine (0.54 ml, 5.16 mmol). A solution of 3-chloro-benzo[d]isothiazole 1,1-dioxide (0.52 g, 2.58 mmol) in dichloromethane (10 ml) was then added dropwise and stirred for 30 min. The solution was warmed to room temperature and washed with water and dried (MgSO$_4$). The solvent was then removed in vacuo. The residue was taken into dichloromethane (15 ml) and imidazol-1-yl-oxo-acetic acid tert-butyl ester (1.0 g, 5.16 mmol) was added. The solution was stirred for 2 hours. The solvent was removed in vacuo. The residue was taken into ethyl acetate (100 ml). The solution was washed with 0.5 N hydrochloric acid solution, saturated sodium bicarbonate and brine, dried (MgSO$_4$) and filtered. The solvent was removed in vacuo. The residue was chromatographed using a mixture of 0–5% ethyl acetate/dichloromethane as eluent, which afforded 0.6 g (34%) of 2-(tert-butoxyoxalyl-amino)-5-(S)-((1,1-dioxo-1H-benzo[d] isothiazol-3-ylamino)methyl)-6-(1-(S)-phenyl-ethyl)-4,5,6,7-tetrahydro-thieno[2,3-c]pyridine-3-carboxylic acid tert-butyl ester as an oil $^1$H-NMR (CDCl$_3$) δ12.50 (s, 1H), 7.94–7.92 (m, 1H), 7.79–7.71 (m, 2H), 7.59–7.50 (m, 1H), 7.38–7.27 (m, 4H), 6.86 (d, 1H, J=4 Hz), 4.14 (d, 1H, J=12 Hz), 3.95 (d, 1H, J=17 Hz), 3.88 (q, 1H, J=6 Hz), 3.70–3.62 (m, 1H), 3.47 (t, 1H, J=13 Hz), 3.34–3.24 (m, 1H), 3.06 (dd, 1H, J=17, 6 Hz), 2.53 (d, 1H, J=17 Hz), 1.62 (s, 9H), 1.61 (s, 9H), 1.44 (d, 3H, J=7 Hz).

A solution of 2-(tert-butoxyoxalyl-amino)-5-(S)-((1,1-dioxo-1H-benzo[d]isothiazol-3-ylamino)methyl)-6-(1-(S)-phenyl-ethyl)-4,5,6,7-tetrahydro-thieno[2,3-c]pyridine-3-carboxylic acid tert-butyl ester (252 mg, 0.37 mmol) in tetrahydrofuran (12 ml) was passed through Raney Ni (0.95 g, 50% Raney Ni-Water washed with methanol (6 ml) and tetrahydrofuran (10 ml) and dried before use). The solvent was removed in vacuo. The residue was dissolved in acetic acid (7 ml) and hydrogenated with 10% Pd/C (250 mg) at 50 psi for 15 hours. The mixture was filtered and the filtrate was added to saturated sodium bicarbonate solution. The solution was then extracted with ethylacetate (3×100 ml). The extracts were combined and dried (MgSO$_4$). The solvent was removed in vacuo. The residue was washed with diethyl ether affording 156 mg (73%) of 2-(tert-butoxyoxalyl-amino)-5-(S)-((1,1-dioxo-1H-benzo[d]isothiazol-3-ylamino)-methyl)-4,5,6,7-tetrahydro-thieno[2,3-c]pyridine-3-carboxylic acid tert-butyl ester as an oil.

$^1$H-NMR (CDCl$_3$) δ12.59 (s, 1H), 7.94–7.90 (m, 1H), 7.70–7.66 (m, 3H), 7.51 (s, 1H), 4.11 (d, 1H, J=12 Hz), 4.08

(q, 2H, J=17 Hz), 3.40 (dd, 1H, J=12, 6 Hz), 3.26–3.18 (m, 1H), 3.18 (d, 1H, J=17 Hz), 2.55 (dd, 1H, J=12, 6 Hz), 1.62 (s, 18H).

LC-MS: $R_t$=3.58 min, m/z: 577 [M+H]$^+$.

A solution of 2-(tert-butoxyoxalyl-amino)-5-(S)-((1,1-dioxo-1H-benzo[d]isothiazol-3-ylamino)methyl)-4,5,6,7-tetrahydro-thieno[2,3-c]pyridine-3-carboxylic acid tert-butyl ester (149 mg, 0.26 mmol) in 50% trifluoroacetic acid/dichloromethane (1 ml) was left in an open flask for 60 hours. The volatiles were removed in vacuo and the residue was washed with dichloromethane to yield 80 mg (54%) of the title compound as a solid trifluoroacetate.

$^1$H-NMR (DMSO-d$_6$) δ12.29 (s, 1H), 9.80 (s, 1H), 9.51 (bs, 2H), 8.19 (d, 1H, J=5 Hz), 8.02–8.00 (m, 1H), 7.89–7.84 (m, 2H), 4.46 (d, 1H, J=16 Hz), 4.30 (d, 1H, J=16 Hz), 3.96–3.80 (m, 3H), 3.30 (d, 1H, J=17 Hz), 2.93 (dd, 1H, J=18, 10 Hz);

LC-MS: $R_t$=0.68 min, m/z: 465 [M+H]$^+$.

Example 45

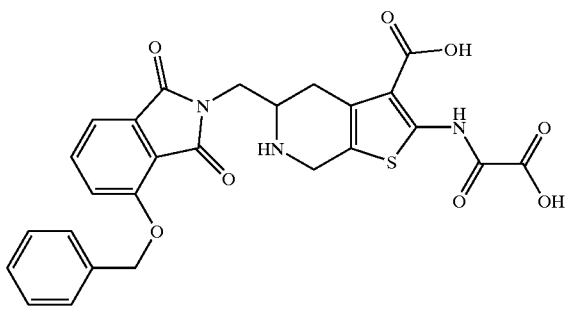

5-(4-Benzyloxy-1,3-dioxo-1,3-dihydro-isoindol-2-ylmethyl)-2-(oxalyl-amino)-4,5,6,7-tetrahydro-thieno[2,3-c]pyridine-3-carboxylic acid The title compound was prepared in a similar way as described in Example 5 as a trifluoroacetate. $^1$H-NMR (400 MHz, DMSO-d$_6$) δ12.31 (s, 1H), 9.25 (bs, 2H), 7.80 (t, 1H, J=8 Hz), 7.59–7.32 (m, 7H), 5.37 (s, 2H), 4.42–4.21 (m, 2H), 3.95–3.70 (m, 3H), 3.4–3.2 (obscure by water, 1H), 2.83–2.75 (m, 1H)

LC-MS: $R_t$=2.16 min, m/z: 536.1 [M+H]$^+$

Example 46

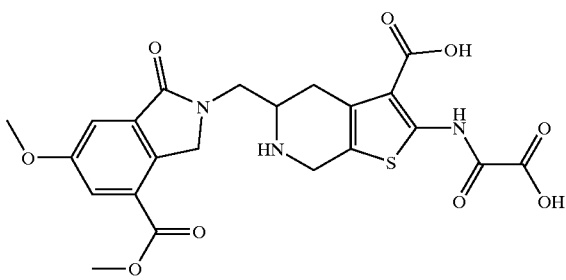

5-(6-Methoxy-4-methoxycarbonyl-1-oxo-1,3-dihydro-isoindol-2-ylmethyl)-2-(oxalyl-amino)-4,5,6,7-tetrahydro-thieno[2,3-c]pyridine-3-carboxylic acid To a solution of 2-amino-5-aminomethyl-6-(4-methoxy-benzyl)-4,5,6,7-tetrahydro-thieno[2,3-c]pyridine-3-carboxylic acid tert-butyl ester (57.4 mg, 0.142 mmol) and diisopropyl ethylamine (49 μl, 0.28 mmol) in acetonitrile (20 ml) at room temperature was added 2-bromomethyl-5-methoxy-isophthalic acid dimethyl ester (3.00 g, 7.45 mmol). The solution was stirred for 16 hours and the solvent evaporated in vacuo. The residue was taken into ethyl acetate (50 ml) and washed with water (2×20 ml), 1 N hydrochloric acid (20 ml), brine, dried (MgSO$_4$), filtered and the solvent evaporated in vacuo. The residue was chromatographed on silica gel column using a mixture of ethyl acetate/hexane (1:1) as eluent, which afforded 62 mg (71%) of 2-amino-6-(4-methoxy-benzyl)-5-(6-methoxy-4-methoxycarbonyl-1-oxo-1,3-dihydro-isoindol-2-ylmethyl)-4,5,6,7-tetrahydro-thieno[2,3-c]pyridine-3-carboxylic acid tert-butyl ester as a solid.

$^1$H-NMR δ(CDCl$_3$): δ7.75 (d, 1H, J=2.4 Hz), 7.55 (d, 1H, J=2.4 Hz), 7.11 (bs, 2H), 6.74 (d, 2H, J=8.0 Hz), 5.97 (s, 2H), 4.71 (d, 1H, J=18.4 Hz), 4.62 (d, 1H, J=18.4 Hz), 4.09 (m, 1H), 3.93 (s, 3H), 3.92 (s, 3H), 3.80 (m, 1H), 3.76 (s, 3H), 3.66–3.40 (m, 5H), 2.80 (d, 1H, J=17.2 Hz), 2.64 (d, 1H, J=17.2 Hz), 1.52 (s, 9H).

To a stirred solution of 2-amino-6-(4-methoxy-benzyl)-5-(6-methoxy-4-methoxycarbonyl-1-oxo-1,3-dihydro-isoindol-2-ylmethyl)-4,5,6,7-tetrahydro-thieno[2,3-c]pyridine-3-carboxylic acid tert-butyl ester (60 mg, 0.10 mmol) in tetrahydrofuran (1.0 ml) was added imidazol-1-yl-oxo-acetic acid tert-butyl ester (60 mg, 0.30 mmol) in tetrahydrofuran (1.0 ml). The mixture was stirred at room temperature for 24 hours. The solvent was removed in vacuo. The residue was taken into ethyl acetate (20 ml) and washed with 0.5 N hydrochloric acid (2×10 ml), saturated sodium bicarbonate (2×10 ml) and brine (10 ml), dried (MgSO$_4$) and filtered. The solvent was removed in vacuo and residue was chromatographed using a gradient ethyl acetate/hexane (10–25%) as eluent, which afforded 40 mg (58%) of 2-(tert-butoxyoxalyl-amino)-6-(4-methoxy-benzyl)-5-(6-methoxy-4-methoxycarbonyl-1-oxo-1,3-dihydro-isoindol-2-ylmethyl)-4,5,6,7-tetrahydro-thieno[2,3-c]pyridine-3-carboxylic acid tert-butyl ester as a solid.

$^1$H-NMR δ(CDCl$_3$): δ12.54 (s, 1H), 7.75 (d, 1H, J=2.4 Hz), 7.55 (d, 1H, J=2.4 Hz), 7.10 (d, 2H, J=8.0 Hz), 6.74 (d, 2H, J=8.0 Hz), 4.74 (d, 1H, J=18.4 Hz), 4.62 (d, 1H, J=18.4 Hz), 4.05–3.90 (m, 2H), 3.94 (s, 3H), 3.92 (s, 3H), 3.82–3.48 (m, 5H), 3.77 (s, 3H), 2.95 (dd, 1H, J=17.2 Hz and J=5.2 Hz), 2.67 (dd, 1H, J=17.2 Hz and J=5.2 Hz), 1.61 (s, 9H), 1.58 (s, 9H).

To a solution of 2-(tert-butoxyoxalyl-amino)-6-(4-methoxy-benzyl)-5-(6-methoxy-4-methoxycarbonyl-1-oxo-1,3-dihydro-isoindol-2-ylmethyl)-4,5,6,7-tetrahydro-thieno[2,3-c]pyridine-3-carboxylic acid tert-butyl ester (38 mg, 0.055 mmol) in 10% formic acid/methanol (1.0 ml) at room temperature under nitrogen was added 10% Pd/C (38 mg). The mixture was stirred for 16 hours and the Pd/C was filtered off and the filtrate evaporated in vacuo. The residue was taken into dichloromethane (1.0 ml) poured into hexane. The precipitate was filtered off, affording 28 mg (82%) of 2-(tert-butoxyoxalyl-amino)-5-(6-methoxy-4-methoxycarbonyl-1-oxo-1,3-dihydro-isoindol-2-ylmethyl)-4,5,6,7-tetrahydro-thieno[2,3-c]pyridine-3-carboxylic acid tert-butyl ester as a solid. $^1$H-NMR δ(CDCl$_3$): δ12.45 (s, 1H), 10.90 (s, 1H), 10.69 (s, H), 7.73 (s, 1H), 7.42 (s, 1H), 4.85 (bs, 2H), 4.65 (bs, 1H), 4.42 (bs, 2H), 3.99 (bs, 2H), 3.96 (s, 3H), 3.89 (s, 3H), 3.35 (bs, 1Hz), 3.21 (bs, 1H), 1.62 (s, 9H), 1.56 (s, 9H).

To a solution of trifluoroacetic acid (0.5 ml) and dichloromethane (0.5 ml) was added 2-(tert-butoxyoxalyl-amino)-

5-(6-methoxy-4-methoxycarbonyl-1-oxo-1,3-dihydro-isoindol-2-ylmethyl)-4,5,6,7-tetrahydro-thieno[2,3-c]pyridine-3-carboxylic acid tert-butyl ester (14 mg, 0.023 mmol). The solution was stirred at room temperature for 40 hours. The reaction mixture was poured into diethyl ether (20 ml). The precipitate was filtered off, which afforded 10 mg (75%) of the title compound as a solid trifluoroacetate.

$^1$H-NMR δ(DMSO-d$_6$): δ12.28 (s, 1H), 9.32 (s, 1H), 9.10 (s, 1H), 7.65 (d, 1H, J=2.4 Hz), 7.50 (d, 1H, J=2.4 Hz), 4.82 (d, 1H, J=17.2 Hz), 4.65 (d, 1H, J=17.6 Hz), 4.40 (d, 1H, J=17.6 Hz), 4.30 (m, 1H), 4.10 (dd, 1H, J=17.2 Hz and J=5.2 Hz), 3.95 (s, 1H), 3.89 (s, 6H), 3.85 (d, 1H, J=17.2 Hz), 2.81 (dd, 1H, J=18 Hz and J=7.2 Hz).

LC-MS: R$_t$=1.30 min; m/z: 504 [M+H]$^+$

Example 47

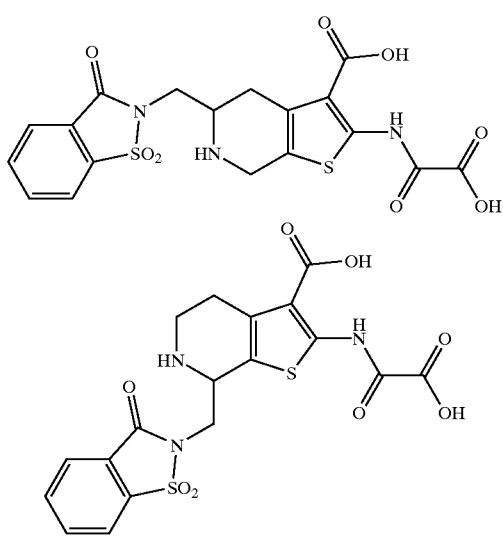

2-(Oxalyl-amino)-5-(1,1,3-trioxo-1,3-dihydro-1H-benzo[d]isothiazol-2-ylmethyl)-4,7-dihydro-5H-thieno[2,3-c]pyridine-3-carboxylic acid and 2-(Oxalyl-amino)-7-(1,1,3-trioxo-1,3-dihydro-1H-benzo[d]isothiazol-2-ylmethyl)-4,7-dihydro-5H-thieno[2,3-c]pyridine-3-carboxylic acid To a solution of 2-aminomethyl-4-(2-spiro[1,3]dioxolane)-piperidine (193 mg, 1.12 mmol) and diisopropyl ethylamine (0.46 ml, 2.55 mmol) in acetonitrile (10 ml) cooled to 0° C. was added 2-chlorosulfonyl-benzoic acid methyl ester (278 mg, 1.18 mmol). The solution was stirred at 25° C. for 24 hours. Solvent was removed in vacuo and the residue was chromatographed using a mixture of ethyl acetate/hexane (1:3) as eluent, which afforded 199 mg (51%) of 2-(4-(2-spiro[1,3]dioxolane)piperidin-2-ylmethyl)-1,1-dioxo-1,2-dihydro-1H-benzo[d]isothiazol-3-one as a solid.

$^1$H-NMR (CDCl$_3$): δ7.99–7.96 (m, 1H), 7.66–7.53 (m, 3H), 5.01 (s, 1H), 4.73 (dm, 1H, J=14.4 Hz), 4.06–3.93 (m, 6H), 3.25 (dd, 1H, J=12.6 Hz), 3.06 (td, 1H, J=13.5 Hz and J=3.6 Hz), 1.93 (dd, 1H, J=14.1 Hz and J=5.7 Hz), 1.87 (dd, 1H, J=14.1 Hz and J=3.0 Hz), 1.76 (dd, 1H, J=13.5 Hz and J=5.1 Hz).

LC-MS: R$_t$=1.78; m/z: 339 [M+H]$^+$.

2-(4-(2-Spiro[1,3]dioxolane)piperidin-2-ylmethyl)-1,1-dioxo-1,2-dihydro-1H-benzo[d]isothiazol-3-one (199 mg, 0.588 mmol) was dissolved in 2 M hydrochloric acid (12 ml) and the solution was heated to 50° C. for 24 hours. The volatiles were removed in vacuo and the residue (341 mg) was treated without further purification with saturated sodium carbonate (12 ml), dichloromethane (8 ml) and di-t-butyl dicarbonate (1.64 g, 7.5 mmol). The mixture was stirred at 35° C. for 3 days and extracted with dichloromethane (30 ml). The organic solution was washed with saturated sodium bicarbonate, brine, dried (MgSO$_4$), filtered and the solvent evaporated in vacuo. The residue was chromatographed on silica gel column using a mixture of ethyl acetate/hexane (1:3) as eluent, which afforded 115 mg (50%) of 4-oxo-2-(1,1,3-trioxo-1,3-dihydro-1H-benzo[d]isothiazol-2-ylmethyl)-piperidine-1-carboxylic acid tert-butyl ester as an oil.

$^1$H-NMR (CDCl$_3$): δ8.06 (dd, 1H, J=6.0, 1.8 Hz), 7.95–7.80 (m, 3H), 5.02 (bs, 1H), 4.35 (bs, 1H), 3.91 (dd, 1H, J=15.0 Hz and J=8.4 Hz), 3.78 (dd, 1H, J=14.7 Hz and J=5.7 Hz), 3.53 (t, 1H, J=10.8 Hz), 2.74 (dd, 1H, J=15.0 Hz and J=7.5 Hz), 2.60–2.38 (m, 3H), 1.32 (s, 9H).

To a solution of 4-oxo-2-(1,1,3-trioxo-1,3-dihydro-1H-benzo[d]isothiazol-2-ylmethyl)-piperidine-1-carboxylic acid tert-butyl ester (115 mg, 0.292 mmol) in absolute ethanol (5 ml) was added t-butyl cyanoacetate (57 l, 0.41 mmol), sulfur (13 mg, 0.41 mmol) and morpholine (55 μl, 0.63 mmol). The solution was stirred at 50° C. for 14 hours. The solvent was evaporated in vacuo and the residue was chromatographed on silica gel column using a mixture of ethyl acetate/hexane (1:4) as eluent, which afforded 100 mg (62%) of 2-amino-5-(1,1,3-trioxo-1,3-dihydro-1H-benzo[d]isothiazol-2-ylmethyl)-4,7-dihydro-5H-thieno[2,3-c]pyridine-3,6-dicarboxylic acid di-tert-butyl ester and 2-amino-7-(1,1,3-trioxo-1,3-dihydro-1H-benzo[d]isothiazol-2-ylmethyl)-4,7-dihydro-5H-thieno[2,3-c]pyridine-3,6-dicarboxylic acid di-tert-butyl ester as a mixture.

$^1$H-NMR (CDCl$_3$): δ8.10–8.00 (m, 1H), 7.98–7.77 (m, 2.8H), 7.66–7.58 (m, 0.2H), 6.11 (s, 0.4H), 6.06 (s, 0.6H), 5.59 (m, 0.2H), 5.39 (t, 0.3H, J=5.7 Hz) 5.23 (bs, 0.3H), 5.04 (bs, 0.4H), 4.77 (d, 0.4H, J=14.4 Hz), 4.60 (d, 0.4H, J=14.4 Hz), 4.45–4.18 (m, 1H), 4.02–3.82 (m, 1.5H), 3.64 (dd, 0.5H, J=14.7 Hz and J=5.2 Hz), 3.30–2.60 (m, 2H), 1.54 (s, 7H), 1.53 (s, 2H), 1.26 (s, 7H), 1.21 (s, 2H).

To a stirred solution of the above 2-amino-5-(1,1,3-trioxo-1,3-dihydro-1H-benzo[d]isothiazol-2-ylmethyl)-4,7-dihydro-5H-thieno[2,3-c]pyridine-3,6-dicarboxylic acid di-tert-butyl ester and 2-amino-7-(1,1,3-trioxo-1H-benzo[d]isothiazol-2-ylmethyl)-4,7-dihydro-5H-thieno[2,3-c]pyridine-3,6-dicarboxylic acid di-tert-butyl ester mixture (100 mg, 0.18 mmol) in acetonitrile (7 ml) was added imidazol-1-yl-oxo-acetic acid tert-butyl ester (290 mg, 1.46 mmol) in acetonitrile (1 ml). The mixture was stirred at room temperature for 16 hours. The solvent was removed in vacuo and the residue was taken into ethyl acetate. The solution was washed with 0.5 N hydrochloric acid solution, saturated sodium bicarbonate, brine, dried MgSO$_4$) and filtered. The solvent was removed in vacuo and the residue was chromatographed on silicagel using a mixture of ethyl acetate/hexane (1:4) as eluent, which provided 98 mg (80%) of a mixture of 2-(tert-butoxyoxalyl-amino)-5-(1,1,3-trioxo-1,3-dihydro-1H-benzo[d]isothiazol-2-ylmethyl)-4,7-dihydro-5H-thieno[2,3-c]pyridine-3,6-dicarboxylic acid di-tert-butyl ester and 2-(tert-butoxyoxalyl-amino)-7-(1,1,3-trioxo-1,3-dihydro-1H-benzo[d]isothiazol-2-ylmethyl)-4,7-dihydro-5H-thieno[2,3-c]pyridine-3,6-dicarboxylic acid di-tert-butyl ester as a solid.

$^1$H-NMR (CDCl$_3$): δ12.60 (s, 0.3H), 12.54 (s, 0.7H), 8.12–8.06 (m, 1H), 7.98–7.80 (m, 2.8H), 7.66–7.58 (m, 0.2H), 5.83 (bs, 0.1H), 5.61 (t, 0.2H), 5.40–4.54 (m, 0.9H), 4.53–4.40 (m, 0.8H), 4.02–3.70 (m, 1.42H), 3.66 (dd, 0.58H, J=14.7 Hz and J=5.2 Hz), 3.30–2.99 (m, 3H), 1.68 (s, 6H), 1.62 (s, 6H), 1.60 (s, 6H), 1.31 (s, 4.5H), 1.25 (s, 4.5H)

LC-MS: $R_t$=4.45; m/z: 678 [M+H]$^+$.

To a solution of trifluoroacetic acid (4 ml) and dichloromethane (2 ml) was added the mixture of 2-(tert-butoxyoxalyl-amino)-5-(1,1,3-trioxo-1,3-dihydro-1H-benzo[d]isothiazol-2-ylmethyl)-4,7-dihydro-5H-thieno[2,3-c]pyridine-3,6-dicarboxylic acid di-tert-butyl ester and 2-(tert-butoxyoxalyl-amino)-7-(1,1,3-trioxo-1,3-dihydro-1H-benzo[d]isothiazol-2-ylmethyl)-4,7-dihydro-5H-thieno[2,3-c]pyridine-3,6-dicarboxylic acid di-tert-butyl ester (78 mg, 0.12 mmol). The solution was stirred at room temperature for 24 hours. The solvent was then evaporated in vacuo, which afforded 50 mg (72%) of the title compounds as a mixture of trifluoroacetates.

$^1$H-NMR (DMSO-d$_6$): δ12.32 (s, 1H), 9.75–9.20 (m, 2H), 8.40 (t, 1H, J=6.0 Hz), 8.22–8.02 (m, 3H), 5.03 (bs, 0.5H), 4.52 (d, 1H), 4.38–4.10 (m, 2H), 3.88 (bs, 0.5H), 3,70–3.64 (m, 0.5H), 3.44–3.34 (m, 0.5H), 3.20–2.90 (m, 2H).

LC-MS: $R_t$=1.28 min, m/z: 466 [M+H]$^+$

Example 48

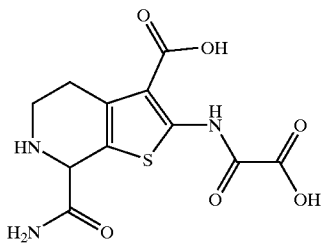

7-(R)-Carbamoyl-2-(oxalyl-amino)-4,5,6,7-tetrahydro-thieno[2,3-c]pyridine-3-carboxylic acid To a solution of 2-(S)-4-oxo-piperidine-1,2-dicarboxylic acid 1-tert butyl ester (18.4 g, 75.6 mmol) and triethylamine (12.65 mL, 90.79 mmol) in tetrahydrofuran (50 mL) cooled to −20° C. was added isobutylchloro-formate (11.81 mL, 90.79 mmol) and the mixture was stirred for 10 min at −20° C. before a 25% solution of ammonia in water (100 mL) was added. The temperature was kept at −20° C. for 30 min before the cooling bath was removed and the reaction mixture was allowed to reach room temperature and stirring was continued for another hour. The reaction mixture was extracted with ethyl acetate (6×50 mL) and the combined organic phases were dried (MgSO$_4$). The solvent was removed in vacuo and the residue was purified by column chromatography (SiO$_2$, Flash 40, ethyl acetate) to give 8.51 g (46%) of 2-(S)-carbamoyl-4-oxo-piperidine-1-carboxylic acid 1-tert-butyl ester.

A solution of 2-(S)-carbamoyl-4-oxo-piperidine-1-carboxylic acid 1-tert butyl ester (3.51 g, 14.48 mmol), tert-butyl cyanoacetate (2.04 g, 14.48 mmol), sulphur (0.464 g, 14.48 mmol) and diisopropyl ethylamine (2.5 mL, 14.48 mmol) in methanol (20 mL) was heated 16 hours at 40° C. under N$_2$. The volatiles were removed in vacuo and the residue was purified using column chromatography (SiO$_2$, Flash 40, petroleum ether/ethyl acetate 3:1) to give 1.33 g (23%) of a mixture 2-amino-5-(S)-carbamoyl-4,7-dihydro-5H-thieno[2,3-c]pyridine-3,6-di-carboxylic acid di-tert-butyl ester and 2-amino-7-(R)-carbamoyl-4,7-dihydro-5H-thieno[2,3-c]pyridine-3,6-di-carboxylic acid di-tert-butyl ester isomers.

0.5 g (1.25 mmol) of the above mixture was dissolved dichloromethane (10 mL) and imidazole-1-yl-oxo-acetic acid tert-butyl ester (0.74 g, 3.77 mmol) and triethylamine (525 μL, 3.77 mmol) was added. The reaction mixture was stirred for 16 hours at room temperature before the volatiles were removed in vacuo. The residue was purified by column chromatography (SiO$_2$, Flash 40, petroleum ether/ethyl acetate (4:1)) too give 75 mg (11%) of 2-(tert-butoxyoxalyl-amino)-7-(R)-carbamoyl-4,7-dithydro-5H-thieno[2,3-c]pyridine-3,6-dicarboxylic acid di-tert-butyl ester.

This was dissolved in a mixture of trifluoacetic acid/dichloromethane (1:1) (10 mL) and stirred for 16 hours at room temperature before the solvent was removed in vacuo. The residue was recrystallized from methanol to give 24 mg (39%) of the title compound.

LC-MS: $R_t$=1.56 min, m/z: 314 [M+H]$^+$

Calculated for $C_{11}H_{11}N_3O_6S$, 0.25×$C_2HF_3O_2$, 0.75×$H_2O$ C, 38.88%; H, 3.62%; N, 11.83%; Found: C, 38.92%; H, 3.92%; N, 11.81%.

Example 49

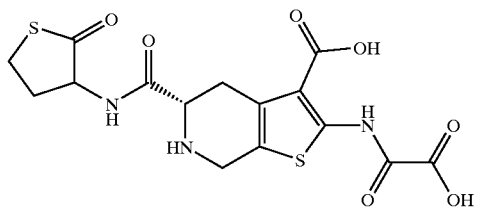

2-(Oxalyl-amino)-5-(S)-(2-oxo-tetrahydro-thiophen-3-ylcarbamoyl)-4,5,6,7-tetrahydro-thieno[2,3-c]pyridine-3-carboxylic acid A solution of 2-amino-4,7-dihydro-5H-thieno[2,3-c]pyridine-3,5-(S),6-tri-carboxylic acid 3,6-di-tert-butyl ester (0.30 g, 0.75 mmol) and triethylamine (0.21 mL, 1.51 mmol) in tetrahydrofuran (10 mL) was cooled to −20° C. before isobutyl chloroformate (103 μL, 0.75 mmol) was added. The reaction mixture was stirred 15 min at −20° C. before homocystein hydrochloride (116 mg, 0.75 mmol) was added. The cooling bath was removed and the reaction mixture was left for 16 hours at room temperature. The solvent was removed in vacuo and the residue was subjected to column chromatography (SiO$_2$, Flash 40, heptane/ethyl acetate 2:1) to give 212 mg (56%) of 2-amino-5-(S)-(2-oxo-tetrahydro-thiophen-3-ylcarbamoyl)-4,7-dihydro-5H-thieno[2,3-c]pyridine-3,6-dicarboxylic acid di-tert-butyl ester A solution of 2-amino-5-(S)-(2-oxo-tetrahydro-thiophen-3-ylcarbamoyl)-4,7-dihydro-5H-thieno[2,3-c]pyridine-3,6-dicarboxylic acid di-tert-butyl ester (200 mg, 0.40 mmol), imidazole-1-yl-oxo-acetic acid tert-butyl ester (235 mg, 1.20 mmol) and triethylamine (168 μL, 1.20 mmol) in dichloromethane (10 mL) was stirred for 16 hours at room temperature before the solvent was removed in vacuo. The residue was purified by column chromatography (SiO$_2$, Flash 40, heptane/ethyl acetate 2:1) to give 250 mg (100%) of 2-(tert-butoxyoxalyl-amino)-5-(S)-(2-oxo-tetrahydro-thiophen-3-ylcarbamoyl)-4,7-dihydro-5H-thieno[2,3-c]pyridine-3,6-dicarboxylic acid di-tert-butyl ester.

This was dissolved in a mixture of trifluoroacetic acid/dichloromethane (1:1) (3 mL) and stirred for 16 hours at room temperature before diethyl ether (6 mL) was added. The precipitate was filtered off and washed with diethyl ether to give 172 mg (81%) of the title compound as a solid trifluoroacetate.

LC-MS; $R_t$=0.41 min, m/z: 414 [M+H]$^+$

Calculated for $C_{15}H_{15}N_3O_7S_2$, 1.5×$C_2HF_3O_2$, $H_2O$; C, 35.88%; H, 3.10%; N, 6.97%; Found: C, 35.91%; H, 3.54%; N, 6.97%.

Example 50

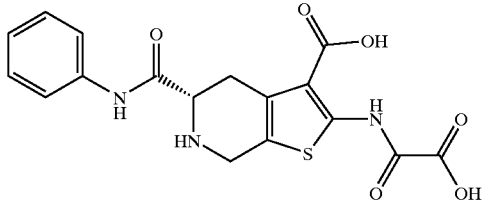

2-(Oxalyl-amino)-5-(S)-phenylcarbamoyl-4,5,6,7-tetrahydro-thieno[2,3-c]pyridine-3-carboxylic acid A solution of 2-amino-4,5,6,7-tetrahydro-thieno[2,3-c]-pyridine-3,5-(S),6-tricarboxylic acid 3,5-di-tert-butyl ester (300 mg, 0.75 mmol) and triethylamine (210 μL, 1.51 mmol) in tetrahydrofuran (10 mL) was cooled to −20° C. before isobutylchloroformate (103 mg, 0.75 mmol) was introduced. The reaction mixture was stirred for 20 min before aniline (70 mg, 0.75 mmol) was added. The cooling bath was removed and the reaction was left for 16 hours at room temperature before the solvent was removed in vacuo. The residue was partitioned between ethyl acetate (50 mL) and water (50 mL). The organic phase was dried (MgSO$_4$) and the solvent was removed in vacuo. The residue was dissolved in dichloromethane (10 mL) and imidazole-1-yl-oxo-acetic acid tert-butyl ester (443 mg, 2.26 mmol) and triethylamine (315 μL, 2.26 mmol) was added. The reaction mixture was stirred 16 hours at room temperature before the solvent was removed in vacuo. The residue was purified by column chromatography (SiO$_2$, Flash 40, heptane/ethyl acetate (3:1) to give 250 mg 2-(tert-butoxyoxalyl-amino)-5-(S)-phenylcarbamoyl-4,7-dihydro-5H-thieno[2,3-c] pyridine-3,6-dicarboxylic acid di-tert-butyl ester.

2-(tert-Butoxyoxalyl-amino)-5-(S)-phenylcarbamoyl-4,7-dihydro-5H-thieno[2,3-c]pyridine-3,6-dicarboxylic acid di-tert-butyl ester was dissolved in a mixture of trifluoroacetic acid/dichloromethane (1:1) (3 mL) and stirred for 16 hours at room temperature before di-ethyl ether (6 mL) was added. The precipitate was filtered off and washed with diethyl ether to give 155 mg (41%) of the title compound as a solid trifluoroacetate.

LC-MS; $R_t$=0.86 min, m/z: 390 [M+H]$^+$

Calculated for $C_{17}H_{15}N_3O_6S$, 1.5×$C_2HF_3O_2$, $H_2O$; C, 41.53%; H, 3.22%; N, 7.26%; Found: C, 41.77%; H, 3.29%; N, 7.28%.

Example 51

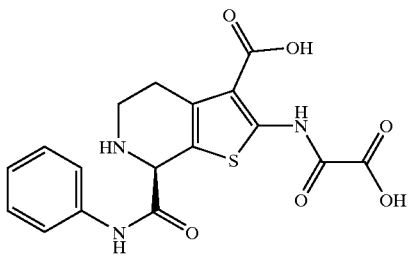

2-(Oxalyl-amino)-7-(R)-phenylcarbamoyl-4,5,6,7-tetrahydro-thieno[2,3-c]pyridine-3-carboxylic acid To a solution of 2-(S)-4-oxo-piperidine-1,2-dicarboxylic acid 1-tert butyl ester (2.06 g, 8.47 mmol) and triethylamine (1.42 mL, 10.16 mmol) in tetrahydrofuran (20 mL) cooled to −20° C. was added isobutylchloroformate (1.39 g, 10.16 mmol) and the mixture was stirred for 10 min at −20° C. before aniline (946 mg, 10.16 mmol) was added. The cooling bath was removed and the reaction mixture was stirred for 16 hours at room temperature before the solvent was removed in vacuo. The residue was divided between water (50 mL) and ethyl acetate (50 mL). The organic phase was washed with saturated sodium chloride (25 mL) and dried (MgSO$_4$). After filtration and concentration in vacuo the residue was purified using column chromatography (SiO$_2$, Flash 40, petroleum ether/ethyl acetate 5:1) to give 1.3 g (48%) of 4-oxo-2-(S)-phenyl-carbamoyl-piperidine-1-carboxylic acid tert-butyl ester.

A solution of 4-oxo-2-(S)-phenylcarbamoyl-piperidine-1-carboxylic acid tert-butyl ester (1.3 g, 4.08 mmol), tert-butylcyanoacetate (0.58 g, 4.08 mmol), sulphur (0.133 g, 4.08 mmol) and diisopropyl ethylamine (0.7 mL, 4.08 mmol) in methanol (10 mL) was heated under nitrogen to 40° C. for 16 hours before the solvent was removed in vacuo. The residue was subjected to column chromatography (SiO$_2$, Flash 40, petroleum ether/ethyl acetate 6:1) to give 0.70 g (36%) of a mixture of 2-amino-5-(S)-phenylcarbamoyl-4,7-dihydro-5H-thieno[2,3-c]pyridine-3,6-di-carboxylic acid di-tert-butyl ester and 2-amino-7-(R)-phenylcarbamoyl-4,7-dihydro-5H-thieno[2,3-c]pyridine-3,6-di-carboxylic acid di-tert-butyl ester isomers.

The above mixture was dissolved in dichloromethane (20 mL) and imidazole-1-yl-oxo-acetic acid tert-butyl ester (872 mg, 4.44 mmol) and triethylamine (618 μL, 4.44 mmol) was added. The reaction mixture was stirred 16 hours before the solvent was removed in vacuo and the residue was subjected to column chromatography (SiO$_2$, Flash 40, petroleum ether/ethyl acetate 5:1) to give 0.50 g (56%) as a mixture of 2-(tert-butoxyoxalyl-amino)-5-(S)-phenylcarbamoyl-4,7-dihydro-5H-thieno[2,3-c]pyridine-3,6-di-carboxylic acid di-tert-butyl ester and 2-(tert-butoxyoxalyl-amino)-7-(R)-phenylcarbamoyl-4,7-dihydro-5H-thieno[2,3-c]pyridine-3,6-di-carboxylic acid di-tert-butyl ester.

300 mg of the mixture was dissolved in a mixture of trifluoacetic acid/dichloromethane (1:1) (6.0 mL) and the solution was stirred for 16 hours at room temperature before the solvent was removed in vacuo. The residue was purified on preparative HPLC to give 70 mg (34%) of the title compound as a solid trifluoroacetate.

LC-MS; $R_t$=0.95 min, m/z: 390 [M+H]$^+$

Calculated for $C_{17}H_{15}N_3O_6S$, $C_2HF_3O_2$, $H_2O$; C, 43.77%; H, 3.48%; N, 8.06%; Found: C, 43.92%; H, 3.44%; N, 7.97%.

Example 52

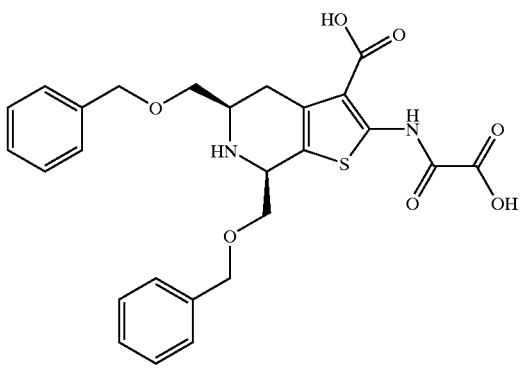

5-(R),7-(R)-Bis-benzyloxmethyl-2-(oxalin-amino)-4,5,6,7-tetrahydro-thieno[2,3-c]pyridine-3-carboxylic acid Benzyloxyacetaldehyde (0.90 9; 6.0 mmol) and dimethyl (2-oxomethyl)-phosphonate (1.0 g; 6.0 mmol) were dissolved in a mixture of tetrahydrofuran (25 ml) and water (20 ml). 1N Aqueous potassium hydroxide (6 ml) was added and the mixture was stirred for 30 min. Di-chloromethane (50 ml) was added and the organic phase was separated, dried (MgSO$_4$) and evaporated in vacuo leaving 5-benzyloxypent-3-en-2-one.

$^1$H-NMR: (CDCl$_3$): δ2.25 (s, 3H); 4.19 (dd, 2H); 4.55 (s, 2H); 6.34 (dt; 1H); 6.70 (dt, 1H); 7.26 (m, 5H).

5-benzyloxypent-3-en-2-one was dissolved in methanol (5 ml) and ammonium acetate (13 mmol, 1.03 g) was mixed together with benzyloxyacetaldehyde (1.8 g; 12 mmol) and acetic acid (0.69 ml) and the mixture was stirred for 2 days. The solvent was removed in vacuo and the residue was chromatographed on silica using gradient elution from 100% di-chloromethane to 100% ethyl acetate. A fraction (411 mg) contained (according to LC-MS; m/z 340.4) 2,5-di (benzyloxymethyl)-4-piperidone in an impure state was isolated. The crude mixture was dissolved in ethanol (3 ml) and tert-butylcyanoacetate (400 mg), sulfur (100 mg) and triethylamine was added and the mixture was stirred at room temperature overnight. The mixture was filtered and the solvent removed in vacuo. The residue was chromatographed on silica in a mixture of dichloromethane/(7% of 25% aqueous ammonia in ethanol) (40:1), which afforded 0.14 g of 2-amino-5-(R),7-(R)-bis-benzyloxymethyl4,5,6,7-tetrahydro-thieno[2,3-c]pyridine-3-carboxylic acid tert-butyl ester as an oil.

LC-MS: R$_t$: 6.03 min; m/z: 495.2 [M+H]$^+$

2-Amino-5-(R),7-(R)-Bis-benzyloxymethyl -4,5,6,7-tetrahydro-thieno[2,3-c]pyridine-3-carboxylic acid tert-butyl ester (0.14 9; 0.28 mmol) was dissolved in dichloromethane (5 ml) and treated with imidazol-1-yl-oxo-acetic acid tert-butyl ester (0.1 g; 0.5 mmol) and triethylamine (70 μl; 0.5 mmol), and stirred overnight, washed with water, dried (MgSO$_4$) and the solvent removed in vacuo. The residue was chromatographed on silica using ethyl acetate/dichloromethane (1:3) as eluent. The residue was treated with trifluoroacetic acid (0.5 ml) in dichloromethane (0.5 ml) and stirred for 4 hours. Evaporation of the solvent in vacuo afforded 37 mg of the title compound.

LC-MS: R$_t$: 4.74 min; m/z: 511.4 [M+H]$^+$.

Example 53

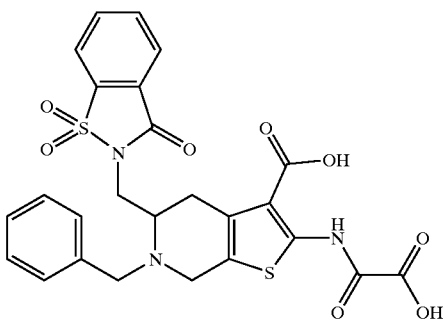

6-Benzyl-2-(oxalyl-amino)-5-(1,1,3-trioxo-1,3-dihydro-1,6-benzo[d]isothiazol-2-ylmethyl)-4,5,6,7-tetrahydro-thieno[2,3-c]pyridine-3-carboxylic acid 1-Benzyl4-oxo-piperidine-2-carboxylic acid ethyl ester (2.9 g; 11.1 mmol) (prepared in a similar way as described in "GENERAL CHIRAL SYNTHESIS" for 4-oxo-1-((S)-1-phenyl-ethyl)-piperidine-(R)-2-carboxylic acid ethyl ester using benzylamine instead of 1-(S)-phenethylamine) was dissolved in abs. ethanol (50 ml) and sulfur (0.35 g, 11.1 mmol), triethylamine (1.6 ml, 11.1 mmol), and tert-butylcyanoacetate (1.7 g, 11.1 mmol) were added and the mixture was stirred 2 days at room temperature. The solvent was removed in vacuo and the residue was chromatographed on silica using a mixture of ethyl actetate/heptane (1:4) as eleuent leaving a mixture (700 mg; 1:1 based on NMR) of 2-amino-6-benzyl-4,5,6,7-tetrahydro-thieno[2,3-c]pyridine-3,7-dicarboxylic acid 3-tert-butyl ester-7-ethyl ester and 2-amino-6-benzyl-4,5,6,7-tetrahydro-thieno[2,3-c]pyridine-3,7-dicarboxylic acid 3-tert-butyl ester 5-ethyl ester which was used in the next step without separation. To this mixture was added tetrahydrofuran (5 ml) and lithium borohydride (1.1 ml of a 2M solution in tetrahydrofuran) and the mixture was stirred 18 hours. More lithium borohydride (5.0 ml of a 2M solution in tetrahydrofuran) was added and the mixture stirred for an additiona 4 days. Ethyl acetate (10 ml) was added dropwise and after 1 hour the mixture was poured onto water (100 ml) and extracted with dichloromethane (2×100 ml) and chromatographed on silica (using ethylacetate/heptane 1:1 as eluent), which afforded a mixture of 2-amino-6-benzyl-7-hydroxymethyl-4,5,6,7-tetrahydro-thieno[2,3-c]pyridine-3-carboxylic acid tert-butyl ester and 2-amino-6-benzyl-5-hydroxymethyl-4,5,6,7-tetrahydro-thieno[2,3-c]pyridine-3-carboxylic acid tert-butyl ester (in total 187 mg). To this mixture was added dry tetrahydrofuran (10 ml), 2,3-dihydro-1,2-benzisothiazol-3-one-1,1-dioxide (100 mg; 0.55 mmol), triphenylphosphine (144 mg 0.55 mmol) and the mixture was cooled with ice. Diethyl azodicarboxylate (86 μl) was added and the mixture was stirred overnight at room temperature. The solvent was evaporated in vacuo and the residue was chromatographed on silica using a mixture of ethyl acetate/heptane (1:1) as eluent leaving 94 mg of 2-amino-6-benzyl-5-(1,1,3-trioxo-1,3-dihydro-1,6-benzo[d]isothiazol-2-ylmethyl)-4,5,6,7-tetrahydro-thieno[2,3-c]pyridine-3-carboxylic acid tert-butyl ester.

$^1$H-NMR: (CDCl$_3$): δ1.52 (s, 9H); 2.75 (dd, 1H); 2.90 (dd, 1H); 3.55 (d, 1H); 3.72 (m, 4H); 3.94 (d, 1H); 4.12 (d, 1H); 5.97 (s, 2H); 7.14–7.37 (m, 5H); 7.80–8.0 (m, 4H).

LC-MS: R$_t$ 5.47 min, m/z: 540.4 [M+H]$^+$

2-Amino-6-benzyl-5-(1,1,3-trioxo-1,3-dihydro-1,6-benzo[d]isothiazol-2-ylmethyl)-4,5,6,7-tetrahydro-thieno[2,3-c]

pyridine-3-carboxylic acid tert-butyl ester (94 mg; 0.17 mmol) was dissolved in dichloromethane (5 ml) and treated with imidazol-1-yl-oxo-acetic acid tert-butyl ester (0.07 g; 0.3 mmol) and triethylamine (49 μl; 0.3 mmol), and stirred overnight, washed with water, 1N aqueous citric acid, dried (MgSO$_4$) and the solvent removed in vacuo leaving 104 mg of 2-(tert-butoxyoxalyl-amino)-6-benzyl-5-(1,1,3-trioxo-1,3-dihydro-1,6-benzo[d]isothiazol-2-ylmethyl)-4,5,6,7-tetrahydro-thieno[2,3-c]pyridine-3-carboxylic acid tert-butyl ester as an oil.

LC-MS: R$_t$: 5.50 min, m/z: 668.6 [M+H]$^+$ 2-(tert-Butoxyoxalyl-amino)-6-benzyl-5-(1,1,3-trioxo-1,3-dihydro-1,6-benzo[d]isothiazol-2-ylmethyl)-4,5,6,7-tetrahydro-thieno[2,3-c]pyridine-3-carboxylic acid tert-butyl ester (100 mg; 0.15 mmol) was treated with trifluoroacetic acid (1 m) in dichloro-methane (4 ml) and stirred for 2 days. Evaporation of the solvent in vacuo afforded 90 mg of the title compound as a solid trifluoroacetate.

Calc. for $C_{25}H_{21}N_3O_8S_2$, $1.5 \times C_2HF_3O_2$, $0.5 \times H_2O$ C, 45.72%; H, 3.22%; N, 5.71%. Found: C, 45.48%; H, 3.46%; N, 5.72%

LC-MS: R$_t$: 4.16 min; m/z: 556.2 [M+H]$^+$

What is claimed is:
1. A compound of Formula 1

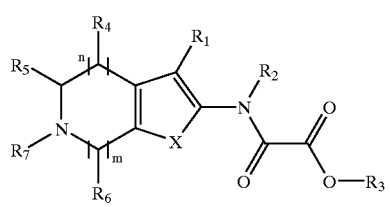

Formula 1 wherein
n is 0, 1 or 2;
m is 1 or 2;
X is S or O;
R$_1$ is hydrogen or COOR$_3$, or R$_1$ is selected from the group consisting of the following 5-membered heterocycles:

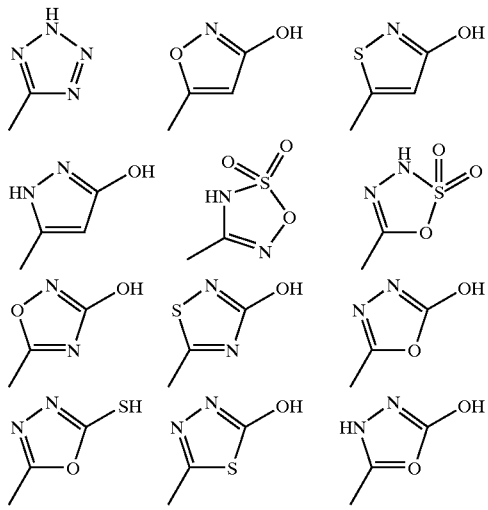

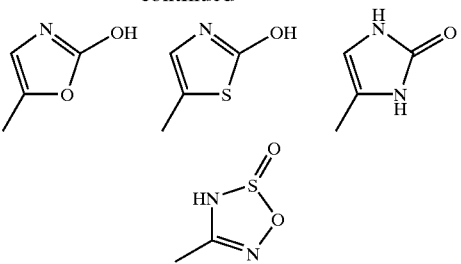

R$_2$ is hydrogen, C$_1$–C$_6$alkyl, hydroxy or NR$_8$R$_9$;
R$_3$ is hydrogen, C$_1$–C$_6$alkyl, arylC$_1$–C$_6$alkyl, C$_1$–C$_6$alkylcarbonyloxyC$_1$–C$_6$alkyl or C$_1$–C$_6$alkylcarbonyloxyarylC$_1$–C$_6$alkyl;
R$_4$, R$_5$ and R$_6$ are independently hydrogen, trihalomethyl, C$_1$–C$_6$alkyl, aryl, arylC$_1$–C$_6$alkyl, hydroxy, oxo, carboxy, carboxyC$_1$–C$_6$alkyl, C$_1$–C$_6$alkyloxycarbonyl, aryloxycarbonyl, arylC$_1$–C$_6$alkyloxycarbonyl, C$_1$–C$_6$alkyloxy, C$_1$–C$_6$alkyloxyC$_1$–C$_6$alkyl, aryloxy, arylC$_1$–C$_6$alkyloxy, arylC$_1$–C$_6$alkyloxyC$_1$–C$_6$alkyl, thio, C$_1$–C$_6$alkyl-thio, C$_1$–C$_6$alkylthioC$_1$–C$_6$alkyl, arylthio, arylC$_1$–C$_6$alkylthio, arylC$_1$–C$_6$alkylthioC$_1$–C$_6$alkyl, NR$_8$R$_9$, R$_8$R$_9$NC$_1$–C$_6$alkyl, C$_1$–C$_6$alkylaminoC$_1$–C$_6$alkyl, arylaminoC$_1$–C$_6$alkyl, arylC$_1$–C$_6$alkylaminoC$_1$–C$_6$alkyl, di(arylC$_1$–C$_6$alkyl)aminoC$_1$–C$_6$alkyl, C$_1$–C$_6$alkylcarbonyl, C$_1$–C$_6$alkylcarbonylC$_1$–C$_6$alkyl, arylC$_1$–C$_6$alkylcarbonyl, arylC$_1$–C$_6$alkylcarbonylC$_1$–C$_6$alkyl, C$_1$–C$_6$alkylcarboxy, C$_1$–C$_6$alkylcarboxyC$_1$–C$_6$-alkyl, arylcarboxy, arylcarboxyC$_1$–C$_6$alkyl, arylC$_1$–C$_6$alkylcarboxy, arylC$_1$–C$_6$alkyl-carboxyC$_1$–C$_6$alkyl, C$_1$–C$_6$alkylcarbonylamino, C$_1$–C$_6$alkylcarbonylaminoC$_1$–C$_6$alkyl, -carbonylNR$_8$C$_1$–C$_6$alkylCOR$_{12}$, arylC$_1$–C$_6$alkylcarbonylamino, arylC$_1$–C$_6$alkyl-carbonylaminoC$_1$–C$_6$alkyl, arylcarbonylaminoC$_1$–C$_6$alkyl, CONR$_8$R$_9$, or C$_1$–C$_6$alkyl-CONR$_8$R$_9$ wherein the alkyl and aryl groups are optionally substituted as defined in the definition section and R$_{12}$ is NR$_8$R$_9$, or C$_1$–C$_6$alkylNR$_8$R$_9$;
R$_7$ is hydrogen, C$_1$–C$_6$alkyl, aryl, arylC$_1$–C$_6$alkyl, C$_1$–C$_6$alkylcarbonyl, C$_1$–C$_6$alkoxycarbonyl, arylcarbonyl, aryloxocarbonyl, arylC$_1$–C$_6$alkylcarbonyl, aryC$_1$–C$_6$alkoxycarbonyl, C$_1$–C$_6$alkylcarboxy, arylC$_1$–C$_6$alkylcarboxy, R$_{10}$R$_{11}$NcarbonylC$_1$–C$_6$alkyl wherein R$_{10}$ and R$_{11}$ are independently selected from hydrogen, C$_1$–C$_6$alkyl, aryl, arylC$_1$–C$_6$alkyl, C$_1$–C$_6$alkyl-carbonyl, arylcarbonyl, arylC$_1$–C$_6$alkylcarbonyl, C$_1$–C$_6$alkylcarboxy or arylC$_1$–C$_6$alkylcarboxy; wherein the alkyl and aryl groups are optionally substituted as defined in the definition section;
R$_8$ and R$_9$ are independently selected from hydrogen, C$_1$–C$_6$alkyl, aryl, arylC$_1$–C$_6$alkyl, C$_1$–C$_6$alkylcarbonyl, C$_1$–C$_6$alkoxycarbonyl, arylcarbonyl, aryloxocarbonyl, arylC$_1$–C$_6$alkylcarbonyl, arylC$_1$–C$_6$alkoxycarbonyl, C$_1$–C$_6$alkylcarboxy, arylC$_1$–C$_6$alkylcarboxy, R$_{10}$R$_{11}$NcarbonylC$_1$–C$_6$alkyl wherein the alkyl and aryl groups are optionally substituted as defined in the definition section; or $R_8$ and $R_9$ together with the nitrogen to which they are attached form a saturated, partially saturated or aromatic monocyclic, bicyclic or tricyclic ring system containing from 3 to 14 carbon atoms and from 0 to 3 additional heteroatoms selected from nitrogen, oxygen or sulphur, the ring system can optionally be substituted with at least one $C_1$–$C_6$alkyl, aryl, aryl$C_1$–$C_6$alkyl, hydroxy, oxo, $C_1$–$C_6$alkyloxy, aryl$C_1$–$C_6$alkyloxy, $C_1$–$C_6$alkyloxy$C_1$–$C_6$alkyl, $NR_{10}R_{11}$ or $C_1$–$C_6$alkyl-amino$C_1$–$C_6$alkyl, wherein $R_{10}$ and $R_{11}$ are independently selected from hydrogen, $C_1$–$C_6$alkyl, aryl, aryl$C_1$–$C_6$alkyl, $C_1$–$C_6$alkylcarbonyl, arylcarbonyl, aryl$C_1$–$C_6$alkylcarbonyl, $C_1$–$C_6$alkylcarboxy or aryl$C_1$–$C_6$alkylcarboxy; wherein the alkyl and aryl groups are optionally substituted as defined in the definition section; or $R_8$ and $R_9$ are independently a saturated or partial saturated cyclic 5, 6 or 7 membered amine, imide or lactam;

or a salt thereof with a pharmaceutically acceptable acid or base, or any optical isomer or mixture of optical isomers, a racemic mixture, or any tautomeric form, or prodrug thereof.

2. A compound of Formula 1

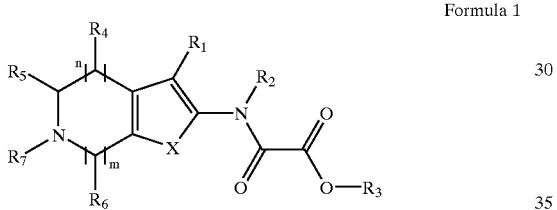

Formula 1 wherein n is 0, 1 or 2;

m is 1 or 2;

X is S or O;

$R_1$ is hydrogen or $COOR_3$, or $R_1$ is selected from the group consisting of the following 5-membered heterocycles:

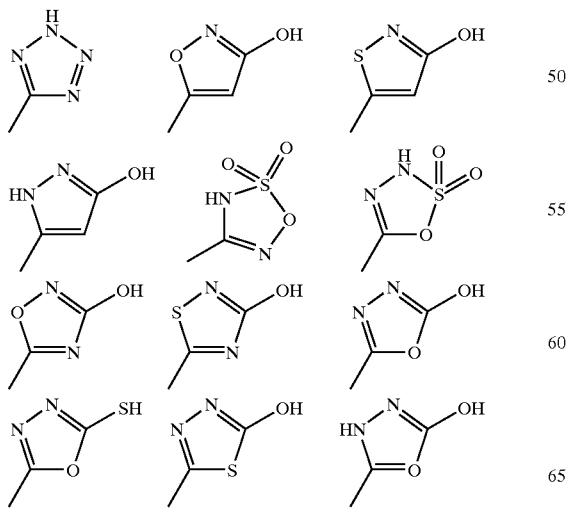

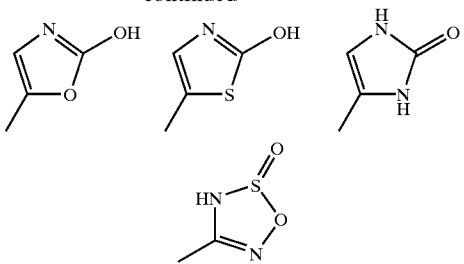

$R_2$ is hydrogen, $C_1$–$C_6$alkyl, hydroxy or $NR_8R_9$;

$R_3$ is hydrogen, $C_1$–$C_6$alkyl, aryl$C_1$–$C_6$alkyl, $C_1$–$C_6$alkylcarbonyloxy$C_1$–$C_6$alkyl or $C_1$–$C_6$alkylcarbonyloxyaryl$C_1$–$C_6$alkyl;

$R_4$, $R_5$ and $R_6$ are independently hydrogen, trihalomethyl, $C_1$–$C_6$alkyl, aryl, aryl$C_1$–$C_6$alkyl, hydroxy, oxo, carboxy, carboxy$C_1$–$C_6$alkyl, $C_1$–$C_6$alkyloxycarbonyl, aryloxycarbonyl, aryl$C_1$–$C_6$alkyloxycarbonyl, $C_1$–$C_6$alkyloxy, $C_1$–$C_6$alkyloxy$C_1$–$C_6$alkyl, aryloxy, aryl$C_1$–$C_6$alkyloxy, aryl$C_1$–$C_6$alkyloxy$C_1$–$C_6$alkyl, thio, $C_1$–$C_6$alkyl-thio, $C_1$–$C_6$alkylthio$C_1$–$C_6$alkyl, arylthio, aryl$C_1$–$C_6$alkylthio, aryl$C_1$–$C_6$alkylthio$C_1$–$C_6$alkyl, $NR_8R_9$, $C_1$–$C_6$alkylamino$C_1$–$C_6$alkyl, aryl$C_1$–$C_6$alkylamino$C_1$–$C_6$alkyl, di(aryl$C_1$–$C_6$alkyl)amino$C_1$–$C_6$alkyl, $C_1$–$C_6$alkylcarbonyl, $C_1$–$C_6$alkylcarbonyl$C_1$–$C_6$alkyl, aryl$C_1$–$C_6$alkylcarbonyl, aryl$C_1$–$C_6$alkylcarbonyl$C_1$–$C_6$alkyl, $C_1$–$C_6$alkylcarboxy, $C_1$–$C_6$alkylcarboxy$C_1$–$C_6$-alkyl, arylcarboxy, arylcarboxy$C$–$C_6$alkyl, aryl$C_1$–$C_6$alkylcarboxy, aryl$C_1$–$C_6$alkylcarboxy$C_1$–$C_6$alkyl, $C_1$–$C_6$alkylcarbonylamino, $C_1$–$C_6$alkylcarbonylamino$C_1$–$C_6$alkyl, -carbonyl$NR_8C_1$–$C_6$alkyl$COR_{12}$, aryl$C_1$–$C_6$alkylcarbonyl-amino, aryl$C_1$–$C_6$alkylcarbonylamino$C_1$–$C_6$alkyl, $CONR_8R_9$, or $C_1$–$C_6$alkyl-$CONR_8R_9$ wherein the alkyl and aryl groups are optionally substituted and $R_{12}$ is $NR_8R_9$, or $C_1$–$C_6$alkyl$NR_8R_9$;

$R_7$ is hydrogen, $C_1$–$C_6$alkyl, aryl, aryl$C_1$–$C_6$alkyl, $C_1$–$C_6$alkylcarbonyl, $C_1$–$C_6$alkoxycarbonyl, arylcarbonyl, aryloxocarbonyl, aryl$C_1$–$C_6$alkylcarbonyl, aryl$C_1$–$C_6$alkoxycarbonyl, $C_1$–$C_6$alkylcarboxy, aryl$C_1$–$C_6$alkylcarboxy, $R_{10}R_{11}$Ncarbonyl$C_1$–$C_6$alkyl wherein $R_{10}$ and $R_{11}$ are independently selected from hydrogen, $C_1$–$C_6$alkyl, aryl, aryl$C_1$–$C_6$alkyl, $C_1$–$C_6$alkylcarbonyl, arylcarbonyl, aryl$C_1$–$C_6$alkylcarbonyl, $C_1$–$C_6$alkylcarboxy or aryl$C_1C_6$alkylcarboxy; wherein the alkyl and aryl groups are optionally substituted;

$R_8$ and $R_9$ are independently selected from hydrogen, $C_1$–$C_6$alkyl, aryl, aryl$C_1$–$C_6$alkyl, $C_1$–$C_6$alkylcarbonyl, $C_1$–$C_6$alkoxycarbonyl, arylcarbonyl, aryloxocarbonyl, aryl$C_1$–$C_6$alkylcarbonyl, aryl$C_1$–$C_6$alkoxycarbonyl, $C_1$–$C_6$alkylcarboxy, aryl$C_1$–$C_6$alkylcarboxy, $R_{10}R_{11}$Ncarbonyl$C_1$–$C_6$alkyl wherein the alkyl and aryl groups are optionally substituted; or $R_8$ and $R_9$ together with the nitrogen to which they are attached form a saturated, partially saturated or aromatic cyclic, bicyclic or tricyclic ring system containing from 3 to 14 carbon atoms and from 0 to 3 additional heteroatoms selected from nitrogen, oxygen or sulphur, the ring system can optionally be substituted with at least one $C_1$–$C_6$alkyl, aryl, aryl$C_1$–$C_6$alkyl, hydroxy, oxo, $C_1$–$C_6$alkyloxy, aryl$C_1$–$C_6$alkyloxy, $C_1$–$C_6$alkyloxy$C_1$–$C_6$alkyl, $NR_{10}R_{11}$ or $C_1$–$C_6$alkylamino$C_1$–$C_6$alkyl, wherein $R_{10}$ and $R_{11}$ are independently selected from hydrogen, $C_1$–$C_6$alkyl, aryl, aryl$C_1$–$C_6$alkyl, $C_1$–$C_6$alkylcarbonyl, arylcarbonyl, aryl$C_1$–$C_6$alkylcarbonyl, $C_1$–$C_6$alkylcarboxy or aryl$C_1$–$C_6$alkylcarboxy; wherein the alkyl and aryl groups are optionally substituted; or $R_8$ and $R_9$ are independently a saturated or partial saturated cyclic 5, 6 or 7 membered amine, imide or lactam;

or a salt thereof with a pharmaceutically acceptable acid or base, or any optical isomer or mixture of optical isomers, a racemic mixture, or any tautomeric form.

3. A compound according to claim 2 wherein X is sulphur.

4. A compound according to claim 3 wherein $R_1$ is $COOR_3$ and $R_2$ is hydrogen.

5. A compound according to claim 4 wherein n and m are 1.

6. A compound according to claim 4 wherein $R_5$ is $C_1$14 $C_6$alkylNR$_8$R$_9$.

7. A compound according to claim 6 wherein $R_4$ and $R_6$ are hydrogen.

8. A compound according to claim 3 wherein $R_1$ is 5-tetrazolyl, $R_2$ is hydrogen, and $R_5$ is $C_1$–$C_6$alkylNR$_8$R$_9$.

9. A compound according to claim 4 wherein $R_6$ is $C_1$–$C_6$alkylNR$_8$R$_9$.

10. A compound according to claim 9 wherein $R_4$ and $R_5$ are hydrogen.

11. A compound according to claim 3 wherein $R_1$ is 5-tetrazolyl, $R_2$ is hydrogen, and $R_6$ is $C_1$–$C_6$alkylNR$_8$R$_9$.

12. A compound according to claim 3 wherein $R_5$ and $R_6$ are $C_1$–$C_6$alkylNR$_8$R$_9$.

13. A compound according to claim 12 wherein $R_1$ is $COOR_3$ and $R_2$ is hydrogen.

14. A compound according to claim 13 wherein n and m are 1.

15. A compound according to claim 12 wherein $R_1$ is 5-tetrazolyl.

16. A compound according to claim 6 wherein $R_8$ and $R_9$ together with the nitrogen to which they are attached form a partially saturated bicyclic ring system containing 8 carbon atoms, the ring system being optionally substituted with two oxo groups.

17. A compound according to claim 16 wherein the ring system is isoindolyl.

18. A compound according to claim 17 wherein $R_7$ is $C_1$–$C_6$alkoxycarbonyl.

19. A compound according to claim 9 wherein $R_8$ and $R_9$ together with the nitrogen to which they are attached form a partially saturated bicyclic ring system containing 8 carbon atoms, the ring system being optionally substituted with two oxo groups.

20. A compound according to claim 19 wherein the ring system is isoindolyl.

21. A compound according to claim 9 wherein $R_8$ and $R_9$ together with the nitrogen to which they are attached form a partially saturated bicyclic ring system containing 7 carbon atoms and one sulfur atom, the ring system being optionally substituted with three oxo groups.

22. A compound according to claim 21 wherein the ring system is 2,3-dihydro-benzo[d]isothiazolyl.

23. A compound according to claim 9 wherein $R_8$ and $R_9$ together with the nitrogen to which they are attached form a partially saturated bicyclic ring system containing 7 carbon atoms and one sulfur atom, the ring system being optionally substituted with two oxo groups.

24. A compound according to claim 22 wherein $R_7$ is $C_1$–$C_6$alkoxycarbonyl.

25. A compound according to claim 9 wherein $R_8$ and $R_9$ together with the nitrogen to which they are attached form a partially saturated bicyclic ring system containing 8 carbon atoms, the ring system being optionally substituted with one oxo group.

26. A compound according to claim 25 wherein the ring system is optionally substituted isoindolyl.

27. A compound according to claim 25 wherein the ring system is optionally substituted 1-oxo-1,3-dihydro-isoindolyl.

28. A compound according to claim 22 wherein the $R_7$ is $C_1$–$C_6$alkoxycarbonyl.

29. A compound according to claim 4 wherein $R_5$ and $R_6$ are $C_1$–$C_6$alkylNR$_8$R$_9$.

30. A compound according to claim 1 wherein X is sulphur.

31. A compound according to claim 1 wherein $R_1$ is $COOR_3$ and $R_2$ is hydrogen; wherein $R_3$ is defined as above.

32. A compound according to claim 1 wherein n and m are 1.

33. A compound according to claim 1 wherein $R_5$ is $C_1$–$C_6$alkylNR$_8$R$_9$.

34. A compound according to claim 1 wherein $R_4$ and $R_6$ are hydrogen.

35. A compound according to claim 1 wherein $R_1$ is 5-tetrazolyl, $R_2$ is hydrogen, and $R_5$ is $C_1$–$C_6$alkylNR$_8$R$_9$.

36. A compound according to claim 1 wherein $R_6$ is $C_1$–$C_6$alkylNR$_8$R$_9$.

37. A compound according to claim 1 wherein $R_4$ and $R_5$ are hydrogen.

38. A compound according to claim 1 wherein $R_1$ is 5-tetrazolyl, $R_2$ is hydrogen, and $R_6$ is $C_1$–$C_6$alkylNR$_8$R$_9$.

39. A compound according to claim 1 wherein $R_5$ and $R_6$ are $C_1$–$C_6$alkylNR$_8$R$_9$.

40. A compound according to claim 1 wherein $R_1$ is $COOR_3$ and $R_2$ is hydrogen.

41. A compound according to claim 1 wherein n and m are 1.

42. A compound according to claim 1 wherein $R_1$ is 5-tetrazolyl.

43. A compound according to claim 1 wherein $R_8$ and $R_9$ together with the nitrogen to which they are attached form a partially saturated bicyclic ring system containing 8 carbon atoms, the ring system being optionally substituted with two oxo groups.

44. A compound according to claim 1 wherein the ring system is isoindolyl.

45. A compound according to claim 1 wherein $R_7$ is $C_1$–$C_6$alkoxycarbonyl.

46. A compound according to claim 1 wherein $R_8$ and $R_9$ together with the nitrogen to which they are attached form a partially saturated bicyclic ring system containing 8 carbon atoms, the ring system being optionally substituted with two oxo groups.

47. A compound according to claim 1 wherein $R_8$ and $R_9$ together with the nitrogen to which they are attached form a partially saturated bicyclic ring system containing 7 carbon atoms and one sulfur atom, the ring system being optionally substituted with three oxo groups.

48. A compound according to claim 1 wherein the ring system is 2,3-dihydro-benzo[d]isothiazolyl.

49. A compound according to claim 1 wherein $R_8$ and $R_9$ together with the nitrogen to which they are attached form a partially saturated bicyclic ring system containing 7 carbon atoms and one sulfur atom, the ring system being optionally substituted with two oxo groups.

50. A compound according to claim 1 wherein $R_8$ and $R_9$ together with the nitrogen to which they are attached form a partially saturated bicyclic ring system containing 8 carbon atoms, the ring system being optionally substituted with one oxo group.

51. A compound according to claim 1 wherein the ring system is optionally substituted isoindolyl.

52. A compound according to claim 1 wherein the ring system is optionally substituted 1-oxo-1,3-dihydro-isoindolyl.

53. A compound according to claim 1 wherein $R_5$ and $R_6$ are $C_1$–$C_6$alkyl$NR_8R_9$.

54. A compound according to claim 1 wherein $R_5$ is 1,3-dihydro-isoindol, substituted with 1 or 2 oxo groups at the atom positions adjacent to the nitrogen atom and optionally substituted with hydroxy, $C_{1-6}$-alkyloxy, aryl$C_{1-6}$-alkyloxy or $C_{1-6}$-alkylcarboxy, and wherein $R_7$ is hydrogen, alkyl, alkyloxycarbonyl, arylalkyl or aryl wherein aryl is optionally substituted with methoxy.

55. A compound according to claim 1 wherein $R_5$ is 1,1,3-trioxo-1,2-dihydro-1H-benzo[d]isothiazol-2-yl and wherein $R_7$ is hydrogen or arylalkyl.

56. A compound according to claim 1 wherein $R_5$ or $R_6$ is arylaminoalkyl, wherein aryl is 1,1-dioxo-1,2-dihydro-1H-benzo[d]isothiazol-3-yl.

57. A compound according to claim 1 $R_5$ or $R_6$ is arylcarbonylaminoalkyl, wherein aryl is phenyl, indol-3-yl, indol-2-yl, 1,2,3-triazol-4-yl, quinolin-4-yl or naphth-1-yl wherein aryl is optionally substituted, and wherein $R_7$ is hydrogen or arylalkyl optionally substituted with methoxy.

58. A compound according to claim 1 wherein $R_5$ is arylalkylaminoalkyl wherein aryl is phenyl, dibenzofuranyl, naphth-2-yl or indo-3-yl, and wherein alkyl and aryl are optionally substituted, and wherein $R_7$ is hydrogen or arylalkyl optionally substituted with methoxy.

59. A compound according to claim 1 wherein $R_6$ is alkyl$NR_8R_9$, wherein $R_8$ is alkylcarbonyl and $R_9$ is arylalkyl, wherein aryl is optionally substituted.

60. A compound according to claim 1 selected from the following:

5-(1,3-Dioxo-1,3-dihydro-isoindol-2-ylmethyl)-2-(oxalyl-amino)-4,5,6,7-tetrahydro-thieno[2,3-c]pyridine-3,6-dicarboxylic acid 6-ethyl ester;
5-(1,3-Dioxo-1,3-dihydro-isoindol-2-ylmethyl)-2-(oxalyl-amino)-4,5,6,7-tetrahydro-thieno[2,3-c]pyridine-3-carboxylic acid;
(L)-5-(1,3-Dioxo-1,3-dihydro-isoindol-2-ylmethyl)-2-(oxalyl-amino)-4,5,6,7-tetrahydro-thieno[2,3-c]pyridine-3-carboxylic acid;
7-(1,3-Dioxo-1,3-dihydro-isoindol-2-ylmethyl)-2-(oxalyl-amino)-4,5,6,7-tetrahydro-thieno[2,3-c]pyridine-3-carboxylic acid;
5-(4-Hydroxy-1,3-dioxo-1,3-dihydro-isoindol-2-ylmethyl)-2-(oxalyl-amino)-4,5,6,7-tetrahydro-thieno[2,3-c]pyridine-3-carboxylic acid;
2-(Oxalyl-amino)-5-(1-oxo-1,3-dihydro-isoindol-2-ylmethyl)-4,5,6,7-tetrahydro-thieno[2,3-c]pyridine-3-carboxylic acid;
2-(Oxalyl-amino)-7-(1,1,3-trioxo-1,3-dihydro-1H-benzo[d]isothiazol-2-ylmethyl)-4,5,6,7-tetrahydro-thieno[2,3-c]pyridine-3-carboxylic acid;
7-(1,1-Dioxo-1,3-dihydro-1H-benzo[d]isothiazol-2-ylmethyl)-2-(oxalyl-amino)-4,5,6,7-tetrahydro-thieno[2,3-c]pyridine-3-carboxylic acid;
5-(7-Hydroxy-1-oxo-1,3-dihydro-isoindol-2-ylmethyl)-2-(oxalyl-amino)-4,5,6,7-tetrahydro-thieno[2,3-c]pyridine-3-carboxylic acid;

or a pharmaceutically acceptable salt thereof.

61. A compound according to claim 1 selected from the following:

5-(1,3-Dioxo-1,3-dihydro-isoindol-2-ylmethyl)-2-(oxalyl-amino)-4,5,6,7-tetrahydro-thieno[2,3-c]pyridine-3,6-dicarboxylic acid 6-ethyl ester;
5-(1,3-Dioxo-1,3-dihydro-isoindol-2-ylmethyl )-2-(oxalyl-amino)-4,5,6,7-tetrahydro-thieno[2,3c]pyridine-3-carboxylic acid;
(S)-5-(1,3-Dioxo-1,3-dihydro-isoindol-2-ylmethyl)-2-(oxalyl-amino)-4,5,6,7-tetrahydro-thieno[2,3-c]pyridine-3-carboxylic acid;
7-(1,3-Dioxo-1,3-dihydro-isoindol-2-ylmethyl)-2-(oxalyl-amino)-4,5,6,7-tetrahydro-thieno[2,3-c]pyridine-3-carboxylic acid;
5-(4-Hydroxy-1,3-dioxo-1,3-dihydro-isoindol-2-ylmethyl)-2-(oxalyl-amino)-4,5,6,7-tetrahydro-thieno[2,3-c]pyridine-3-carboxylic acid;
2-(Oxalyl-amino)-5-(1-oxo-1,3-dihydro-isoindol-2-ylmethyl)-4,5,6,7-tetrahydro-thieno[2,3-c]pyridine-3-carboxylic acid;
5-(4-Hydroxy-1-oxo-1,3-dihydro-isoindol-2-ylmethyl)-2-(oxalyl-amino)-4,5,6,7-tetrahydro-thieno[2,3-c]pyridine-3-carboxylic acid;
5-(4-Hydroxy-1-oxo-1,3-dihydro-isoindol-2-ylmethyl)-6-methyl-2-(oxalyl-amino)-4,5,6,7-tetrahydro-thieno[2,3-c]pyridine-3-carboxylic acid;
5-((1,1-Dioxo-1H-benzo[d]isothiazol-3-ylamino)-methyl)-2-(oxalyl-amino)-4,5,6,7-tetrahydro-thieno[2,3-c]pyridine-3-carboxylic acid;
7-((1,1-Dioxo-1H-benzo[d]isothiazol-3-ylamino)-methyl)-2-(oxalyl-amino)-4,5,6,7-tetrahydro-thieno[2,3-c]pyridine-3-carboxylic acid;
5-(7-Methoxy-1-oxo-1,3-dihydro-isoindol-2-ylmethyl)-2-(oxalyl-amino)-4,5,6,7-tetrahydro-thieno[2,3-c]pyridine-3-carboxylic acid;
5-(7-Hydroxy-1-oxo-1,3-dihydro-isoindol-2-ylmethyl)-2-(oxalyl-amino)-4,5,6,7-tetrahydro-thieno[2,3-c]pyridine-3-carboxylic acid;
5-(7-Benzyloxy-1-oxo-1,3-dihydro-isoindol-2-ylmethyl)-2-(oxalyl-amino)-4,5,6,7-tetrahydro-thieno[2,3-c]pyridine-3-carboxylic acid;
5-(7-Hydroxy-1-oxo-1,3-dihydro-isoindol-2-ylmethyl)-6-(4-methoxy-benzyl)-2-(oxalyl-amino)-4,5,6,7-tetrahydro-thieno[2,3-c]pyridine-3-carboxylic acid;
5-(1,3-Dioxo-1,3-dihydro-isoindol-2-ylmethyl)-6-(4-methoxy-benzyl)-2-(oxalyl-amino)-4,5,6,7-tetrahydro-thieno[2,3-c]pyridine-3-carboxylic acid;
7-(7-Hydroxy-1-oxo-1,3-dihydro-isoindol-2-ylmethyl)-2-(oxalyl-amino)-4,5,6,7-tetrahydro-thieno[2,3-c]pyridine-3-carboxylic acid;
7-(7-Hydroxy-1-oxo-1,3-dihydro-isoindol-2-ylmethyl)-6-(4-methoxy-benzyl)-2-(oxalyl-amino)-4,5,6,7-tetrahydro-thieno[2,3-c]pyridine-3-carboxylic acid;
7-(1,3-Dioxo-1,3-dihydro-isoindol-2-ylmethyl)-6-(4-methoxy-benzyl)-2-(oxalyl-amino)-4,5,6,7-tetrahydro-thieno[2,3-c]pyridine-3-carboxylic acid;
5-(S)-(7-Methoxy-1-oxo-1,3-dihydro-isoindol-2-ylmethyl)-2-(oxalyl-amino)-4,5,6,7-tetrahydro-thieno[2,3-c]pyridine-3-carboxylic acid;
5-(R)-(7-Methoxy-1-oxo-1,3-dihydro-isoindol-2-ylmethyl)-2-(oxalyl-amino)-4,5,6,7-tetrahydro-thieno[2,3-c]pyridine-3-carboxylic acid;

5-(4-Benzyloxy-1,3-dioxo-1,3-dihydro-isoindol-2-ylmethyl)-2-(oxalyl-amino)-4,5,6,7-tetrahydro-thieno[2,3-c]pyridine-3-carboxylic acid;

5-(6-Methoxy-4-methoxycarbonyl-1-oxo 1,3-dihydro-isoindol-2-ylmethyl)-2-(oxalyl-amino)-4,5,6,7-tetrahydro-thieno[2,3-c]pyridine-3-carboxylic acid;

2-(Oxalyl-amino)-5-(1,1,3-trioxo-1,3-dihydro-1H-benzo[d]isothiazol-2-ylmethyl)-4,7-dihydro-5H-thieno[2,3-c]pyridine-3-carboxylic acid;

2-(Oxalyl-amino)-7-(1,1,3-trioxo-1,3-dihydro-1H-benzo[d]isothiazol-2-ylmethyl)-4,7-dihydro-5H-thieno[2,3-c]pyridine-3-carboxylic acid;

7-Carbamoyl-2-(oxalyl-amino)-4,5,6,7-tetrahydro-thieno[2,3-c]pyridine-3-carboxylic acid;

2-(Oxalyl-amino)-5-(2-oxo-tetrahydro-thiophen-3-ylcarbamoyl)-4,5,6,7-tetrahydro-thieno[2,3-c]pyridine-3-carboxylic acid;

2-(Oxalyl-amino)-5-phenylcarbamoyl-4,5,6,7-tetrahydro-thieno[2,3-c]pyridine-3-carboxylic acid;

2-(Oxalyl-amino)-7-phenylcarbamoyl-4,5,6,7-tetrahydro-thieno[2,3-c]pyridine-3-carboxylic acid;

or a pharmaceutically acceptable salt thereof.

62. A compound according to claim 1 selected from the following:

5-(1,3-Dioxo-1,3-dihydro-isoindol-2-ylmethyl)-2-(oxalyl-amino)-4,5,6,7-tetrahydro-thieno[2,3-c]pyridine-3,6-dicarboxylic acid 6-ethyl ester;

5-(1,3-Dioxo-1,3-dihydro-isoindol-2-ylmethyl)-2-(oxalyl-amino)-4,5,6,7-tetrahydro-thieno[2,3-c]pyridine-3-carboxylic acid;

5-(S)-(1,3-Dioxo-1,3-dihydro-isoindol-2-ylmethyl)-2-(oxalyl-amino)-4,5,6,7-tetrahydro-thieno[2,3-c]pyridine-3-carboxylic acid;

7-(1,3-Dioxo-1,3-dihydro-isoindol-2-ylmethyl)-2-(oxalyl-amino)-4,5,6,7-tetrahydro-thieno[2,3-c]pyridine-3-carboxylic acid;

5-(4-Hydroxy-1,3-dioxo-1,3-dihydro-isoindol-2-ylmethyl)-2-(oxalyl-amino)-4,5,6,7-tetrahydro-thieno[2,3-c]pyridine-3-carboxylic acid;

7-(4-Hydroxy-1,3-dioxo-1,3-dihydro-isoindol-2-ylmethyl)-2-(oxalyl-amino)-4,5,6,7-tetrahydro-thieno[2,3-c]pyridine-3-carboxylic acid;

2-(Oxalyl-amino)-5-(S)-(1-oxo-1,3-dihydro-isoindol-2-ylmethyl)-4,5,6,7-tetrahydro-thieno[2,3-c]pyridine-3-carboxylic acid;

5-(4-Hydroxy-1-oxo-1,3-dihydro-isoindol-2-ylmethyl)-2-(oxalyl-amino)-4,5,6,7-tetrahydro-thieno[2,3-c]pyridine-3-carboxylic acid;

5-(4-Hydroxy-1-oxo-1,3-dihydro-isoindol-2-ylmethyl)-6-methyl-2-(oxalyl-amino)-4,5,6,7-tetrahydro-thieno[2,3-c]pyridine-3-carboxylic acid;

5-((1,1-Dioxo-1H-benzo[d]isothiazol-3-ylamino)methyl)-2-(oxalyl-amino)-4,5,6,7-tetrahydro-thieno[2,3-c]pyridine-3-carboxylic acid;

7-((1,1-Dioxo-1H-benzo[d]isothiazol-3-ylamino)methyl)-2-(oxalyl-amino)-4,5,6,7-tetrahydro-thieno[2,3-c]pyridine-3-carboxylic acid;

5-(7-Methoxy-1-oxo-1,3-dihydro-isoindol-2-ylmethyl)-2-(oxalyl-amino)-4,5,6,7-tetrahydro-thieno[2,3-c]pyridine-3-carboxylic acid;

5-(7-Hydroxy-1-oxo-1,3-dihydro-isoindol-2-ylmethyl)-2-(oxalyl-amino)-4,5,6,7-tetrahydro-thieno[2,3-c]pyridine-3-carboxylic acid;

5-(7-Benzyloxy-1-oxo-1,3-dihydro-isoindol-2-ylmethyl)-2-(oxalyl-amino)-4,5,6,7-tetrahydro-thieno[2,3-c]pyridine-3-carboxylic acid;

5-(7-Hydroxy-1-oxo-1,3-dihydro-isoindol-2-ylmethyl)-6-(4-methoxy-benzyl)-2-(oxalyl-amino)-4,5,6,7-tetrahydro-thieno[2,3-c]pyridine-3-carboxylic acid;

5-(1,3-Dioxo-1,3-dihydro-isoindol-2-ylmethyl)-6-(4-methoxy-benzyl)-2-(oxalyl-amino)-4,5,6,7-tetrahydro-thieno[2,3-c]pyridine-3-carboxylic acid;

7-(7-Hydroxy-1-oxo-1,3-dihydro-isoindol-2-ylmethyl)-2-(oxalyl-amino)-4,5,6,7-tetrahydro-thieno[2,3-c]pyridine-3-carboxylic acid;

7-(7-Hydroxy-1-oxo-1,3-dihydro-isoindol-2-ylmethyl)-6-(4-methoxy-benzyl)-2-(oxalyl-amino)-4,5,6,7-tetrahydro-thieno[2,3-c]pyridine-3-carboxylic acid;

7-(1,3-Dioxo-1,3-dihydro-isoindol-2-ylmethyl)-6-(4-methoxy-benzyl)-2-(oxalyl-amino)-4,5,6,7-tetrahydro-thieno[2,3-c]pyridine-3-carboxylic acid;

7-(((5-Benzyloxy-1H-indole-2-carbonyl)amino)methyl)-6-(4-methoxy-benzyl)-2-(oxalyl-amino)-4,5,6,7-tetrahydro-thieno[2,3-c]pyridine-3-carboxylic acid;

7-(((6-Bromo-2-p-tolyl-quinoline-4-carbonyl)amino)methyl)-6-(4-methoxy-benzyl)-2-(oxalyl-amino)-4,5,6,7-tetrahydro-thieno[2,3-c]pyridine-3-carboxylic acid;

6-(4-Methoxy-benzyl)-7-(((5-methyl-2-phenyl-2H-[1,2,3]triazole-4-carbonyl)amino)methyl)-2-(oxalyl-amino)-4,5,6,7-tetrahydro-thieno[2,3-c]pyridine-3-carboxylic acid;

7-(((1H-Indole-3-carbonyl)amino)methyl)-6-(4-methoxy-benzyl )-2-(oxalyl-amino)-4,5,6,7-tetrahydro-thieno[2,3-c]pyridine-3-carboxylic acid;

7-((4-Ethoxy-2-hydroxy-benzoylamino)methyl)-6-(4-methoxy-benzyl)-2-(oxalyl-amino)-4,5,6,7-tetrahydro-thieno[2,3-c]pyridine-3-carboxylic acid;

7-((4-Benzoylamino-benzoylamino)methyl)-6-(4-methoxy-benzyl)-2-(oxalyl-amino)-4,5,6,7-tetrahydro-thieno[2,3-c]pyridine-3-carboxylic acid;

7-(((Biphenyl-4-carbonyl)-amino)methyl)-6-(4-methoxy-benzyl)-2-(oxalyl-amino)-4,5,6,7-tetrahydro-thieno[2,3-c]pyridine-3-carboxylic acid;

7-(((1H-indole-2-carbonyl)amino)methyl)-6-(4-methoxy-benzyl)-2-(oxalyl-amino)-4,5,6,7-tetrahydro-thieno[2,3-c]pyridine-3-carboxylic acid;

7-((3-Biphenyl-4-yl-acryloylamino)methyl)-6-(4-methoxy-benzyl)-2-(oxalyl-amino)-4,5,6,7-tetrahydro-thieno[2,3-c]pyridine-3-carboxylic acid;

6-(4-Methoxy-benzyl)-7-(((5-methoxy-1H-indole-2-carbonyl)amino)methyl)-2-(oxalyl-amino)-4,5,6,7-tetrahydro-thieno[2,3-c]pyridine-3-carboxylic acid;

7-((4-Benzyl-benzoylamino)methyl)-6-(4-methoxy-benzyl)-2-(oxalyl-amino)-4,5,6,7-tetrahydro-thieno[2,3-c]pyridine-3-carboxylic acid;

6-(4-Methoxy-benzyl)-7-(((naphthalene-1-carbonyl)amino)methyl)-2-(oxalyl-amino)-4,5,6,7-tetrahydro-thieno[2,3-c]pyridine-3-carboxylic acid;

6-(4-Methoxy-benzyl)-5-((2-naphthalen-2-yl-ethylamino)methyl)-2-(oxalyl-amino)-4,5,6,7-tetrahydro-thieno[2,3-c]pyridine-3-carboxylic acid;

5-((2-Benzo[1,3]dioxol-5-yl-acetylamino)methyl)-2-(oxalyl-amino)-4,5,6,7-tetrahydro-thieno[2,3-c]pyridine-3-carboxylic acid;

5-((2-Dibenzofuran-2-yl-ethyl)amino)methyl)-6-(4-methoxy-benzyl)-2-(oxalyl-amino)-4,5,6,7-tetrahydro-thieno[2,3-c]pyridine-3-carboxylic acid;

6-(4-Methoxy-benzyl)-5-((2-(5-methoxy-2-methyl-1H-indol-3-yl)-acetylamino)methyl)-2-(oxalyl-amino)-4,5,6,7-tetrahydro-thieno[2,3-c]pyridine-3-carboxylic acid;

5-((2-(1H-indol-3-yl)-2-oxo-acetylamino)methyl)-2-(Oxalyl-amino)-4,5,6,7-tetrahydro-thieno[2,3-c]pyridine-3-carboxylic acid;

5-(R)-(7-Methoxy-1-oxo-1,3-dihydro-isoindol-2-ylmethyl)-2-(oxalyl-amino)-4,5,6,7-tetrahydro-thieno[2,3-c]pyridine-3-carboxylic acid;

5-(S)-(7-Methoxy-1-oxo-1,3-dihydro-isoindol-2-ylmethyl)-2-(oxalyl-amino)-4,5,6,7-tetrahydro-thieno[2,3-c]pyridine-3-carboxylic acid;
5-(S)-(4-Hydroxy-1-oxo-1,3-dihydro-isoindol-2-ylmethyl)-2-(oxalyl-amino)-4,5,6,7-tetrahydro-thieno[2,3-c]pyridine-3-carboxylic acid;
2-(S)-(Oxalyl-amino)-5-((4-phenoxy-benzylamino)methyl)-4,5,6,7-tetrahydro-thieno[2,3-c]pyridine-3-carboxylic acid;
5-(S)-((4-Acetylamino-benzylamino)methyl)-2-(oxalyl-amino)-4,5,6,7-tetrahydro-thieno[2,3-c]pyridine-3-carboxylic acid;
7-(S)-((Acetyl-(4-phenoxy-benzyl)amino)methyl)-2-(oxalyl-amino)-4,5,6,7-tetrahydro-thieno[2,3-c]pyridine-3-carboxylic acid;
7-(S)-((Acetyl-benzyl-amino)methyl)-2-(oxalyl-amino)-4,5,6,7-tetrahydro-thieno[2,3-c]pyridine-3-carboxylic acid;
5-(S)-((1,1-Dioxo-1H-benzo[d]isothiazol-3-ylamino)methyl)-2-(oxalyl-amino)-4,5,6,7-tetrahydro-thieno[2,3-c]pyridine-3-carboxylic acid;
5-(4-Benzyloxy-1,3-dioxo-1,3-dihydro-isoindol-2-ylmethyl)-2-(oxalyl-amino)-4,5,6,7-tetrahydro-thieno[2,3-c]pyridine-3-carboxylic acid;
5-(6-Methoxy-4-methoxycarbonyl-1-oxo-1,3-dihydro-isoindol-2-ylmethyl)-2-(oxalyl-amino)-4,5,6,7-tetrahydro-thieno[2,3-c]pyridine-3-carboxylic acid;
2-(Oxalyl-amino)-5-(1,1,3-trioxo-1,3-dihydro-1H-benzo[d]isothiazol-2-ylmethyl)-4,7-dihydro-5H-thieno[2,3-c]pyridine-3-carboxylic acid;
2-(Oxalyl-amino)-7-(1,1,3-trioxo-1,3-dihydro-1H-benzo[d]isothiazol-2-ylmethyl)-4,7-dihydro-5H-thieno[2,3-c]pyridine-3-carboxylic acid;
7-(R)-Carbamoyl-2-(oxalyl-amino)-4,5,6,7-tetrahydro-thieno[2,3-c]pyridine-3-carboxylic acid;
2-(Oxalyl-amino)-5-(S)-(2-oxo-tetrahydro-thiophen-3-ylcarbamoyl)-4,5,6,7-tetrahydro-thieno[2,3-c]pyridine-3-carboxylic acid;
2-(Oxalyl-amino)-5-(S)-phenylcarbamoyl-4,5,6,7-tetrahydro-thieno[2,3-c]pyridine-3-carboxylic acid;
2-(Oxalyl-amino)-7-(R)-phenylcarbamoyl-4,5,6,7-tetrahydro-thieno[2,3-c]pyridine-3-carboxylic acid;
5-(R),7-(R)-Bis-benzyloxymethyl-2-(oxalyl-amino)-4,5,6,7-tetrahydro-thieno[2,3-c]pyridine-3-carboxylic acid;
6-Benzyl-2-(oxalyl-amino)-5-(1,1,3-trioxo-1,3-dihydro-1,6-benzo[d]isothiazol-2-ylmethyl)-4,5,6,7-tetrahydro-thieno[2,3-c]pyridine-3-carboxylic acid;
or a salt thereof with a pharmaceutically acceptable acid or base, or any optical isomer or mixture of optical isomers, a racemic mixture, or any tautomeric form, or prodrug thereof.

63. Compounds according to claim 1 which act as inhibitors of Protein Tyrosine Phosphatases.

64. A pharmaceutical composition comprising an effective amount of a compound of claim 1 together with one or more pharmaceutically acceptable carriers or diluents.

65. The pharmaceutical composition according to claim 64 in the form of an oral dosage unit or parenteral dosage unit.

66. The pharmaceutical composition according to claim 64 wherein the compound is administered as a dose in a range from about 0.05 to 1000 mg.

67. A method of treating type I diabetes, type II diabetes, impaired glucose tolerance, insulin resistance or obesity, comprising administering to a subject in need thereof an effective amount of a compound of claim 1.

68. A method of treating immune dysfunctions including autoimmunity, diseases with dysfunctions of the coagulation system, allergic diseases, osteoporosis, proliferative disorders including cancer and psoriasis, diseases with decreased or increased synthesis or effects of growth hormone, diseases with decreased or increased synthesis of hormones or cytokines that regulate the release of/or response to growth hormone, diseases of the brain including Alzheimer's disease and schizophrenia, and infectious diseases, comprising administering to a subject in need thereof an effective amount of a compound of claim 1.

69. A method for preparing a compound of formula 1, comprising:

A)

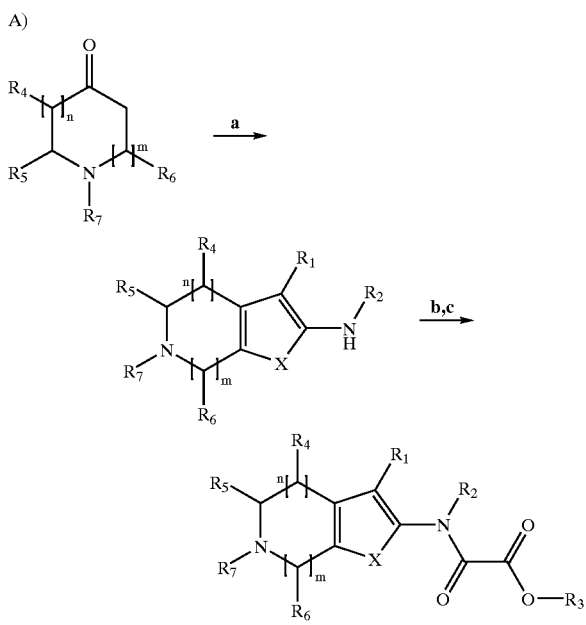

a) NCCH$_2$COOR$_3$, sulphur, morpholine or triethylamine, ethanol; b) R$_3$OCOCOimidazole, tetrahydrofuran; c) 25% trifluoroacetic acid/dichloromethane; wherein n, m, X, R$_1$, R$_2$, R$_3$, R$_4$, R$_5$, R$_6$ and R$_7$ are defined in claim 1, or

B)

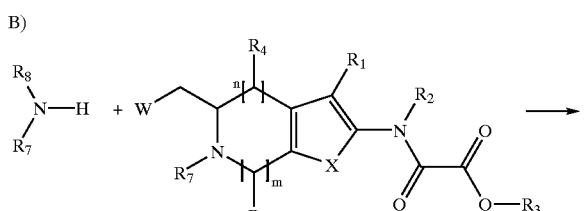

(I)                (II)

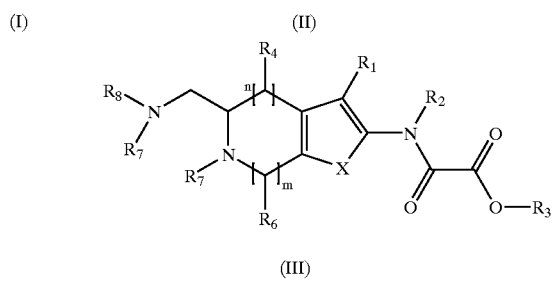

(III)

allowing an amine (I) and a substituted oxalylamide (II) to react under basic conditions (e.g. K$_2$CO$_3$, in N,N-dimethylformamide or methylethylketone) or under Mitsunobu conditions (Oyo Mitsunobu, *Synthesis*, (1981) 1–28) to yield (III) wherein W is OH, OSO$_2$Me or halo, and n, m, X, $R_1$, $R_2$, $R_3$, $R_4$, $R_6$, $R_7$ and $R_8$ are defined in claim 1, or

C)

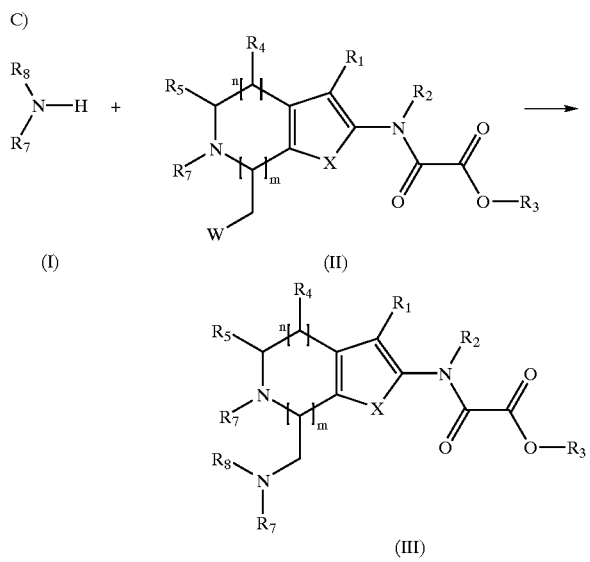

allowing an amine (I) and a substituted oxalylamide (II) to react under basic conditions (e.g. $K_2CO_3$, in N,N-dimethylformamide or methylethylketone) or under Mitsunobu conditions (Oyo Mitsunobu, *Synthesis*, (1981) 1–28) to yield (III) wherein W is OH, $OSO_2Me$ or halo, and n, m, X, $R_1$, $R_2$, $R_3$, $R_4$, $R_5$, $R_7$ and $R_8$ are defined in claim 1.

70. A method of treating type I diabetes, type II diabetes, impaired glucose tolerance, insulin resistance or obesity comprising administering to a subject in need thereof an effective amount of a compound of claim 1 and an insulin sensitizer to said subject.

71. A method of treating type I diabetes, type II diabetes, impaired glucose tolerance, insulin resistance or obesity comprising administering to a subject in need thereof an effective amount of a compound of claim 1 and an agent stimulating insulin release from β cells to said subject.

72. A method of treating type I diabetes, type II diabetes, impaired glucose tolerance, insulin resistance or obesity, comprising administering to a subject in need thereof an effective amount of a compound of claim 1 and an antiobesity agent such as orlistat to said subject.

73. The method according to claim 70, wherein the insulin sensitizer is a thiazolidinedione or (−) 3-[4-[2-Phenoxazin-10-yl)ethoxy]phenyl]-2-ethoxypropanoic acid or a pharmaceutically acceptable salts thereof.

74. The method according to claim 73, wherein the thiazolidinedione is seleceted from troglitazone, ciglitazone, pioglitazone, rosiglitazone, and 5-[[4-[3-Methyl-4-oxo-3,4-dihydro-2-quinazolinyl]methoxy]phenyl-methyl]thiazolidine-2,4-dione or a pharmaceutically acceptable salt thereof.

75. The method according to claim 70, wherein the insulin sensitizer is (−) 3-[4-[2-Phenoxazin-10-yl)ethoxy]phenyl]-2-ethoxypropanoic acid or a pharmaceutically acceptable salts thereof.

76. The method according to claim 75, wherein the insulin sensitizer is the arginine salt of (−) 3-[4-[2-Phenoxazin-10-yl)ethoxy]phenyl]-2-ethoxypropanoic acid.

77. The method according to claim 71, wherein the agent stimulating insulin release from β cells is repaglinide.

* * * * *

UNITED STATES PATENT AND TRADEMARK OFFICE
CERTIFICATE OF CORRECTION

PATENT NO. : 6,410,556 B1
DATED : June 25, 2002
INVENTOR(S) : Andersen et al.

It is certified that error appears in the above-identified patent and that said Letters Patent is hereby corrected as shown below:

Column 107,
Line 23, "R5 is $C_1 14$" should read -- R5 is $C_1$-$C_6$ --.

Column 108,
Line 4, "according to claim 22" should read -- according to claim 20 --.

Column 116,
Line 19, "is seleceted from" should read -- is selected from --.

Signed and Sealed this

Twenty-third Day of December, 2003

JAMES E. ROGAN
*Director of the United States Patent and Trademark Office*